(12) United States Patent
Church et al.

(10) Patent No.: US 10,640,789 B2
(45) Date of Patent: May 5, 2020

(54) RNA-GUIDED TRANSCRIPTIONAL REGULATION

(71) Applicant: President and Fellows of Harvard College, Cambridge, MA (US)

(72) Inventors: George M. Church, Brookline, MA (US); Prashant G. Mali, Somerville, MA (US); Kevin M. Esvelt, Auburndale, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/049,451

(22) Filed: Feb. 22, 2016

(65) Prior Publication Data

US 2016/0237456 A1 Aug. 18, 2016

Related U.S. Application Data

(63) Continuation of application No. 14/319,530, filed on Jun. 30, 2014, which is a continuation of application No. PCT/US2014/040868, filed on Jun. 4, 2014.

(60) Provisional application No. 61/830,787, filed on Jun. 4, 2013.

(51) Int. Cl.
| | |
|---|---|
| *C12N 15/113* | (2010.01) |
| *C12N 15/115* | (2010.01) |
| *C12N 15/90* | (2006.01) |
| *C12N 9/22* | (2006.01) |
| *C12N 15/01* | (2006.01) |
| *C12N 15/10* | (2006.01) |
| *C12N 15/63* | (2006.01) |
| *C12N 15/11* | (2006.01) |

(52) U.S. Cl.
CPC .......... *C12N 15/907* (2013.01); *C12N 9/22* (2013.01); *C12N 15/102* (2013.01); *C12N 15/11* (2013.01); *C12N 15/113* (2013.01); *C12N 15/635* (2013.01); *C12N 2310/20* (2017.05); *C12N 2310/3513* (2013.01); *C12Y 301/00* (2013.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 9,257,135 B2 * | 2/2016 | Ong | G11B 5/012 |
| 9,267,135 B2 * | 2/2016 | Church | C12N 15/01 |
| 2010/0076057 A1 | 3/2010 | Sontheimer et al. | |
| 2011/0189776 A1 | 8/2011 | Terns et al. | |
| 2011/0223638 A1 | 9/2011 | Wiedenheft et al. | |
| 2013/0130248 A1 | 5/2013 | Haurwitz et al. | |
| 2013/0253040 A1 | 9/2013 | Miller et al. | |
| 2014/0068797 A1 * | 3/2014 | Doudna | C12N 15/102 800/18 |
| 2014/0179770 A1 * | 6/2014 | Zhang | C12N 15/86 514/44 R |
| 2014/0273226 A1 | 9/2014 | Wu | |
| 2014/0273233 A1 | 9/2014 | Chen et al. | |
| 2014/0315985 A1 | 10/2014 | May et al. | |
| 2014/0342457 A1 * | 11/2014 | Mali | C12N 15/10 435/441 |
| 2016/0024524 A1 * | 1/2016 | Joung | C12N 9/22 435/462 |

FOREIGN PATENT DOCUMENTS

| | | |
|---|---|---|
| WO | 2008/108989 A2 | 9/2008 |
| WO | 2010/054108 A2 | 5/2010 |
| WO | 2011/143124 A2 | 11/2011 |
| WO | 2012/164565 A1 | 12/2012 |
| WO | 2013/098244 A1 | 7/2013 |
| WO | 2013/126794 A1 | 8/2013 |
| WO | 2013/141680 A1 | 9/2013 |
| WO | 2013/142578 A1 | 9/2013 |
| WO | 2013/176772 A1 | 11/2013 |
| WO | 2014/022702 A2 | 2/2014 |
| WO | 2014/065596 A1 | 5/2014 |

(Continued)

OTHER PUBLICATIONS

Al-Attar et al., Clustered Regularly Interspaced Short Palindromic Repeats (CRISPRs): The Hallmark of an Ingenious Antiviral Defense Mechanism in Prokaryotes, Bioi Chem. (20 11) vol. 392, Issue 4, pp. 277-289.

(Continued)

*Primary Examiner* — Julie Wu

(74) *Attorney, Agent, or Firm* — Banner & Witcoff, Ltd.

(57) ABSTRACT

Methods of modulating expression of a target nucleic acid in a cell are provided including introducing into the cell a first foreign nucleic acid encoding one or more RNAs complementary to DNA, wherein the DNA includes the target nucleic acid, introducing into the cell a second foreign nucleic acid encoding a nuclease-null Cas9 protein that binds to the DNA and is guided by the one or more RNAs, introducing into the cell a third foreign nucleic acid encoding a transcriptional regulator protein or domain, wherein the one or more RNAs, the nuclease-null Cas9 protein, and the transcriptional regulator protein or domain are expressed, wherein the one or more RNAs, the nuclease-null Cas9 protein and the transcriptional regulator protein or domain co-localize to the DNA and wherein the transcriptional regulator protein or domain regulates expression of the target nucleic acid.

32 Claims, 65 Drawing Sheets
(28 of 65 Drawing Sheet(s) Filed in Color)
Specification includes a Sequence Listing.

(56) References Cited

FOREIGN PATENT DOCUMENTS

| | | | |
|---|---|---|---|
| WO | 2014/089290 A1 | 6/2014 | |
| WO | 2014/093595 A1 | 6/2014 | |
| WO | 2014/093622 A2 | 6/2014 | |
| WO | 2014/093661 A2 | 6/2014 | |
| WO | 2014/093694 A1 | 6/2014 | |
| WO | 2014/099744 A1 | 6/2014 | |
| WO | 2014/113493 A1 | 7/2014 | |
| WO | 2014/150624 A1 | 9/2014 | |
| WO | 2014/191518 A1 | 12/2014 | |
| WO | 2014/197568 A2 | 12/2014 | |

OTHER PUBLICATIONS

Ansari et al, Rioboactivators: Transcription activation by non-coding RNA, Grit Rev Biochem Mol Bioi. 2009 ; 44(1 ): 50-61.

Carroll, "A CRISPR Approach to Gene Targeting" 20(9) Molecular Therapy 1658-1660 (Sep. 2012).

Cheng, AW et al. Multiplexed Activation of Endogenous Genes by CRISP R-on, An RNA-Guided Transcriptional Activator System. Cell Research. Aug. 27, 2013. vol. 23; pp. 1163-1171. DOI: 10.1038/cr.2013.122.

Cong, Let al. Multiplex Genome Engineering Using CRISPR/Cas Systems. Science. Jan. 3, 2013, vol. 339; pp. 819-823; abstract; p. 821, third column; p. 822, first column, first paragraph; figure 4. DOI: 10.1126/science.1231143.

CRISPR in the Lab: A Practical Guide [online]. Addgene. Sep. 4, 2014. Retrieved on Dec. 4, 2014. Retrieved from the Internet: <URL: https://www.addgene.org/CRISPR/guide/>.

Gasiunas, G et aL Cas9-crRNA Ribonucleoprotein Complex Mediates Specific DNA Cleavage for Adaptive Immunity in Bacteria. PNAS. Sep. 4, 2012. vol. 109, No. 39; pp. E2579-E2586; p. E2583, first column, first paragraph. DOI: 1 0.1073/pnas.1208507109.

Hale et al., Essential Features and Rational Design of CRISPR RNAs That Function With the Cas RAMP Module Complex to Cleave RNAs, Molecular Cell, (20 12) vol. 45, Issue 3, 292-302.

Hatoum-Aslan, et al. 'Mature clustered, regularly interspaced, short palindromic repeats RNA 5,9, 14 (crRNA) length is measured by a ruler mechanism anchored at the precursor processing site' Proceedings of the National Academy of Sciences. vol. 108, No. 52. pp. 21218-21222. Dec. 2011. entire document.

International Search Report and Written Opinion issued in corresponding International Application No. PCT/US14/40868, dated Dec. 31, 2014.

Jinek , et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/content/2/e00471 >. entire document.

Jinek, M et al. A Programmable Dual-RNA-Guided DNA Endonuclease in Adaptive Bacterial Immunity. Science. Jun. 28, 2012, vol. 337; pp. 816-821; DOI: 10.1126/science.1225829.

Leman, AR et al. The Replication Forie Understanding the Eukaryotic Replication Machinery and the Challenges to Genome Duplication. Genes. Jan. 29, 2013. vol. 4; pp. 1-32; figure 1; DOI: 10.3390/genes4010001.

Liu et al, Cell-Penetrating Peptide-Mediated Delivery of TALEN Proteins via Bioconjugation for Genome Engineering, PLOS One, 2014, vol. 9(1), pp. 1-7.

Makarova et al., "Evolution and classification of the CRISPR-Cas systems" 9(6) Nature Reviews Microbiology 467-477 (1-23) (Jun. 2011).

Mali, P. et al. CAS9 Transcriptional Activators for Target Specificity Screening and Paired Nickases for Cooperative Genome Engineering. Nature Biotechnology. Aug. 1, 2013. vol. 31; pp. 833-838; entire document. DOI: 10.1038/nbt.2675.

Mali, P. et al. RNA-Guided Human Genome Engineering via Cas9. Science. Jan. 3, 2013,vol. 339; pp. 323-826; abstract; p. 823, second column, second to third paragraph; p. 823, third column, second paragraph to third paragraph; figure 1; Supplementary material, p. 4, first paragraph; p. 7, first paragraph; Supplementary figures S1, S3. DOI: 10.1126/science.1232033.

Qi, L et al. Repurposing CRISPR as an RNA-Guided Platform for Sequence-Specific Control of Gene Expression. Cell. Feb. 28, 2013. vol. 152; pp. 1173-1183; figures 2, 4. DOI: 10.1 016/j.cell.2013.02. 022.

Ramakrishna et al, Gene disruption by cell-penetrating peptide-mediated delivery of Cas9 protein and guide RNA, Genome Res. published online Apr. 2, 2014, pp. 1-20 plus figures.

Ran, FA et al. Double Nicking by RNA-Guided CRISPR Cas9 for Enhanced Genome Editing Specificity. Cell. Sep. 12, 2013. vol. 154; pp. 1380-1389. DOI: 10.1016/j.ce11.2013.08.021.

Rho, Mina et al. 'Diverse CRISPRs Evolving in Human Microbiomes.' PLoS Genetics. vol. 8, No. 6. 1-14 pp. 1-12. Jun. 2012. entire document.

Sapranauskas et al (Nucleic Acids Research, 2011, 39:9275-9282).

Sontheimer Erik, Project 7: Establishing RNA-Directed DNA Targeting in Eukaryotic Cells; Project dates: Nov. 16, 2011 to Dec. 31, 2012 (Feb. 4, 2012).

The Delivery Problem, Nature Biotechnology, 2006, vol. 24(3), pp. 305-306.

Tiley, LS et al. The VP16 Transcription Activation Domain Is Functional When Targeted to a Promoter-Proximal RNA Sequence. Genes and Development. 1992. vol. 6; pp. 2077-2087; abstract; p. 2077, first column, first paragraph.

Trafton, A. Editing the Genome With High Precision [online]. MIT News office. Jan. 3, 2013 [retrieved on Dec. 4, 2014). Retrieved from the Internet: <URL:http:/lnewsoffice. Trafton .edut20 13/editing-the-genome-with-high-precision-01 03 >;pp. 1-3; p. 3, third paragraph.

U.S. Appl. No. 61/781,598, filed Mar. 14, 2013, Haurwitz, R.

U.S. Appl. No. 61/794,422, filed Mar. 15, 2013, Davis, G. et al.

Wiedenheft eta!., "RNA-guided genetic silencing systems in bacteria and archaea" 482 Nature 331-338 (Feb. 16, 2012).

Gilbert, Luke A., et al.,"CRISPR-Mediated Modular RNA-Guided Regulation of Transcription in Eukaryotes," Cell, vol. 154, No. 2, Jul. 1, 2013 (Jul. 1, 2013), pp. 442-451.

Maeder, Morgan L., et al.,"Robust, synergistic regulation of human gene expression using TALE activators," HHS Public Access Author Manuscript, vol. 10, No. 3, Feb. 10, 2013 (Feb. 10, 2013), pp. 243-245.

Mali, P. et al., "Supplementary Materials for RNA-Guided Human Genome Engineering via Cas9," Science, vol. 339, No. 6121, Jan. 3, 2013 (Jan. 3, 2013), pp. 1-36.

Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.

\* cited by examiner

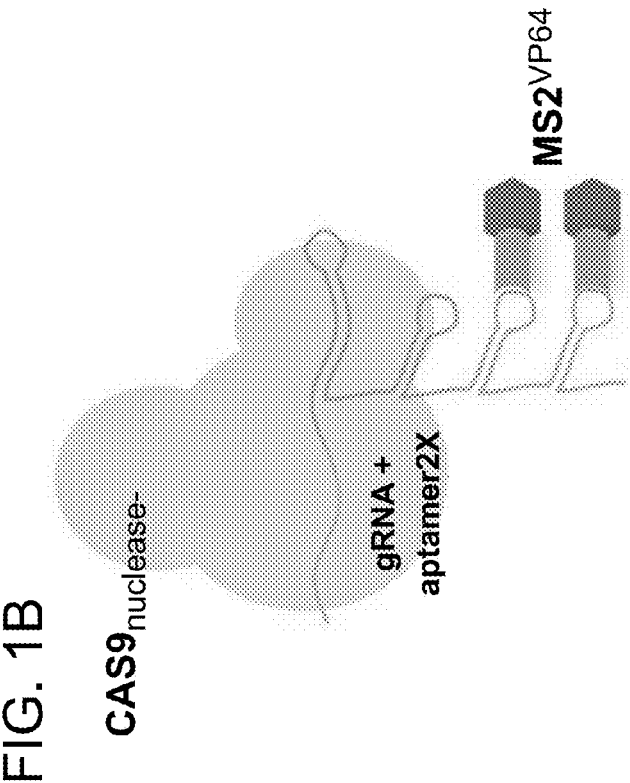
FIG. 1A
FIG. 1B
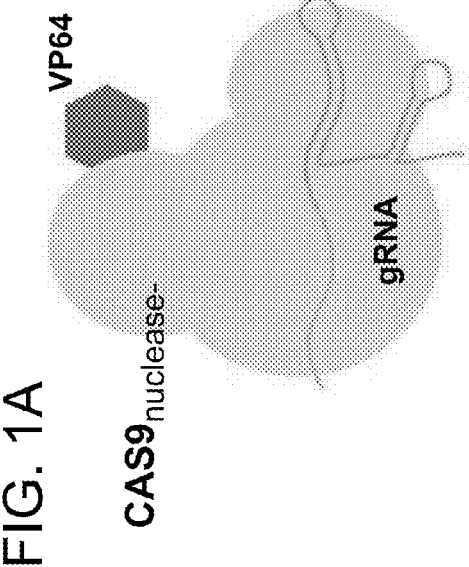
FIG. 1C
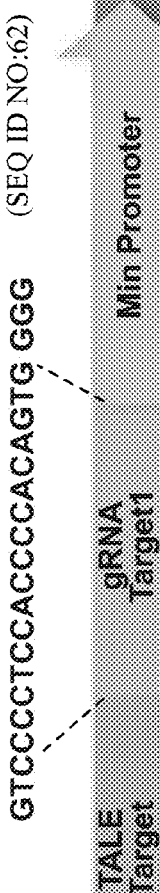
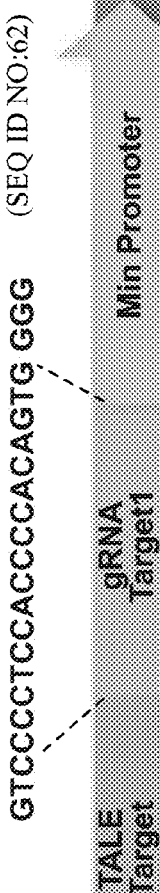

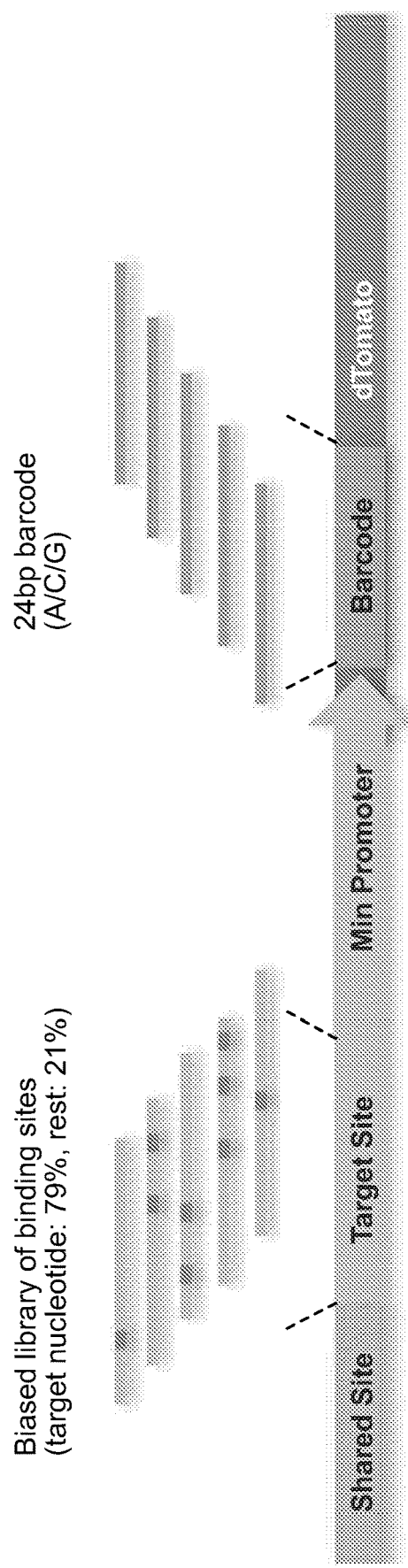

18mer TALE$^{VP64}$: one base mismatch match, mismatch=A, mismatch=C, mismatch=G, mismatch=T

18mer TALE$^{VP64}$: two base mismatch

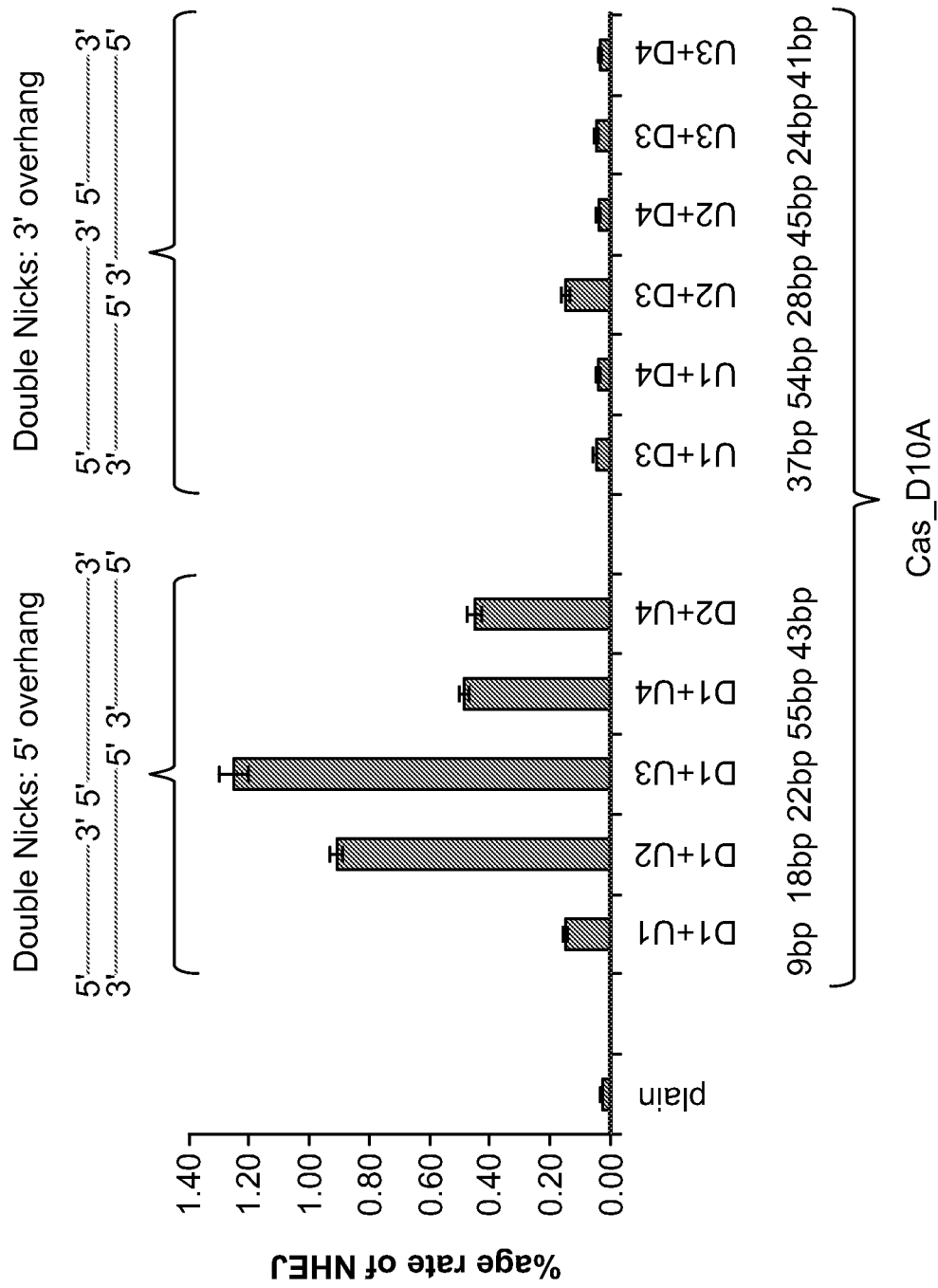

(SEQ ID NO:64)
TAATACTTTTATCTGTCCCCACCCCACAGTGGGGCCACTAGGGACACAGGAATTGGTGACAGAAAGCCCC

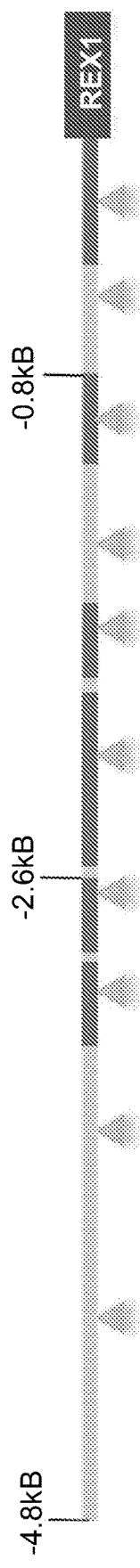
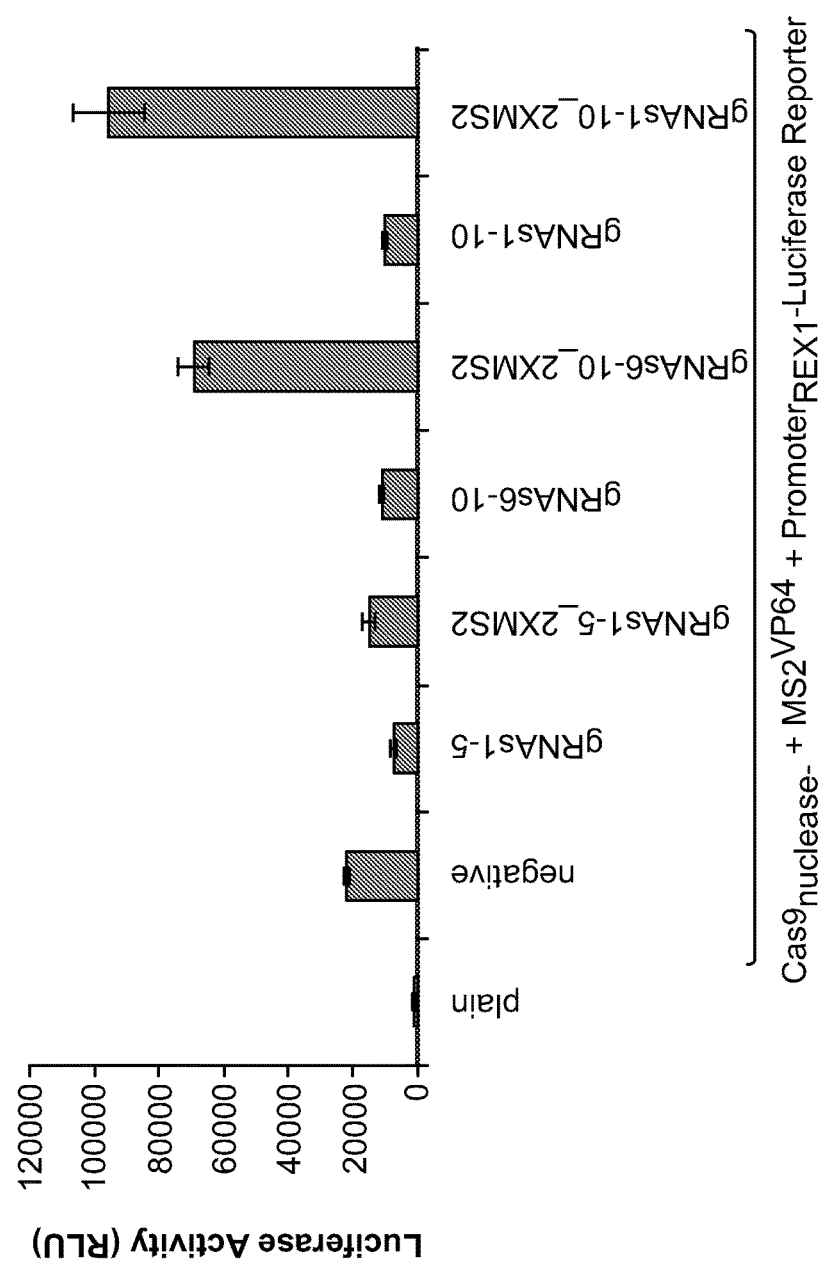
FIG. 7A
FIG. 7B

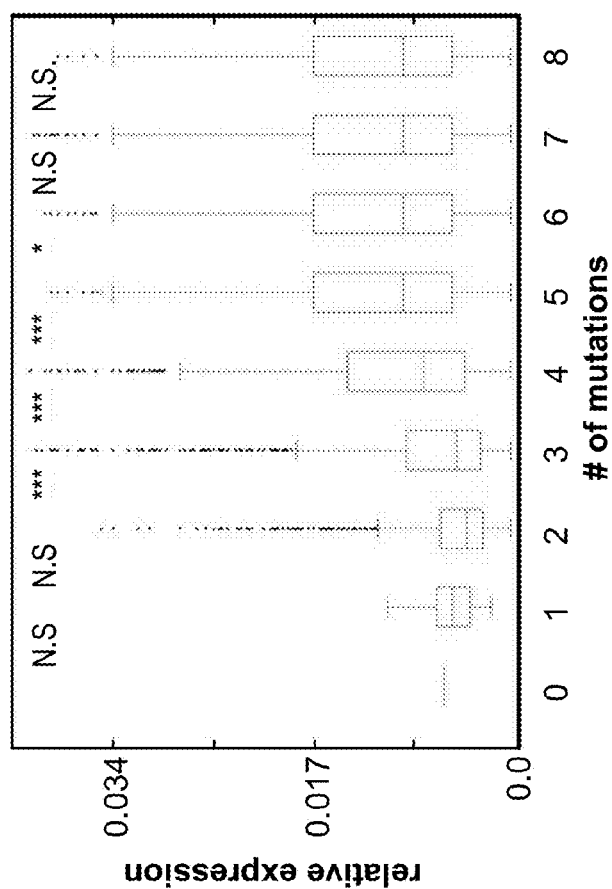
FIG. 14A
Target    : GAGATGATCGCCCCTTCTTC TGG (SEQ ID NO:88)
gRNA3     : GAGATGATCGCCCCTTCTTC    (SEQ ID NO:89)
gRNA3mut: GTGATGACCGGCCGTTCTTC    (SEQ ID NO:90)
FIG. 14B
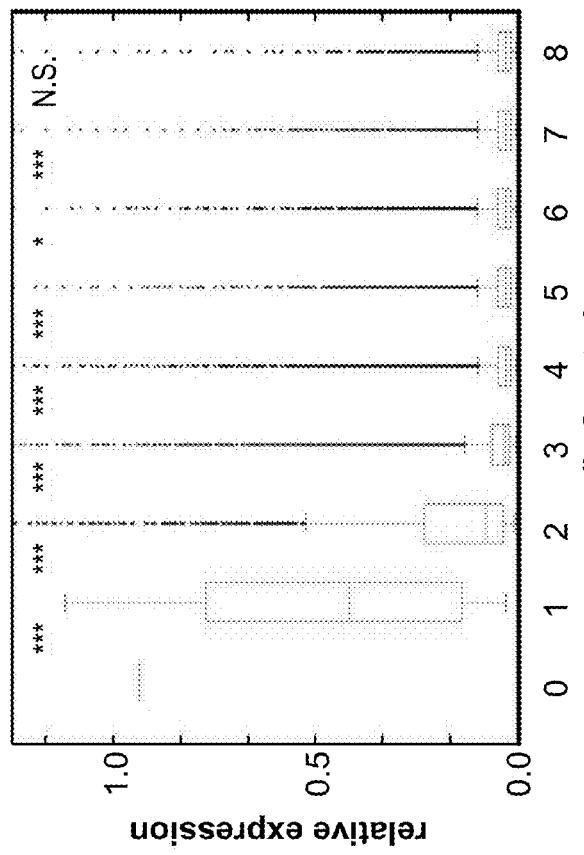
FIG. 14C

FIG. 15B-2

(SEQ ID NO:94)
GUCCCUCCACCCCACAGUC (SEQ ID NO:95)
GUCCCUCCACCCCACAGAG (SEQ ID NO:96)
GUCCCUCCACCCCACACUG (SEQ ID NO:97)
GUCCCUCCACCCCACUGUG (SEQ ID NO:98)
GUCCCUCCACCCAGAGUG (SEQ ID NO:99)
GUCCCUCCACCCCUCAGUG (SEQ ID NO:100)
GUCCCUCCACCCGACAGUG (SEQ ID NO:101)
GUCCCUCCACCGCACAGUG (SEQ ID NO:102)
GUCCCUCCACGCCACAGUG (SEQ ID NO:103)
GUCCCUCCAGCCCACAGUG (SEQ ID NO:104)
GUCCCUCCUCCCCACAGUG (SEQ ID NO:105)
GUCCCUCGACCCCACAGTG (SEQ ID NO:106)
GUCCCUCCACCCCACAGAC (SEQ ID NO:107)
GUCCCUCCACCCCACUCUG (SEQ ID NO:108)
GUCCCUCCACCCUGAGUG (SEQ ID NO:109)
GUCCCUCCACCGGACAGUG (SEQ ID NO:110)
GUCCCUCCAGGCCACAGUG (SEQ ID NO:111)
GUCCCUCGUCCCCACAGUG

FIG. 15C
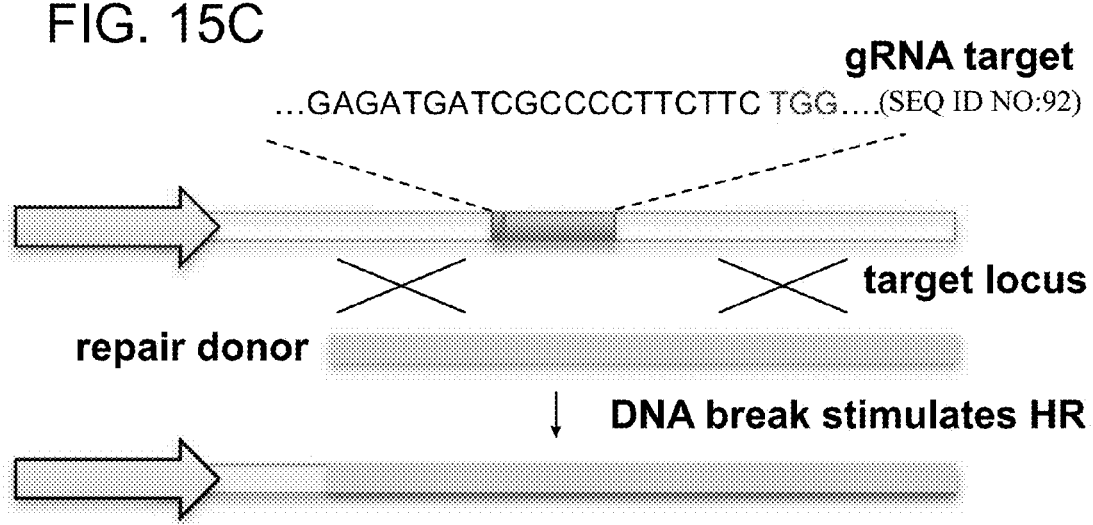
FIG. 15D-1
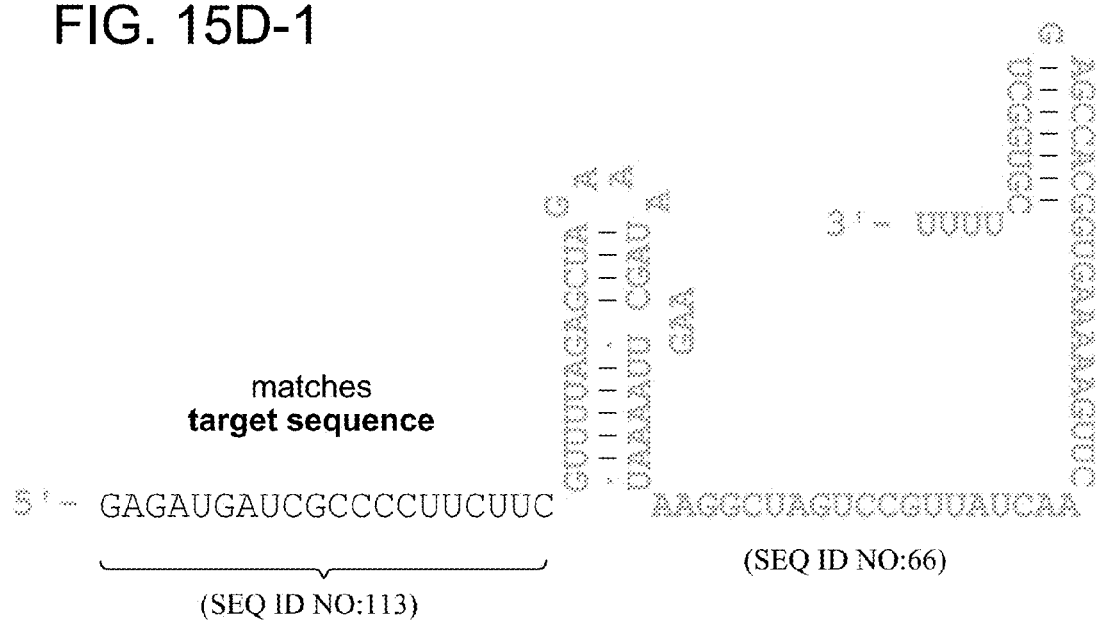
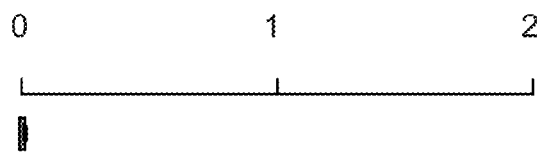

FIG. 15D-2

(SEQ ID NO:114)
GAGAUGAUCGCCCCUUCUUG (SEQ ID NO:115)
GAGAUGAUCGCCCCUUCUAC (SEQ ID NO:116)
GAGAUGAUCGCCCCUUCAUC (SEQ ID NO:117)
GAGAUGAUCGCCCCUUGUUC (SEQ ID NO:118)
GAGAUGAUCGCCCCUACUUC (SEQ ID NO:119)
GAGAUGAUCGCCCCAUCUUC (SEQ ID NO:120)
GAGAUGAUCGCCCGUUCUUC (SEQ ID NO:121)
GAGAUGAUCGCCGCUUCUUC (SEQ ID NO:122)
GAGAUGAUCGCGCCUUCUUC (SEQ ID NO:123)
GAGAUGAUCGGCCCUUCUUC (SEQ ID NO:124)
GAGAUGAUCCCCCUUCUUC (SEQ ID NO:125)
GAGAUGAUGGCCCCUUCUUC (SEQ ID NO:126)
GAGAUGAUCGCCCCUUCUAG (SEQ ID NO:127)
GAGAUGAUCGCCCCUUGAUC (SEQ ID NO:128)
GAGAUGAUCGCCCAACUUC (SEQ ID NO:129)
GAGAUGAUCGCCGGUUCUUC (SEQ ID NO:130)
GAGAUGAUCGGGCCUUCUUC (SEQ ID NO:131)
GAGAUGAUGCCCCUUCUUC

FIG. 16B-1

```
        AGCCACGGUGAAAAAGUUC
       G|||||||
        UCGGUGC
                 AAAAA
              3' --
                                              AAGGCUAGUCCGUUAUCAA
                                              (SEQ ID NO:66)
                        GAA
              A     UAAAUU CGAU
             A  A   ||||||  |||||
            G    GUUUAGCUA
                            matches
                            target sequence
        5' -- GGGGCCACUAGGGACAGGAU
                  (SEQ ID NO:133)
```

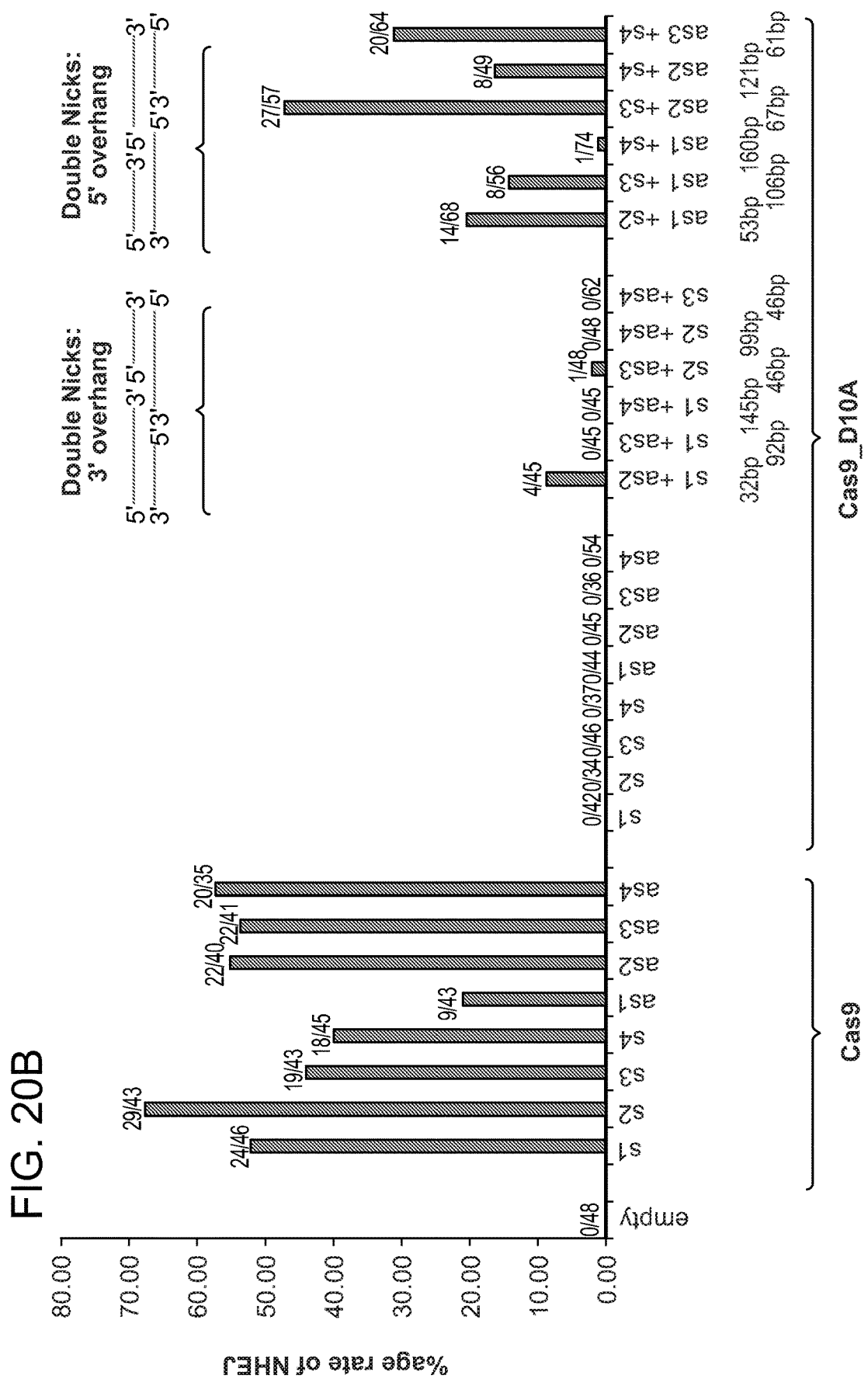

FIG. 21A as1 + s2

```
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGG------TTCTGGGTACTT    (SEQ ID NO:160)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGCgagccaccttatattcccagggCGGTTAATGTGGCTCTGGTTCTGGGTACTT    (SEQ ID NO:161)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:162)
GGGATCCTGTGTCCCCG----T----C----T----GG----------------------------TT----CT--GG----G--TACTT    (SEQ ID NO:187)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:163)
GGGATCCTGTGTCCCCGAGCTGGGACCACCTTATATTCCCAGGGC----------------------------------TTCTGGGTACTT    (SEQ ID NO:159)
GGGATCCTGTGTCCCCGAGCTGGGACCACCTTATATTCCCAGGGC----------------------------CGGTTAATGTGGCTCTGGTTCTGGGTACTT    (SEQ ID NO:159)
GGGATCCTGTGTCCCCGAGCTGGGACCACCTTATA----------------------------CGGTTAATGTGGCTCTGGTTCTGGGTACTT    (SEQ ID NO:159)
GGGATC--T--TGT--------------------------------------------GGTACTT    (SEQ ID NO:164)
GGGATCCTGTGTCCCCGAGCTGGGACCACCTTATATTCCCAGGGC----------------------------CGGTTAATGTGGCTCTGGTTCTGGGTACTT    (SEQ ID NO:159)
```

FIG. 21B

```
as2 + e3
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA (SEQ ID NO:165)
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATGAATCTGGCTCTGGTTCTGGTTCTGGGTACTTTTATCTGTCCCCTCCACCCCA-----CAGT----GGGGCC----ACT--A (SEQ ID NO:166) GACAGAAAA
AGGGCCGGTTAATG-----TGGCTCTGGTTCTGGTTCTGGGTACTTTTATCTGTCCCC------------- (SEQ ID NO:167) ----------GATTGGTGACAGAAAA
AGGGCCGGTT------------------------------------------------------------- (SEQ ID NO:168) ----CAGGACAGGAGGATTGGTGACAGAAAA
AGGGCCGGTT------------------------------------------------------------- (SEQ ID NO:165)
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATG-----TGGCTCTGGTTCTGGTTCTGGGTACTTTTATCTGTCCCC------------- (SEQ ID NO:169) ----------GATTGGTGACAGAAAA
AGGGCCGGTTAATG-----TGGC------------------------------------------------ (SEQ ID NO:170) ----------GATTGGTGACAGAAAA
AGGGCCGGTTAATG-----TGGCTCTGGTTCTGGTTCTGGGTACTTTTATCTGTCCCC------------- (SEQ ID NO:171)
AGGGCCGGTTAATG-----TGGCTCTGGTTCTGGTTCTGGGTACTTTTATCTGTCCCCTCCACCCCA-----CAGT----GGGG (SEQ ID NO:165) ACAGGACAGGAGGATTGGTGACAxxAAAA
AGGGCCGGTTAATG-----TGGCTCTGGTTCTGGTTCTGGGTACTTTTATCTGTCCCCTCCACCCCA-----CAGT----GGGGCC----ACT--AGGGACAGGAGGATTGGTGACAGAAAA
AGGGCCGGTTAATG------------------------------------------------------------ (SEQ ID NO:172)
AGGGCCGGTTAATG-----TGGCTCTGGTTCTGGTTCTGGGTACTTTTATCTGTCCCCTCCACCCCA------ (SEQ ID NO:173) --------TGGTGACAGAAAA
AGGGCCGGTTAATG-----TGGCTCTGGTTCTGGTTCTGGGTACTTTTATCTGTCCCCTCCACCCCAxxxCAGTCxGxCCCTCCACCCxCAGGACAGGAGGATTGGTGACAGAAAA
AGGGCCGGTTAATG-----TGGCTCTGGTTCTGGTTCTGGGTACTTTTATCTGTCCCCTCCACC--------A (SEQ ID NO:174) CC----ACT--AGGGACAGGAGGATTGGTGACAGAAAA
```

FIG. 21C

```
as3 + s4
                                       (SEQ ID NO:175)
CCCACAGTGGGGCCACTA------------GG--GACAGGATTGTTGAC-AGAAAAGCCCCAT--------------------------------------------------------------------------ACCCC
                                       (SEQ ID NO:176)
CCCACAGTGGGGCCACTA------------GG--GACAGGATTGTTGAC-AGAAAAGCCCCAT--------------------------------------------------------------------------ACCCC
                                       (SEQ ID NO:176)
CCCACAGTGGGGCCACTA------------------------------------GTAGAACAGCCCCATCCTTAGGCCTCCCCATCCTTAGGCCTCCTCCTTCCTCCTAGTCTCCTGATATTGGGTCTAACCCC
                                       (SEQ ID NO:177)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCAC-----------------------------------------------------------CCTTAGGCCTCCCCATCCTTAGGCCTCCTCCTTCCTCCTAGTCTCCTGATATTGGGTCTAACCCC
                                       (SEQ ID NO:179)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------G---GACAGGATTGTTGAC-AAAAAAGCCCCATCCTTAGGCCTCCCCATCCTTA GCCTCCTCCTTCCTCCTAGTCTCCTGATATTGGGTCTAACCCC
                                       (SEQ ID NO:181)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:182)
CCCACAGTGGGGCCACTA------------GG--GAC-----------------------------------------AGGCCTCCCCATCCTTAGGCCTCCTCCTTCCTCCTAGTCTCCTGATATTGGGTCTAACCCC
                                       (SEQ ID NO:183)
CCCACAGTGGGGCCACTAGGGACACGGG--GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:178)
CCC---------------------------------------------------------------------------------------------------------TGATATTGGGTCTAACCCC
                                       (SEQ ID NO:178)
CCCACAGTGGGGCCACTA-----------------ACAGGATTGTTGAC-AGAAAAGCCCCATCCTTAGGCCTCCCCATCCTTAGGCCTCCTCCTTCCTCCTAGTCTCCTGATATTGGGTCTAACCCC
                                       (SEQ ID NO:184)
CCCACAGTGGGGCCACTA------------GG--GACAGGATTGTTGAC-AGAAAAGCCCCATCCTTAGGCCTCCCCATCCTTAGGCCTCCTCCTTCCTCCTAGTCTCCTGATATTGGGTCTAACCCC
```

RNA-GUIDED TRANSCRIPTIONAL REGULATION

RELATED APPLICATION DATA

This application is a continuation of U.S. patent application Ser. No. 14/319,530, filed on Jun. 30, 2014, which is a continuation of PCT application no. PCT/US2014/040868, designating the United States and filed Jun. 4, 2014; which claims the benefit U.S. Provisional Patent Application No. 61/830,787 filed on Jun. 4, 2013; each of which are hereby incorporated by reference in their entireties.

STATEMENT OF GOVERNMENT INTERESTS

This invention was made with government support under Grant No. P50 HG005550 from the National Institutes of health and DE-FG02-02ER63445 from the Department of Energy. The government has certain rights in the invention.

REFERENCE TO AN ELECTRONIC SEQUENCE LISTING

The contents of the electronic sequence listing (Sequence_Listing 10498_00766_ST25_REPLACEMENT.txt; Size: 71,475 bytes; and Date of Creation: Feb. 13, 2020) is herein incorporated by reference in its entirety.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012): Sapranauskas, R. et al. The *Streptococcus thermophilus* CRISPR/Cas system provides immunity in *Escherichia coli*. Nucleic acids research 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

SUMMARY

Aspects of the present disclosure are directed to a complex of a guide RNA, a DNA binding protein and a double stranded DNA target sequence. According to certain aspects, DNA binding proteins within the scope of the present disclosure include a protein that forms a complex with the guide RNA and with the guide RNA guiding the complex to a double stranded DNA sequence wherein the complex binds to the DNA sequence. This aspect of the present disclosure may be referred to as co-localization of the RNA and DNA binding protein to or with the double stranded DNA. In this manner, a DNA binding protein-guide RNA complex may be used to localize a transcriptional regulator protein or domain at target DNA so as to regulate expression of target DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding an RNA guided nuclease-null DNA binding protein that binds to the DNA and is guided by the one or more RNAs, introducing into the cell a third foreign nucleic acid encoding a transcriptional regulator protein or domain, wherein the one or more RNAs, the RNA guided nuclease-null DNA binding protein, and the transcriptional regulator protein or domain are expressed, wherein the one or more RNAs, the RNA guided nuclease-null DNA binding protein and the transcriptional regulator protein or domain co-localize to the DNA and wherein the transcriptional regulator protein or domain regulates expression of the target nucleic acid.

According to one aspect, the foreign nucleic acid encoding an RNA guided nuclease-null DNA binding protein further encodes the transcriptional regulator protein or domain fused to the RNA guided nuclease-null DNA binding protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion. According to one aspect, the guide RNA includes a spacer sequence and a tracer mate sequence. The guide RNA may also include a tracr sequence, a portion of which hybridizes to the tracr mate sequence. The guide RNA may also include a linker nucleic acid sequence which links the tracer mate sequence and the tracr sequence to produce the tracrRNA-crRNA fusion. The spacer sequence binds to target DNA, such as by hybridization.

According to one aspect, the guide RNA includes a truncated spacer sequence. According to one aspect, the guide RNA includes a truncated spacer sequence having a 1 base truncation at the 5' end of the spacer sequence. According to one aspect, the guide RNA includes a truncated spacer sequence having a 2 base truncation at the 5' end of the spacer sequence. According to one aspect, the guide RNA includes a truncated spacer sequence having a 3 base truncation at the 5' end of the spacer sequence. According to one aspect, the guide RNA includes a truncated spacer sequence having a 4 base truncation at the 5' end of the spacer sequence. Accordingly, the spacer sequence may have a 1 to 4 base truncation at the 5' end of the spacer sequence.

According to certain embodiments, the spacer sequence may include between about 16 to about 20 nucleotides which hybridize to the target nucleic acid sequence. According to certain embodiments, the spacer sequence may include about 20 nucleotides which hybridize to the target nucleic acid sequence.

According to certain aspects, the linker nucleic acid sequence may include between about 4 and about 6 nucleic acids.

According to certain aspects, the tracr sequence may include between about 60 to about 500 nucleic acids. According to certain aspects, the tracr sequence may include between about 64 to about 500 nucleic acids. According to certain aspects, the tracr sequence may include between about 65 to about 500 nucleic acids. According to certain aspects, the tracr sequence may include between about 66 to about 500 nucleic acids. According to certain aspects, the tracr sequence may include between about 67 to about 500 nucleic acids. According to certain aspects, the tracr sequence may include between about 68 to about 500 nucleic acids. According to certain aspects, the tracr sequence may include between about 69 to about 500 nucleic acids. According to certain aspects, the tracr sequence may include between about 70 to about 500 nucleic acids. According to certain aspects, the tracr sequence may include between about 80 to about 500 nucleic acids. According to certain aspects, the tracr sequence may include between about 90 to about 500 nucleic acids. According to certain aspects, the tracr sequence may include between about 100 to about 500 nucleic acids.

According to certain aspects, the tracr sequence may include between about 60 to about 200 nucleic acids. According to certain aspects, the tracr sequence may include between about 64 to about 200 nucleic acids. According to certain aspects, the tracr sequence may include between about 65 to about 200 nucleic acids. According to certain aspects, the tracr sequence may include between about 66 to about 200 nucleic acids. According to certain aspects, the tracr sequence may include between about 67 to about 200 nucleic acids. According to certain aspects, the tracr sequence may include between about 68 to about 200 nucleic acids. According to certain aspects, the tracr sequence may include between about 69 to about 200 nucleic acids. According to certain aspects, the tracr sequence may include between about 70 to about 200 nucleic acids. According to certain aspects, the tracr sequence may include between about 80 to about 200 nucleic acids. According to certain aspects, the tracr sequence may include between about 90 to about 200 nucleic acids. According to certain aspects, the tracr sequence may include between about 100 to about 200 nucleic acids.

An exemplary guide RNA is depicted in FIG. 5B.

According to one aspect, the DNA is genomic DNA, mitochondrial DNA, viral DNA, or exogenous DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding an RNA guided nuclease-null DNA binding protein of a Type II CRISPR System that binds to the DNA and is guided by the one or more RNAs, introducing into the cell a third foreign nucleic acid encoding a transcriptional regulator protein or domain, wherein the one or more RNAs, the RNA guided nuclease-null DNA binding protein of a Type II CRISPR System, and the transcriptional regulator protein or domain are expressed, wherein the one or more RNAs, the RNA guided nuclease-null DNA binding protein of a Type II CRISPR System and the transcriptional regulator protein or domain co-localize to the DNA and wherein the transcriptional regulator protein or domain regulates expression of the target nucleic acid.

According to one aspect, the foreign nucleic acid encoding an RNA guided nuclease-null DNA binding protein of a Type II CRISPR System further encodes the transcriptional regulator protein or domain fused to the RNA guided nuclease-null DNA binding protein of a Type II CRISPR System. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding a nuclease-null Cas9 protein that binds to the DNA and is guided by the one or more RNAs, introducing into the cell a third foreign nucleic acid encoding a transcriptional regulator protein or domain, wherein the one or more RNAs, the nuclease-null Cas9 protein, and the transcriptional regulator protein or domain are expressed, wherein the one or more RNAs, the nuclease-null Cas9 protein and the transcriptional regulator protein or domain co-localize to the DNA and wherein the transcriptional regulator protein or domain regulates expression of the target nucleic acid.

According to one aspect, the foreign nucleic acid encoding a nuclease-null Cas9 protein further encodes the transcriptional regulator protein or domain fused to the nuclease-null Cas9 protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to one aspect a cell is provided that includes a first foreign nucleic acid encoding one or more RNAs complementary to DNA, wherein the DNA includes a target nucleic acid, a second foreign nucleic acid encoding an RNA guided nuclease-null DNA binding protein, and a third foreign nucleic acid encoding a transcriptional regulator protein or domain wherein the one or more RNAs, the RNA guided nuclease-null DNA binding protein and the transcriptional regulator protein or domain are members of a co-localization complex for the target nucleic acid.

According to one aspect, the foreign nucleic acid encoding an RNA guided nuclease-null DNA binding protein further encodes the transcriptional regulator protein or domain fused to an RNA guided nuclease-null DNA binding protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, the RNA guided nuclease-null DNA binding protein is an RNA guided nuclease-null DNA binding protein of a Type II CRISPR System. According to certain aspects, the RNA guided nuclease-null DNA binding protein is a nuclease-null Cas9 protein.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase and being guided by the two or more RNAs, wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase of a Type II CRISPR System and being guided by the two or more RNAs, wherein the two or more RNAs and the at least one RNA guided DNA binding protein nickase of a Type II CRISPR System are expressed and wherein the at least one RNA guided DNA binding protein nickase of a Type II CRISPR System co-localizes with the two or more RNAs to the DNA target nucleic acid and nicks the DNA target nucleic acid resulting in two or more adjacent nicks.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one Cas9 protein nickase having one inactive nuclease domain and being guided by the two or more RNAs, wherein the two or more RNAs and the at least one Cas9 protein nickase are expressed and wherein the at least one Cas9 protein nickase co-localizes with the two or more RNAs to the DNA target nucleic acid and nicks the DNA target nucleic acid resulting in two or more adjacent nicks.

According to the methods of altering a DNA target nucleic acid, the two or more adjacent nicks are on the same strand of the double stranded DNA. According to one aspect, the two or more adjacent nicks are on the same strand of the double stranded DNA and result in homologous recombination. According to one aspect, the two or more adjacent nicks are on different strands of the double stranded DNA. According to one aspect, the two or more adjacent nicks are on different strands of the double stranded DNA and create double stranded breaks. According to one aspect, the two or more adjacent nicks are on different strands of the double stranded DNA and create double stranded breaks resulting in nonhomologous end joining. According to one aspect, the two or more adjacent nicks are on different strands of the double stranded DNA and are offset with respect to one another. According to one aspect, the two or more adjacent nicks are on different strands of the double stranded DNA and are offset with respect to one another and create double stranded breaks. According to one aspect, the two or more adjacent nicks are on different strands of the double stranded DNA and are offset with respect to one another and create double stranded breaks resulting in nonhomologous end joining. According to one aspect, the method further includes introducing into the cell a third foreign nucleic acid encoding a donor nucleic acid sequence wherein the two or more nicks results in homologous recombination of the target nucleic acid with the donor nucleic acid sequence.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase and being guided by the two or more RNAs, and wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase of a Type II CRISPR system and being guided by the two or more RNAs, and wherein the two or more RNAs and the at least one RNA guided DNA binding protein nickase of a Type II CRISPR System are expressed and wherein the at least one RNA guided DNA binding protein nickase of a Type II CRISPR System co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one Cas9 protein nickase having one inactive nuclease domain and being guided by the two or more RNAs, and wherein the two or more RNAs and the at least one Cas9 protein nickase are expressed and wherein the at least one Cas9 protein nickase co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a cell is provided including a first foreign nucleic acid encoding two or more RNAs with each RNA being complementary to an adjacent site in a DNA target nucleic acid, and a second foreign nucleic acid encoding at least one RNA guided DNA binding protein nickase, and wherein the two or more RNAs and the at least one RNA guided DNA binding protein nickase are members of a co-localization complex for the DNA target nucleic acid.

According to one aspect, the RNA guided DNA binding protein nickase is an RNA guided DNA binding protein nickase of a Type II CRISPR System. According to one aspect, the RNA guided DNA binding protein nickase is a Cas9 protein nickase having one inactive nuclease domain.

According to one aspect, the cell is a eukaryotic cell. According to one aspect, the cell is a yeast cell, a plant cell or an animal cell. According to one aspect, the cell is a mammalian cell.

According to one aspect, the RNA includes between about 10 to about 500 nucleotides. According to one aspect, the RNA includes between about 20 to about 100 nucleotides.

According to one aspect, the target nucleic acid is associated with a disease or detrimental condition.

According to one aspect, the two or more RNAs are guide RNAs. According to one aspect, the two or more RNAs are tracrRNA-crRNA fusions.

According to one aspect, the DNA target nucleic acid is genomic DNA, mitochondrial DNA, viral DNA, or exogenous DNA.

Further features and advantages of certain embodiments of the present invention will become more fully apparent in the following description of embodiments and drawings thereof, and from the claims.

BRIEF DESCRIPTION OF THE DRAWINGS

The patent or application file contains drawings executed in color. Copies of this patent or patent application publication with the color drawings will be provided by the Office upon request and payment of the necessary fee. The foregoing and other features and advantages of the present embodiments will be more fully understood from the following detailed description of illustrative embodiments taken in conjunction with the accompanying drawings in which:

FIG. 1A and FIG. 1B are schematics of RNA-guided transcriptional activation. FIG. 1C is a design of a reporter construct. FIGS. 1E-1 and 1E-2 show assay data by FACS and IF demonstrating gRNA sequence-specific transcriptional activation from reporter constructs in the presence of Cas9N, MS2-VP64 and gRNA bearing the appropriate MS2 aptamer binding sites.

FIG. 2A depicts a methodology for evaluating the landscape of targeting by Cas9-gRNA complexes and TALEs.

FIG. 3B depicts data showing percentage rate of non-homologous end joining for off-set nicks leading to 5' overhangs and off-set nicks leading to 3' overhangs.

FIGS. 5B-1 and 5B-2 depict guide RNAs with random sequence insertions and percentage rate of homologous recombination

FIG. 7A is a schematic of guide RNAs for the REX1 gene. FIG. 7B depicts transcriptional activation for a promoter-luciferase reporter construct.

FIGS. 10A-1 and 10A-2 depict data from a nuclease mediated HR assay confirming that 18-mer TALEs tolerate multiple mutations in their target sequences.

FIG. 14A depicts the specificity profile of two gRNAs (wild-type) and mutants. Sequence differences are highlighted in red. FIGS. 14B and 14C depict that this assay was specific for the gRNA being evaluated (data re-plotted from FIG. 13D).

FIGS. 15A, 15B-1, 15B-2, 15C, 15D-1, and 15D-2 depict gRNA2 (FIGS. 15A-B) and gRNA3 (FIGS. 15C-D) bearing single or double-base mismatches (highlighted in red) in the spacer sequence versus the target.

FIGS. 16A, 16B-1, 16B2, 16C, 16D-1, and 16D-2 depict a nuclease assay of two independent gRNA that were tested: gRNA1 (FIGS. 16A-B) and gRNA3 (FIGS. 16C-D) bearing truncations at the 5' end of their spacer.

FIGS. 19A, 19B-1, 19B-2, 19C-1, and 19C-2 depict a comparison of TALE monomer specificity versus TALE protein specificity.

FIGS. 20A-20B depict data related to off-set nicking.

FIGS. 21A-21C are directed to off-set nicking and NHEJ profiles.

DETAILED DESCRIPTION

Figures 1, 1D:
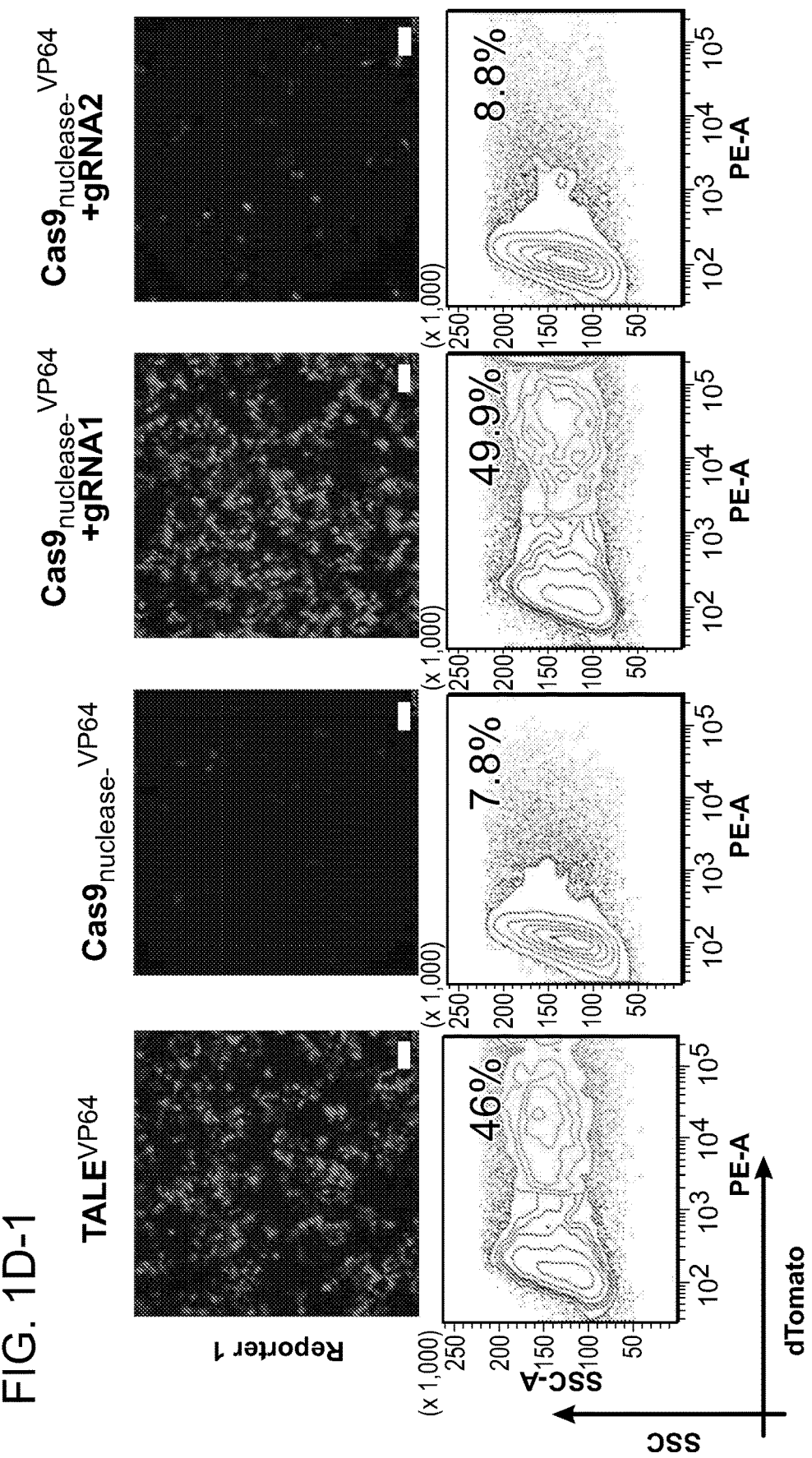
FIGS. 1D-1 and 1D-2 show data demonstrating that Cas9N-VP64 fusions display RNA-guided transcriptional activation as assayed by both fluorescence-activated cell sorting (FACS) and immunofluorescence assays (IF).

Embodiments of the present disclosure are based on the use of DNA binding proteins to co-localize transcriptional regulator proteins or domains to DNA in a manner to regulate a target nucleic acid. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. According to certain aspects, the DNA binding protein may be a nuclease-null DNA binding protein. According to this aspect, the nuclease-null DNA binding protein may result from the alteration or modification of a DNA binding protein having nuclease activity. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain. According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein of a Type II CRISPR System which lacks nuclease activity. An exemplary DNA binding protein is a nuclease-null Cas9 protein. An exemplary DNA binding protein is a Cas9 protein nickase.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei 191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma mobile* 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum ruby un* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni* doylci 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system, which has been rendered nuclease null or which has been rendered a nickase as described herein.

The Cas9 protein may be referred by one of skill in the art in the literature as Csn1. The *S. pyogenes* Cas9 protein sequence that is the subject of experiments described herein is shown below. See Deltcheva et al., Nature 471, 602-607 (2011) hereby incorporated by reference in its entirety (SEQ ID NO: 1)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

```
INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD—
```

According to certain aspects of methods of RNA-guided genome regulation described herein, Cas9 is altered to reduce, substantially reduce or eliminate nuclease activity. According to one aspect, Cas9 nuclease activity is reduced, substantially reduced or eliminated by altering the RuvC nuclease domain or the HNH nuclease domain. According to one aspect, the RuvC nuclease domain is inactivated. According to one aspect, the HNH nuclease domain is inactivated. According to one aspect, the RuvC nuclease domain and the HNH nuclease domain are inactivated. According to an additional aspect, Cas9 proteins are provided where the RuvC nuclease domain and the HNH nuclease domain are inactivated. According to an additional aspect, nuclease-null Cas9 proteins are provided insofar as the RuvC nuclease domain and the HNH nuclease domain are inactivated. According to an additional aspect, a Cas9 nickase is provided where either the RuvC nuclease domain or the HNH nuclease domain is inactivated, thereby leaving the remaining nuclease domain active for nuclease activity. In this manner, only one strand of the double stranded DNA is cut or nicked.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinke et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 or Cas9N and exhibits reduced or eliminated nuclease activity, or nuclease activity is absent or substantially absent within levels of detection. According to this aspect, nuclease activity for a Cas9N may be undetectable using known assays, i.e. below the level of detection of known assays.

According to one aspect, the nuclease null Cas9 protein includes homologs and orthologs thereof which retain the ability of the protein to bind to the DNA and be guided by the RNA. According to one aspect, the nuclease null Cas9 protein includes the sequence as set forth for naturally occurring Cas9 from *S. pyogenes* and having one or more or all of D10, H840, D839 and H863 substituted with alanine and protein sequences having at least 30%, 40%, 50%, 60%, 70%, 80%, 90%, 95%, 98% or 99% homology thereto and being a DNA binding protein, such as an RNA guided DNA binding protein.

According to one aspect, the nuclease null Cas9 protein includes the sequence as set forth for naturally occurring Cas9 from *S. pyogenes* excepting the protein sequence of the RuvC nuclease domain and the HNH nuclease domain and also protein sequences having at least 30%, 40%, 50%, 60%, 70%, 80%, 90%, 95%, 98% or 99% homology thereto and being a DNA binding protein, such as an RNA guided DNA binding protein. In this manner, aspects of the present disclosure include the protein sequence responsible for DNA binding, for example, for co-localizing with guide RNA and binding to DNA and protein sequences homologous thereto, and need not include the protein sequences for the RuvC nuclease domain and the HNH nuclease domain (to the extent not needed for DNA binding), as these domains may be either inactivated or removed from the protein sequence of the naturally occurring Cas9 protein to produce a nuclease null Cas9 protein.

Figure 4A:
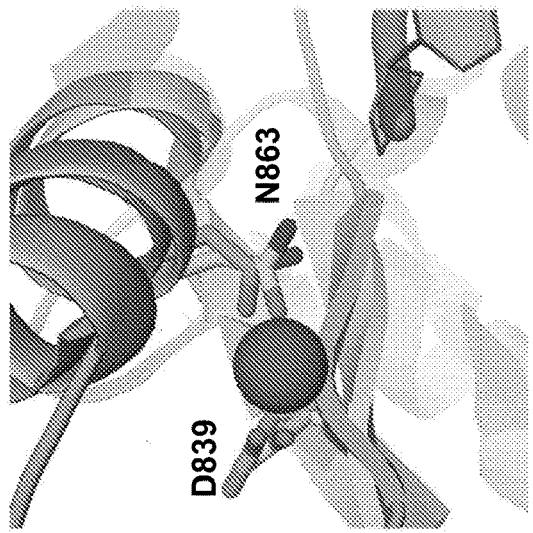
FIG. 4A is a schematic of a metal coordinating residue in RuvC PDB ID: 4EP4 (blue) position D7 (left), a schematic of HNH endonuclease domains from PDB IDs: 3M7K (orange) and 4H9D (cyan) including a coordinated Mg-ion (gray sphere) and DNA from 3M7K (purple) (middle) and a list of mutants analyzed (right).
Figure 4A:
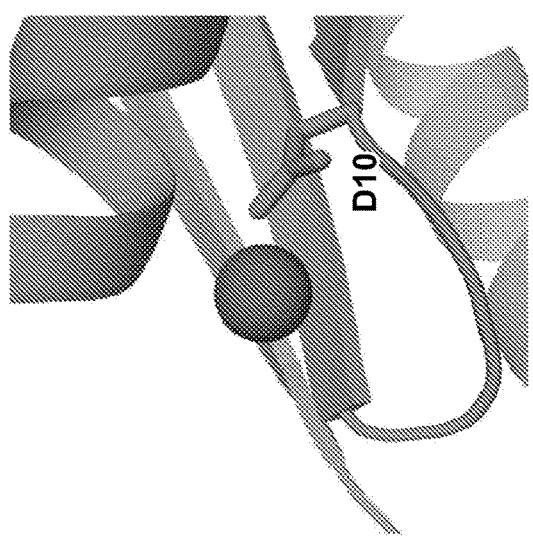

For purposes of the present disclosure, FIG. 4A depicts metal coordinating residues in known protein structures with homology to Cas9. Residues are labeled based on position in Cas9 sequence. Left: RuvC structure, PDB ID: 4EP4 (blue) position D7, which corresponds to D10 in the Cas9 sequence, is highlighted in a Mg-ion coordinating position. Middle: Structures of HNH endonuclease domains from PDB IDs: 3M7K (orange) and 4H9D (cyan) including a coordinated Mg-ion (gray sphere) and DNA from 3M7K (purple). Residues D92 and N113 in 3M7K and 4H9D positions D53 and N77, which have sequence homology to Cas9 amino acids D839 and N863, are shown as sticks. Right: List of mutants made and analyzed for nuclease activity: Cas9 wildtype; $Cas9_{m1}$ which substitutes alanine for D10; $Cas9_{m2}$ which substitutes alanine for D10 and alanine for H840; $Cas9_{m3}$ which substitutes alanine for D10, alanine for H840, and alanine for D839; and Cas9m4 which substitutes alanine for D10, alanine for H840, alanine for D839, and alanine for N863.

Figure 4B:
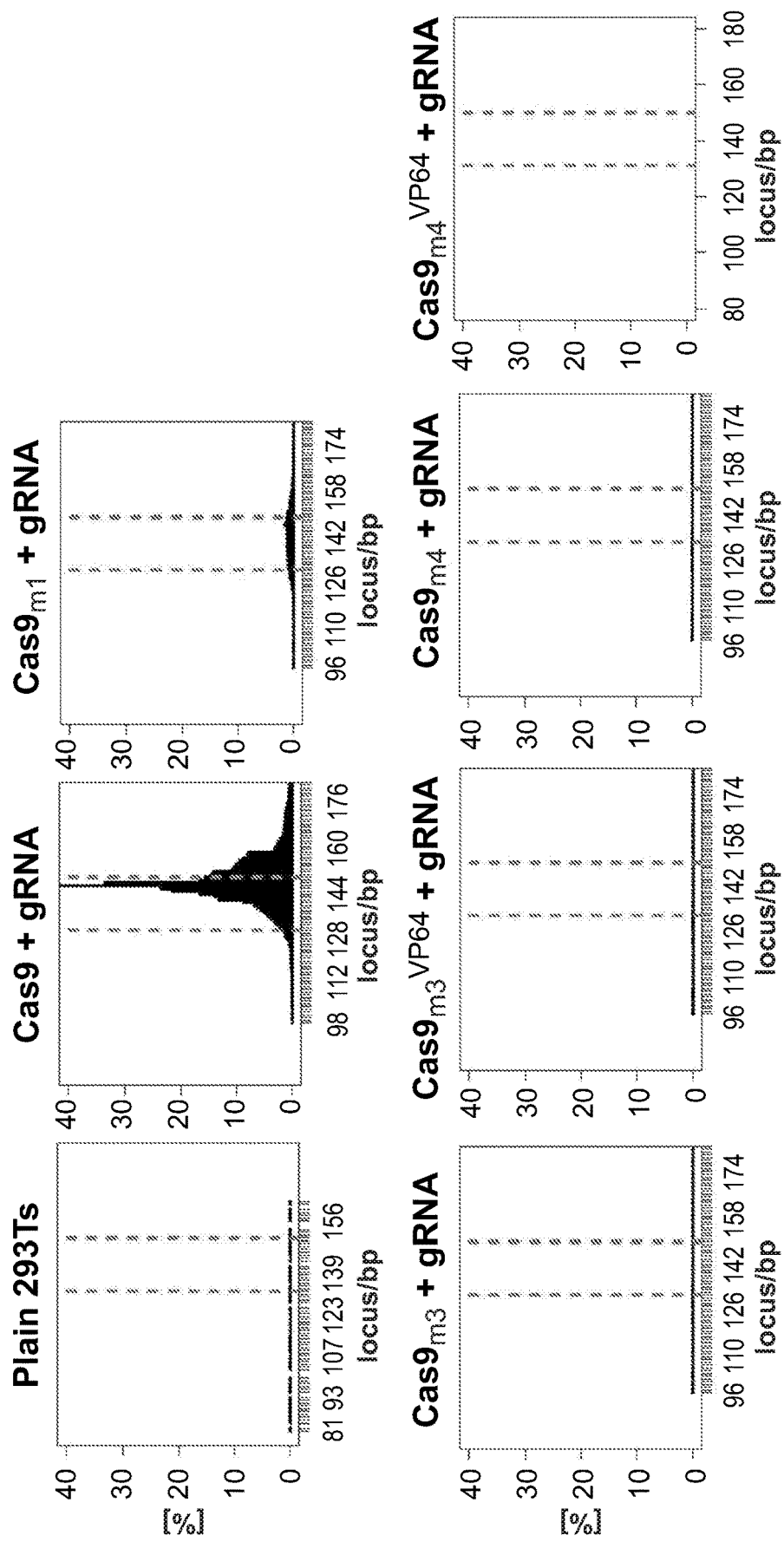
FIG. 4B depicts data showing undetectable nuclease activity for Cas9 mutants m3 and m4, and also their respective fusions with VP64.
Figure 4C:
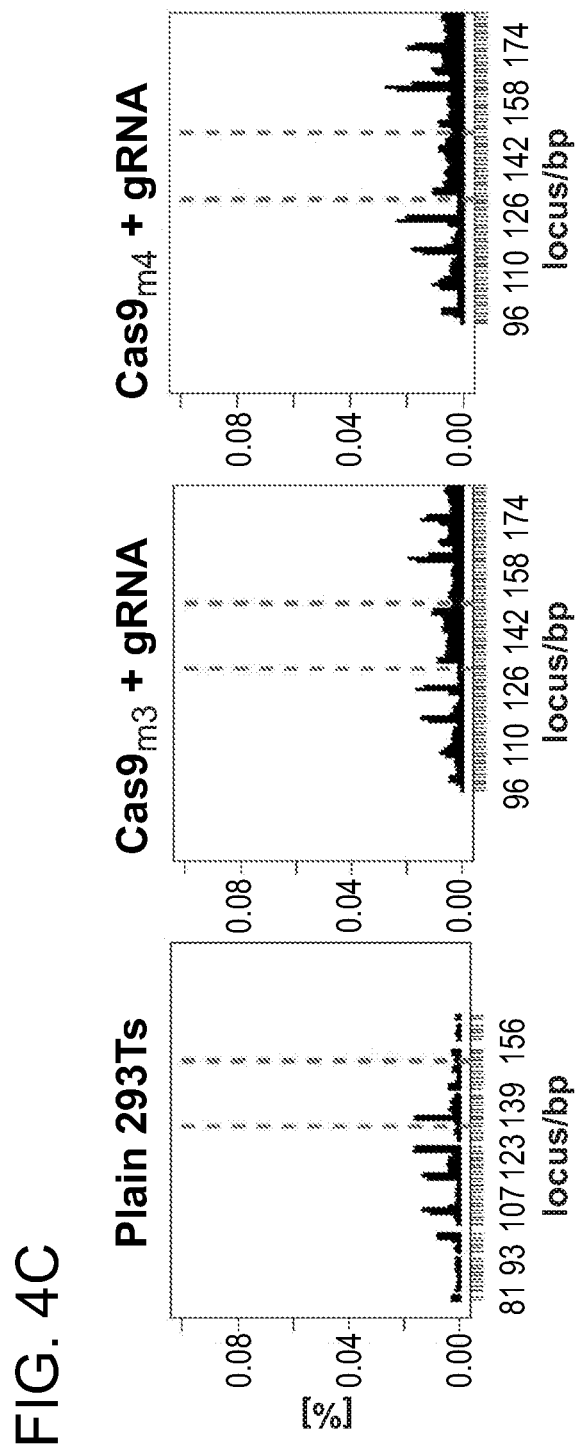
FIG. 4C is a higher-resolution examination of the data in FIG. 4B.

As shown in FIG. 4B, the Cas9 mutants: m3 and m4, and also their respective fusions with VP64 showed undetectable nuclease activity upon deep sequencing at targeted loci. The plots show the mutation frequency versus genomic position, with the red lines demarcating the gRNA target. FIG. 4C is a higher-resolution examination of the data in FIG. 4B and confirms that the mutation landscape shows comparable profile as unmodified loci.

According to one aspect, an engineered Cas9-gRNA system is provided which enables RNA-guided genome regulation in human cells by tethering transcriptional activation domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA.

According to one aspect, a Cas9N-fusion protein capable of transcriptional activation is provided. According to one aspect, a VP64 activation domain (see Zhang et al., Nature Biotechnology 29, 149-153 (2011) hereby incorporated by reference in its entirety) is joined, fused, connected or otherwise tethered to the C terminus of Cas9N. According to one method, the transcriptional regulatory domain is provided to the site of target genomic DNA by the Cas9N protein. According to one method, a Cas9N fused to a transcriptional regulatory domain is provided within a cell along with one or more guide RNAs. The Cas9N with the transcriptional regulatory domain fused thereto bind at or near target genomic DNA. The one or more guide RNAs bind at or near target genomic DNA. The transcriptional regulatory domain regulates expression of the target gene. According to a specific aspect, a Cas9N-VP64 fusion activated transcription of reporter constructs when combined with gRNAs targeting sequences near the promoter, thereby displaying RNA-guided transcriptional activation.

According to one aspect, a gRNA-fusion protein capable of transcriptional activation is provided. According to one aspect, a VP64 activation domain is joined, fused, connected or otherwise tethered to the gRNA. According to one method, the transcriptional regulatory domain is provided to the site of target genomic DNA by the gRNA. According to one method, a gRNA fused to a transcriptional regulatory domain is provided within a cell along with a Cas9N protein. The Cas9N binds at or near target genomic DNA. The one or more guide RNAs with the transcriptional regulatory protein or domain fused thereto bind at or near target genomic DNA. The transcriptional regulatory domain regulates expression of the target gene. According to a specific aspect, a Cas9N protein and a gRNA fused with a transcriptional regulatory domain activated transcription of reporter constructs, thereby displaying RNA-guided transcriptional activation.

Figures 1, 1D, 2:
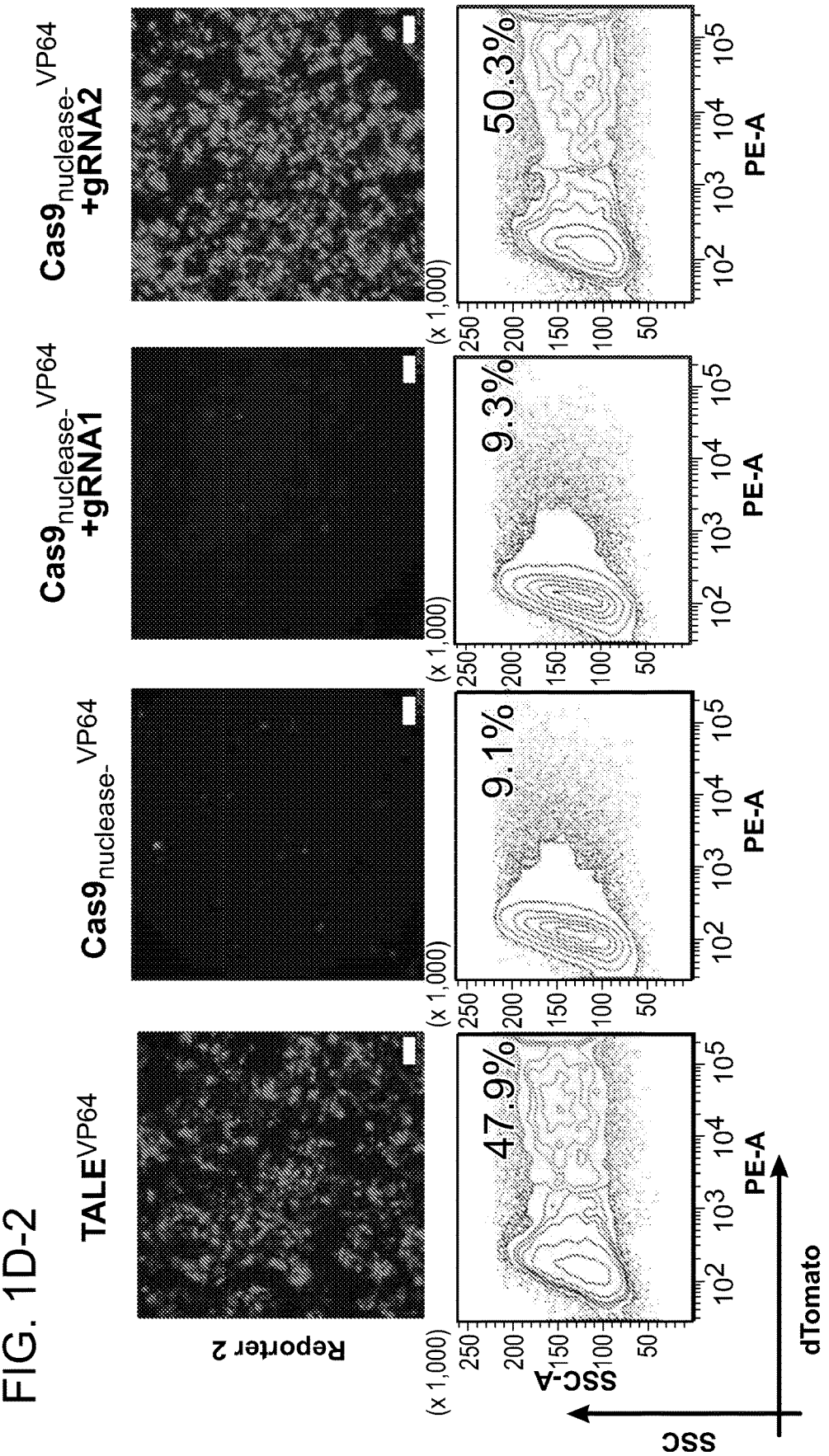
Figure 5A:
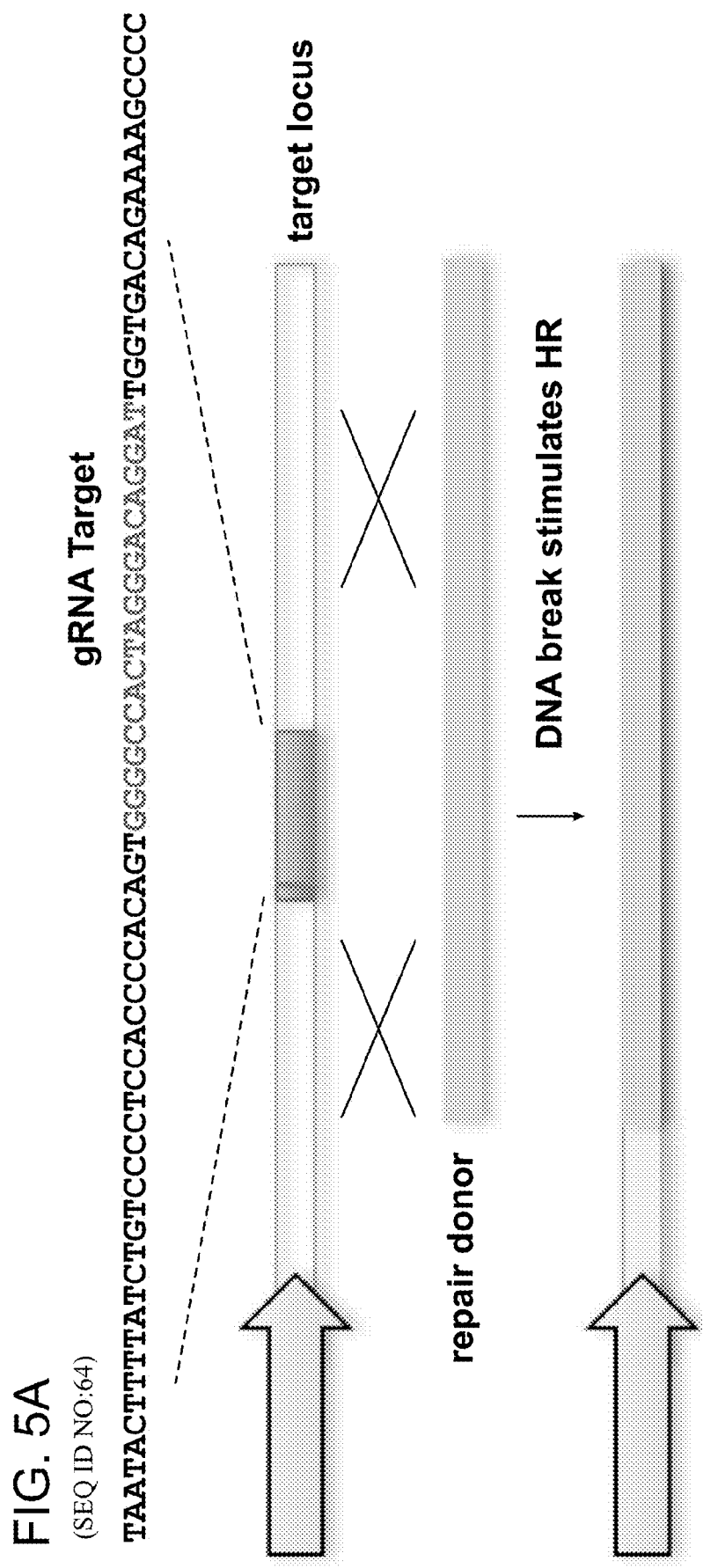
FIG. 5A is a schematic of a homologous recombination assay to determine Cas9-gRNA activity.
Figures 1, 5B:
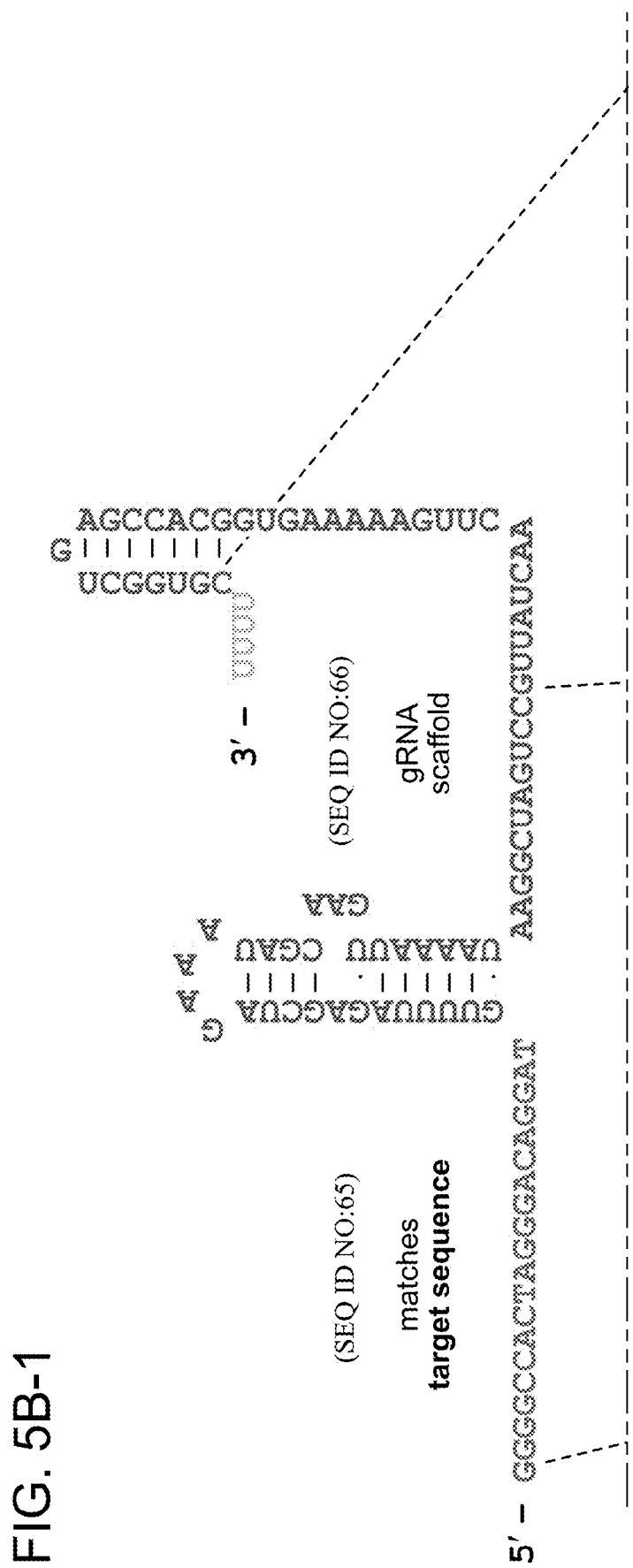
Figures 2, 5B:
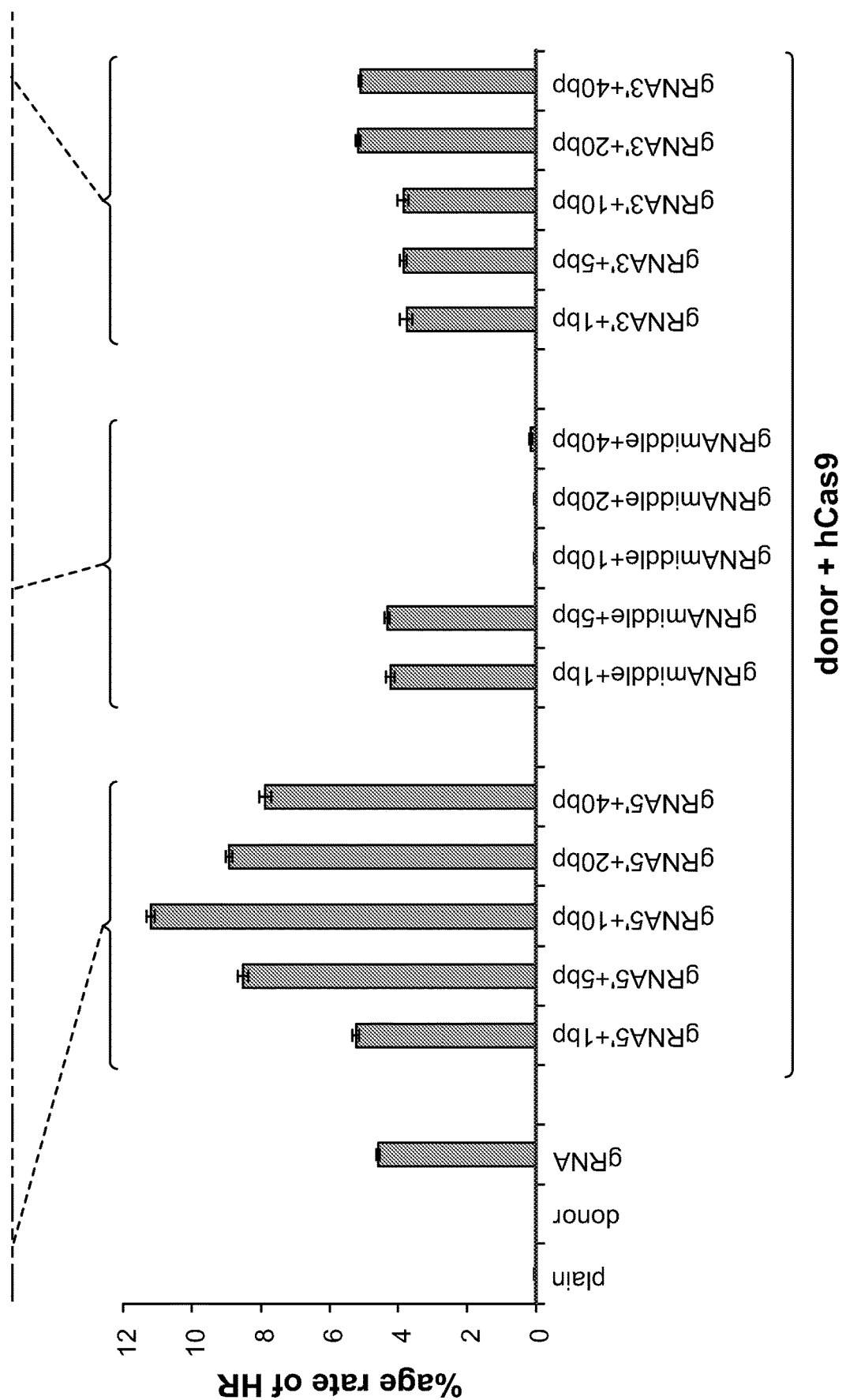

The gRNA tethers capable of transcriptional regulation were constructed by identifying which regions of the gRNA will tolerate modifications by inserting random sequences into the gRNA and assaying for Cas9 function. gRNAs bearing random sequence insertions at either the 5' end of the crRNA portion or the 3' end of the tracrRNA portion of a chimeric gRNA retain functionality, while insertions into the tracrRNA scaffold portion of the chimeric gRNA result in loss of function. See FIG. 5A-B summarizing gRNA flexibility to random base insertions. FIG. 5A is a schematic of a homologous recombination (HR) assay to determine Cas9-gRNA activity. As shown in FIGS. 5B-1 and 5B-2, gRNAs bearing random sequence insertions at either the 5' end of the crRNA portion or the 3' end of the tracrRNA portion of a chimeric gRNA retain functionality, while insertions into the tracrRNA scaffold portion of the chimeric gRNA result in loss of function. The points of insertion in the gRNA sequence are indicated by red nucleotides. Without wishing to be bound by scientific theory, the increased activity upon random base insertions at the 5' end may be due to increased half-life of the longer gRNA.

To attach VP64 to the gRNA, two copies of the MS2 bacteriophage coat-protein binding RNA stem-loop were appended to the 3' end of the gRNA. See Fusco et al., Current Biology: CB13, 161-167 (2003) hereby incorporated by reference in its entirety. These chimeric gRNAs were expressed together with Cas9N and MS2-VP64 fusion protein. Sequence-specific transcriptional activation from reporter constructs was observed in the presence of all 3 components.

Figures 1, 1E:
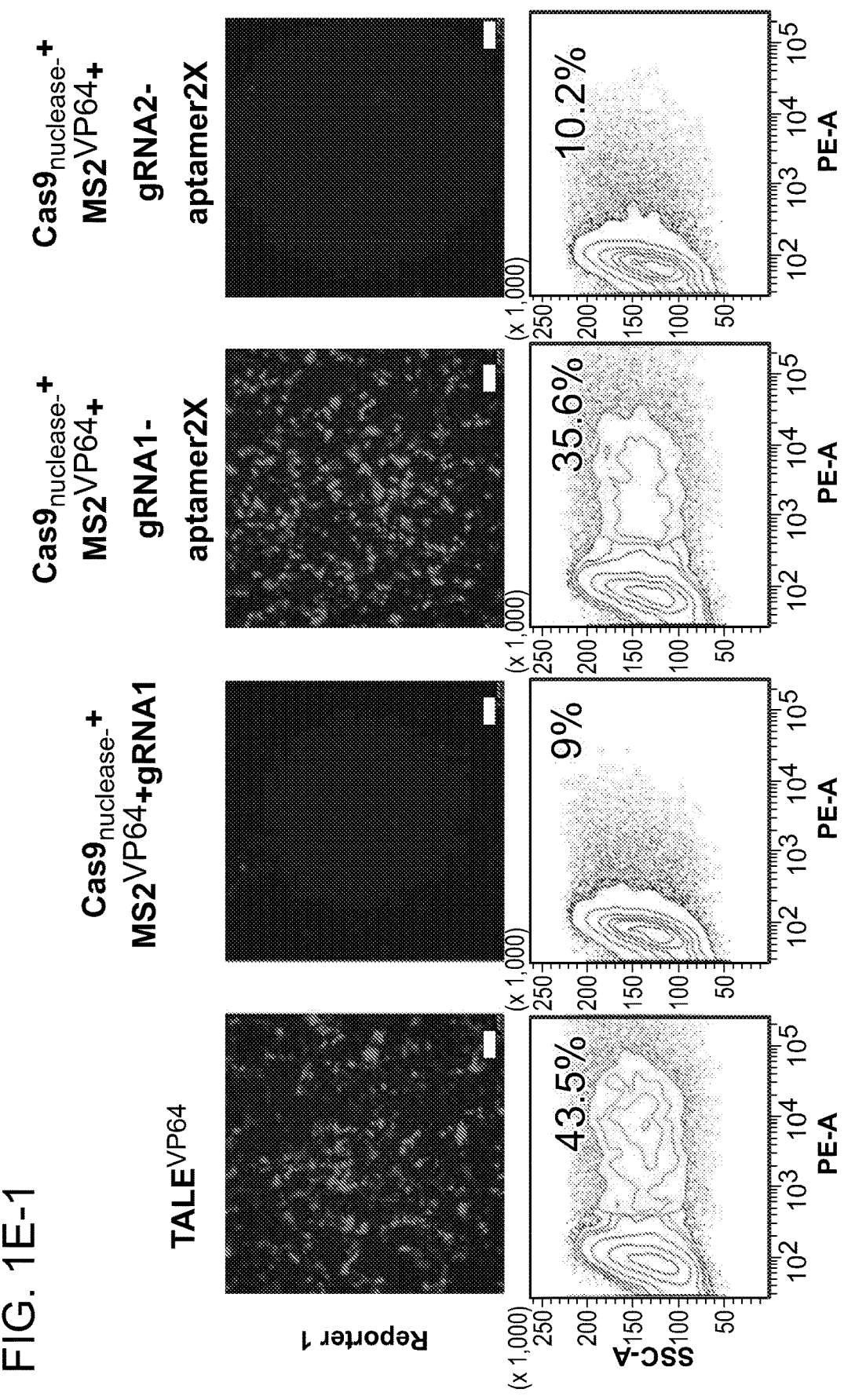
Figures 1, 1E, 2:
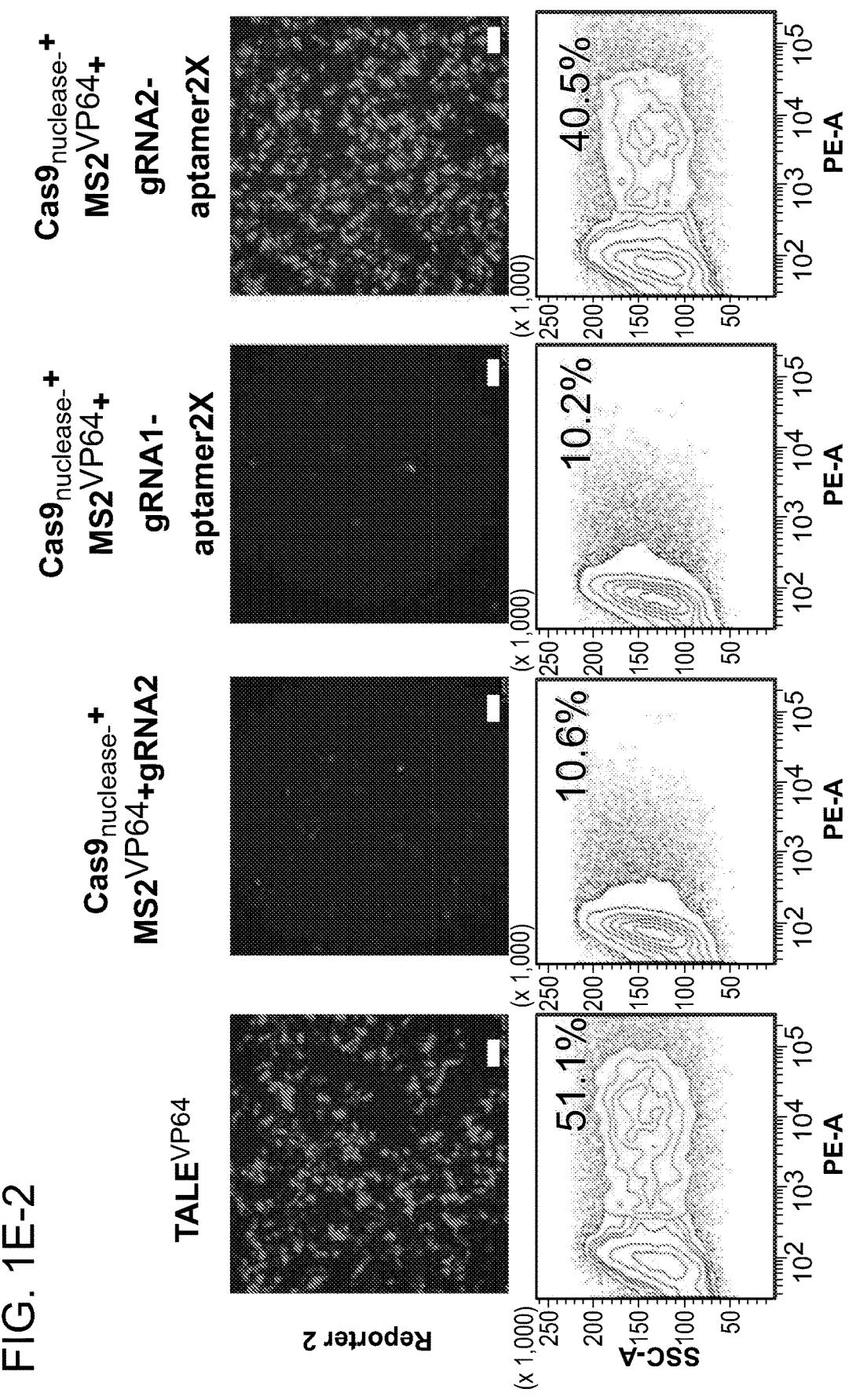

FIG. 1A is a schematic of RNA-guided transcriptional activation. As shown in FIG. 1A, to generate a Cas9N-fusion protein capable of transcriptional activation, the VP64 activation domain was directly tethered to the C terminus of Cas9N. As shown in FIG. 1B, to generate gRNA tethers capable of transcriptional activation, two copies of the MS2 bacteriophage coat-protein binding RNA stem-loop were appended to the 3' end of the gRNA. These chimeric gRNAs were expressed together with Cas9N and MS2-VP64 fusion protein. FIG. 1C shows design of reporter constructs used to assay transcriptional activation. The two reporters bear distinct gRNA target sites, and share a control TALE-TF target site. As shown in FIGS. 1D-1 and 1D-2, Cas9N-VP64 fusions display RNA-guided transcriptional activation as assayed by both fluorescence-activated cell sorting (FACS) and immunofluorescence assays (IF). Specifically, while the control TALE-TF activated both reporters, the Cas9N-VP64 fusion activates reporters in a gRNA sequence specific manner. As shown in FIGS. 1E-1 and 1E-2, gRNA sequence-specific transcriptional activation from reporter constructs only in the presence of all 3 components: Cas9N, MS2-VP64 and gRNA bearing the appropriate MS2 aptamer binding sites was observed by both FACS and IF.

Figure 1F:
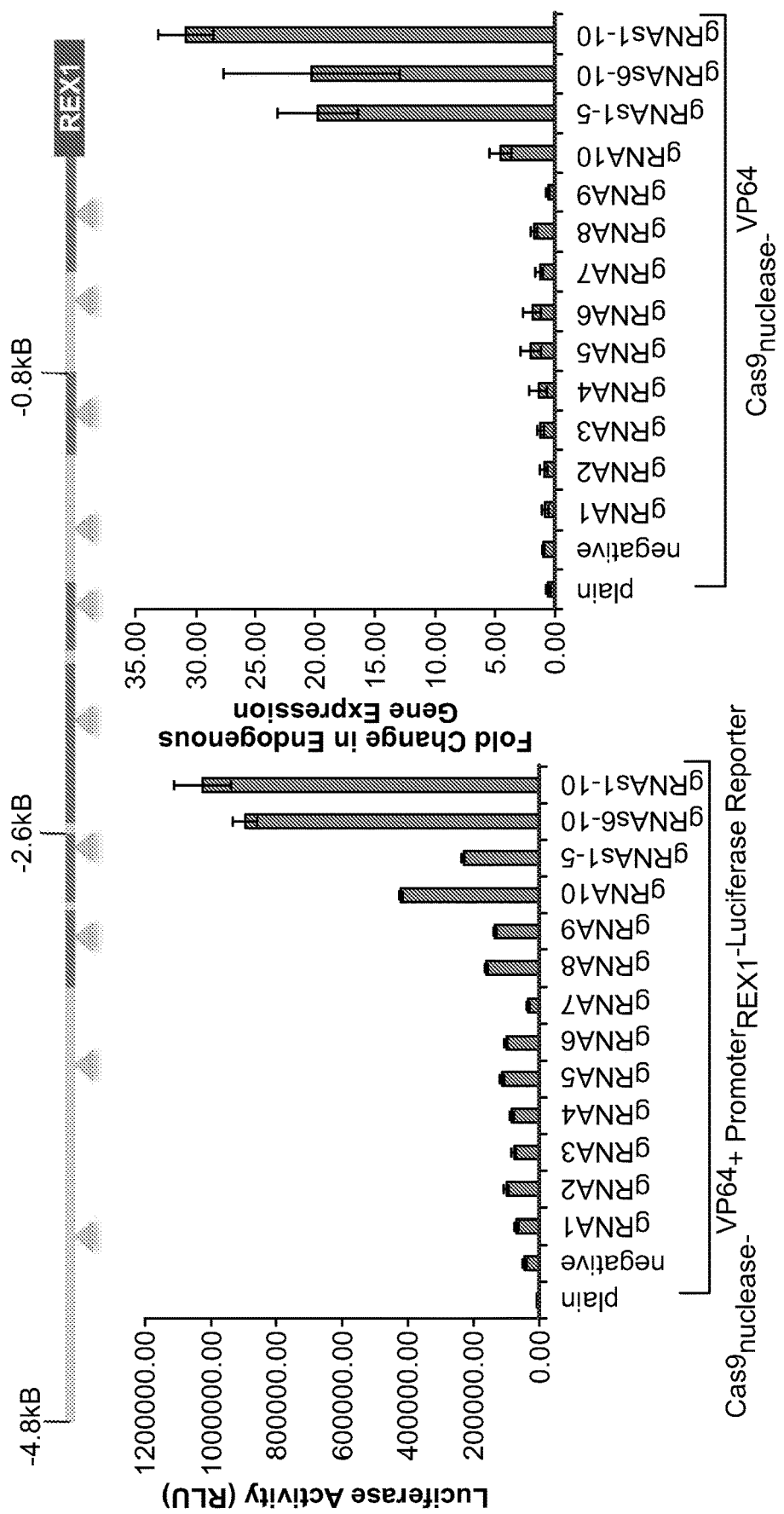
FIG. 1F depicts data demonstrating transcriptional induction by individual gRNAs and multiple gRNAs.

According to certain aspects, methods are provided for regulating endogenous genes using Cas9N, one or more gRNAs and a transcriptional regulatory protein or domain. According to one aspect, an endogenous gene can be any desired gene, referred to herein as a target gene. According to one exemplary aspect, genes target for regulation included ZFP42 (REX1) and POU5F1 (OCT4), which are both tightly regulated genes involved in maintenance of pluripotency. As shown in FIG. 1F, 10 gRNAs targeting a ~5 kb stretch of DNA upstream of the transcription start site (DNase hypersensitive sites are highlighted in green) were designed for the REX1 gene. Transcriptional activation was assayed using either a promoter-luciferase reporter construct (see Takahashi et al., Cell 131 861-872 (2007) hereby incorporated by reference in its entirety) or directly via qPCR of the endogenous genes.

Figures 6A, 6B:
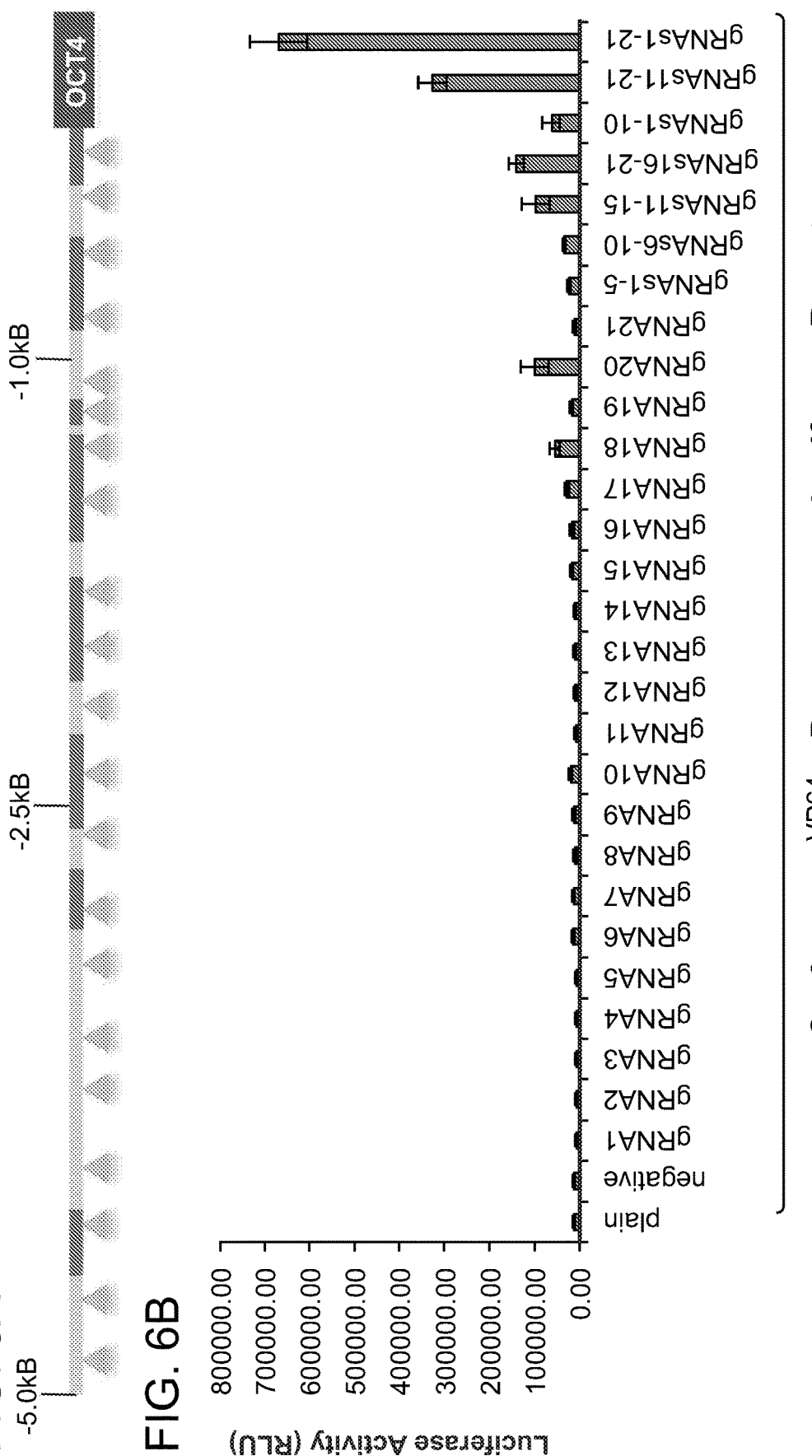
FIG. 6A is a schematic of guide RNAs for the OCT4 gene.
FIG. 6B depicts transcriptional activation for a promoter-luciferase reporter construct.
Figure 6C:
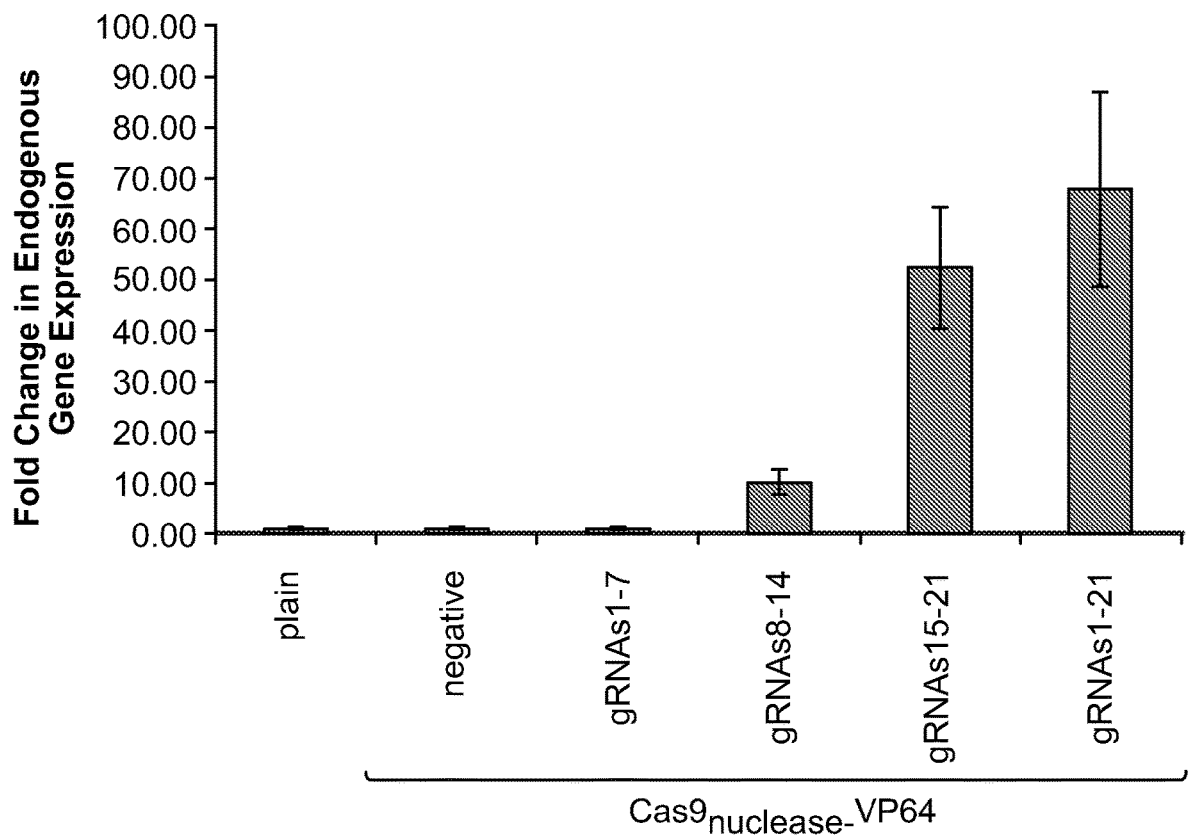
FIG. 6C depicts transcriptional activation via qPCR of endogenous genes.

FIG. 6A-C is directed to RNA-guided OCT4 regulation using Cas9N-VP64. As shown in FIG. 6A, 21 gRNAs targeting a ~5 kb stretch of DNA upstream of the transcription start site were designed for the OCT4 gene. The DNase hypersensitive sites are highlighted in green. FIG. 6B shows transcriptional activation using a promoter-luciferase reporter construct. FIG. 6C shows transcriptional activation directly via qPCR of the endogenous genes. While introduction of individual gRNAs modestly stimulated transcription, multiple gRNAs acted synergistically to stimulate robust multi-fold transcriptional activation.

Figure 7C:
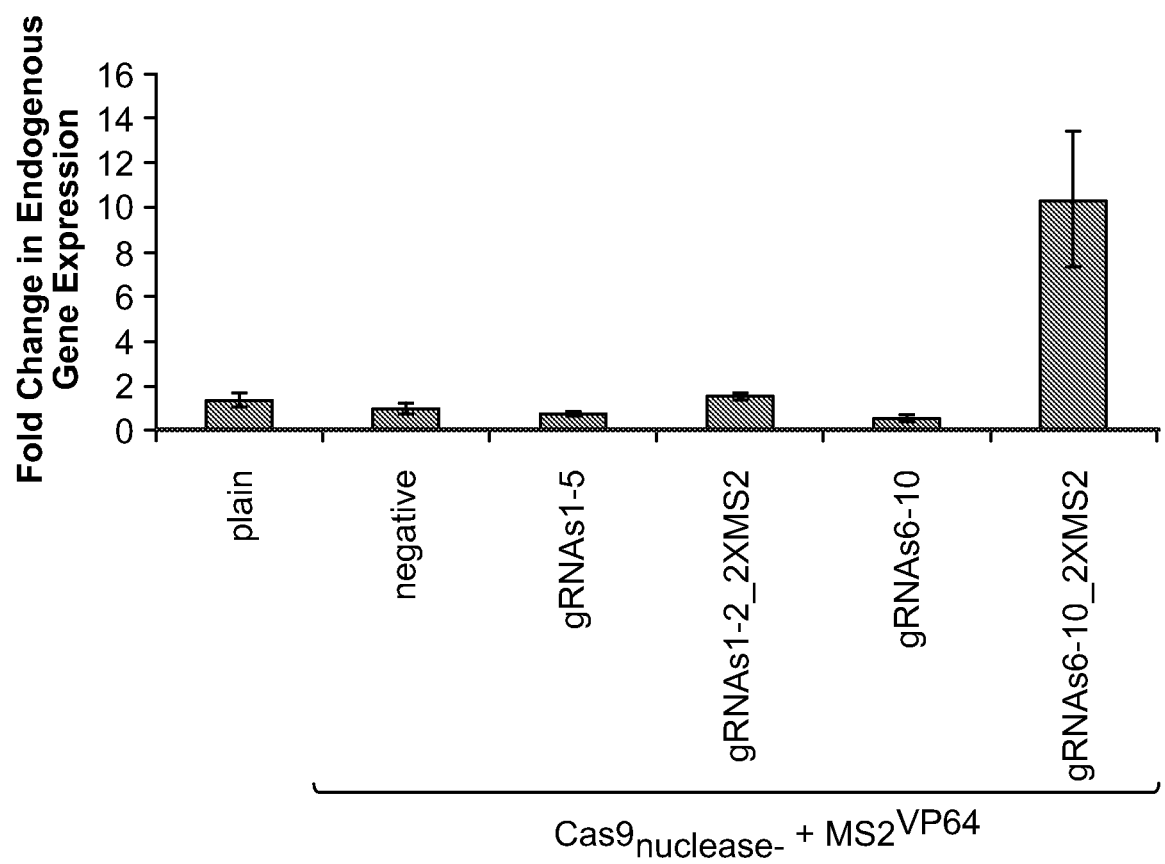
FIG. 7C depicts transcriptional activation via qPCR of endogenous genes.

FIG. 7A-C is directed to RNA-guided REX1 regulation using Cas9N, MS2-VP64 and gRNA+2×-MS2 aptamers. As shown in FIG. 7A, 10 gRNAs targeting a ~5 kb stretch of DNA upstream of the transcription start site were designed for the REX1 gene. The DNase hypersensitive sites are highlighted in green. FIG. 7B shows transcriptional activation using a promoter-luciferase reporter construct. FIG. 7C shows transcriptional activation directly via qPCR of the endogenous genes. While introduction of individual gRNAs modestly stimulated transcription, multiple gRNAs acted synergistically to stimulate robust multi-fold transcriptional activation. In one aspect, the absence of the 2×-MS2 aptamers on the gRNA does not result in transcriptional activation. See Maeder et al., *Nature Methods* 10, 243-245 (2013) and Perez-Pinera et al., *Nature Methods* 10, 239-242 (2013) each of which are hereby incorporated by reference in its entirety.

Accordingly, methods are directed to the use of multiple guide RNAs with a Cas9N protein and a transcriptional regulatory protein or domain to regulate expression of a target gene.

Both the Cas9 and gRNA tethering approaches were effective, with the former displaying ~1.5-2 fold higher potency. This difference is likely due to the requirement for 2-component as opposed to 3-component complex assembly. However, the gRNA tethering approach in principle enables different effector domains to be recruited by distinct gRNAs so long as each gRNA uses a different RNA-protein interaction pair. See Karyer-Bibens et al., *Biology of the Cell/Under the Auspices of the European Cell Biology Organization* 100, 125-138 (2008) hereby incorporated by reference in its entirety. According to one aspect of the present disclosure, different target genes may be regulated using specific guide RNA and a generic Cas9N protein, i.e. the same or a similar Cas9N protein for different target genes. According to one aspect, methods of multiplex gene regulation are provided using the same or similar Cas9N.

Methods of the present disclosure are also directed to editing target genes using the Cas9N proteins and guide RNAs described herein to provide multiplex genetic and epigenetic engineering of human cells. With Cas9-gRNA targeting being an issue (see Jiang et al., *Nature Biotechnology* 31, 233-239 (2013) hereby incorporated by reference in its entirety), methods are provided for in-depth interrogation of Cas9 affinity for a very large space of target sequence variations. Accordingly, aspects of the present disclosure provide direct high-throughput readout of Cas9 targeting in human cells, while avoiding complications introduced by dsDNA cut toxicity and mutagenic repair incurred by specificity testing with native nuclease-active Cas9.

Further aspects of the present disclosure are directed to the use of DNA binding proteins or systems in general for the transcriptional regulation of a target gene. One of skill in the art will readily identify exemplary DNA binding systems based on the present disclosure. Such DNA binding systems need not have any nuclease activity, as with the naturally occurring Cas9 protein. Accordingly, such DNA binding systems need not have nuclease activity inactivated. One exemplary DNA binding system is TALE. As a genome editing tool, usually TALE-FokI dimers are used, and for genome regulation TAEL-VP64 fusions have been shown to be highly effective. According to one aspect, TALE specificity was evaluated using the methodology shown in FIG. 2A. A construct library in which each element of the library comprises a minimal promoter driving a dTomato fluorescent protein is designed. Downstream of the transcription start site m, a 24 bp (A/C/G) random transcript tag is inserted, while two TF binding sites are placed upstream of the promoter: one is a constant DNA sequence shared by all library elements, and the second is a variable feature that bears a 'biased' library of binding sites which are engineered to span a large collection of sequences that present many combinations of mutations away from the target sequence the programmable DNA targeting complex was designed to bind. This is achieved using degenerate oligonucleotides engineered to bear nucleotide frequencies at each position such that the target sequence nucleotide appears at a 79% frequency and each other nucleotide occurs at 7% frequency. See Patwardhan et al., *Nature Biotechnology* 30, 265-270 (2012) hereby incorporated by reference in its entirety. The reporter library is then sequenced to reveal the associations between the 24 bp dTomato transcript tags and their corresponding 'biased' target site in the library element. The large diversity of the transcript tags assures that sharing of tags between different targets will be extremely rare, while the biased construction of the target sequences means that sites with few mutations will be associated with more tags than sites with more mutations. Next, transcription of the dTomato reporter genes is stimulated with either a control-TF engineered to bind the shared DNA site, or the target-TF that was engineered to bind the target site. The abundance of each expressed transcript tag is measured in each sample by conducting RNAseq on the stimulated cells, which is then mapped back to their corresponding binding sites using the association table established earlier. The control-TF is expected to excite all library members equally since its binding site is shared across all library elements, while the target-TF is expected to skew the distribution of the expressed members to those that are preferentially targeted by it. This assumption is used in step 5 to compute a normalized expression level for each binding site by dividing the tag counts obtained for the target-TF by those obtained for the control-TF.

Figure 2B:
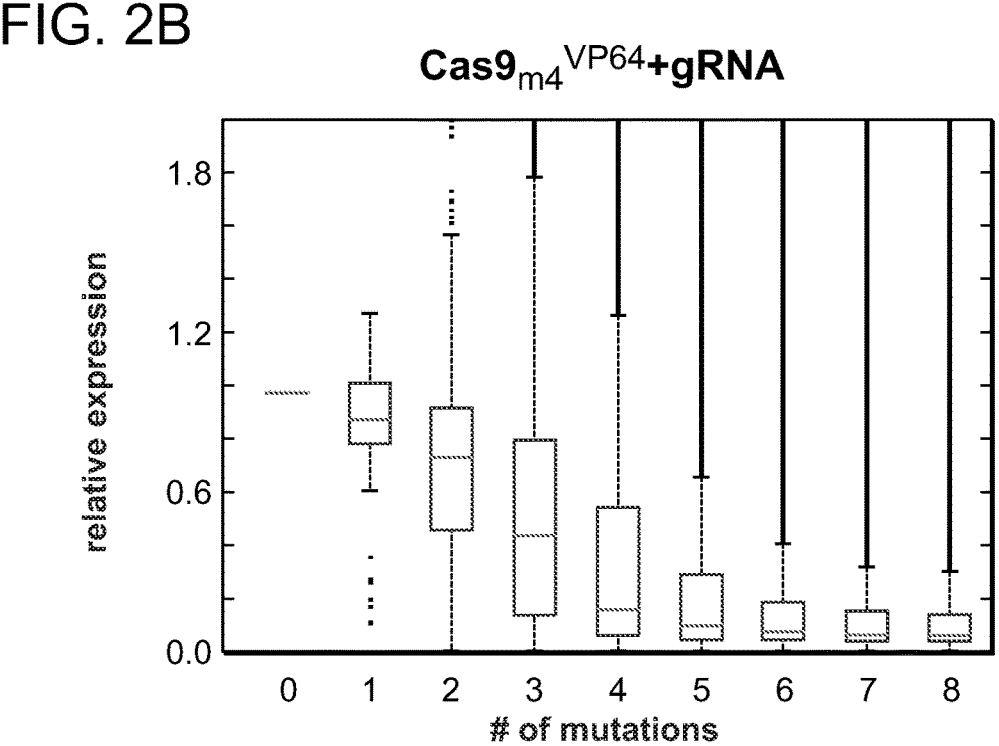
FIG. 2B depicts data demonstrating that a Cas9-gRNA complex is on average tolerant to 1-3 mutations in its target sequences.
Figure 2C:
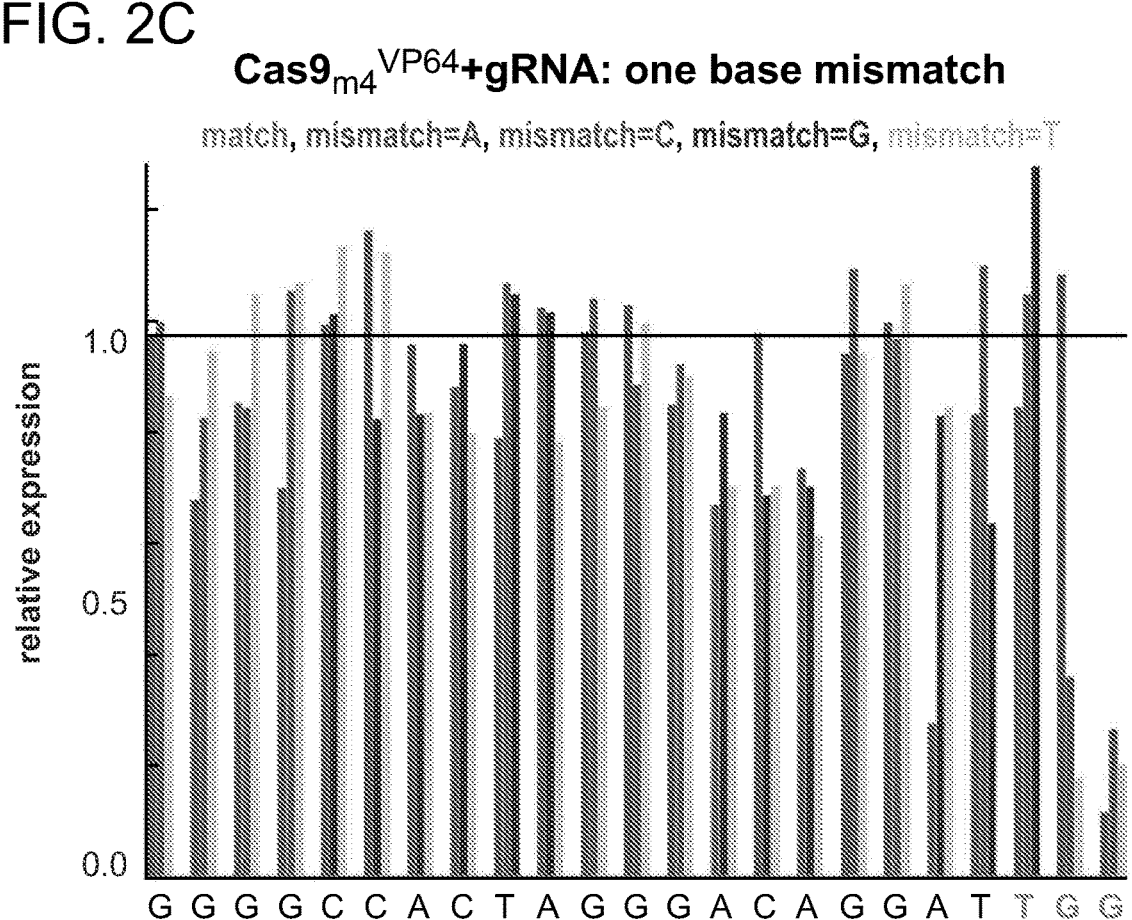
FIG. 2C depicts data demonstrating that the Cas9-gRNA complex is largely insensitive to point mutations, except those localized to the PAM sequence.
Figure 2D:
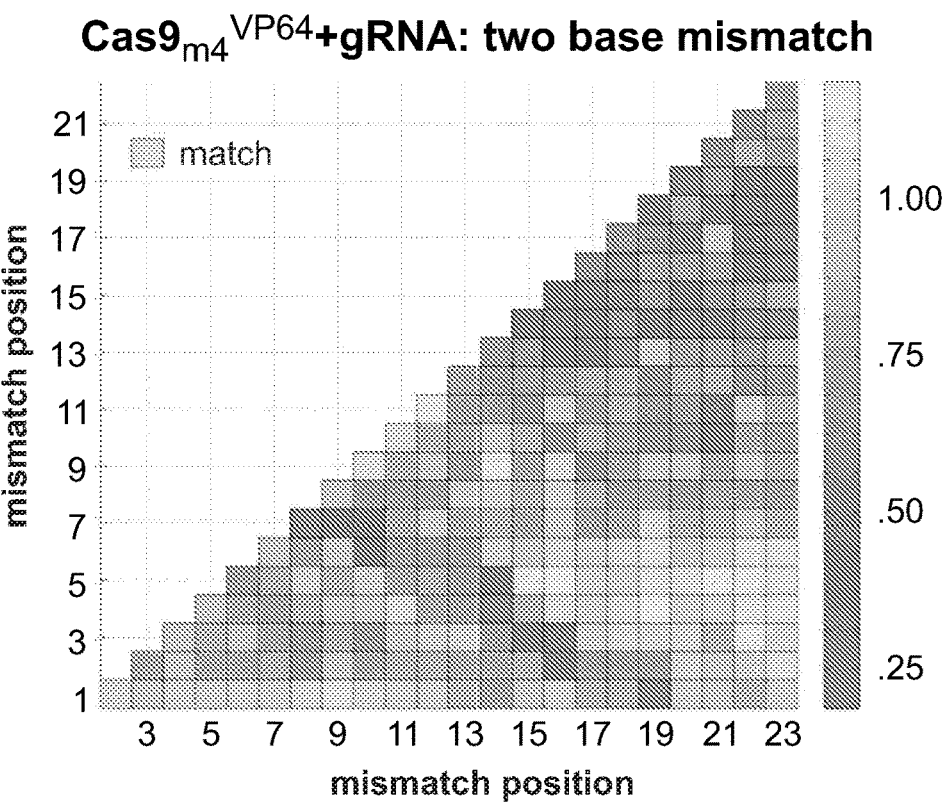
FIG. 2D depicts heat plot data demonstrating that introduction of 2 base mismatches significantly impairs the Cas9-gRNA complex activity.

As shown in FIG. 2B, the targeting landscape of a Cas9-gRNA complex reveals that it is on average tolerant to 1-3 mutations in its target sequences. As shown in FIG. 2C, the Cas9-gRNA complex is also largely insensitive to point mutations, except those localized to the PAM sequence. Notably this data reveals that the predicted PAM for the *S. pyogenes* Cas9 is not just NGG but also NAG. As shown in FIG. 2D, introduction of 2 base mismatches significantly impairs the Cas9-gRNA complex activity, however only when these are localized to the 8-10 bases nearer the 3' end of the gRNA target sequence (in the heat plot the target sequence positions are labeled from 1-23 starting from the 5' end).

Figure 2E:
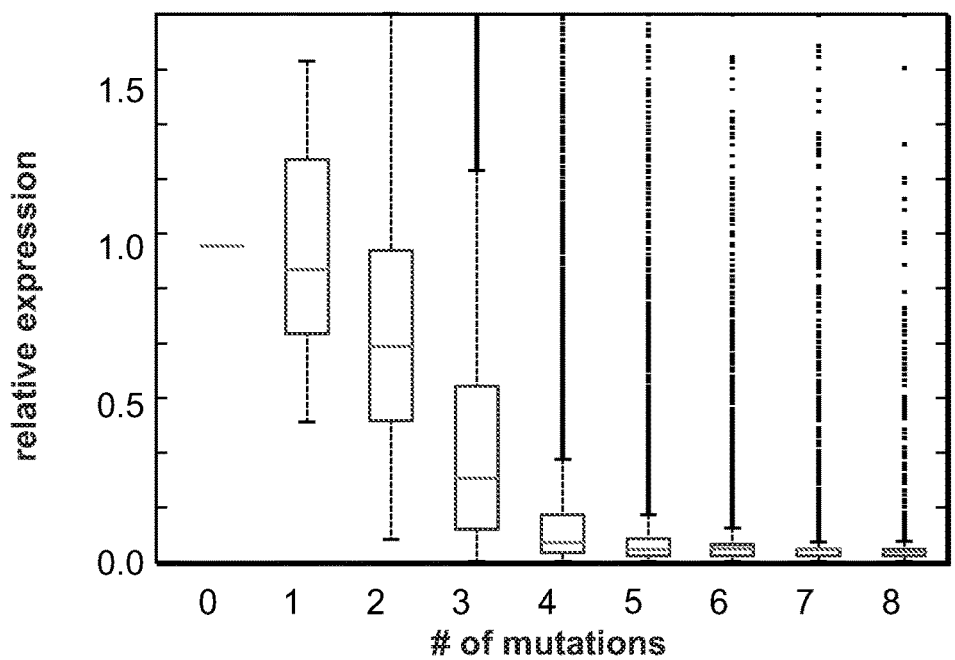
FIG. 2E depicts data demonstrating that an 18-mer TALE reveals is on average tolerant to 1-2 mutations in its target sequence.
Figure 2F:
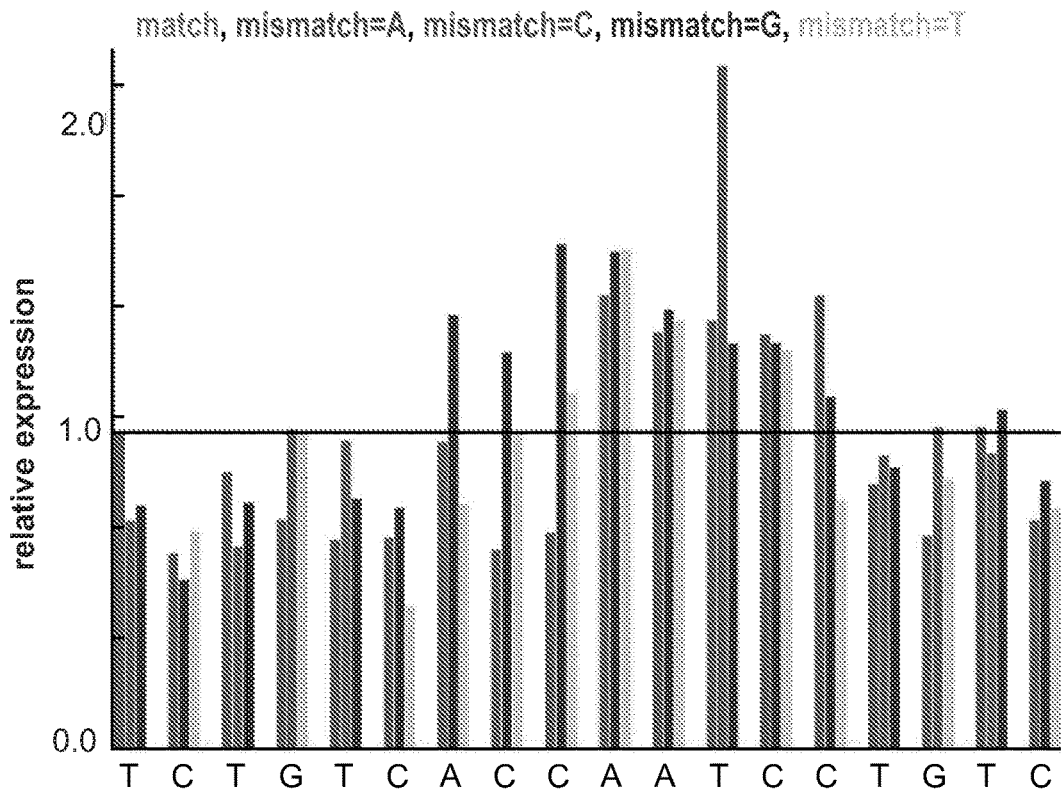
FIG. 2F depicts data demonstrating the 18-mer TALE is, similar to the Cas9-gRNA complexes, largely insensitive to single base mismatched in its target.
Figure 2G:
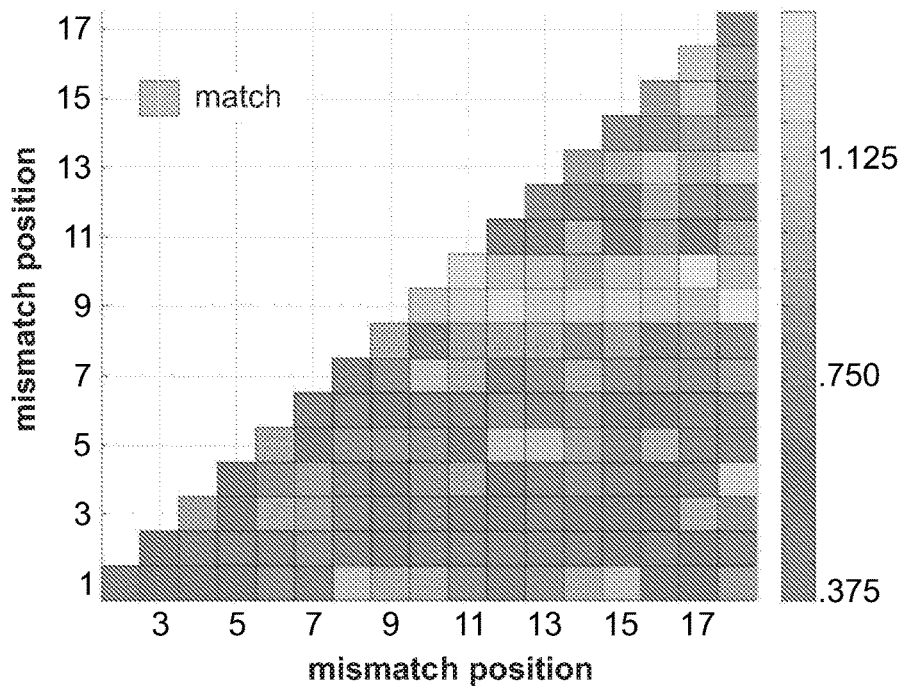
FIG. 2G depicts heat plot data demonstrating that introduction of 2 base mismatches significantly impairs the 18-mer TALE activity.

The mutational tolerance of another widely used genome editing tool, TALE domains, was determined using the transcriptional specificity assay described herein. As shown in FIG. 2E, the TALE off-targeting data for an 18-mer TALE reveals that it can tolerate on average 1-2 mutations in its target sequence, and fails to activate a large majority of 3 base mismatch variants in its targets. As shown in FIG. 2F, the 18-mer TALE is, similar to the Cas9-gRNA complexes, largely insensitive to single base mismatched in its target. As shown in FIG. 2G, introduction of 2 base mismatches significantly impairs the 18-mer TALE activity. TALE activity is more sensitive to mismatches nearer the 5' end of its target sequence (in the heat plot the target sequence positions are labeled from 1-18 starting from the 5' end).

Figures 1, 10A:
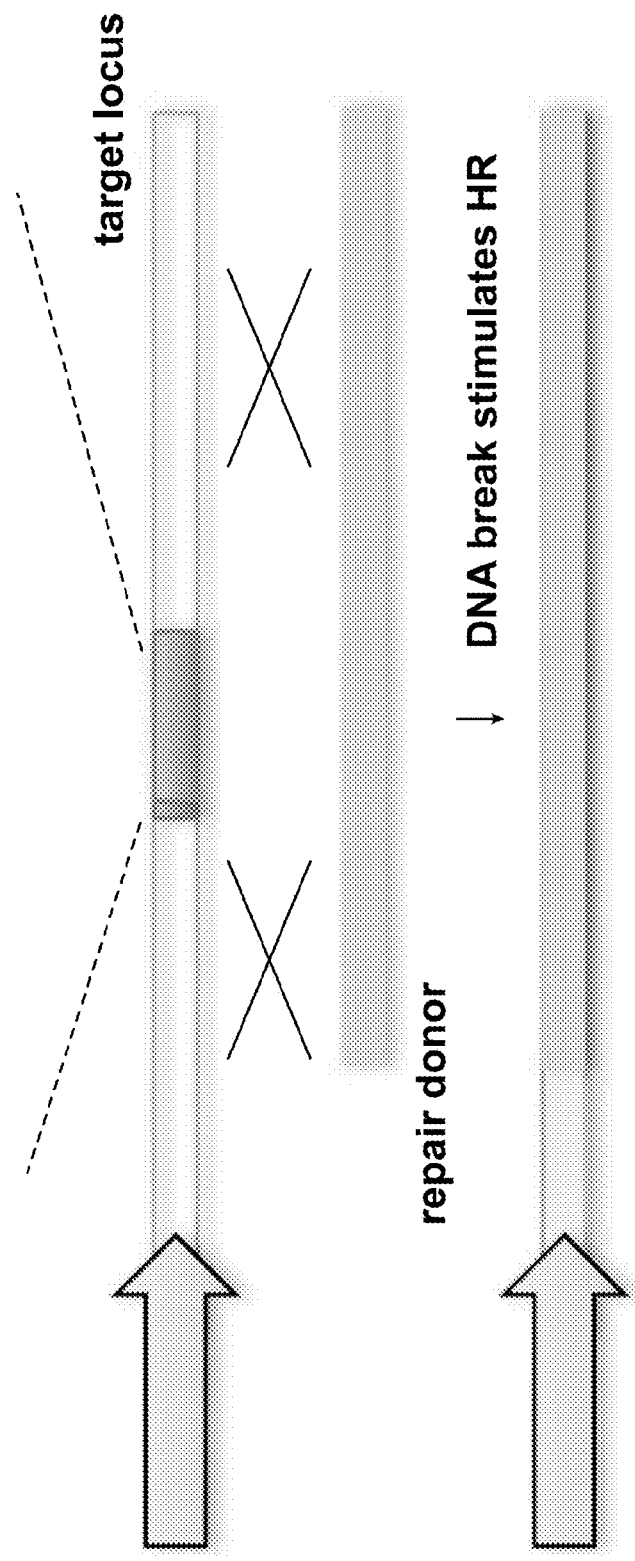
Figures 2, 10A:
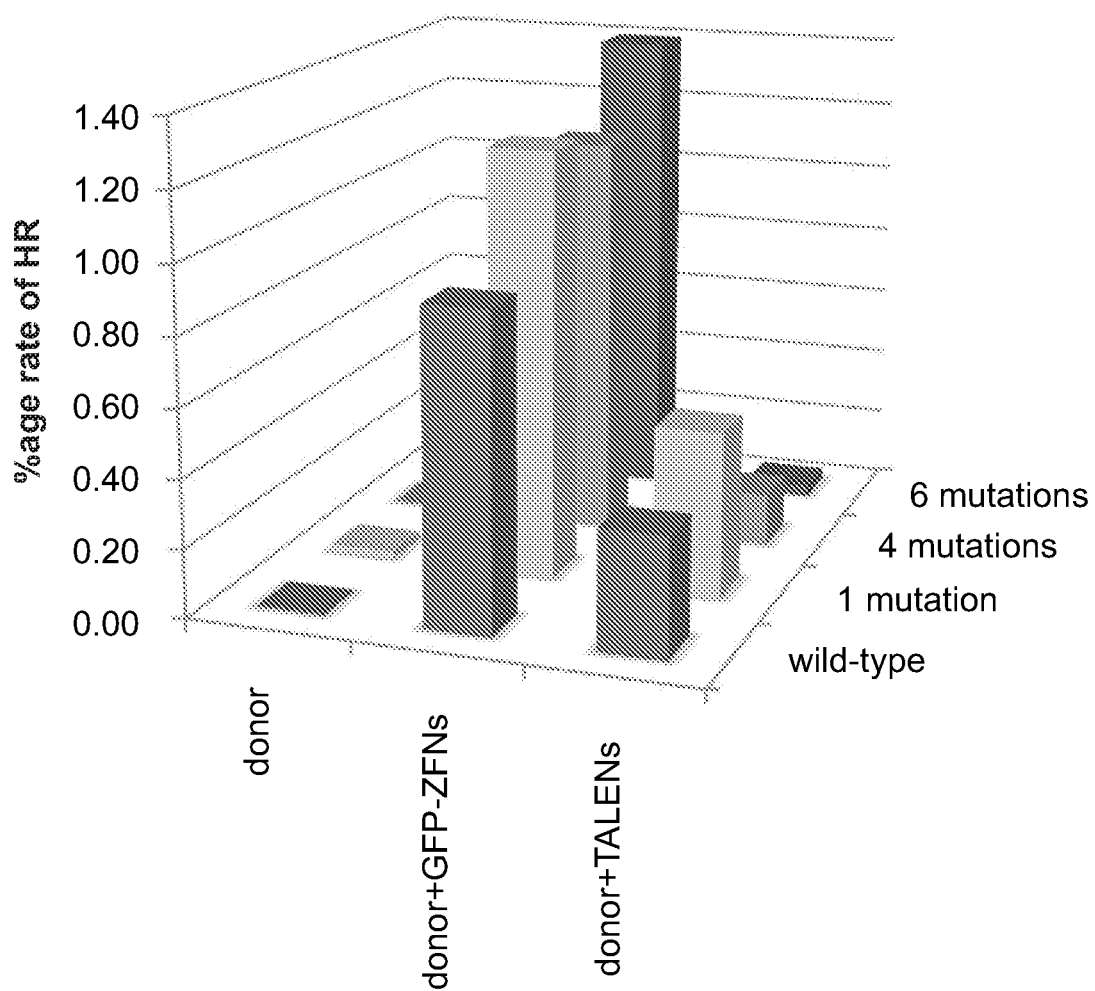
Figure 10B:
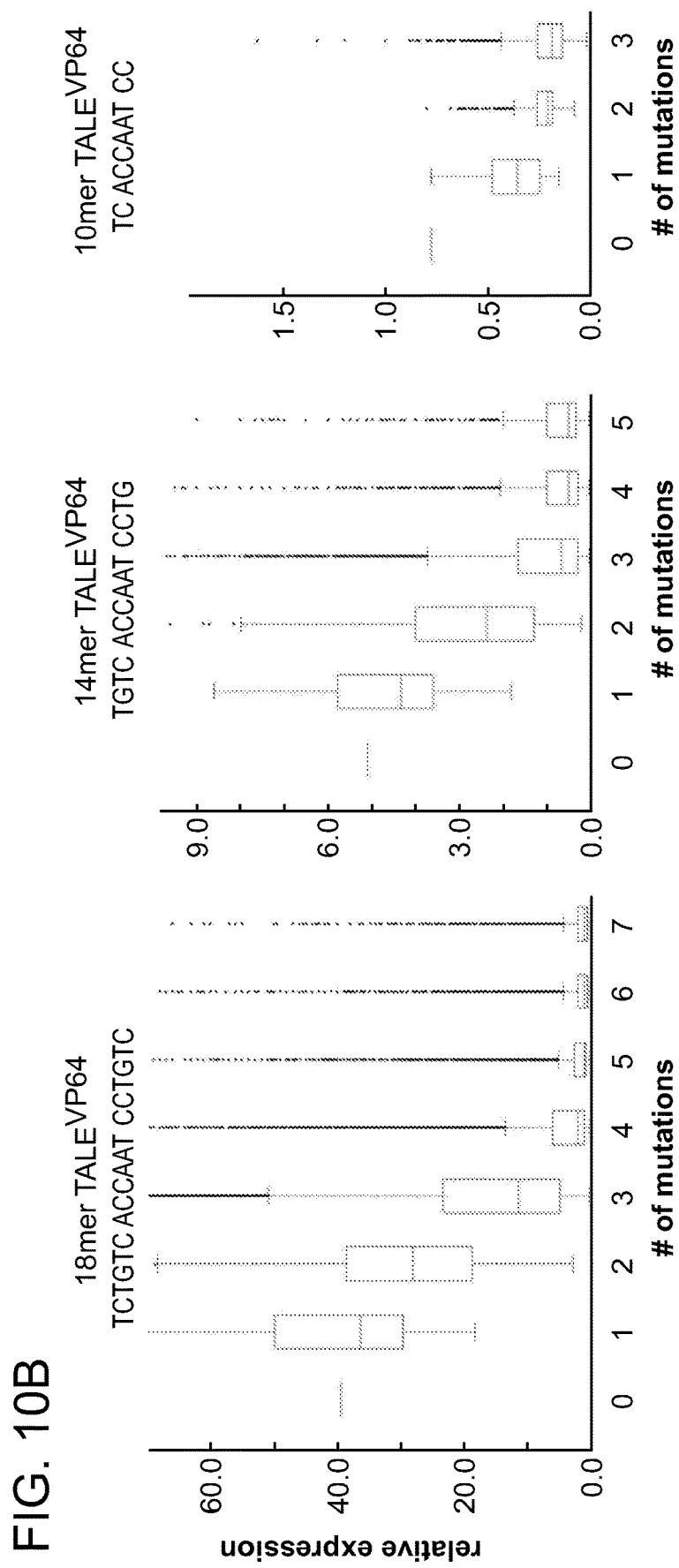
FIG. 10B depicts data from analysis of the targeting landscape of TALEs of 3 different sizes (18-mer, 14-mer and 10-mer).
Figure 10C:
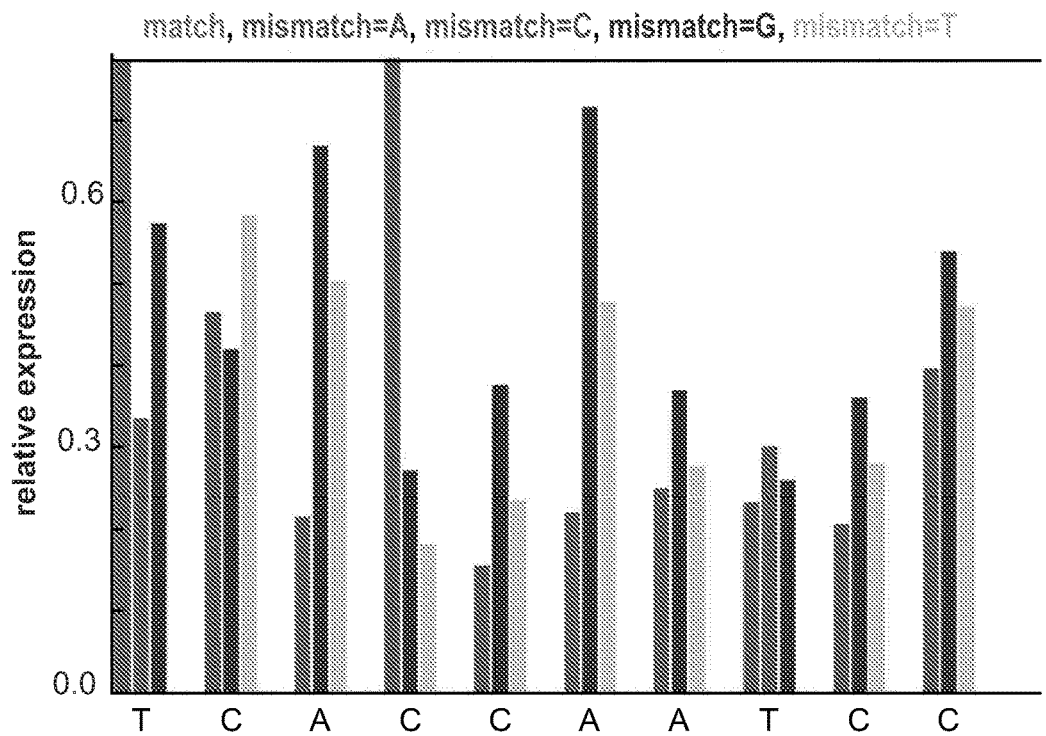
FIG. 10C depicts data for 10-mer TALEs show near single-base mismatch resolution.
Figure 10D:
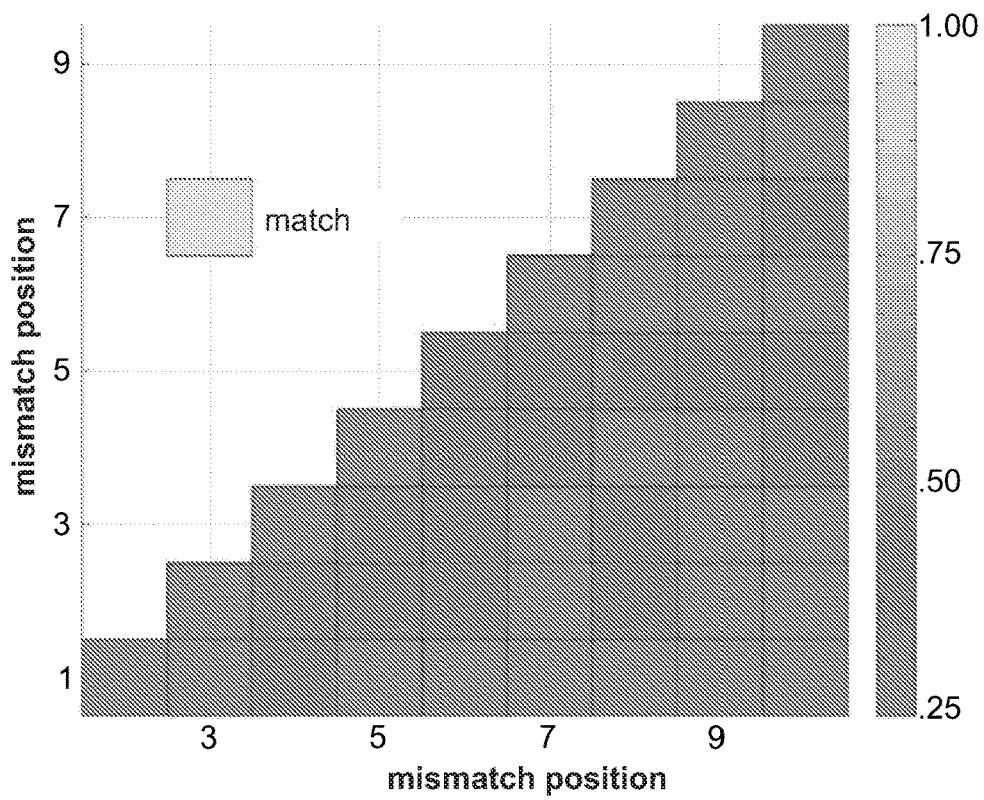
FIG. 10D depicts heat plot data for 10-mer TALEs show near single-base mismatch resolution.

Results were confirmed using targeted experiments in a nuclease assay which is the subject of FIGS. 10A-C directed to evaluating the landscape of targeting by TALEs of different sizes. As shown in FIGS. 10A-1 and 10A-2, using a nuclease mediated HR assay, it was confirmed that 18-mer TALEs tolerate multiple mutations in their target sequences. As shown in FIG. 10B, using the approach described in FIG. 2, the targeting landscape of TALEs of 3 different sizes (18-mer, 14-mer and 10-mer) was analyzed. Shorter TALEs (14-mer and 10-mer) are progressively more specific in their targeting but also reduced in activity by nearly an order of magnitude. As shown in FIGS. 10C and 10D, 10-mer TALEs show near single-base mismatch resolution, losing almost all activity against targets bearing 2 mismatches (in the heat plot the target sequence positions are labeled from 1-10 starting from the 5' end). Taken together, these data imply that engineering shorter TALEs can yield higher specificity in genome engineering applications, while the requirement for FokI dimerization in TALE nuclease applications is essential to avoid off-target effect. See Kim et al., *Proceedings of the National Academy of Sciences of the United States of America* 93, 1156-1160 (1996) and Pattanayak et al., *Nature Methods* 8, 765-770 (2011) each of which are hereby incorporated by reference in its entirety.

Figure 8A:
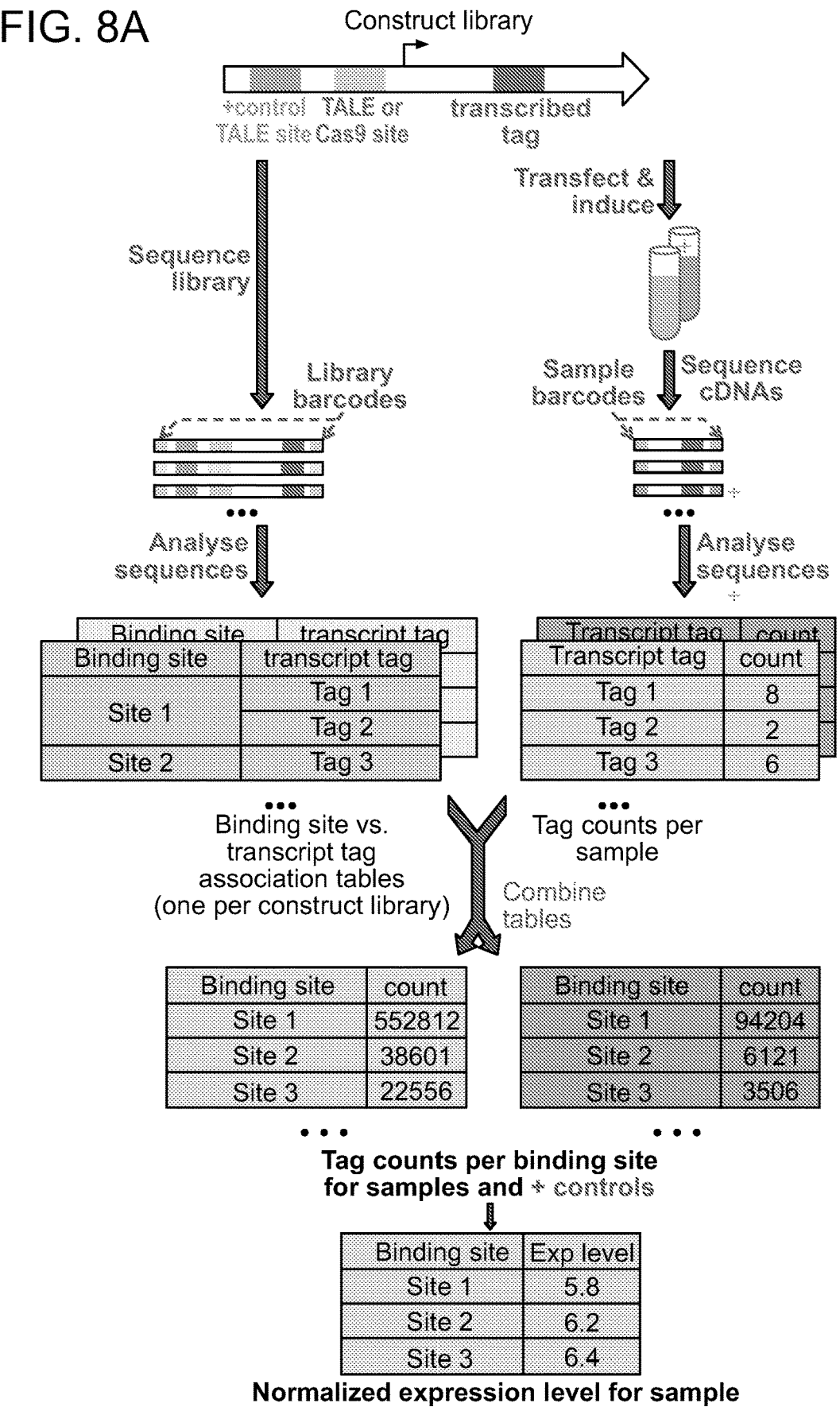
FIG. 8A depicts in schematic a high level specificity analysis processing flow for calculation of normalized expression levels.
Figure 8B:
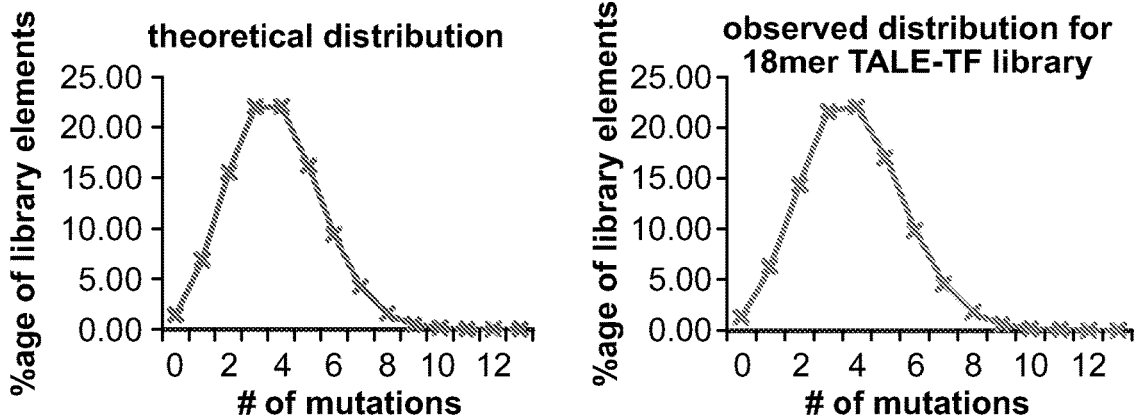
FIG. 8B depicts data of distributions of percentages of binding sites by numbers of mismatches generated within a biased construct library. Left: Theoretical distribution. Right: Distribution observed from an actual TALE construct library.
Figure 8C:
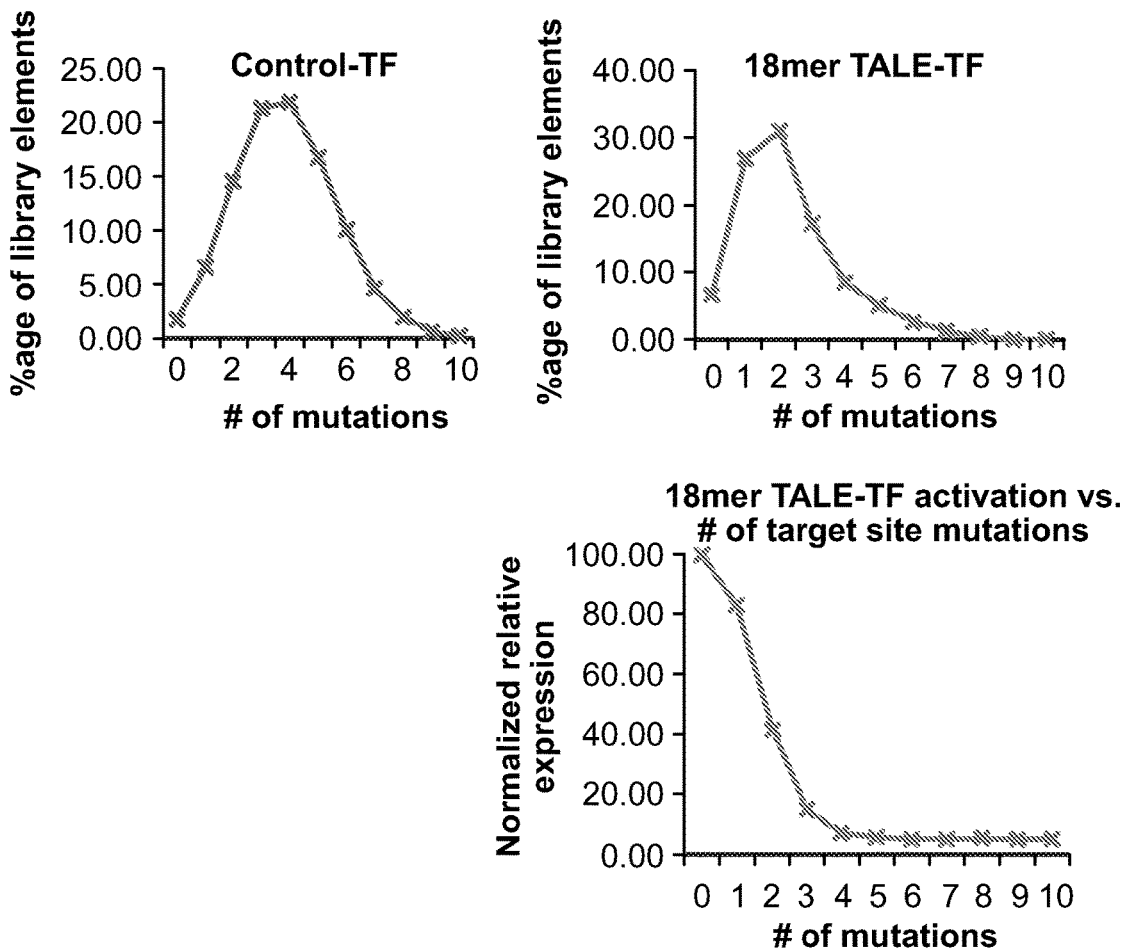
FIG. 8C depicts data of distributions of percentages of tag counts aggregated to binding sites by numbers of mismatches. Left: Distribution observed from the positive control sample. Right: Distribution observed from a sample in which a non-control TALE was induced.

FIG. 8A-C is directed to high level specificity analysis processing flow for calculation of normalized expression levels illustrated with examples from experimental data. As shown in FIG. 8A, construct libraries are generated with a biased distribution of binding site sequences and random sequence 24 bp tags that will be incorporated into reporter gene transcripts (top). The transcribed tags are highly degenerate so that they should map many-to-one to Cas9 or TALE binding sequences. The construct libraries are sequenced ($3^{rd}$ level, left) to establish which tags co-occur with binding sites, resulting in an association table of binding sites vs. transcribed tags ($4^{th}$ level, left). Multiple construct libraries built for different binding sites may be sequenced at once using library barcodes (indicated here by the light blue and light yellow colors; levels 1-4, left). A construct library is then transfected into a cell population and a set of different Cas9/gRNA or TALE transcription factors are induced in samples of the populations ($2^{nd}$ level, right). One sample is always induced with a fixed TALE activator targeted to a fixed binding site sequence within the construct (top level, green box); this sample serves as a positive control (green sample, also indicated by a + sign). cDNAs generated from the reporter mRNA molecules in the induced samples are then sequenced and analyzed to obtain tag counts for each tag in a sample ($3^{rd}$ and $4^{th}$ level, right). As with the construct library sequencing, multiple samples, including the positive control, are sequenced and analyzed together by appending sample barcodes. Here the light red color indicates one non-control sample that has been sequenced and analyzed with the positive control (green). Because only the transcribed tags and not the construct binding sites appear in each read, the binding site vs. tag association table obtained from construct library sequencing is then used to tally up total counts of tags expressed from each binding site in each sample ($5^{th}$ level). The tallies for each non-positive control sample are then converted to normalized expression levels for each binding site by dividing them by the tallies obtained in the positive control sample. Examples of plots of normalized expression levels by numbers of mismatches are provided in FIGS. 2B and 2E, and in FIG. 9A and FIG. 10B. Not covered in this overall process flow are several levels of filtering for erroneous tags, for tags not associable with a construct library, and for tags apparently shared with multiple binding sites. FIG. 8B depicts example distributions of percentages of binding sites by numbers of mismatches generated within a biased construct library. Left: Theoretical distribution. Right: Distribution observed from an actual TALE construct library. FIG. 8C depicts example distributions of percentages of tag counts aggregated to binding sites by numbers of mismatches. Left: Distribution observed from the positive control sample. Right: Distribution observed from a sample in which a non-control TALE was induced. As the positive control TALE binds to a fixed site in the construct, the distribution of aggregated tag counts closely reflects the distribution of binding sites in FIG. 8B, while the distribution is skewed to the left for the non-control TALE sample because sites with fewer mismatches induce higher expression levels. Below: Computing the relative enrichment between these by dividing the tag counts obtained for the target-TF by those obtained for the control-TF reveals the average expression level versus the number of mutations in the target site.

Figure 9A:
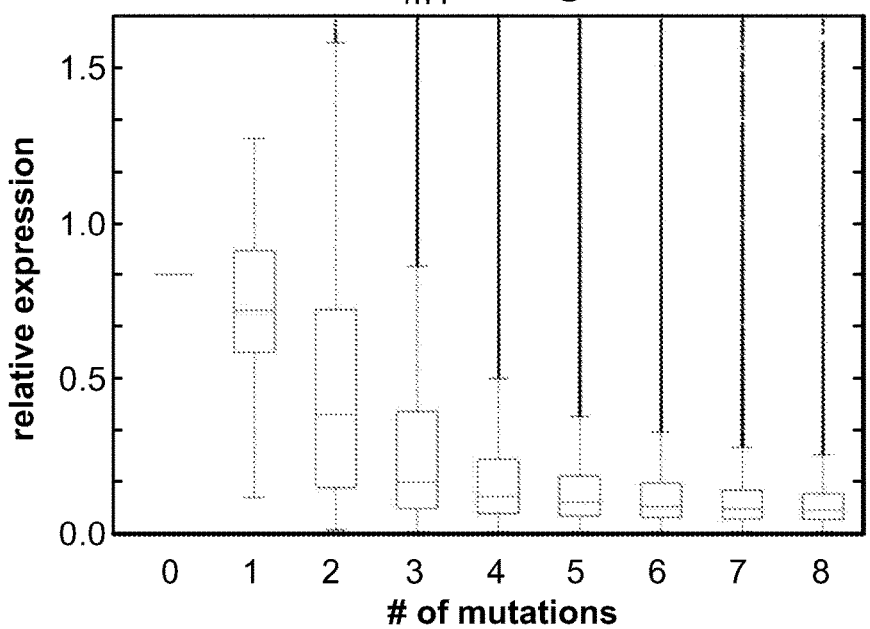
FIG. 9A depicts data for analysis of the targeting landscape of a Cas9-gRNA complex showing tolerance to 1-3 mutations in its target sequence.
Figure 9B:
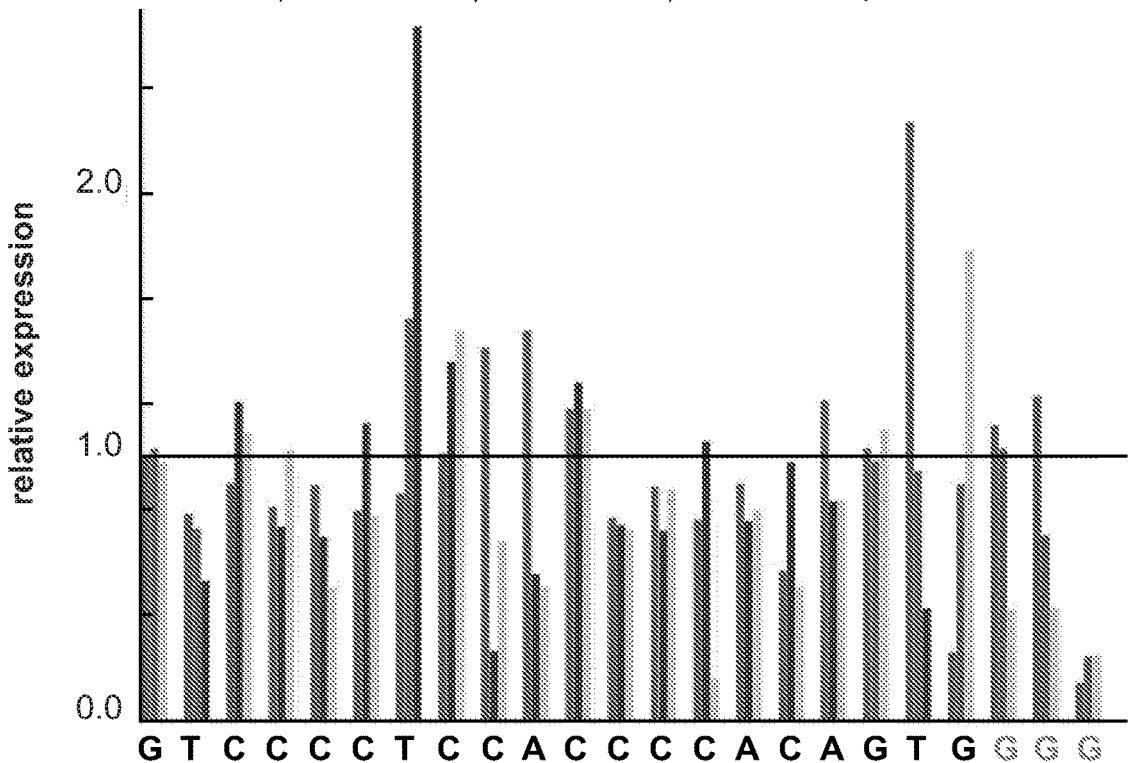
FIG. 9B depicts data for analysis of the targeting landscape of a Cas9-gRNA complex showing insensitivity to point mutations, except those localized to the PAM sequence.
Figure 9C:
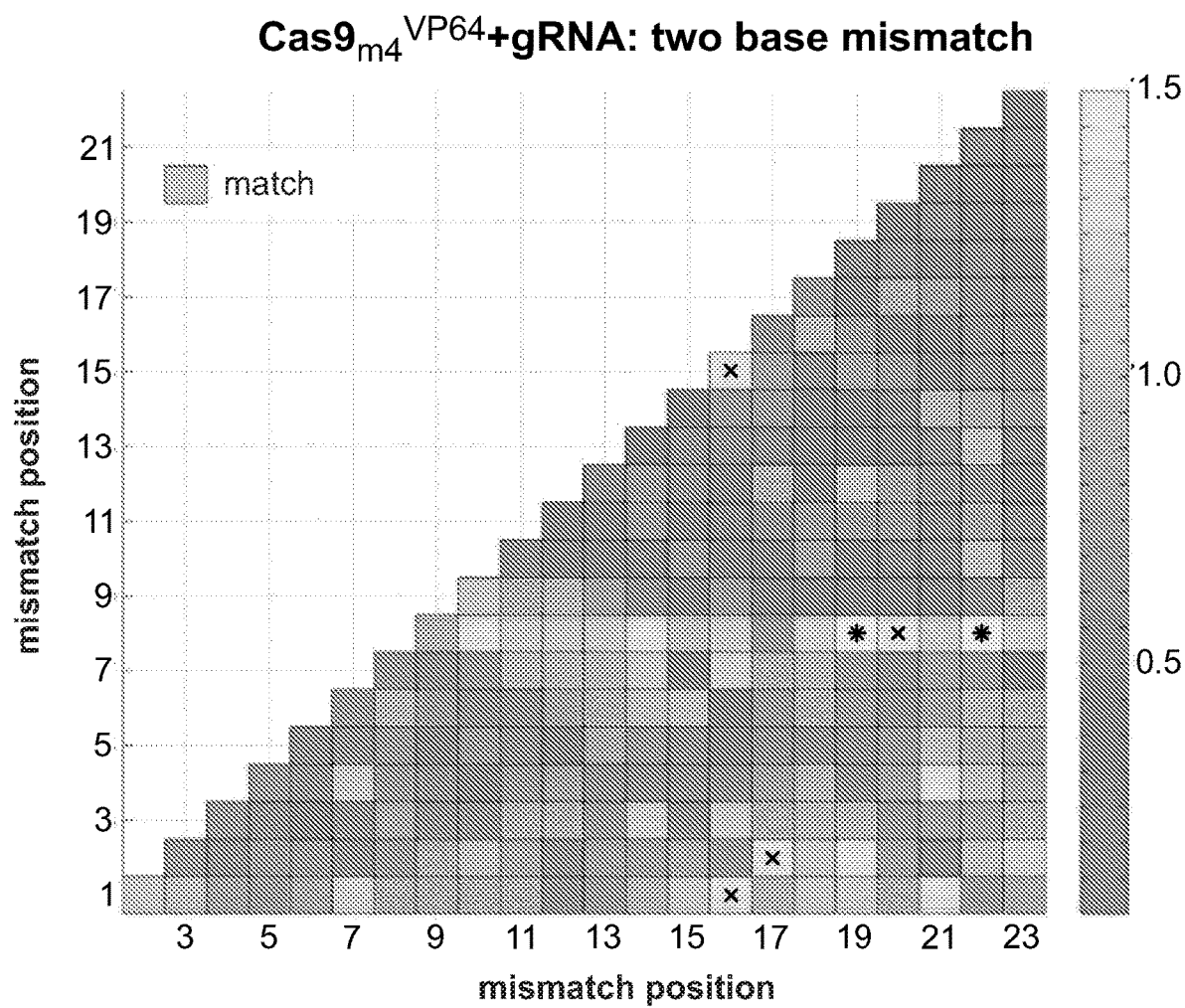
FIG. 9C depicts heat plot data for analysis of the targeting landscape of a Cas9-gRNA complex showing that introduction of 2 base mismatches significantly impairs activity.
Figure 9D:
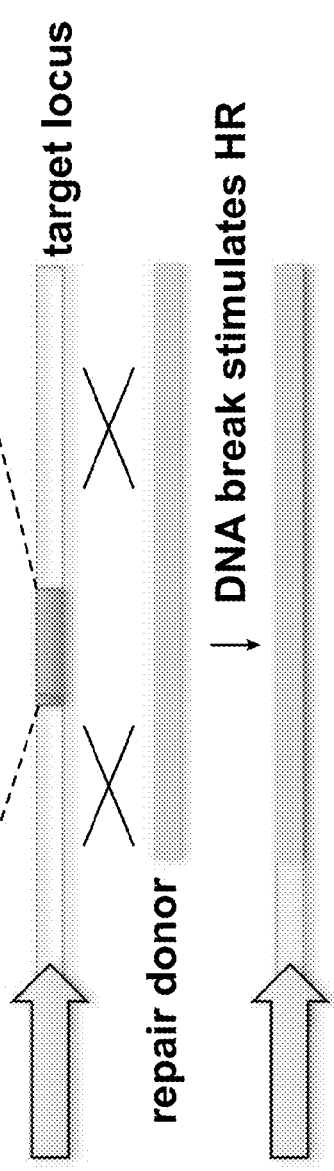
FIG. 9D depicts data from a nuclease mediated HR assay confirming that the predicted PAM for the S. pyogenes Cas9 is NGG and also NAG.
Figure 9D:
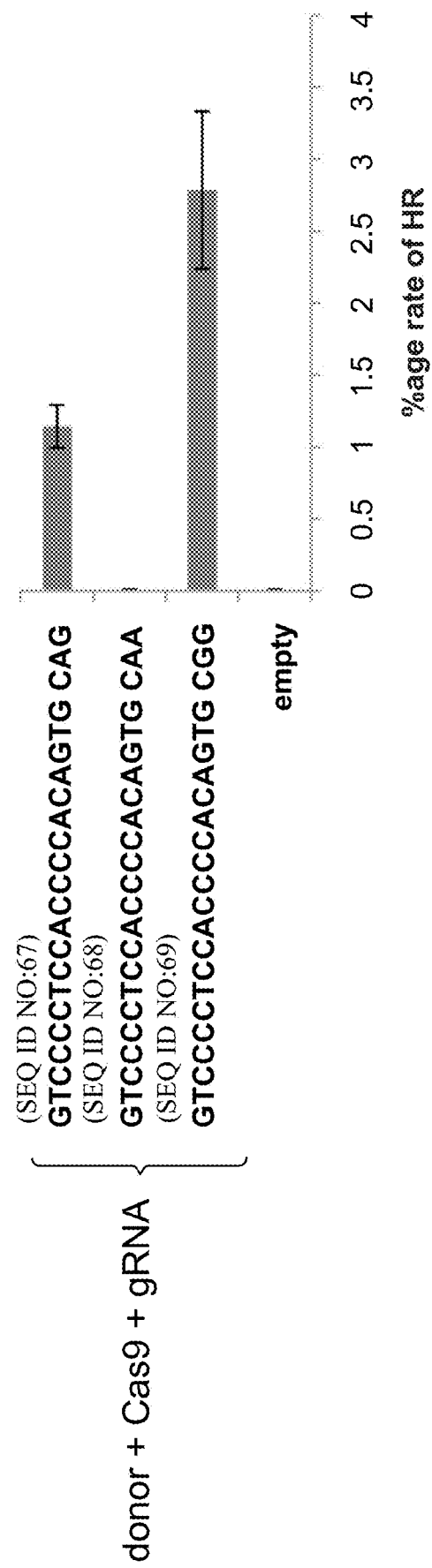

These results are further reaffirmed by specificity data generated using a different Cas9-gRNA complex. As shown in FIG. 9A, a different Cas9-gRNA complex is tolerant to 1-3 mutations in its target sequence. As shown in FIG. 9B, the Cas9-gRNA complex is also largely insensitive to point mutations, except those localized to the PAM sequence. As shown in FIG. 9C, introduction of 2 base mismatches however significantly impairs activity (in the heat plot the target sequence positions are labeled from 1-23 starting from the 5' end). As shown in FIG. 9D, it was confirmed using a nuclease mediated HR assay that the predicted PAM for the *S. pyogenes* Cas9 is NGG and also NAG.

According to certain aspects, binding specificity is increased according to methods described herein. Because synergy between multiple complexes is a factor in target gene activation by Cas9N-VP64, transcriptional regulation applications of Cas9N is naturally quite specific as individual off-target binding events should have minimal effect. According to one aspect, off-set nicks are used in methods of genome-editing. A large majority of nicks seldom result in NHEJ events, (see Certo et al., *Nature Methods* 8, 671-676 (2011) hereby incorporated by reference in its entirety) thus minimizing the effects of off-target nicking. In contrast, inducing off-set nicks to generate double stranded breaks (DSBs) is highly effective at inducing gene disruption. According to certain aspects, 5' overhangs generate more significant NHEJ events as opposed to 3' overhangs. Similarly, 3' overhangs favor HR over NHEJ events, although the total number of HR events is significantly lower than when a 5' overhang is generated. Accordingly, methods are provided for using nicks for homologous recombination and off-set nicks for generating double stranded breaks to minimize the effects of off-target Cas9-gRNA activity.

Figure 3A:
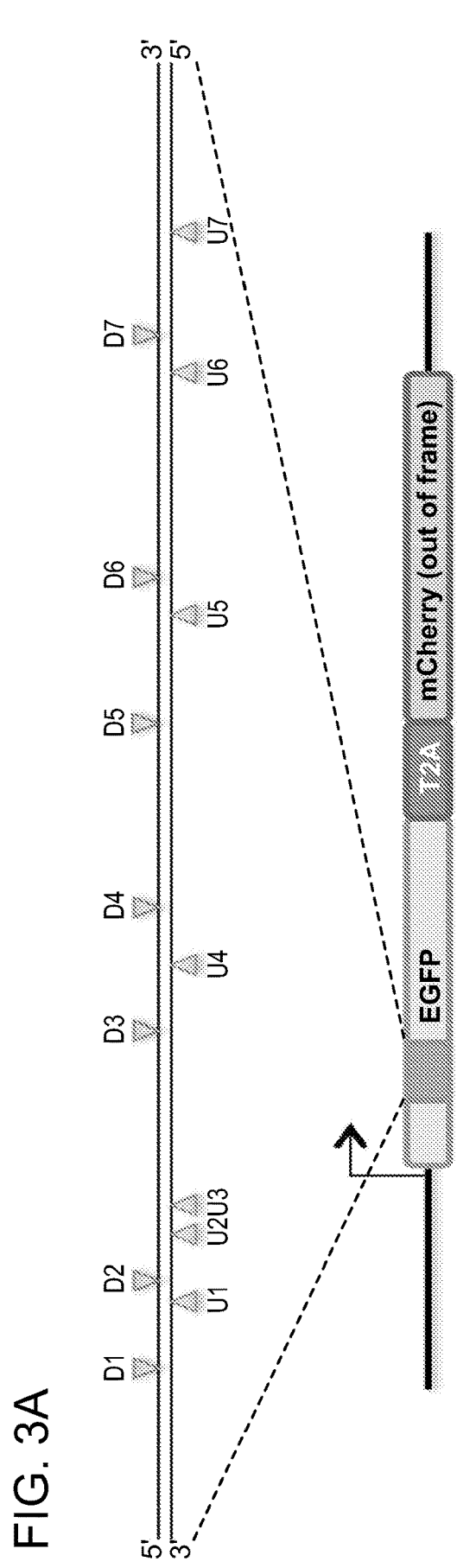
FIG. 3A depicts a schematic of a guide RNA design.
Figure 3C:
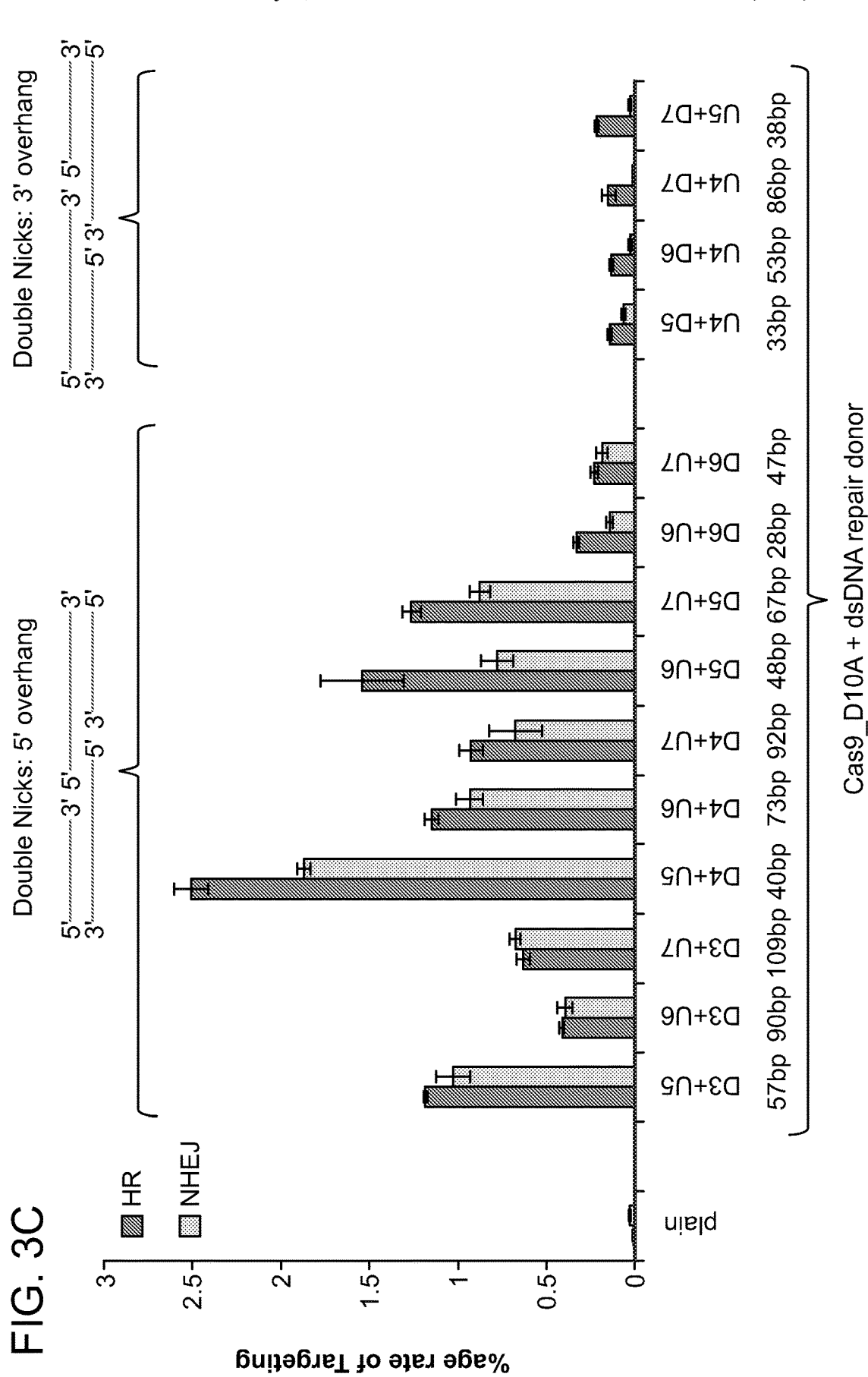
FIG. 3C depicts data showing percentage rate of targeting for off-set nicks leading to 5' overhangs and off-set nicks leading to 3' overhangs.

FIG. 3A-C is directed to multiplex off-set nicking and methods for reducing the off-target binding with the guide RNAs. As shown in FIG. 3A, the traffic light reporter was used to simultaneously assay for HR and NHEJ events upon introduction of targeted nicks or breaks. DNA cleavage events resolved through the HDR pathway restore the GFP sequence, whereas mutagenic NHEJ causes frameshifts rendering the GFP out of frame and the downstream mCherry sequence in frame. For the assay, 14 gRNAs covering a 200 bp stretch of DNA: 7 targeting the sense strand (U1-7) and 7 the antisense strand (D1-7) were designed. Using the Cas9D10A mutant, which nicks the complementary strand, different two-way combinations of the gRNAs were used to induce a range of programmed 5' or 3' overhangs (the nicking sites for the 14 gRNAs are indicated). As shown in FIG. 3B, inducing off-set nicks to generate double stranded breaks (DSBs) is highly effective at inducing gene disruption. Notably off-set nicks leading to 5' overhangs result in more NHEJ events as opposed to 3' overhangs. As shown in FIG. 3C, generating 3' overhangs also favors the ratio of HR over NHEJ events, but the total number of HR events is significantly lower than when a 5' overhang is generated.

Figure 11A:
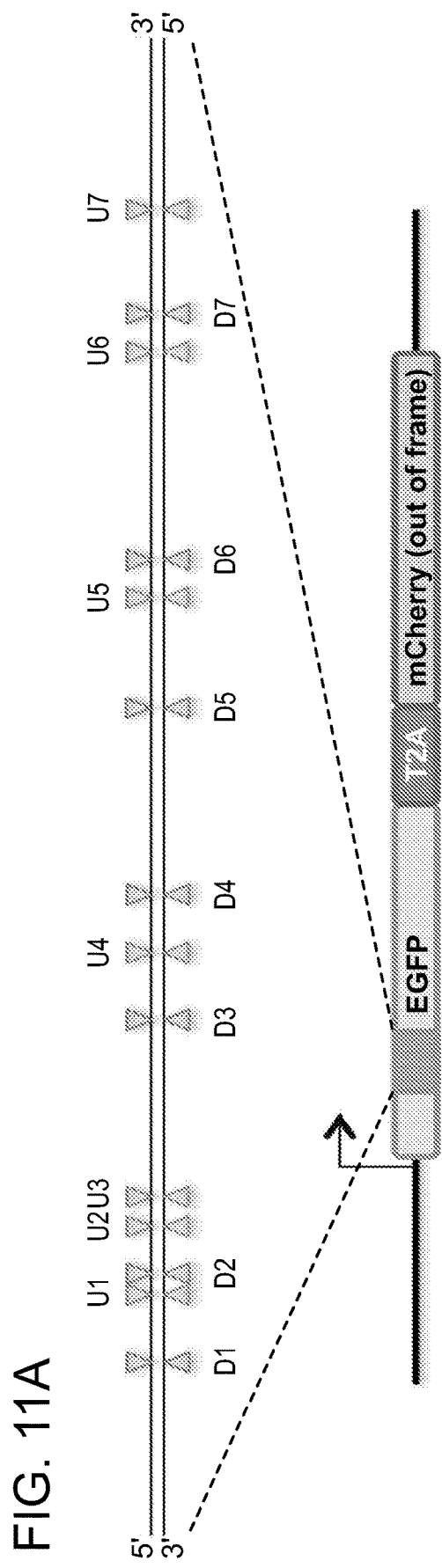
FIG. 11A depicts designed guide RNAs.
Figure 11B:
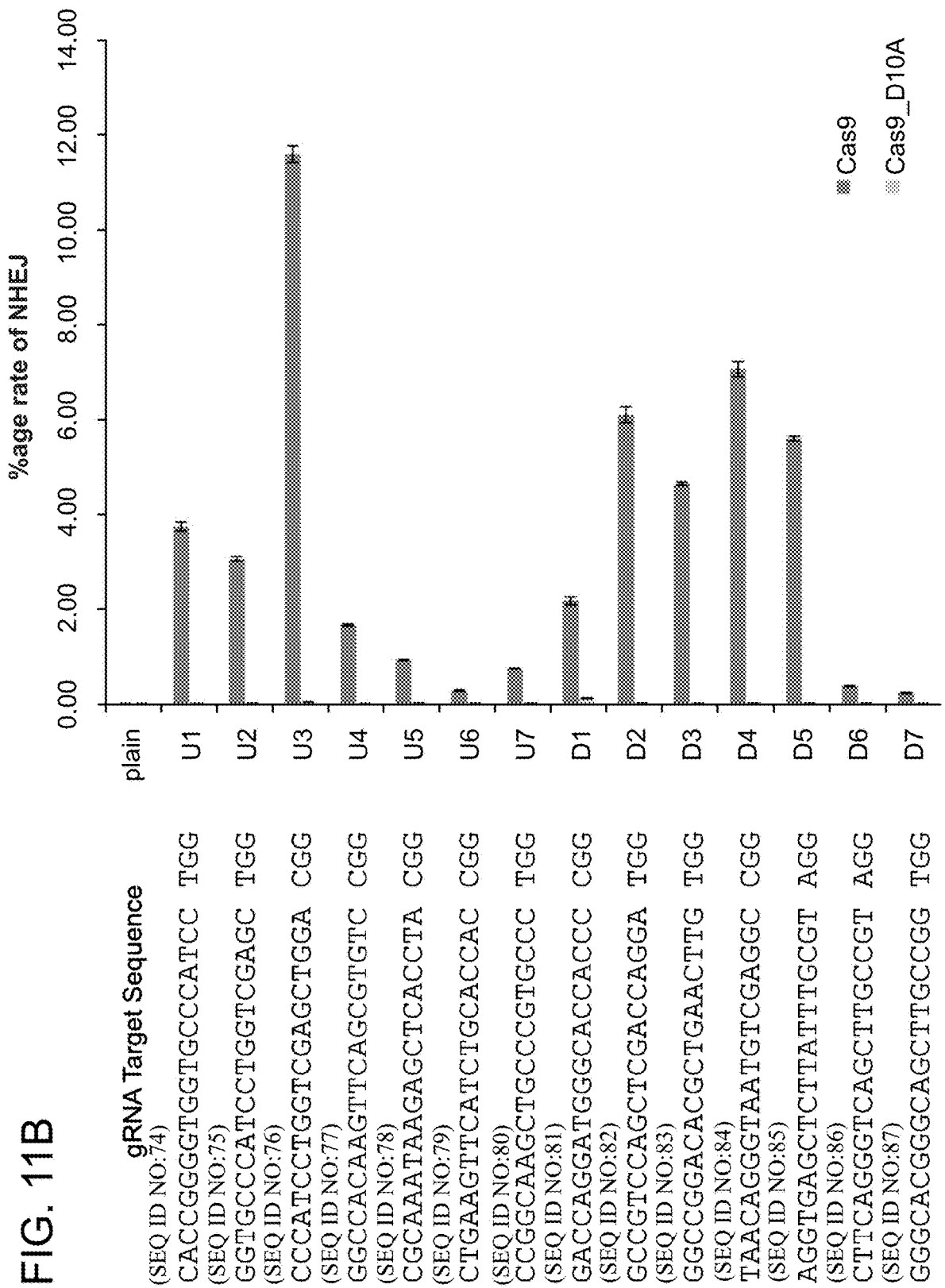
FIG. 11B depicts percentage rate of non-homologous end joining for various guide RNAs.

FIG. 11A-B is directed to Cas9D10A nickase mediated NHEJ. As shown in FIG. 11A, the traffic light reporter was used to assay NHEJ events upon introduction of targeted nicks or double-stranded breaks. Briefly, upon introduction of DNA cleavage events, if the break goes through mutagenic NHEJ, the GFP is translated out of frame and the downstream mCherry sequences are rendered in frame resulting in red fluorescence. 14 gRNAs covering a 200 bp stretch of DNA: 7 targeting the sense strand (U1-7) and 7 the antisense strand (D1-7) were designed. As shown in FIG. 11B, it was observed that unlike the wild-type Cas9 which results in DSBs and robust NHEJ across all targets, most nicks (using the Cas9D10A mutant) seldom result in NHEJ events. All 14 sites are located within a contiguous 200 bp stretch of DNA and over 10-fold differences in targeting efficiencies were observed.

According to certain aspects, methods are described herein of modulating expression of a target nucleic acid in a cell that include introducing one or more, two or more or a plurality of foreign nucleic acids into the cell. The foreign nucleic acids introduced into the cell encode for a guide RNA or guide RNAs, a nuclease-null Cas9 protein or proteins and a transcriptional regulator protein or domain. Together, a guide RNA, a nuclease-null Cas9 protein and a transcriptional regulator protein or domain are referred to as a co-localization complex as that term is understood by one of skill in the art to the extent that the guide RNA, the nuclease-null Cas9 protein and the transcriptional regulator protein or domain bind to DNA and regulate expression of a target nucleic acid. According to certain additional aspects, the foreign nucleic acids introduced into the cell encode for a guide RNA or guide RNAs and a Cas9 protein nickase. Together, a guide RNA and a Cas9 protein nickase are referred to as a co-localization complex as that term is understood by one of skill in the art to the extent that the guide RNA and the Cas9 protein nickase bind to DNA and nick a target nucleic acid.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Further, cells include any in which it would be beneficial or desirable to regulate a target nucleic acid. Such cells may include those which are deficient in expression of a particular protein leading to a disease or detrimental condition. Such diseases or detrimental conditions are readily known to those of skill in the art. According to the present disclosure, the nucleic acid responsible for expressing the particular protein may be targeted by the methods described herein and a transcriptional activator resulting in upregulation of the target nucleic acid and corresponding expression of the particular protein. In this manner, the methods described herein provide therapeutic treatment.

Target nucleic acids include any nucleic acid sequence to which a co-localization complex as described herein can be useful to either regulate or nick. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Transcriptional regulator proteins or domains which are transcriptional activators include VP16 and VP64 and others readily identifiable by those skilled in the art based on the present disclosure.

Diseases and detrimental conditions are those characterized by abnormal loss of expression of a particular protein. Such diseases or detrimental conditions can be treated by upregulation of the particular protein. Accordingly, methods of treating a disease or detrimental condition are provided where the co-localization complex as described herein associates or otherwise binds to DNA including a target nucleic acid, and the transcriptional activator of the co-localization complex upregulates expression of the target nucleic acid. For example upregulating PRDM16 and other genes promoting brown fat differentiation and increased metabolic uptake can be used to treat metabolic syndrome or obesity. Activating anti-inflammatory genes are useful in autoimmunity and cardiovascular disease. Activating tumor suppressor genes is useful in treating cancer. One of skill in the art will readily identify such diseases and detrimental conditions based on the present disclosure.

The following examples are set forth as being representative of the present disclosure. These examples are not to be construed as limiting the scope of the present disclosure as these and other equivalent embodiments will be apparent in view of the present disclosure, figures and accompanying claims.

Example I

Cas9 Mutants

Sequences homologous to Cas9 with known structure were searched to identify candidate mutations in Cas9 that could ablate the natural activity of its RuvC and HNH domains. Using HHpred (world wide website toolkit.tuebingen.mpg.de/hhpred), the full sequence of Cas9 was queried against the full Protein Data Bank (January 2013). This search returned two different HNH endonucleases that had significant sequence homology to the HNH domain of Cas9: Pad and a putative endonuclease (PDB IDs: 3M7K and 4H9D respectively). These proteins were examined to find residues involved in magnesium ion coordination. The corresponding residues were then identified in the sequence alignment to Cas9. Two Mg-coordinating side-chains in each structure were identified that aligned to the same amino acid type in Cas9. They are 3M7K D92 and N113, and 4H9D D53 and N77. These residues corresponded to Cas9 D839 and N863. It was also reported that mutations of Pad residues D92 and N113 to alanine rendered the nuclease catalytically deficient. The Cas9 mutations D839A and N863A were made based on this analysis. Additionally, HHpred also predicts homology between Cas9 and the N-terminus of a *Thermus thermophilus* RuvC (PDB ID: 4EP4). This sequence alignment covers the previously reported mutation D10A which eliminates function of the RuvC domain in Cas9. To confirm this as an appropriate mutation, the metal binding residues were determined as before. In 4EP4, D7 helps to coordinate a magnesium ion. This position has sequence homology corresponding to Cas9 D10, confirming that this mutation helps remove metal binding, and thus catalytic activity from the Cas9 RuvC domain.

Example II

Plasmid Construction

The Cas9 mutants were generated using the Quikchange kit (Agilent technologies). The target gRNA expression constructs were either (1) directly ordered as individual gBlocks from IDT and cloned into the pCR-BluntII-TOPO vector (Invitrogen); or (2) custom synthesized by Genewiz; or (3) assembled using Gibson assembly of oligonucleotides into the gRNA cloning vector (plasmid #41824). The vectors for the HR reporter assay involving a broken GFP were constructed by fusion PCR assembly of the GFP sequence bearing the stop codon and appropriate fragment assembled into the EGIP lentivector from Addgene (plasmid #26777). These lentivectors were then used to establish the GFP reporter stable lines. TALENs used in this study were constructed using standard protocols. See Sanjana et al., *Nature Protocols* 7, 171-192 (2012) hereby incorporated by reference in its entirety. Cas9N and MS2 VP64 fusions were performed using standard PCR fusion protocol procedures. The promoter luciferase constructs for OCT4 and REX1 were obtained from Addgene (plasmid #17221 and plasmid #17222).

Example III

Cell Culture and Transfections

HEK 293T cells were cultured in Dulbecco's modified Eagle's medium (DMEM, Invitrogen) high glucose supplemented with 10% fetal bovine serum (FBS, Invitrogen), penicillin/streptomycin (pen/strep, Invitrogen), and non-essential amino acids (NEAA, Invitrogen). Cells were maintained at 37° C. and 5% $CO_2$ in a humidified incubator.

Transfections involving nuclease assays were as follows: $0.4 \times 10^6$ cells were transfected with 2 µg Cas9 plasmid, 2 µg gRNA and/or 2 µg DNA donor plasmid using Lipofectamine 2000 as per the manufacturer's protocols. Cells were harvested 3 days after transfection and either analyzed by FACS, or for direct assay of genomic cuts the genomic DNA of $\sim 1 \times 10^6$ cells was extracted using DNAeasy kit (Qiagen). For these PCR was conducted to amplify the targeting region with genomic DNA derived from the cells and amplicons were deep sequenced by MiSeq Personal Sequencer (Illumina) with coverage >200,000 reads. The sequencing data was analyzed to estimate NHEJ efficiencies.

For transfections involving transcriptional activation assays: $0.4 \times 10^6$ cells were transfected with (1) 2 µg Cas9N-VP64 plasmid, 2 µg gRNA and/or 0.25 µg of reporter construct; or (2) 2 µg Cas9N plasmid, 2 µg MS2-VP64, 2 µg gRNA-2×MS2aptamer and/or 0.25 µg of reporter construct. Cells were harvested 24-48 hrs post transfection and assayed using FACS or immunofluorescence methods, or their total RNA was extracted and these were subsequently analyzed by RT-PCR. Here standard taqman probes from Invitrogen for OCT4 and REX1 were used, with normalization for each sample performed against GAPDH.

For transfections involving transcriptional activation assays for specificity profile of Cas9-gRNA complexes and TALEs: $0.4 \times 10^6$ cells were transfected with (1) 2 µg Cas9N-VP64 plasmid, 2 µg gRNA and 0.25 µg of reporter library; or (2) 2 µg TALE-TF plasmid and 0.25 µg of reporter library; or (3) 2 µg control-TF plasmid and 0.25 µg of reporter library. Cells were harvested 24 hrs post transfection (to avoid the stimulation of reporters being in saturation mode). Total RNA extraction was performed using RNAeasy-plus kit (Qiagen), and standard RT-per performed using Superscript-III (Invitrogen). Libraries for next-generation sequencing were generated by targeted per amplification of the transcript-tags.

Example IV

Computational and Sequence Analysis for Calculation of Cas9-TF and TALE-TF Reporter Expression Levels The high-level logic flow for this process is depicted in FIG. 8A, and additional details are given here. For details on construct library composition, see FIGS. 8A (level 1) and 8B.

Sequencing:

For Cas9 experiments, construct library (FIG. 8A, level 3, left) and reporter gene cDNA sequences (FIG. 8A, level 3, right) were obtained as 150 bp overlapping paired end reads on an Illumina MiSeq, while for TALE experiments, corresponding sequences were obtained as 51 bp non-overlapping paired end reads on an Illumina HiSeq.

Construct Library Sequence Processing: Alignment:

For Cas9 experiments, novoalign V2.07.17 (world wide website novocraft.com/main/index/php) was used to align paired reads to a set of 250 bp reference sequences that corresponded to 234 bp of the constructs flanked by the pairs of 8 bp library barcodes (see FIG. 8A, $3^{rd}$ level, left). In the reference sequences supplied to novoalign, the 23 bp degenerate Cas9 binding site regions and the 24 bp degenerate transcript tag regions (see FIG. 8A, first level) were specified as Ns, while the construct library barcodes were explicitly provided. For TALE experiments, the same procedures were used except that the reference sequences were 203 bp in length and the degenerate binding site regions were 18 bp vs. 23 bp in length. Validity checking: Novoalign output for comprised files in which left and right reads for each read pair were individually aligned to the reference sequences. Only read pairs that were both uniquely aligned to the reference sequence were subjected to additional validity conditions, and only read pairs that passed all of these conditions were retained. The validity conditions included: (i) Each of the two construct library barcodes must align in at least 4 positions to a reference sequence barcode, and the two barcodes must to the barcode pair for the same construct library. (ii) All bases aligning to the N regions of the reference sequence must be called by novoalign as As, Cs, Gs or Ts. Note that for neither Cas9 nor TALE experiments did left and right reads overlap in a reference N region, so that the possibility of ambiguous novoalign calls of these N bases did not arise. (iii) Likewise, no novoalign-called inserts or deletions must appear in these regions. (iv) No Ts must appear in the transcript tag region (as these random sequences were generated from As, Cs, and Gs only). Read pairs for which any one of these conditions were violated were collected in a rejected read pair file. These validity checks were implemented using custom perl scripts.

Induced Sample Reporter Gene cDNA Sequence Processing: Alignment:

SeqPrep (downloaded from world wide website github.com/jstjohn/SeqPrep) was first used to merge the overlapping read pairs to the 79 bp common segment, after which novoalign (version above) was used to align these 79 bp common segments as unpaired single reads to a set of reference sequences (see FIG. 8A, $3^{rd}$ level, right) in which (as for the construct library sequencing) the 24 bp degenerate transcript tag was specified as Ns while the sample barcodes were explicitly provided. Both TALE and Cas9 cDNA sequence regions corresponded to the same 63 bp regions of cDNA flanked by pairs of 8 bp sample barcode sequences. Validity checking: The same conditions were applied as for construct library sequencing (see above) except that: (a) Here, due prior SeqPrep merging of read pairs, validity processing did not have to filter for unique alignments of both reads in a read pair but only for unique alignments of the merged reads. (b) Only transcript tags appeared in the cDNA sequence reads, so that validity processing only applied these tag regions of the reference sequences and not also to a separate binding site region.

Assembly of Table of Binding Sites Vs. Transcript Tag Associations:

Custom perl was used to generate these tables from the validated construct library sequences (FIG. 8A, $4^{th}$ level, left). Although the 24 bp tag sequences composed of A, C, and G bases should be essentially unique across a construct library (probability of sharing=~2.8e-11), early analysis of binding site vs. tag associations revealed that a non-negligible fraction of tag sequences were in fact shared by multiple binding sequences, likely mainly caused by a combination of sequence errors in the binding sequences, or oligo synthesis errors in the oligos used to generate the construct libraries. In addition to tag sharing, tags found associated with binding sites in validated read pairs might also be found in the construct library read pair reject file if it was not clear, due to barcode mismatches, which construct library they might be from. Finally, the tag sequences themselves might contain sequence errors. To deal with these sources of error, tags were categorized with three attributes: (i) safe vs. unsafe, where unsafe meant the tag could be found in the construct library rejected read pair file; shared vs. nonshared, where shared meant the tag was found associated with multiple binding site sequences, and 2+vs. 1-only, where 2+ meant that the tag appeared at least twice among the validated construct library sequences and so presumed to be less likely to contain sequence errors. Combining these three criteria yielded 8 classes of tags associated with each binding site, the most secure (but least abundant) class comprising only safe, nonshared, 2+ tags; and the least secure (but most abundant) class comprising all tags regardless of safety, sharing, or number of occurrences.

Computation of Normalized Expression Levels:

Custom perl code was used to implement the steps indicated in FIG. 8A, levels 5-6. First, tag counts obtained for each induced sample were aggregated for each binding site, using the binding site vs. transcript tag table previously computed for the construct library (see FIG. 8C). For each sample, the aggregated tag counts for each binding site were then divided by the aggregated tag counts for the positive control sample to generate normalized expression levels. Additional considerations relevant to these calculations included:

1. For each sample, a subset of "novel" tags were found among the validity-checked cDNA gene sequences that could not be found in the binding site vs. transcript tag association table. These tags were ignored in the subsequent calculations.

2. The aggregations of tag counts described above were performed for each of the eight classes of tags described above in binding site vs. transcript tag association table. Because the binding sites in the construct libraries were biased to generate sequences similar to a central sequence frequently, but sequences with increasing numbers of mismatches increasingly rarely, binding sites with few mismatches generally aggregated to large numbers of tags, while binding sites with more mismatches aggregated to smaller numbers. Thus, although use of the most secure tag class was generally desirable, evaluation of binding sites with two or more mismatches might be based on small numbers of tags per binding site, making the secure counts and ratios less statistically reliable even if the tags themselves were more reliable. In such cases, all tags were used. Some compensation for this consideration obtains from the fact that the number of separate aggregated tag counts for n mismatching positions grew with the number of combinations of mismatching positions $$\left(\text{equal to } \binom{L}{n} 3^n\right),$$

and so dramatically increases with n; thus the averages of aggregated tag counts for different numbers n of mismatches (shown in FIGS. 2b, 2e, and in FIGS. 9A and 10B) are based on a statistically very large set of aggregated tag counts for n≥2.

3. Finally, the binding site built into the TALE construct libraries was 18 bp and tag associations were assigned based on these 18 bp sequences, but some experiments were conducted with TALEs programmed to bind central 14 bp or 10 bp regions within the 18 bp construct binding site regions. In computing expression levels for these TALEs, tags were aggregated to binding sites based on the corresponding regions of the 18 bp binding sites in the association table, so that binding site mismatches outside of this region were ignored.

Example V

RNA-Guided SOX2 and NANOG Regulation Using Cas9$_N$-VP64

Figure 12A:
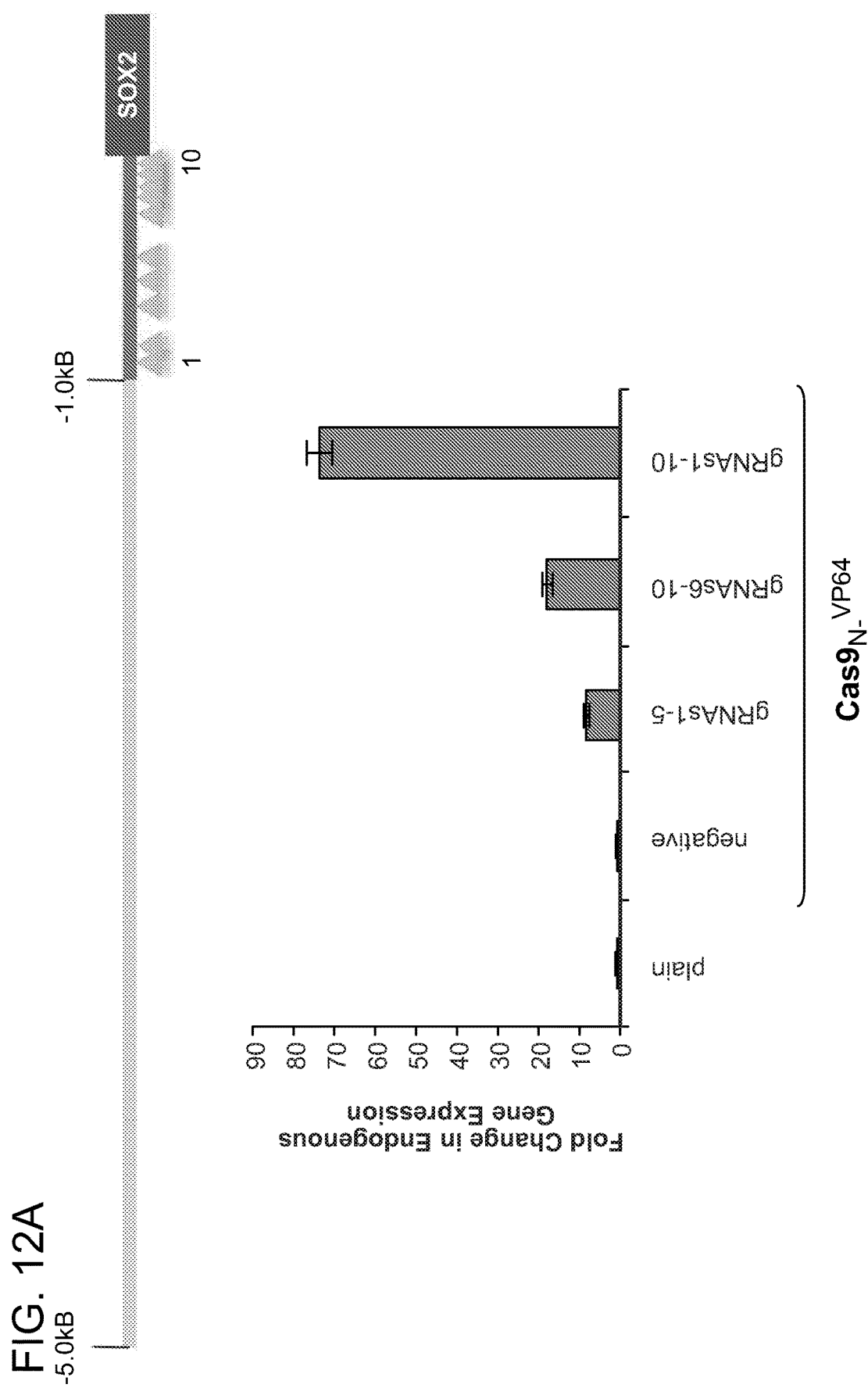
FIG. 12A depicts the Sox2 gene.
Figure 12B:
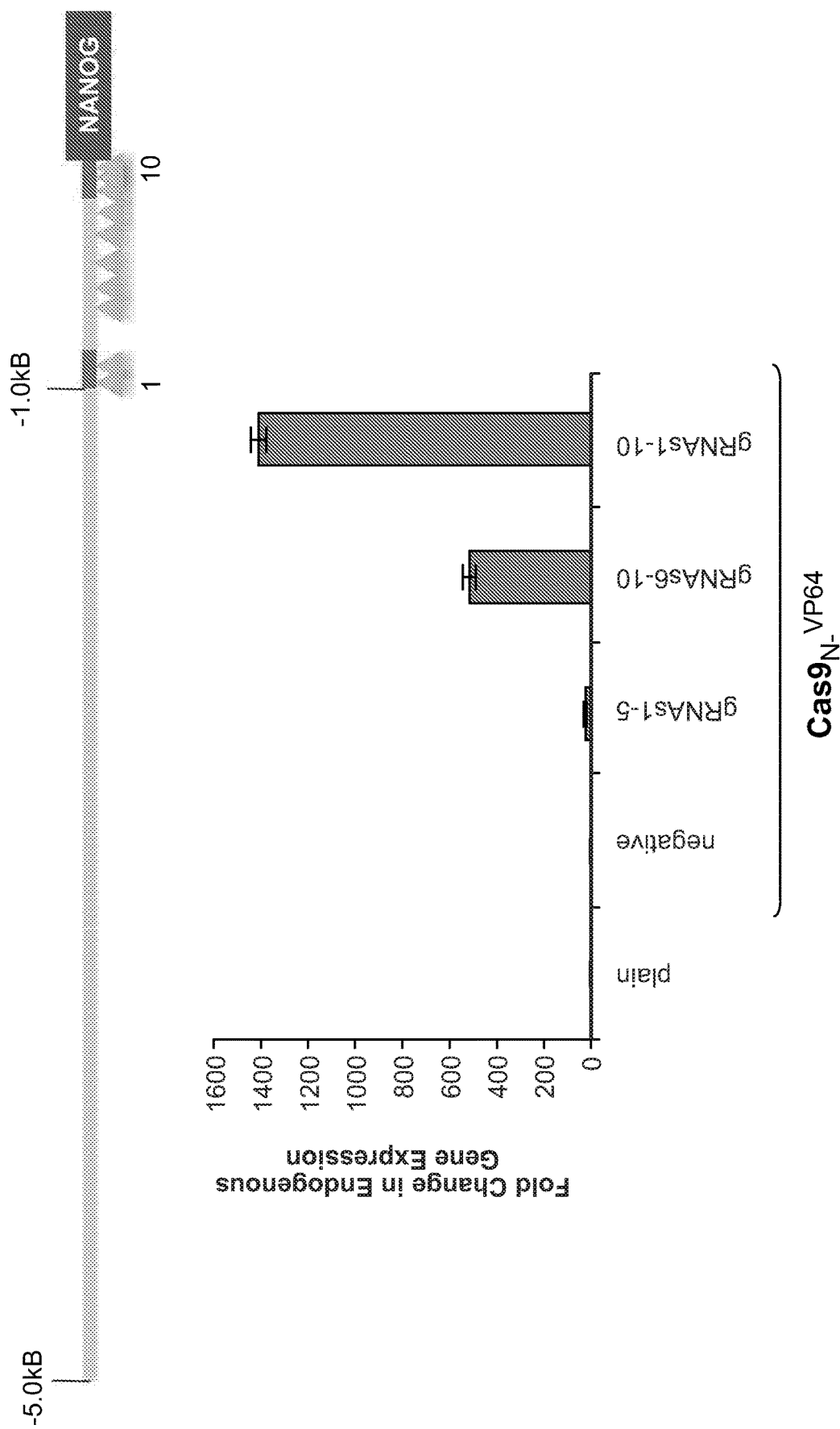
FIG. 12B depicts the Nanog gene.

The sgRNA (aptamer-modified single guide RNA) tethering approach described herein allows different effector domains to be recruited by distinct sgRNAs so long as each sgRNA uses a different RNA-protein interaction pair, enabling multiplex gene regulation using the same Cas9N-protein. For the FIG. 12A SOX2 and FIG. 12B NANOG genes, 10 gRNAs were designed targeting a ~1 kb stretch of DNA upstream of the transcription start site. The DNase hypersensitive sites are highlighted in green. Transcriptional activation via qPCR of the endogenous genes was assayed. In both instances, while introduction of individual gRNAs modestly stimulated transcription, multiple gRNAs acted synergistically to stimulate robust multi-fold transcriptional activation. Data are means+/−SEM (N=3). As shown in FIG. 12A-B, two additional genes, SOX2 and NANOG, were regulated via sgRNAs targeting within an upstream ~1 kb stretch of promoter DNA. The sgRNAs proximal to the transcriptional start site resulted in robust gene activation.

Example VI

Evaluating the Landscape of Targeting by Cas9-gRNA Complexes

Figure 13A:
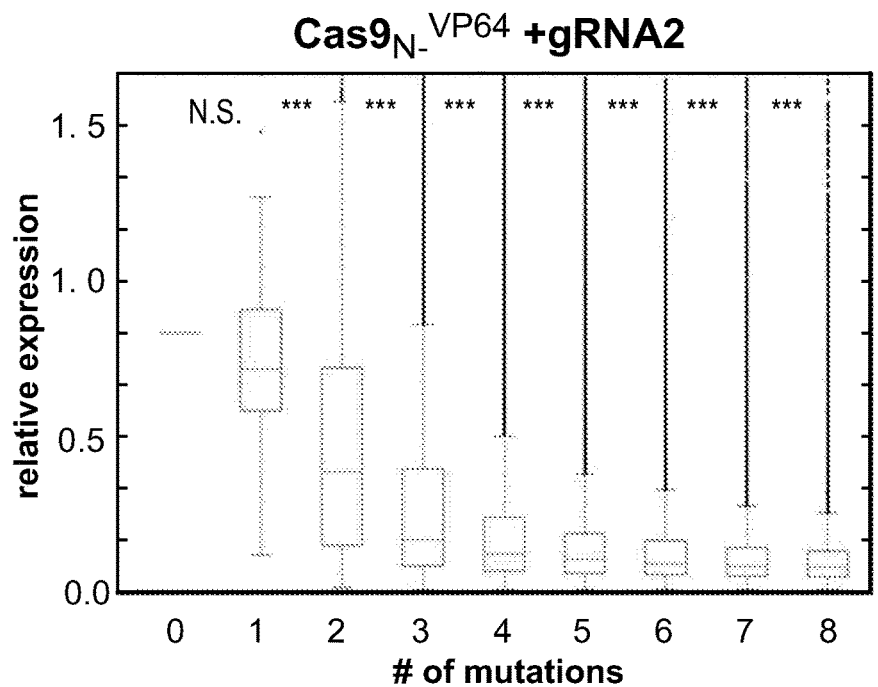
FIGS. 13A-13F depict the targeting landscape of two additional Cas9-gRNA complexes.
Figure 13B:
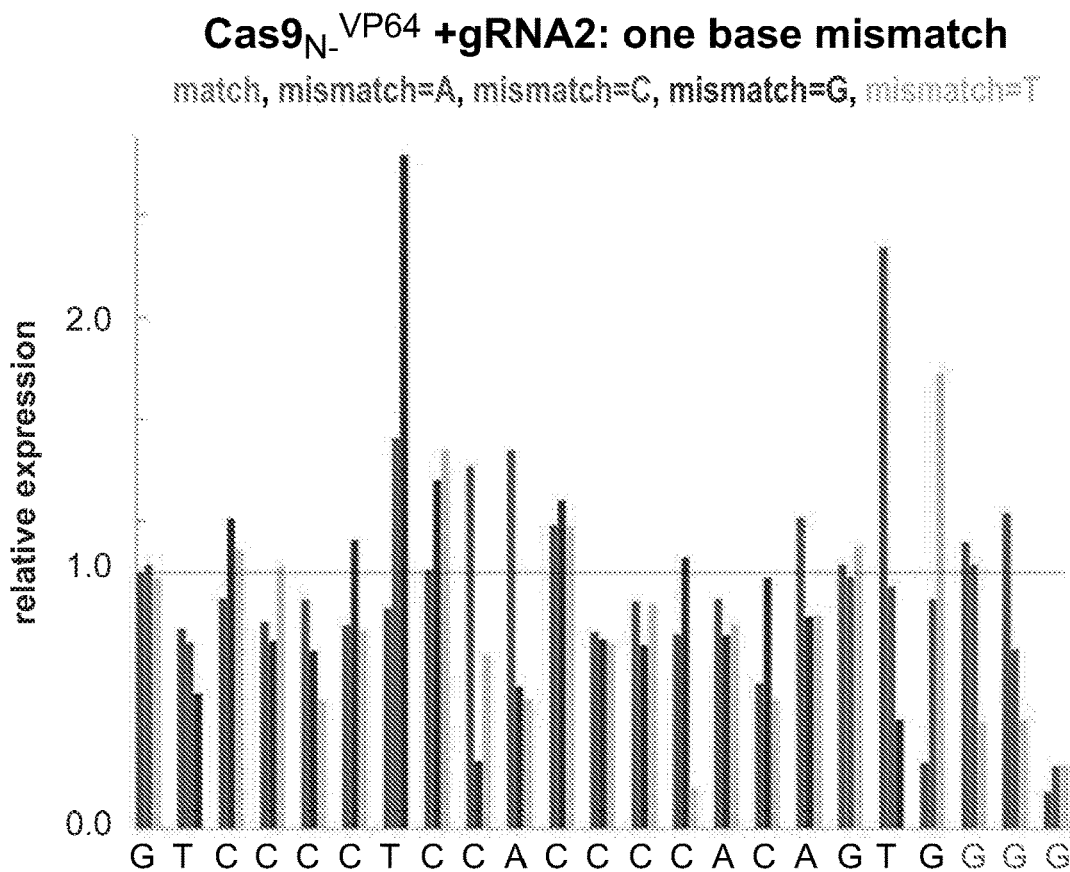
Figure 13C:
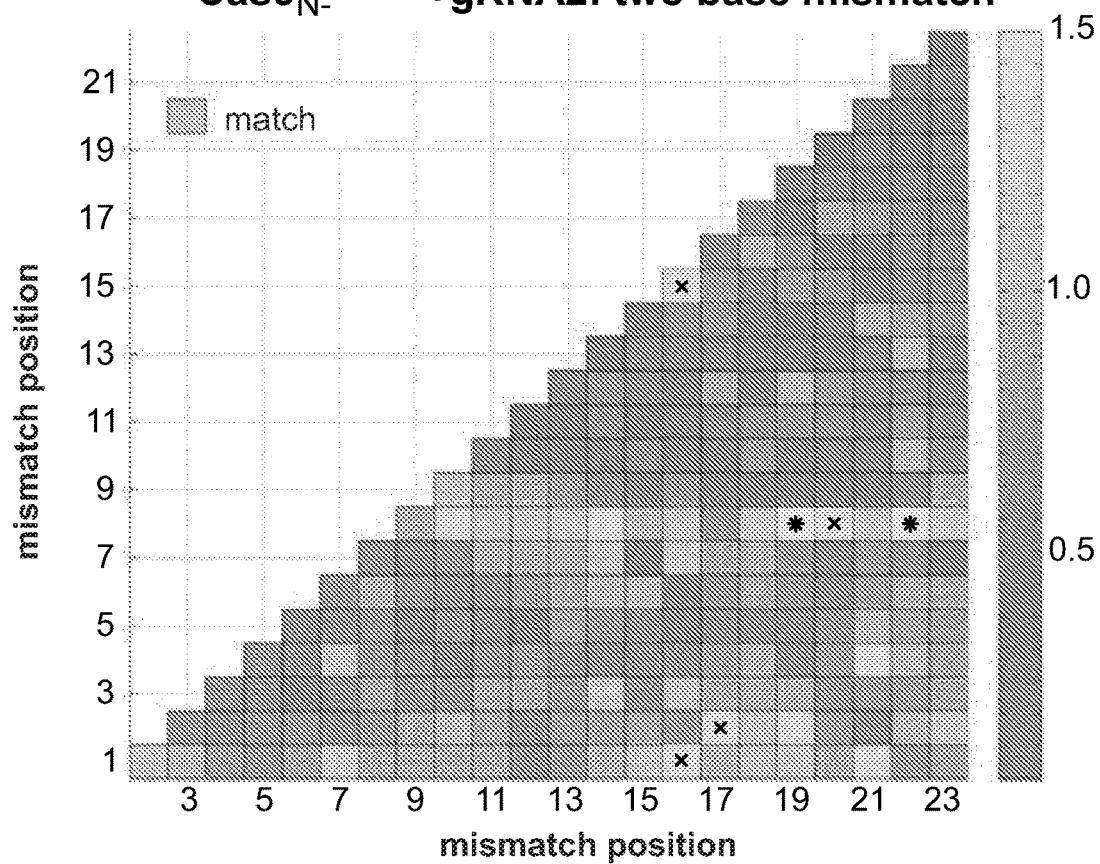
Figure 13D:
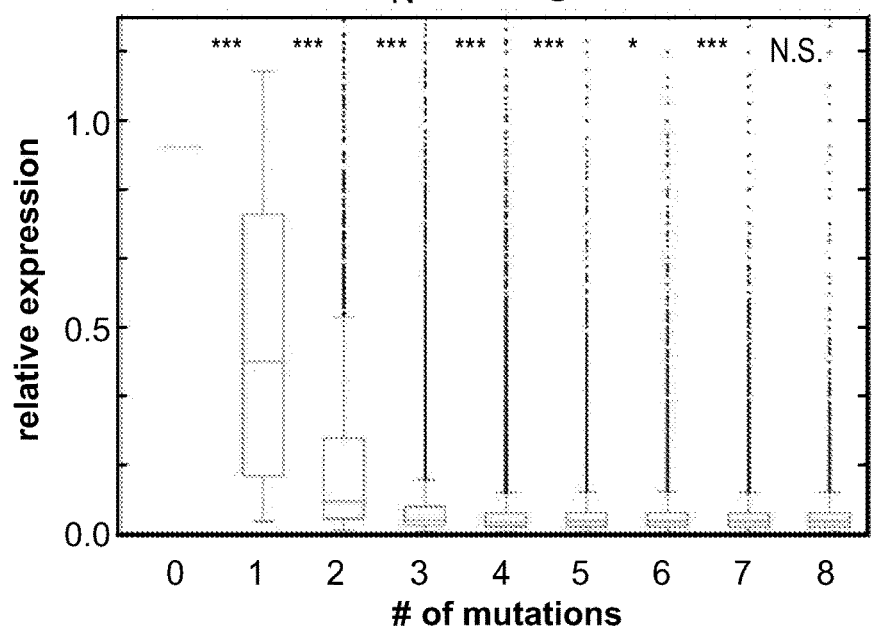
Figure 13E:
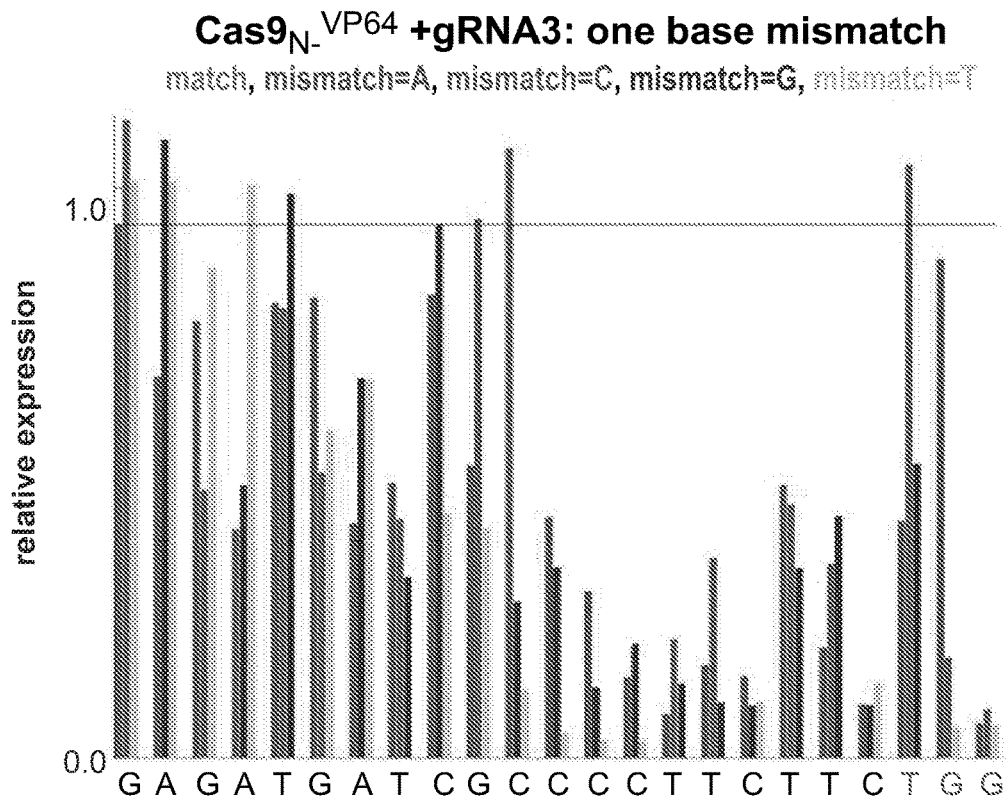
Figure 13F:
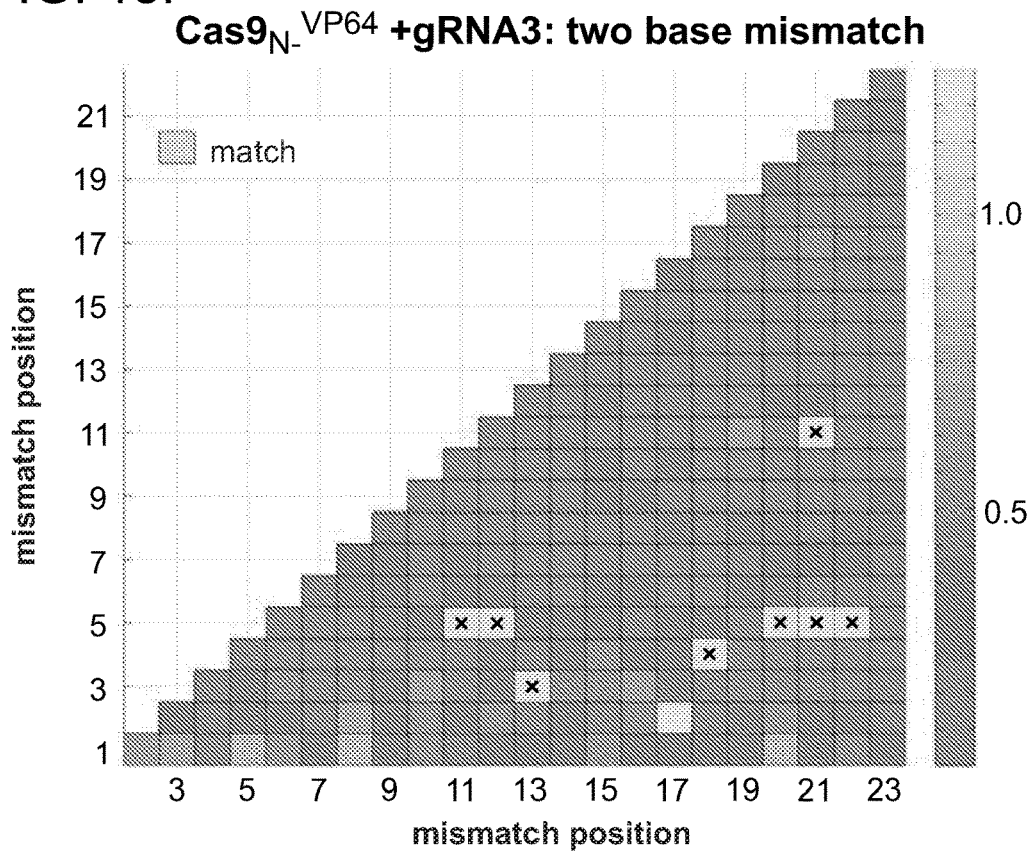
Figure 15A:
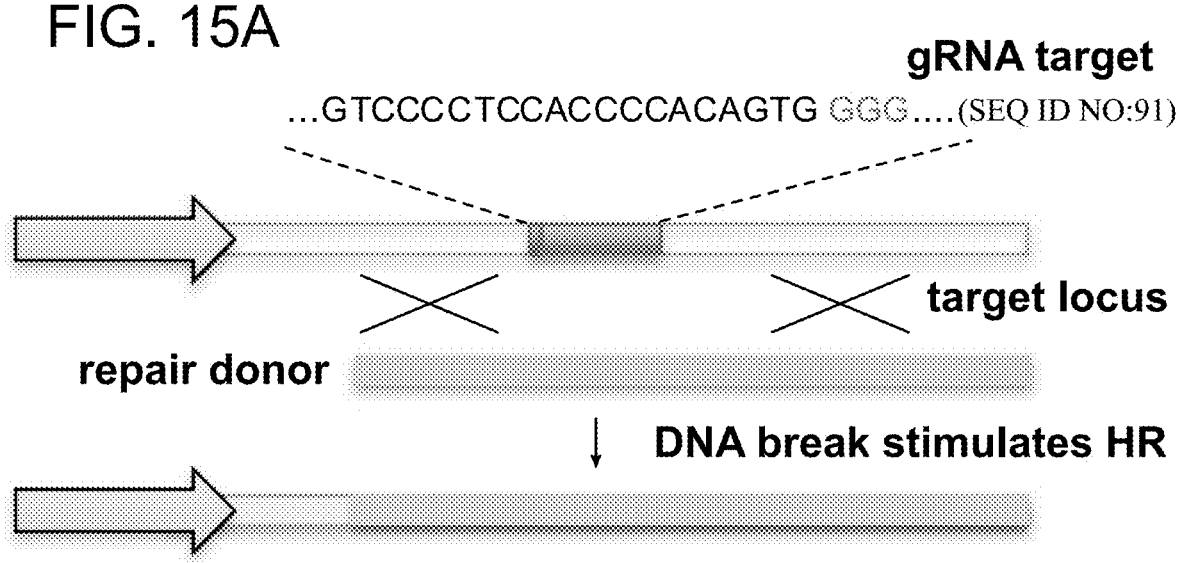
Figures 1, 15B:
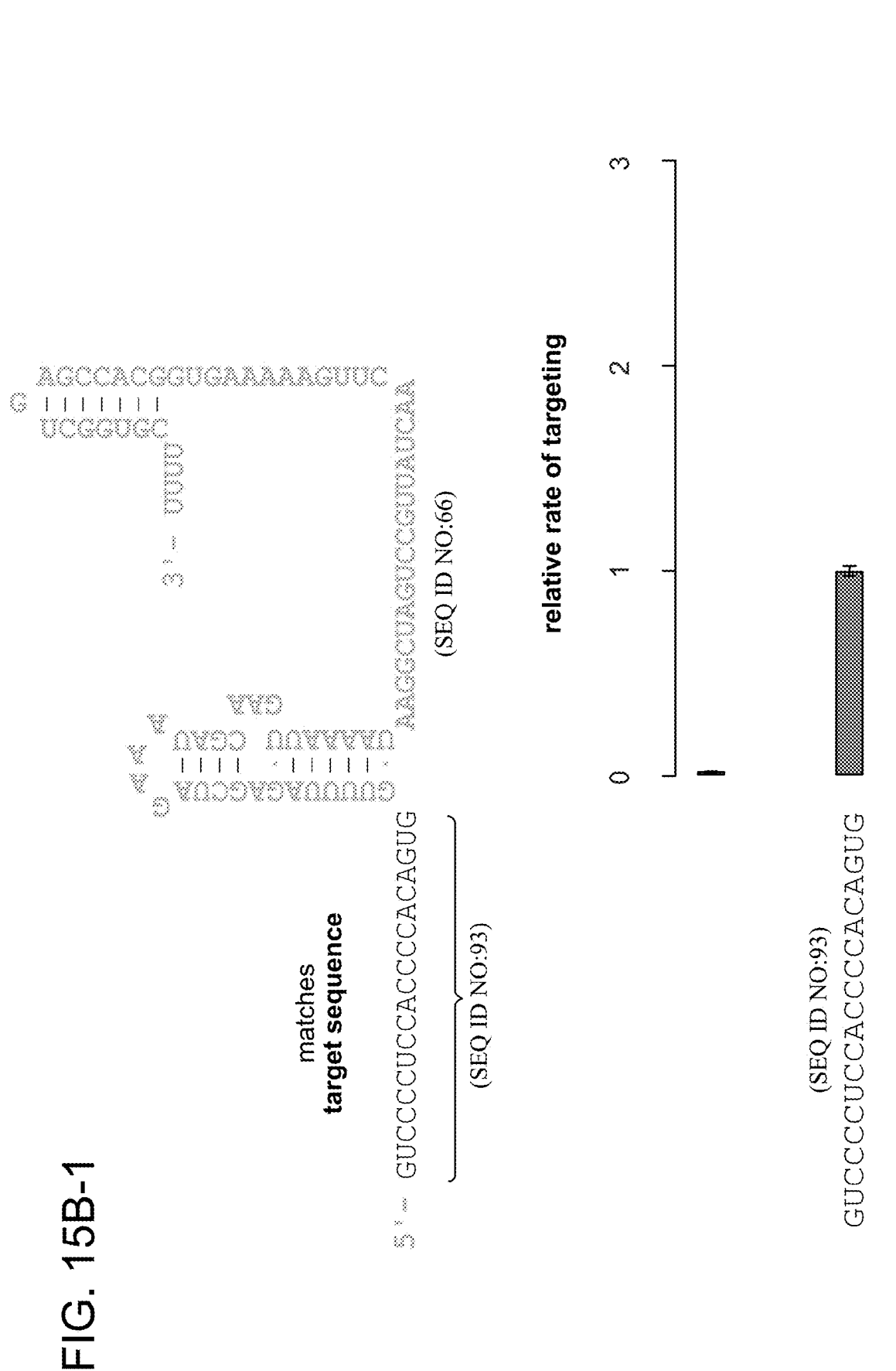
Figure 16A:
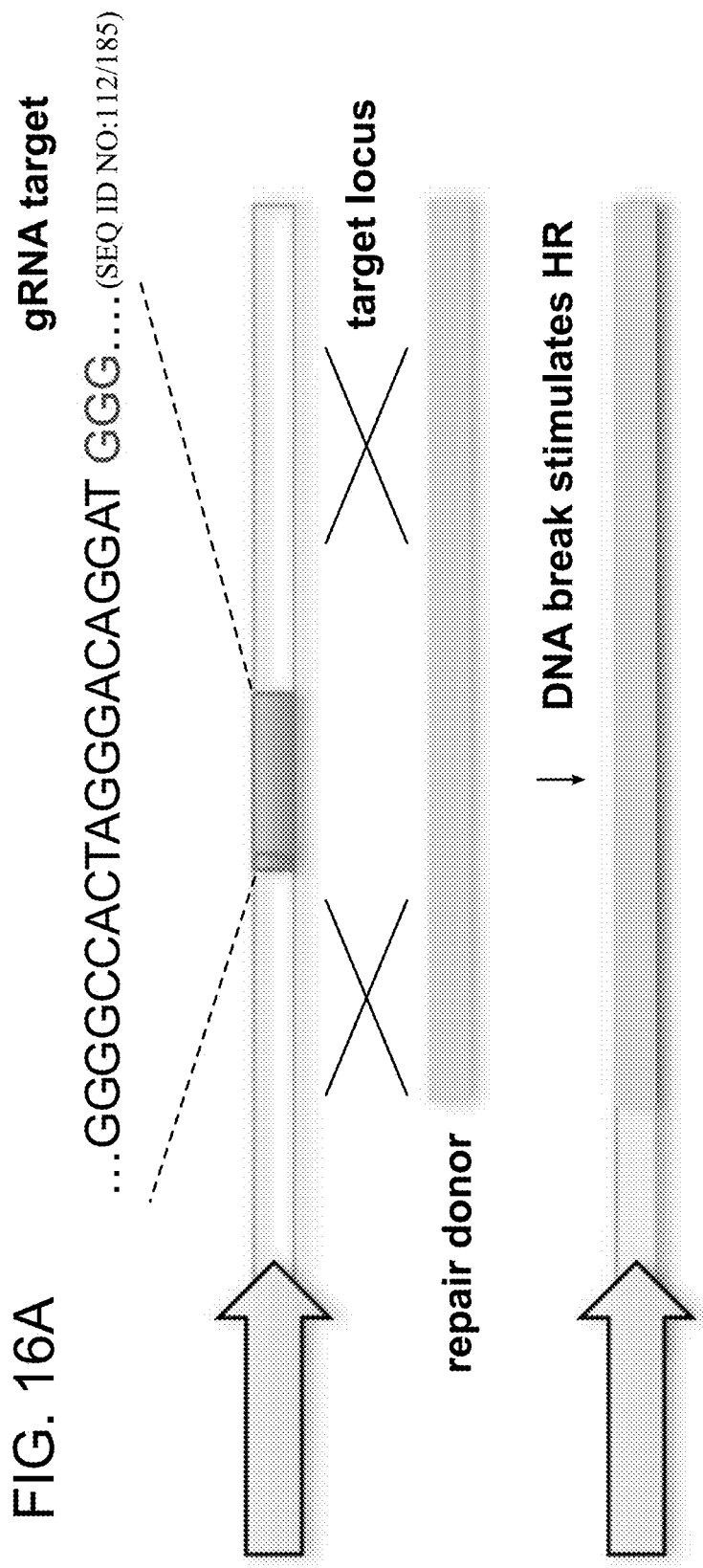
Figures 2, 16B:
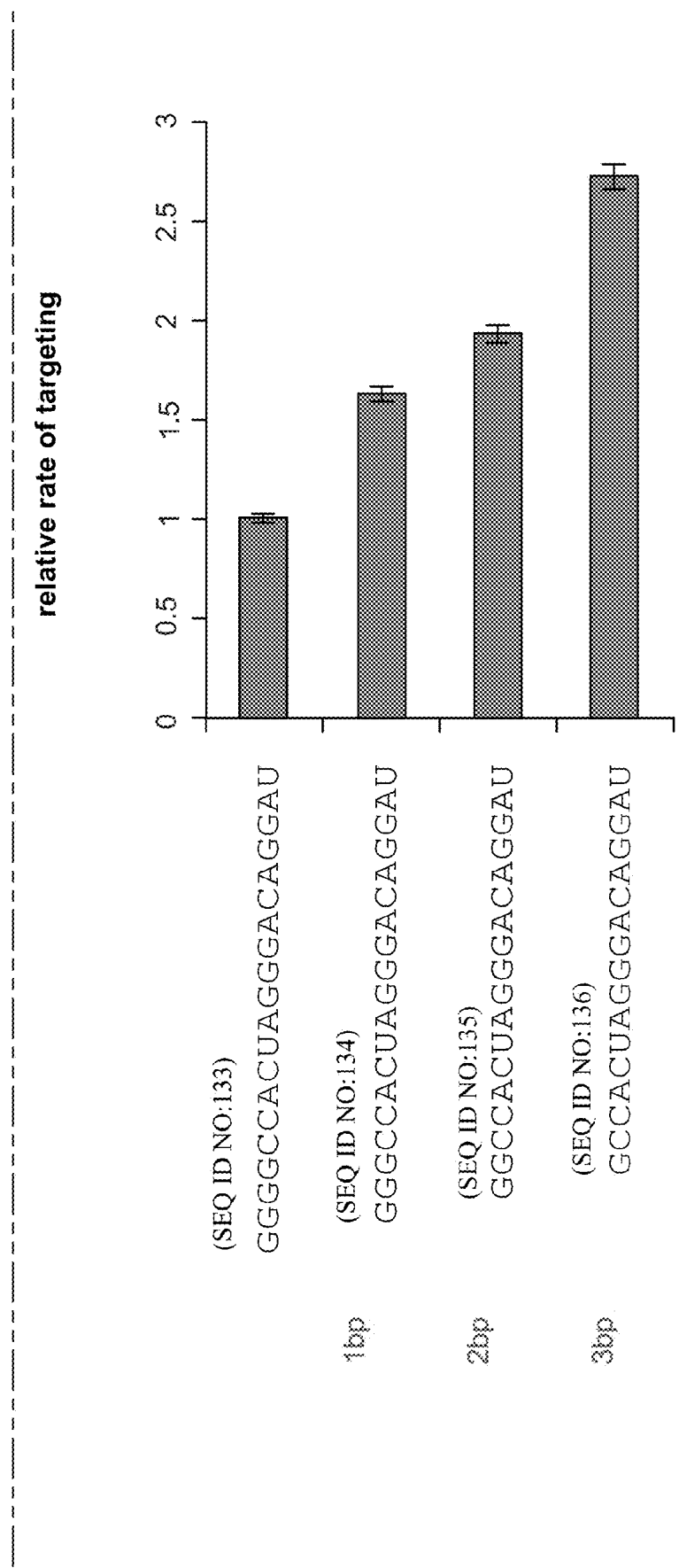
Figure 16C:
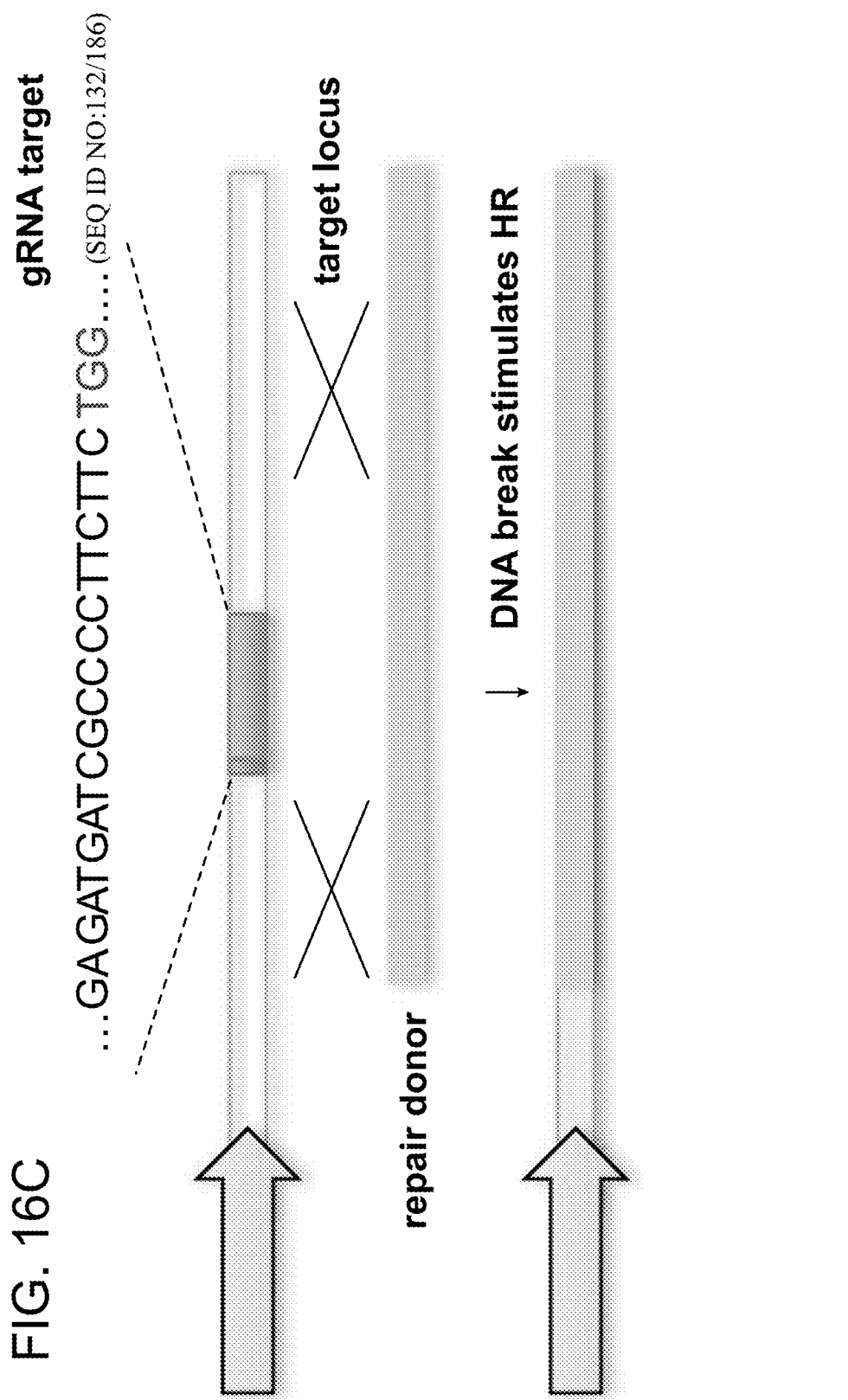
Figures 1, 16D:
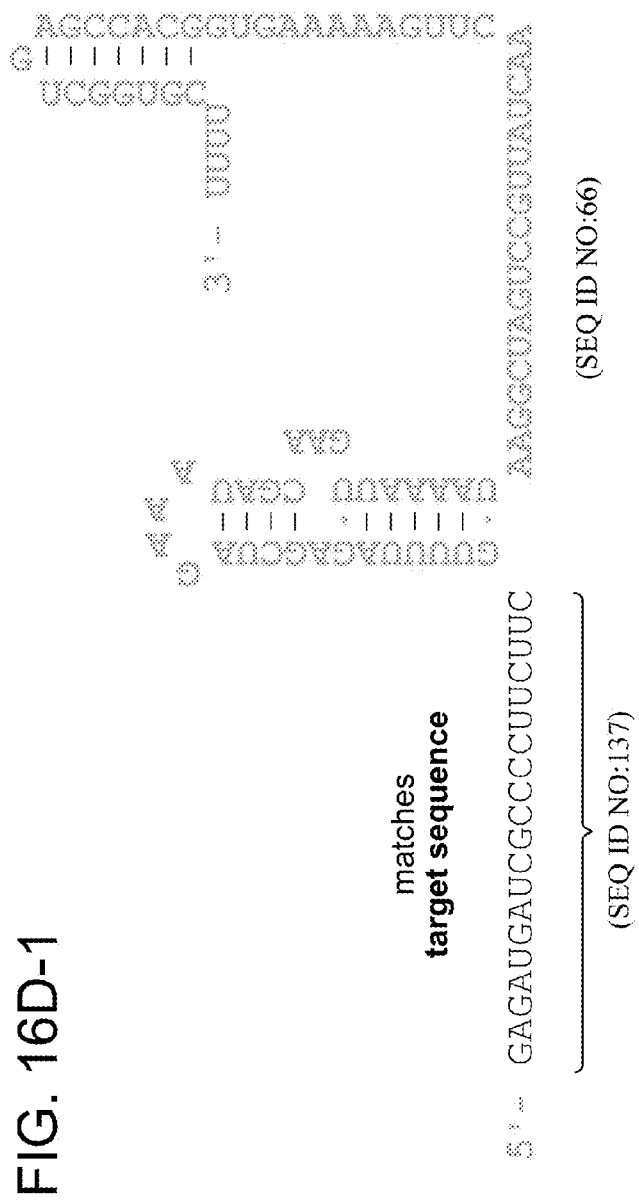
Figures 2, 16D:
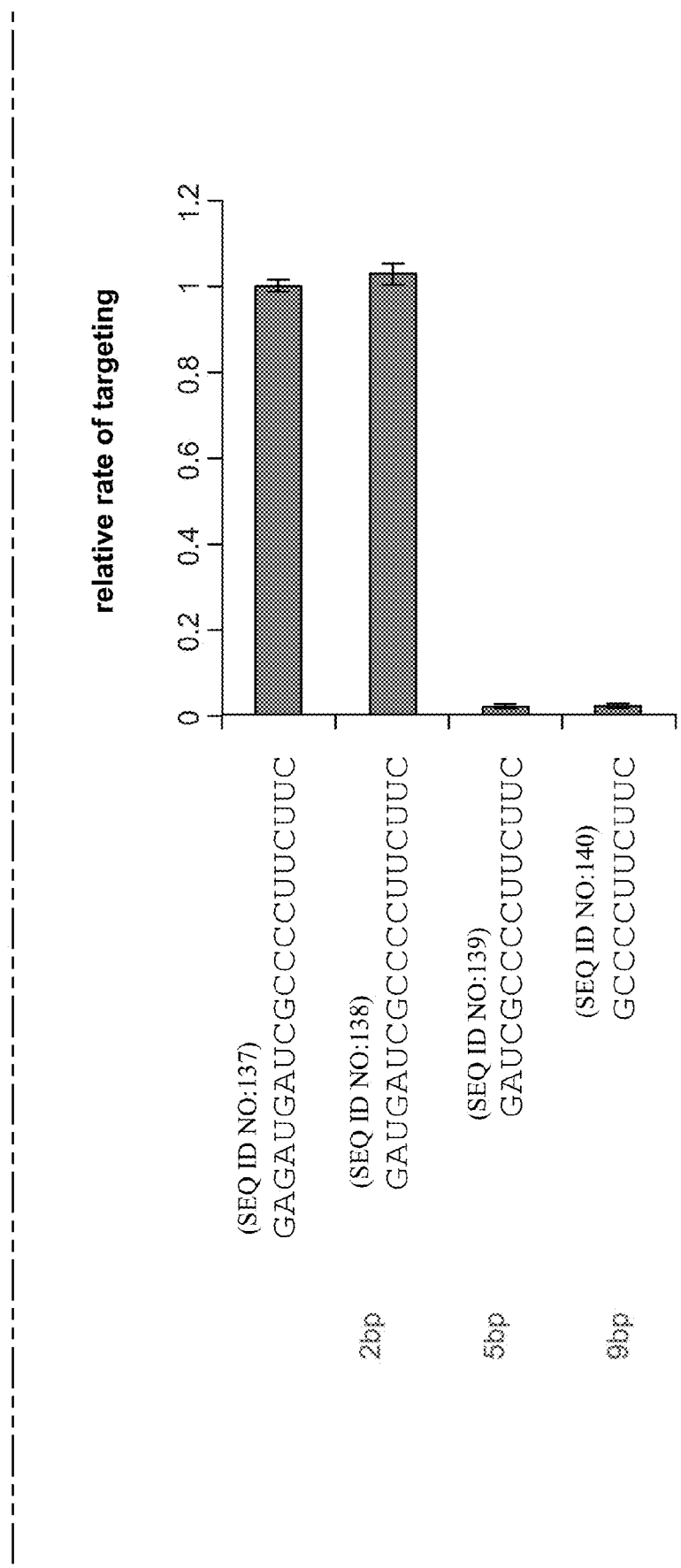

Using the approach described in FIG. 2, the targeting landscape of two additional Cas9-gRNA complexes (FIG. 13A-C) and (FIG. 13D-F) was analyzed. The two gRNAs have vastly different specificity profiles with gRNA2 tolerating up to 2-3 mismatches and gRNA3 only up to 1. These aspects are reflected in both the one base mismatch (FIG. 13B, 13E) and two base mismatch plots (FIG. 13C, 13F). In FIGS. 13C and 13F, base mismatch pairs for which insufficient data were available to calculate a normalized expression level are indicated as gray boxes containing an 'x', while, to improve data display, mismatch pairs whose normalized expression levels are outliers that exceed the top of the color scale are indicated as yellow boxes containing an asterisk '*'. Statistical significance symbols are: * for P<0.0005/n,  for P<0.005/n, * for P<0.05/n, and N.S. (Non-Significant) for P>=0.05/n, where n is the number of comparisons (refer Table 2).

Example VII

Validations, Specificity of Reporter Assay

As shown in FIG. 14A-C, specificity data was generated using two different sgRNA:Cas9 complexes. It was confirmed that the assay was specific for the sgRNA being evaluated, as a corresponding mutant sgRNA was unable to stimulate the reporter library. FIG. 14A: The specificity profile of two gRNAs (wild-type and mutant; sequence differences are highlighted in red) were evaluated using a reporter library designed against the wild-type gRNA target sequence. FIG. 14B: It was confirmed that this assay was specific for the gRNA being evaluated (data re-plotted from FIG. 13D), as the corresponding mutant gRNA is unable to stimulate the reporter library. Statistical significance symbols are: * for P<0.0005/n,  for P<0.005/n, * for P<0.05/n, and N.S. (Non-Significant) for P>=0.05/n, where n is the number of comparisons (refer Table 2). Different sgRNAs can have different specificity profiles (FIGS. 13A, 13D), specifically, sgRNA2 tolerates up to 3 mismatches and sgRNA3 only up to 1. The greatest sensitivity to mismatches was localized to the 3' end of the spacer, albeit mismatches at other positions were also observed to affect activity.

Example VIII

Validations, Single and Double-Base gRNA Mismatches

As shown in FIGS. 15A, 15B-1, 15B-2, 15C, 15D-1, and 15D-2, it was confirmed by targeted experiments that single-base mismatches within 12 bp of the 3' end of the spacer in the assayed sgRNAs resulted in detectable targeting. However, 2 bp mismatches in this region resulted in significant loss of activity. Using a nuclease assay, 2 independent gRNAs were tested: gRNA2 (FIGS. 15A-15B-2) and gRNA3 (FIGS. 15C-15D-2) bearing single or double-base mismatches (highlighted in red) in the spacer sequence versus the target. It was confirmed that single-base mismatches within 12 bp of the 3' end of the spacer in the assayed gRNAs result in detectable targeting, however 2 bp mismatches in this region result in rapid loss of activity. These results further highlight the differences in specificity profiles between different gRNAs consistent with the results in FIG. 13. Data are means+/−SEM (N=3).

Example IX

Validations, 5' gRNA Truncations

As shown in FIGS. 16A, 16B-1, 16B2, 16C, 16D-1, and 16D-2, truncations in the 5' portion of the spacer resulted in retention of sgRNA activity. Using a nuclease assay, 2 independent gRNA were tested: gRNA1 (FIGS. 16A-16B-2) and gRNA3 (FIGS. 16C-16D-2) bearing truncations at the 5' end of their spacer. It was observed that 1-3 bp 5' truncations are well tolerated, but larger deletions lead to loss of activity. Data are means+/−SEM (N=3).

Example X

Validations, S. pyogenes PAM

Figure 17A:
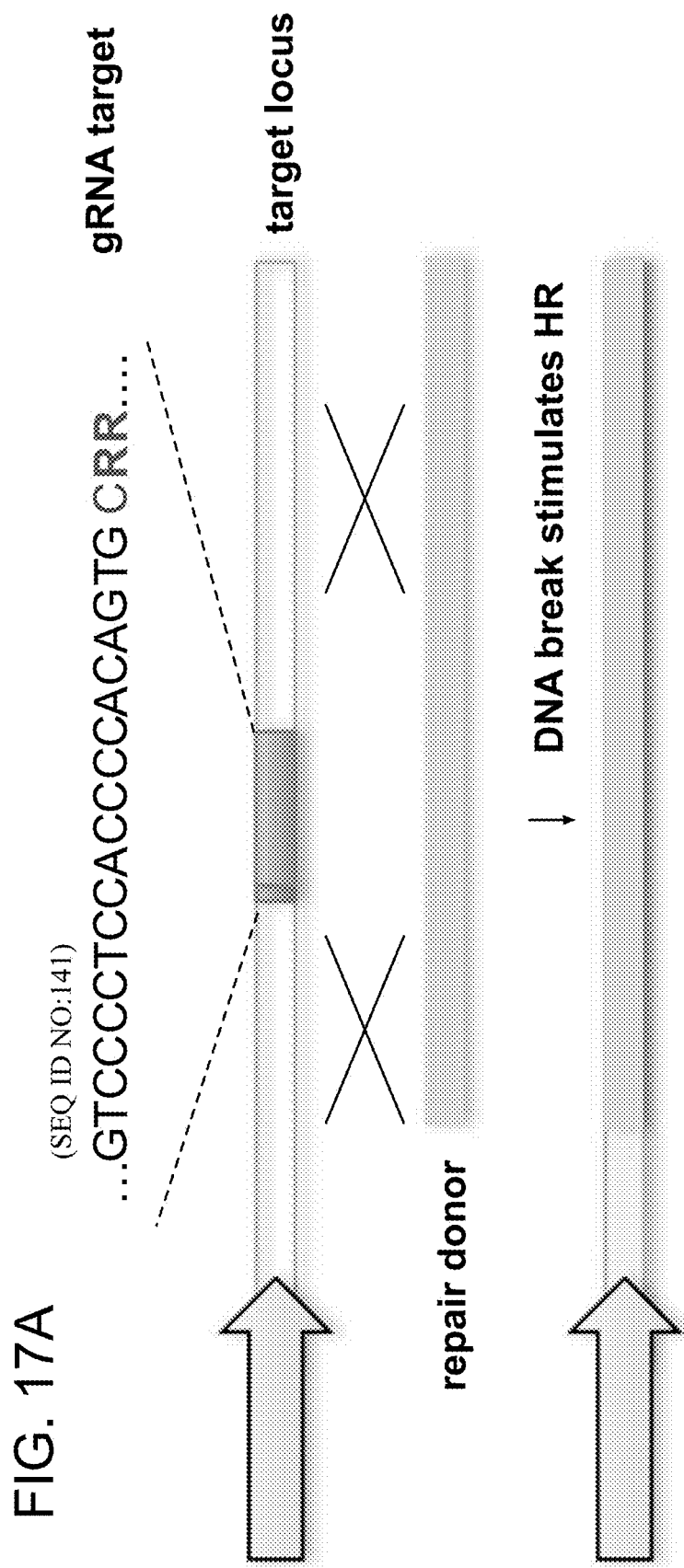
FIGS. 17A-17B depict a nuclease mediated HR assay that shows the PAM for the S. pyogenes Cas9 is NGG and also NAG.
Figure 17B:
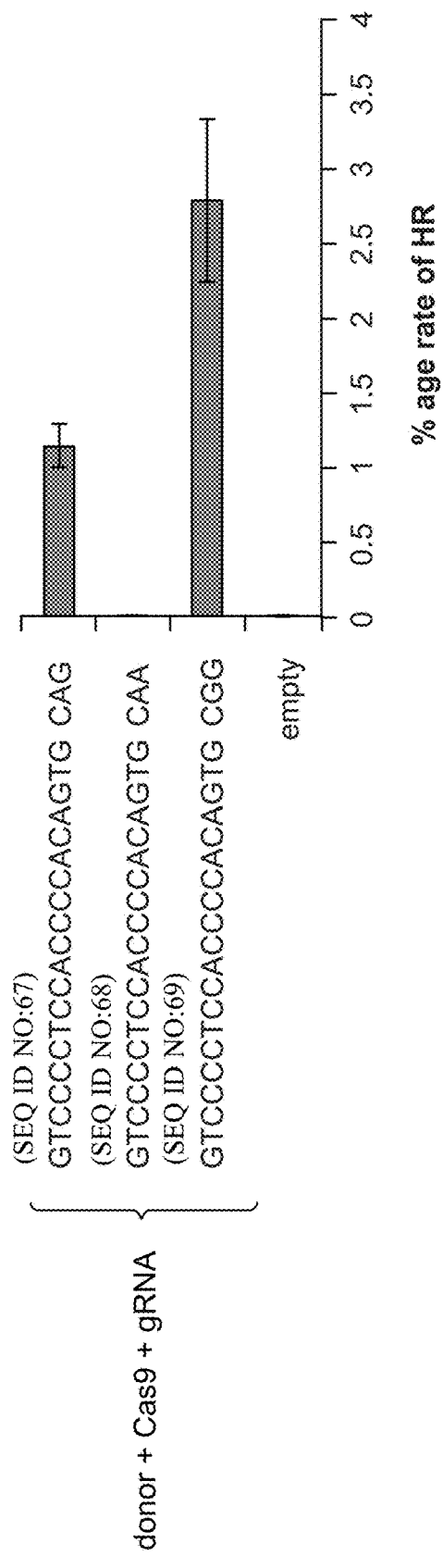

As shown in FIGS. 17A-B, it was confirmed using a nuclease mediated HR assay that the PAM for the S. pyogenes Cas9 is NGG and also NAG. Data are means+/−SEM (N=3). According to an additional investigation, a generated set of about 190K Cas9 targets in human exons that had no alternate NGG targets sharing the last 13 nt of the targeting sequence was scanned for the presence of alternate NAG sites or for NGG sites with a mismatch in the prior 13 nt. Only 0.4% were found to have no such alternate targets.

Example XI

Validations, TALE Mutations

Figure 18A:
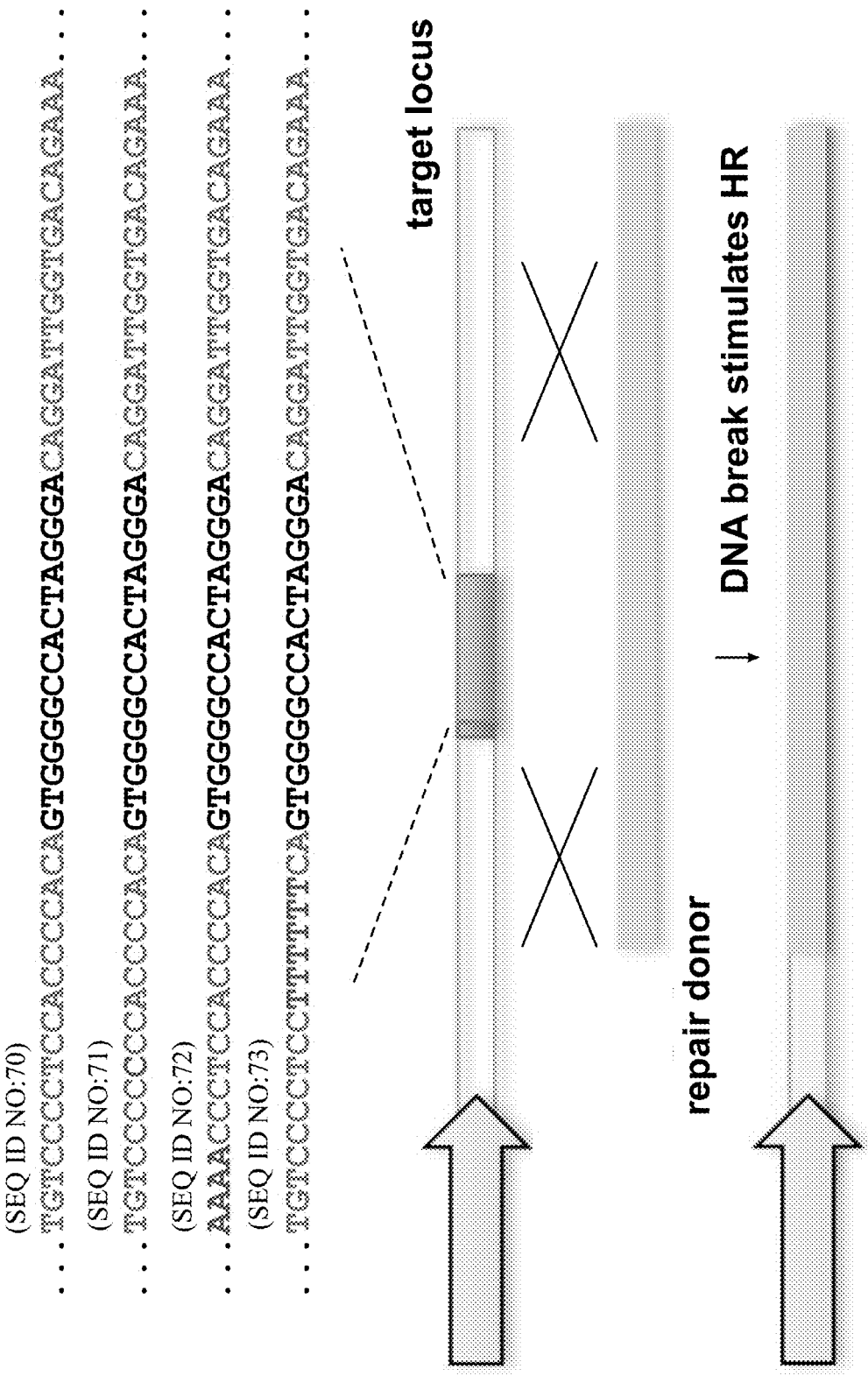
FIGS. 18A-18B depict a nuclease mediated HR assay that confirmed that 18-mer TALEs tolerate multiple mutations in their target sequences.
Figure 18B:
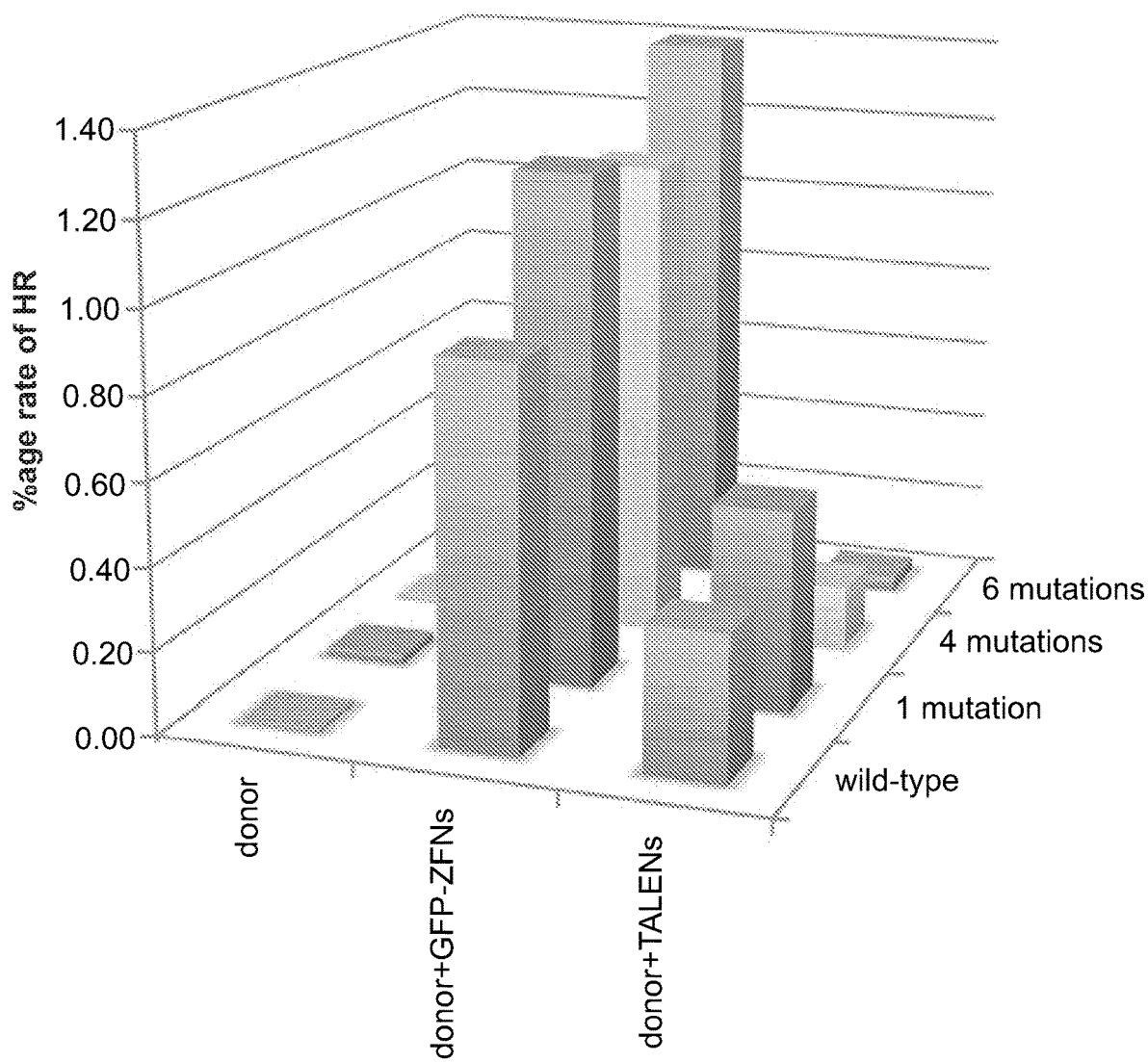

Using a nuclease mediated HR assay (FIG. 18A-B) it was confirmed that 18-mer TALEs tolerate multiple mutations in their target sequences. As shown in FIG. 18A-B certain mutations in the middle of the target lead to higher TALE activity, as determined via targeted experiments in a nuclease assay.

Example XII

TALE Monomer Specificity Versus TALE Protein Specificity

Figure 19A:
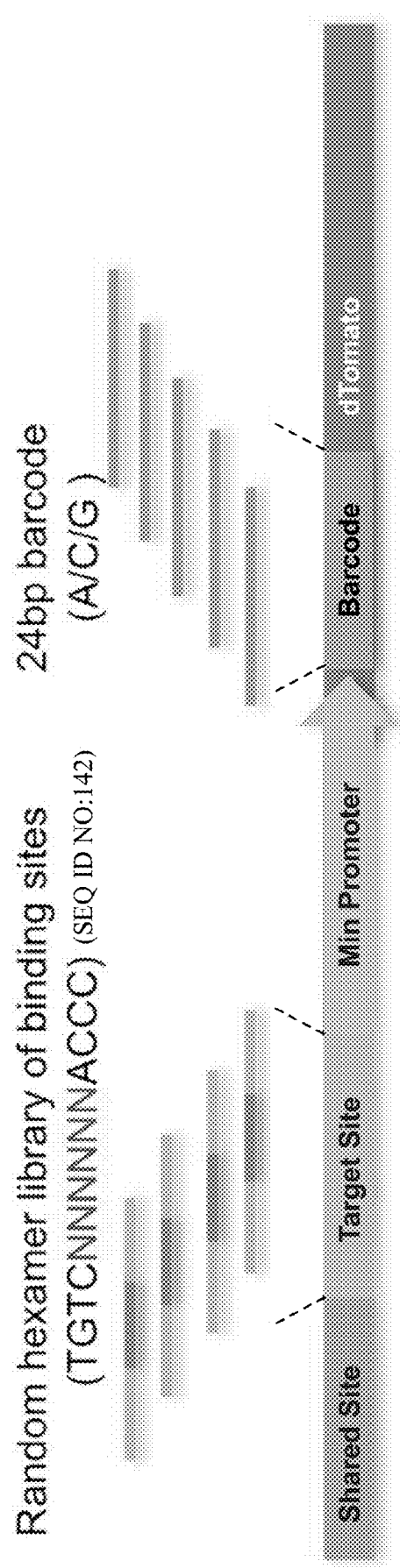
Figures 1, 19B:
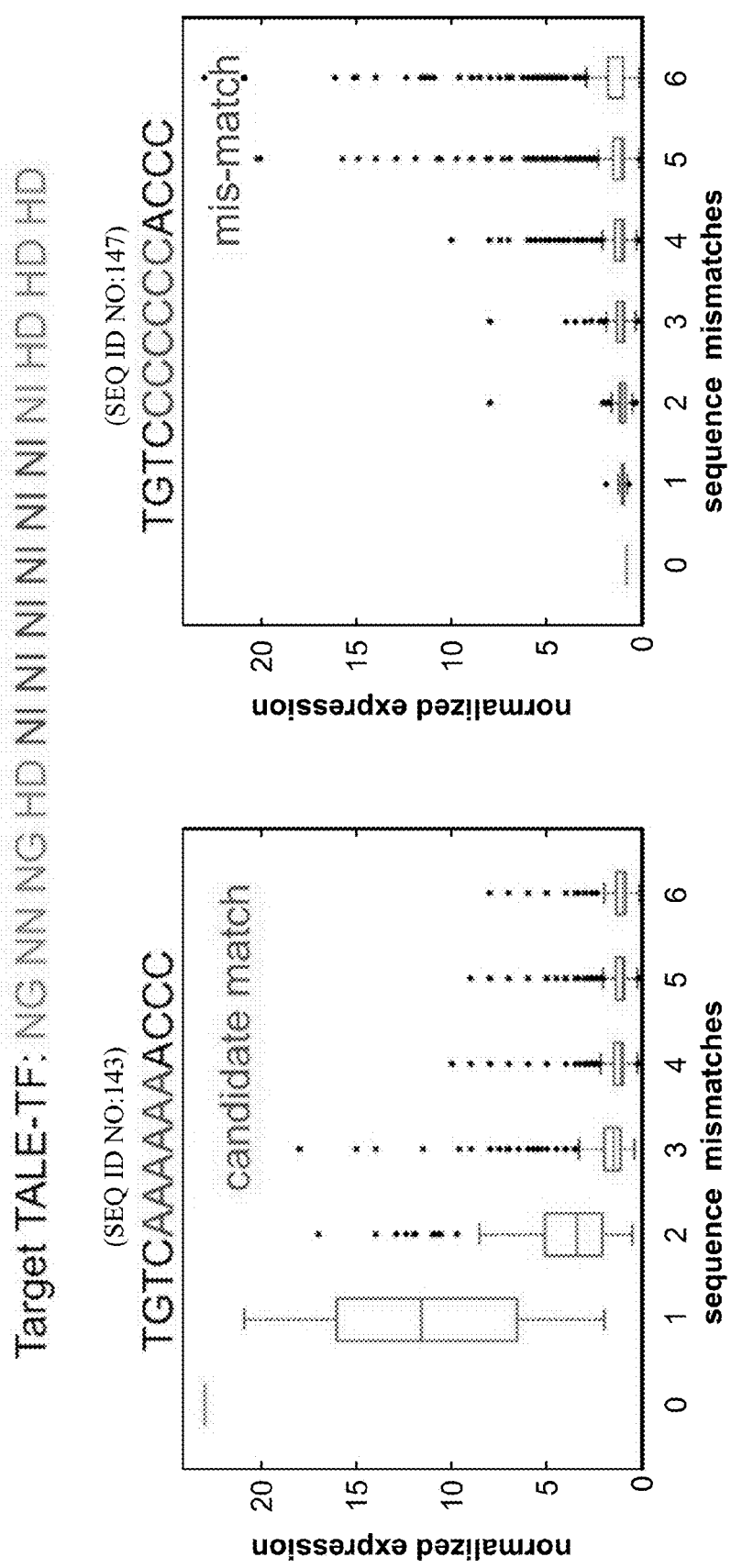
Figures 2, 19B:
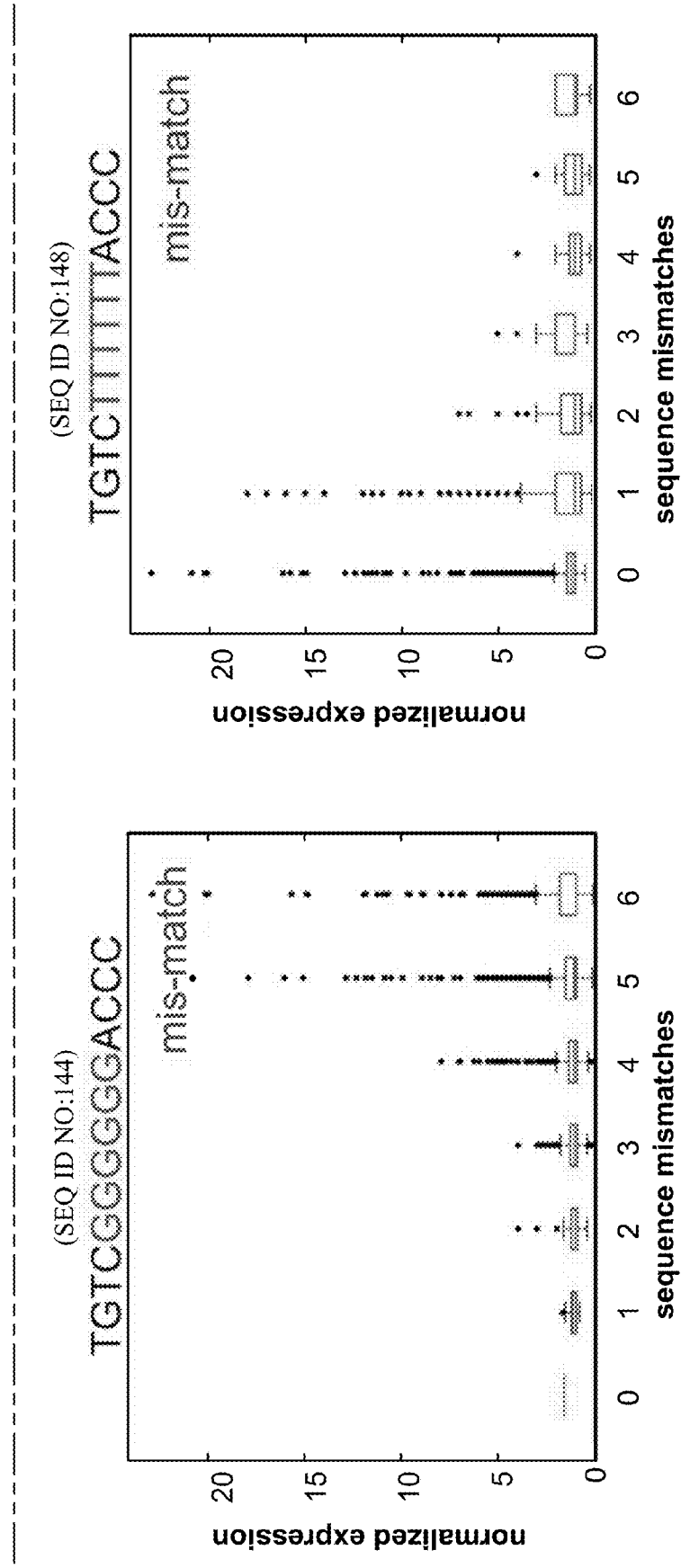
Figures 1, 19C:
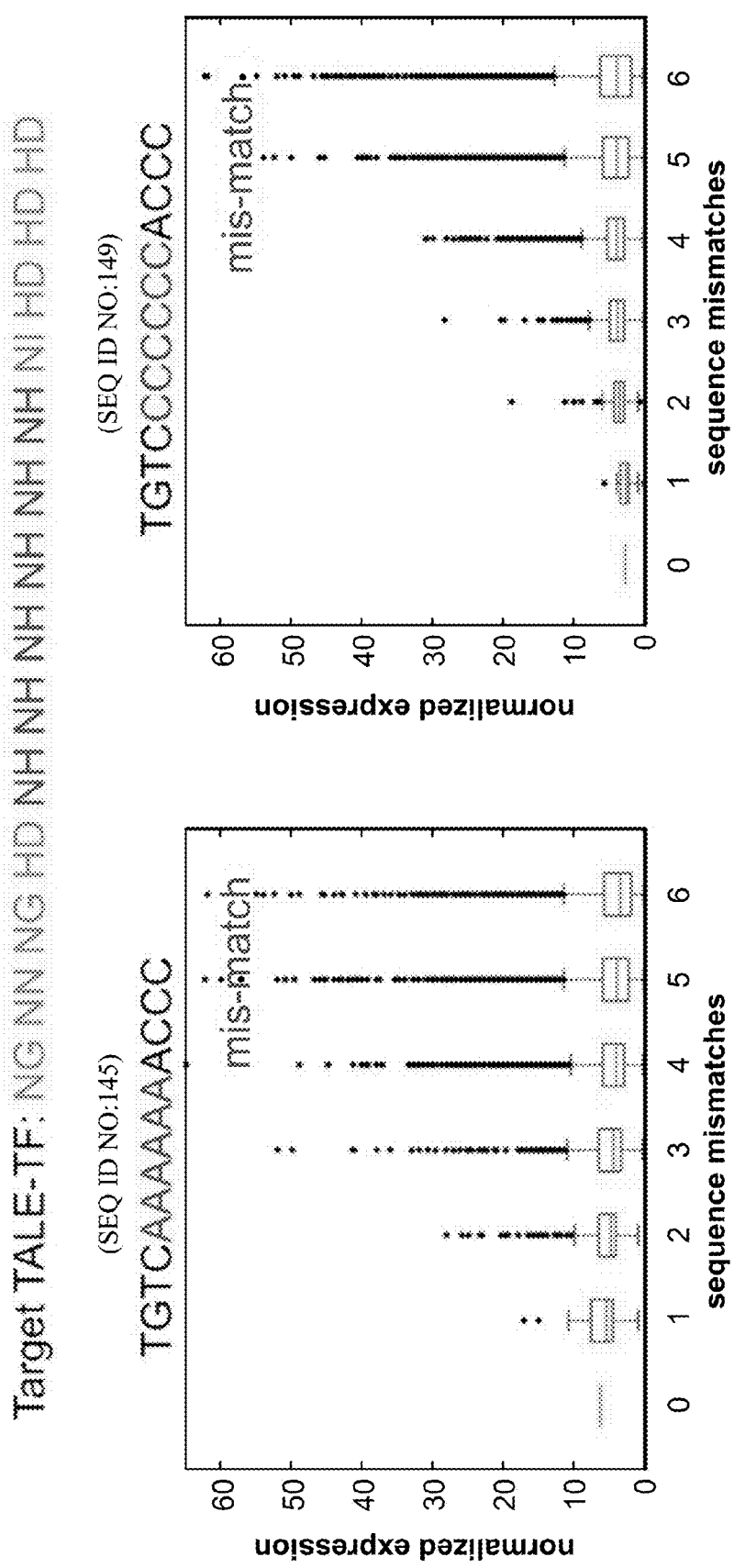
Figures 2, 19C:
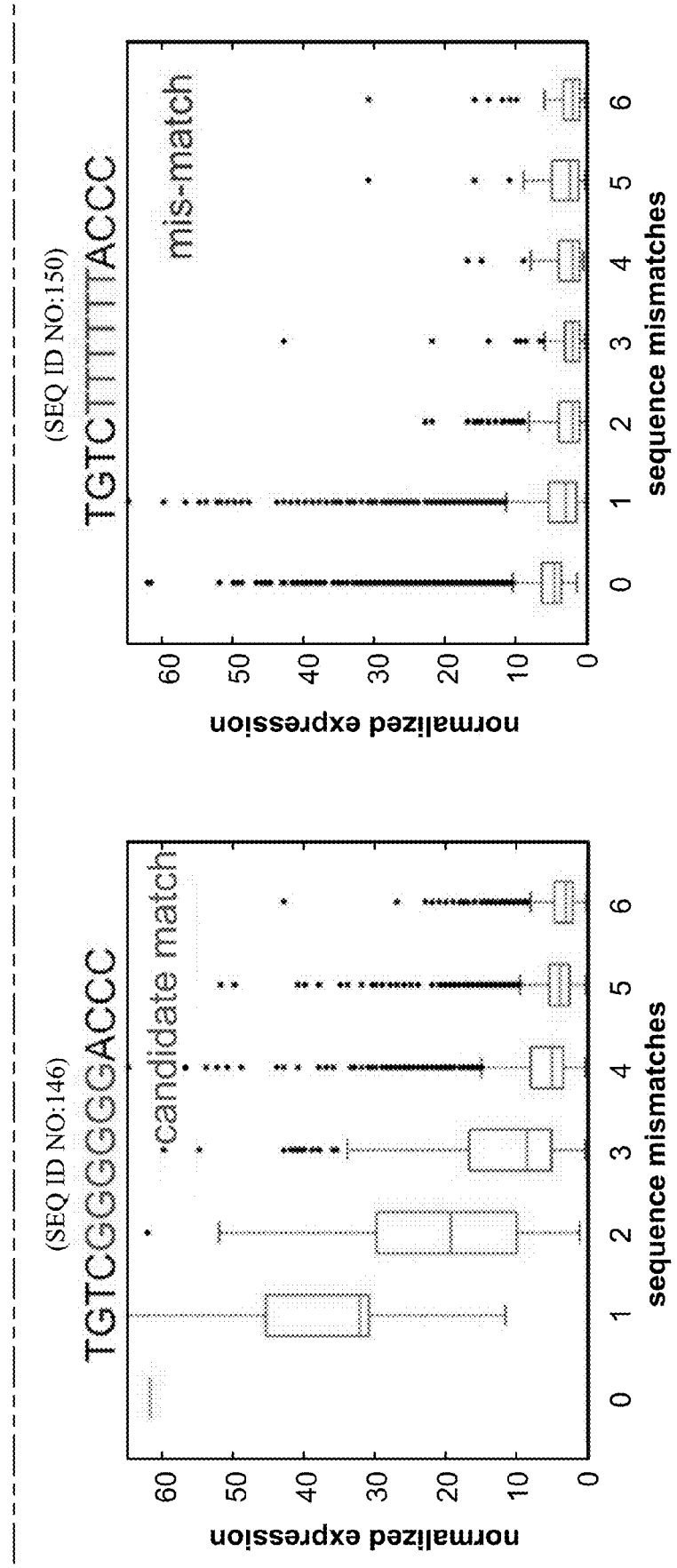

To decouple the role of individual repeat-variable diresidues (RVDs), it was confirmed that choice of RVDs did contribute to base specificity but TALE specificity is also a function of the binding energy of the protein as a whole. FIGS. 19A-19C-2 show a comparison of TALE monomer specificity versus TALE protein specificity. FIG. 19A: Using a modification of approach described in FIG. 2, the targeting landscape of 2 14-mer TALE-TFs bearing a contiguous set of 6 NI or 6 NH repeats was analyzed. In this approach, a reduced library of reporters bearing a degenerate 6-mer sequence in the middle was created and used to assay the TALE-TF specificity. FIGS. 19B-1-19C-2: In both instances, it was noted that the expected target sequence is enriched (i.e. one bearing 6 As for NI repeats, and 6 Gs for NH repeats). Each of these TALEs still tolerate 1-2 mismatches in the central 6-mer target sequence. While choice of monomers does contribute to base specificity, TALE specificity is also a function of the binding energy of the protein as a whole. According to one aspect, shorter engineered TALEs or TALEs bearing a composition of high and low affinity monomers result in higher specificity in genome engineering applications and FokI dimerization in nuclease applications allows for further reduction in off-target effects when using shorter TALEs.

Example XIII

Off-Set Nicking, Native Locus

Figure 20A:
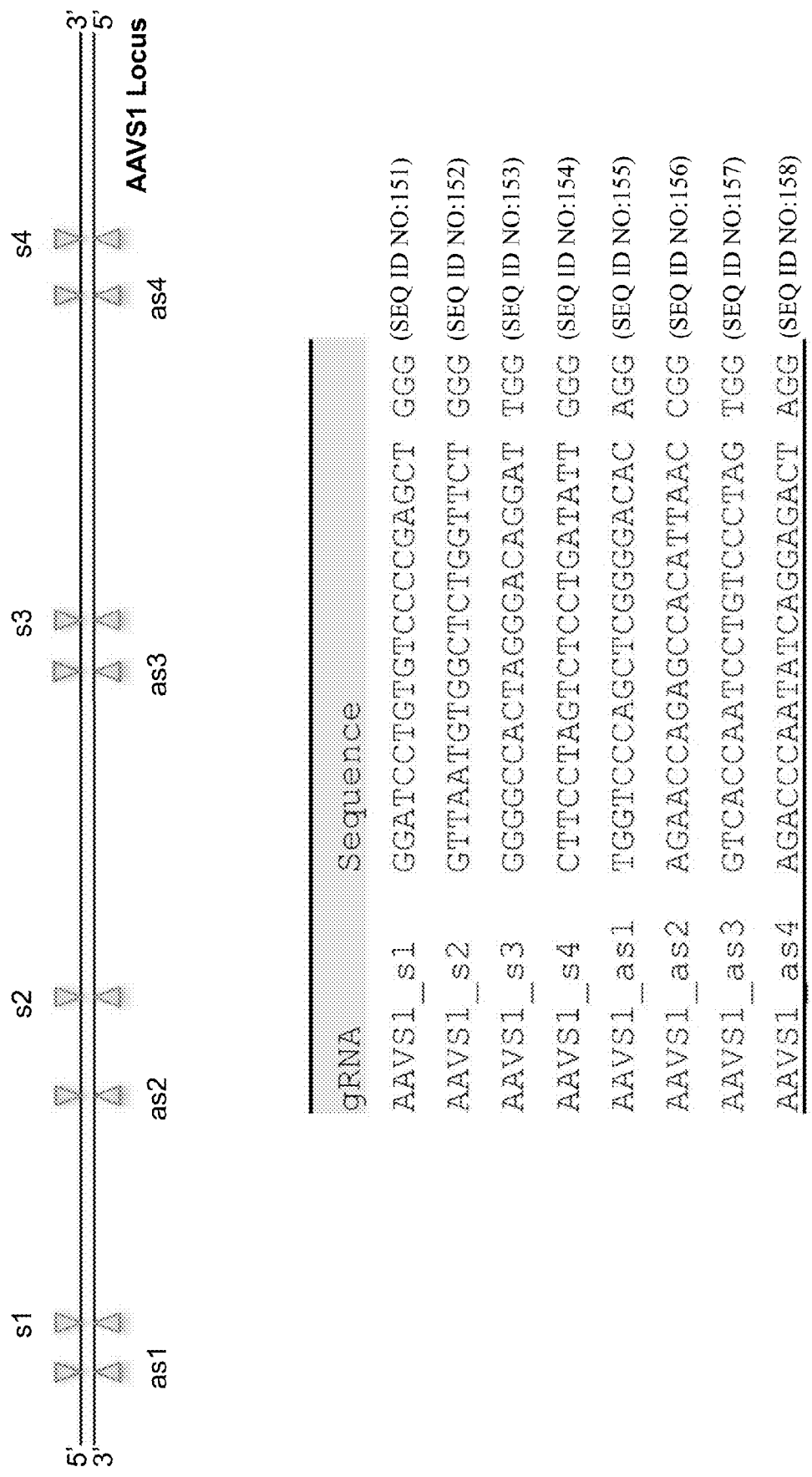

FIG. 20A-B shows data related to off-set nicking. In the context of genome-editing, off-set nicks were created to generate DSBs. A large majority of nicks do not result in non-homologous end joining (NHEJ) mediated indels and thus when inducing off-set nicks, off-target single nick events will likely result in very low indel rates. Inducing off-set nicks to generate DSBs is effective at inducing gene disruption at both integrated reporter loci and at the native AAVS1 genomic locus.

FIG. 20A: The native AAVS1 locus with 8 gRNAs covering a 200 bp stretch of DNA was targeted: 4 targeting the sense strand (s1-4) and 4 the antisense strand (as1-4). Using the Cas9D10A mutant, which nicks the complementary strand, different two-way combinations of the gRNAs was used to induce a range of programmed 5' or 3' overhangs. FIG. 20B: Using a Sanger sequencing based assay, it was observed that while single gRNAs did not induce detectable NHEJ events, inducing off-set nicks to generate DSBs is highly effective at inducing gene disruption. Notably off-set nicks leading to 5' overhangs result in more NHEJ events as opposed to 3' overhangs. The number of Sanger sequencing clones is highlighted above the bars, and the predicted overhang lengths are indicated below the corresponding x-axis legends.

Example XIV

Off-Set Nicking, NHEJ Profiles

FIG. 21A-C is directed to off-set nicking and NHEJ profiles. Representative Sanger sequencing results of three different off-set nicking combinations is shown with positions of the targeting gRNAs highlighted by boxes. Furthermore, consistent with the standard model for homologous recombination (HR) mediated repair, engineering of 5' overhangs via off-set nicks generated more robust NHEJ events than 3' overhangs (FIG. 3B). In addition to a stimulation of NHEJ, robust induction of HR was observed when the 5' overhangs were created. Generation of 3' overhangs did not result in improvement of HR rates (FIG. 3C).

Example XV

TABLE 1 gRNA Targets for Endogenous Gene Regulation Targets in the REX1, OCT4, SOX2 and NANOG promoters used in Cas9-gRNA mediated activation experiments are listed.

| gRNA Name | gRNA Taret |
|---|---|
| REX1 1 | ctggcggatcactcgcggtt agg |
| REX1 2 | cctcggcctccaaaagtgct agg |
| REX1 3 | acgctgattcctgcagatca ggg |
| REX1 4 | ccaggaatacgtatccacca ggg |
| REX1 5 | gccacacccaagcgatcaaa tgg |
| REX1 6 | aaataatacattctaaggta agg |
| PEX1 7 | gctactggggaggctgaggc agg |
| PEX1 8 | tagcaatacagtcacattaa tgg |
| PEX1 9 | ctcatgtgatcccccgtct cgg |
| REX1 10 | ccgggcagagagtgaacgcg cgg |
| Oct4 1 | tcccttccctctcccgtgct tgg |
| OCT4 2 | tctctgcaaagcccctggag agg |
| OCT4 3 | aatgcagttgccgagtgcag tgg |
| OCT4 4 | cctcagcctcctaaagtgct ggg |
| OCT4 5 | gagtacaaatcctctttact agg |
| OCT4 6 | gagcgtctggatttgggata agg |
| OCT4 7 | cagcacctcacctcccagtg agg |
| OCT4 8 | tctaaacccagggaatcat ggg |
| OCT4 9 | cacaaggcagccagggatcc agg |
| OCT4 10 | gatggcaagctgagaaacac tgg |
| OCT4 11 | tgaaatgcacgcatacaatt agg |
| OCT4 12 | ccagtccagacctggccttc tgg |
| OCT4 13 | cccagaaaaacagaccctga agg |
| OCT4 14 | aagggttgagcacttgttta ggg |
| OCT4 15 | atgtctgagttttggttgag agg |
| OCT4 16 | ggtcccttgaaggggaagta ggg |
| OCT4 17 | tggcagtctactcttgaaga tgg |
| OCT4 18 | ggcacagtgccagaggtctg tgg |
| OCT4 19 | taaaaataaaaaaactaaca ggg |
| OCT4 20 | tctgtggggacctgcactg agg |
| 3CT4 21 | ggccagaggtcaaggctagt ggg |
| SOX2 1 | cacgaccgaaacccttctta cgg |
| SOX2 2 | gttgaatgaagacagtctag tgg |
| SOX2 3 | taagaacagagcaagttacg tgg |
| SOX2 4 | tgtaaggtaagagaggagag cgg |

TABLE 1-continued gRNA Targets for Endogenous Gene Regulation Targets in the REX1, OCT4, SOX2 and NANOG promoters used in Cas9-gRNA mediated activation experiments are listed.

| gRNA Name | gRNA Taret |
|---|---|
| SOX2 5 | tgacacaccaactcctgcac tgg |
| SOX2 6 | tttacccacttccttcgaaa agg |
| SOX2 7 | gtggctggcaggctggctct ggg |
| SOX2 8 | ctcccccggcctcccccgcg cgg |
| SOX2 9 | caaaacccaccacccaccct ggg |
| SOX2 10 | aggagccgccgcgcgctgat tgg |
| NANOG 1 | cacacacacccacacgagat ggg |
| NANOG 2 | gaagaagctaaagagccaga ggg |
| NANOG 3 | atgagaatctcaataacctc agg |
| NANOG 4 | tcccgctctgttgcccaggc tgg |
| NANOG 5 | cagacacccaccaccatgcg tgg |
| NANOG 6 | tcccaatttactgggattac agg |
| NANOG 7 | tgatttaaaagttggaaacg tgg |
| NANOG 8 | tctagttccccacctagtct ggg |
| NANOG 9 | gatcaactgagaattcacaa ggg |
| NANOG 10 | cgccaggagggtgggtcta agg |

Example XVI

TABLE 2

Summary of Statistical Analysis of Cas9-gRNA and TALE Specificity Data a

| Figure | Expression level comparison: mutations vs. mutations | | t-test | P-value | Symbol |
|---|---|---|---|---|---|
| 2b | 0 | 1 | 1-samp | 7.8E-05 | ** |
|  | 1 | 2 | 2-samp | 1.4E-06 | *** |
|  | 2 | 3 | 2-samp | 4.0E-61 | *** |
|  | 3 | 4 | 2-samp | 0 | *** |
|  | 4 | 5 | 2-samp | 0 | *** |
|  | 5 | 6 | 2-samp | 1.0E-217 | *** |
|  | 6 | 7 | 2-samp | 1.7E-43 | *** |
|  | 7 | 8 | 2-samp | 3.7E-02 | N.S. |
| 2e | 0 | 1 | 1-samp | 8.9E-01 | N.S. |
|  | 1 | 2 | 2-samp | 1.9E-06 | *** |
|  | 2 | 3 | 2-samp | 5.0E-147 | *** |
|  | 3 | 4 | 2-samp | 0 | *** |
|  | 4 | 5 | 2-samp | 0 | *** |
|  | 5 | 6 | 2-samp | 4.2E-62 | *** |
|  | 6 | 7 | 2-samp | 1.6E-03 | * |
|  | 7 | 8 | 2-samp | 4.7E-01 | N.S. |

TABLE 2-continued

Summary of Statistical Analysis of Cas9-gRNA and TALE Specificity Data

| | | | | | |
|---|---|---|---|---|---|
| S7a | 0 | 1 | 1-samp | 5.2E-02 | N.S. |
|  | 1 | 2 | 2-samp | 2.8E-05 | *** |
|  | 2 | 3 | 2-samp | 3.5E-21 | *** |
|  | 3 | 4 | 2-samp | 1.4E-58 | *** |
|  | 4 | 5 | 2-samp | 8.3E-101 | *** |
|  | 5 | 6 | 2-samp | 6.8E-94 | *** |
|  | 6 | 7 | 2-samp | 1.8E-61 | *** |
|  | 7 | 8 | 2-samp | 8.1E-24 | *** |
| S7d and S8d | 0 | 1 | 1-samp | 2.3E-18 | *** |
|  | 1 | 2 | 2-samp | 2.4E-08 | *** |
|  | 2 | 3 | 2-samp | 6.2E-54 | *** |
|  | 3 | 4 | 2-samp | 4.0E-141 | *** |
|  | 4 | 5 | 2-samp | 1.9E-20 | *** |
|  | 5 | 6 | 2-samp | 1.2E-03 | * |
|  | 6 | 7 | 2-samp | 3.8E-05 | *** |
|  | 7 | 8 | 2-samp | 9.4E-01 | N.S. |
| S8c | 0 | 1 | 1-samp | 7.2E-03 | N.S. |
|  | 1 | 2 | 2-samp | 5.0E-01 | N.S. |
|  | 2 | 3 | 2-samp | 3.9E-84 | *** |
|  | 3 | 4 | 2-samp | 8.5E-153 | *** |
|  | 4 | 5 | 2-samp | 8.6E-76 | *** |
|  | 5 | 6 | 2-samp | 1.6E-03 | * |
|  | 6 | 7 | 2-samp | 7.1E-01 | N.S. |
|  | 7 | 8 | 2-samp | 7.8E-02 | N.S. |
| S13a (left) | 0 | 1 | 1-samp | 7.3E-01 | N.S. |
|  | 1 | 2 | 2-samp | 2.4E-06 | *** |
|  | 2 | 3 | 2-samp | 7.2E-140 | *** |
|  | 3 | 4 | 2-samp | 0 | *** |
|  | 4 | 5 | 2-samp | 0 | *** |
|  | 5 | 6 | 2-samp | 1.0E-72 | *** |
|  | 6 | 7 | 2-samp | 4.0E-03 | * |
| S13a (middle) | 0 | 1 | 1-samp | 9.4E-02 | N.S. |
|  | 1 | 2 | 2-samp | 5.2E-09 | *** |
|  | 2 | 3 | 2-samp | 7.9E-86 | *** |
|  | 3 | 4 | 2-samp | 2.9E-53 | *** |
|  | 4 | 5 | 2-samp | 3.5E-10 | *** |
| S13a (right) | 0 | 1 | 1-samp | 1.3E-13 | *** |
|  | 1 | 2 | 2-samp | 1.1E-04 | *** |
|  | 2 | 3 | 2-samp | 3.7E-08 | *** |

Table 2(a) P-values for comparisons of normalized expression levels of TALE or Cas9-VP64 activators binding to target sequences with particular numbers of target site mutations. Normalized expression levels have been indicated by boxplots in the figures indicated in the Figure column, where the boxes represent the distributions of these levels by numbers of mismatches from the target site. P-values were computed using t-tests for each consecutive pair of numbers of mismatches in each boxplot, where the t-tests were either one sample or two sample t-tests (see Methods). Statistical significance was assessed using Bonferroni-corrected P-value thresholds, where the correction was based on the number of comparisons within each boxplot. Statistical significance symbols are: * for $P < .0005/n$,  for $P < .005/n$, * for $P < .05/n$, and N.S. (Non-Significant) for $P >= .05/n$, where n is the number of comparisons.

b

| | Number position pairs | | |
|---|---|---|---|
| seed start position | both in seed | not both in seed | −log10 P-value |
| 2 | 171 | 19 | 3.11 |
| 3 | 153 | 37 | 1.45 |

TABLE 2-continued

Summary of Statistical Analysis of Cas9-gRNA and TALE Specificity Data

| | | | |
|---|---|---|---|
| 4 | 136 | 54 | 2.01 |
| 5 | 120 | 70 | 3.34 |
| 6 | 105 | 85 | 5.65 |
| 7 | 91 | 99 | 7.34 |
| 8 | 78 | 112 | 5.61 |
| 9 | 66 | 124 | 7.10 |
| 10 | 55 | 135 | 9.72 |
| 11 | 45 | 145 | 9.83 |
| 12 | 35 | 154 | 10.44 |
| 13 | 28 | 162 | 10.72 |
| 14 | 21 | 163 | 8.97 |
| 15 | 15 | 175 | 5.61 |
| 16 | 10 | 180 | 3.34 |
| 17 | 6 | 184 | 2.26 |
| 18 | 3 | 187 | 1.16 |

Table 2(b) Statistical characterization of seed region in Figure 2D: log10(P-values) indicating the degree of separation between expression values for Cas9N VP64 + gRNA binding to target sequences with two mutations for those position pairs mutated within

TABLE 2-continued

Summary of Statistical Analysis of Cas9-gRNA and TALE Specificity Data candidate seed regions at the 3' end of the 20 bp target site vs. all other position pairs. The greatest separation, indicated by the largest −log10 (P-values) (highlighted above), is found in the last 8-9 bp of the target site. These positions may be interpreted as indicating the start of the "seed" region of this target site. See the section "Statistical characterization of seed region" in Methods for information on how the P-values were computed.

Example XVII

Sequences of Proteins and RNAs in the Examples

A. Sequences of the $Cas9_N$-VP64 activator constructs based on the m4 mutant are displayed below. Three versions were constructed with the $Cas9_{m4}^{VP64}$ and $Cas9_{m4}^{VP64}N$ fusion protein formats showing highest activity. Corresponding vectors for the m3 and m2 mutants (FIG. 4A) were also constructed (NLS and VP64 domains are highlighted).

>$Cas9_{m4}^{VP64}$ (SEQ ID NO: 2)

```
gccaccATGGACAAGAAGTACTCCATTGGGCTCGCTATCGGCACAAACAGCGTCGGCTGGGCC

GTCATTACGGACGAGTACAAGGTGCCGAGCAAAAAATTCAAAGTTCTGGGCAATACCGATC

GCCACAGCATAAAGAAGAACCTCATTGGCGCCCTCCTGTTCGACTCCGGGGAGACGGCCGA

AGCCACGCGGCTCAAAAGAACAGCACGGCGCAGATATACCCGCAGAAAGAATCGGATCTGC

TACCTGCAGGAGATCTTTAGTAATGAGATGGCTAAGGTGGATGACTCTTTCTTCCATAGGCT

GGAGGAGTCCTTTTTGGTGGAGGAGGATAAAAAGCACGAGCGCCACCCAATCTTTGGCAAT

ATCGTGGACGAGGTGGCGTACCATGAAAAGTACCCAACCATATATCATCTGAGGAAGAAGC

TTGTAGACAGTACTGATAAGGCTGACTTGCGGTTGATCTATCTCGCGCTGGCGCATATGATC

AAATTTCGGGGACACTTCCTCATCGAGGGGGACCTGAACCCAGACAACAGCGATGTCGACA

AACTCTTTATCCAACTGGTTCAGACTTACAATCAGCTTTTCGAAGAGAACCCGATCAACGCA

TCCGGAGTTGACGCCAAAGCAATCCTGAGCGCTAGGCTGTCCAAATCCCGGCGGCTCGAAA

ACCTCATCGCACAGCTCCCTGGGGAGAAGAAGAACGGCCTGTTTGGTAATCTTATCGCCCTG

TCACTCGGGCTGACCCCCAACTTTAAATCTAACTTCGACCTGGCCGAAGATGCCAAGCTTCA

ACTGAGCAAAGACACCTACGATGATGATCTCGACAATCTGCTGGCCCAGATCGGCGACCAG

TACGCAGACCTTTTTTTGGCGGCAAAGAACCTGTCAGACGCCATTCTGCTGAGTGATATTCT

GCGAGTGAACACGGAGATCACCAAAGCTCCGCTGAGCGCTAGTATGATCAAGCGCTATGAT

GAGCACCACCAAGACTTGACTTTGCTGAAGGCCCTTGTCAGACAGCAACTGCCTGAGAAGTA

CAAGGAAATTTTCTTCGATCAGTCTAAAAATGGCTACGCCGGATACATTGACGGCGGAGCAA

GCCAGGAGGAATTTTACAAATTTATTAAGCCCATCTTGGAAAAAATGGACGGCACCGAGGA

GCTGCTGGTAAAGCTTAACAGAGAAGATCTGTTGCGCAAACAGCGCACTTTCGACAATGGA

AGCATCCCCCACCAGATTCACCTGGGCGAACTGCACGCTATCCTCAGGCGGCAAGAGGATTT

CTACCCCTTTTTGAAAGATAACAGGGAAAAGATTGAGAAAATCCTCACATTTCGGATACCCT
```

```
ACTATGTAGGCCCCCTCGCCCGGGAAATTCCAGATTCGCGTGGATGACTCGCAAATCAGAA

GAGACCATCACTCCCTGGAACTTCGAGGAAGTCGTGGATAAGGGGGCCTCTGCCCAGTCCTT

CATCGAAAGGATGACTAACTTTGATAAAAATCTGCCTAACGAAAAGGTGCTTCCTAAACACT

CTCTGCTGTACGAGTACTTCACAGTTTATAACGAGCTCACCAAGGTCAAATACGTCACAGAA

GGGATGAGAAAGCCAGCATTCCTGTCTGGAGAGCAGAAGAAAGCTATCGTGGACCTCCTCT

TCAAGACGAACCGGAAAGTTACCGTGAAACAGCTCAAAGAAGACTATTTCAAAAAGATTGA

ATGTTTCGACTCTGTTGAAATCAGCGGAGTGGAGGATCGCTTCAACGCATCCCTGGGAACGT

ATCACGATCTCCTGAAAATCATTAAAGACAAGGACTTCCTGGACAATGAGGAGAACGAGGA

CATTCTTGAGGACATTGTCCTCACCCTTACGTTGTTTGAAGATAGGGAGATGATTGAAGAAC

GCTTGAAAACTTACGCTCATCTCTTCGACGACAAAGTCATGAAACAGCTCAAGAGGCGCCGA

TATACAGGATGGGGGCCrGCTGTCAAGAAAACTGATCAATGGGATCCGAGACAAGCAGAGTG

GAAAGACAATCCTGGATTTTCTTAAGTCCGATGGATTTGCCAACCGGAACTTCATGCAGTTG

ATCCATGATGACTCTCTCACCTTTAAGGAGGACATCCAGAAAGCACAAGTTTCTGGCCAGGG

GGACAGTCTTCACGAGCACATCGCTAATCTTGCAGGTAGCCCAGCTATCAAAAAGGGAATA

CTGCAGACCGTTAAGGTCGTGGATGAACTCGTCAAAGTAATGGGAAGGCATAAGCCCGAGA

ATATCGTTATCGAGATGGCCCGAGAGAACCAAACTACCCAGAAGGGACAGAAGAACAGTAG

GGAAAGGATGAAGAGGATTGAAGAGGGTATAAAAGAACTGGGGTCCCAAATCCTTAAGGA

ACACCCAGTTGAAAACACCCAGCTTCAGAATGAGAAGCTCTACCTGTACTACCTGCAGAACG

GCAGGGACATGTACGTGGATCAGGAACTGGACATCAATCGGCTCTCCGACTACGACGTGGC

TGCTATCGTGCCCCAGTCTTTTCTCAAAGATGATTCTATTGATAATAAAGTGTTGACAAGATC

CGATAAAgcTAGAGGGAAGAGTGATAACGTCCCCTCAGAAGAAGTTGTCAAGAAAATGAAA

AATTATTGGCGGCAGCTGCTGAACGCCAAACTGATCACACAACGGAAGTTCGATAATCTGAC

TAAGGCTGAACGAGGTGGCCTGTCTGAGTTGGATAAAGCCGGCTTCATCAAAAGGCAGCTT

GTTGAGACACGCCAGATCACCAAGCACGTGGCCCAAATTCTCGATTCACGCATGAACACCA

AGTACGATGAAAATGACAAACTGATTCGAGAGGTGAAAGTTATTACTCTGAAGTCTAAGCT

GGTCTCAGATTTCAGAAAGGACTTTCAGTTTTATAAGGTGAGAGAGATCAACAATTACCACC

ATGCGCATGATGCCTACCTGAATGCAGTGGTAGGCACTGCACTTATCAAAAAATATCCCAAG

CTTGAATCTGAATTTGTTTACGGAGACTATAAAGTGTACGATGTTAGGAAAATGATCGCAAA

GTCTGAGCAGGAAATAGGCAAGGCCACCGCTAAGTACTTCTTTTACAGCAATATTATGAATT

TTTTCAAGACCGAGATTACACTGGCCAATGGAGAGATTCGGAAGCGACCACTTATCGAAAC

AAACGGAGAAACAGGAGAAATCGTGTGGGACAAGGGTAGGGATTTCGCGACAGTCCGGAA

GGTCCTGTCCATGCCGCAGGTGAACATCGTTAAAAAGACCGAAGTACAGACCGGAGGCTTC

TCCAAGGAAAGTATCCTCCCGAAAAGGAACAGCGACAAGCTGATCGCACGCAAAAAAGATT

GGGACCCCAAGAAATACGGCGGATTCGATTCTCCTACAGTCGCTTACAGTGTACTGGTTGTG

GCCAAAGTGGAGAAAGGGAAGTCTAAAAAACTCAAAAGCGTCAAGGAACTGCTGGGCATC

ACAATCATGGAGCGATCAAGCTTCGAAAAAAACCCCATCGACTTTCTCGAGGCGAAAGGAT

ATAAAGAGGTCAAAAAAGACCTCATCATTAAGCTTCCCAAGTACTCTCTCTTTGAGCTTGAA

AACGGCCGGAAACGAATGCTCGCTAGTGCGGGCGAGCTGCAGAAAGGTAACGAGCTGGCAC

TGCCCTCTAAATACGTTAATTTCTTGTATCTGGCCAGCCACTATGAAAAGCTCAAAGGGTCTC

CCGAAGATAATGAGCAGAAGCAGCTGTTCGTGGAACAACACAAACACTACCTTGATGAGAT

CATCGAGCAAATAAGCGAATTCTCCAAAAGAGTGATCCTCGCCGACGCTAACCTCGATAAG
```

-continued

GTGCTTTCTGCTTACAATAAGCACAGGGATAAGCCCATCAGGGAGCAGGCAGAAAACATTA

TCCACTTGTTTACTCTGACCAACTTGGGCGCGCCTGCAGCCTTCAAGTACTTCGACACCACCA

TAGACAGAAAGCGGTACACCTCTACAAAGGAGGTCCTGGACGCCACACTGATTCATCAGTC

AATTACGGGGCTCTATGAAACAAGAATCGACCTCTCTCAGCTCGGTGGAGACAGCAGGGCT

GACCCCAAGAAGAAGAGGAAGGTGGAGGCCAGCGGTTCCGGACGGGCTGACGCATTGGAC

GATTTTGATCTGGATATGCTGGGAAGTGACGCCCTCGATGATTTTGACCTTGACATGCTTGGTTCG

GATGCCCTTGATGACTTTGACCTCGACATGCTCGGCAGTGACGCCCTTGATGATTTCGACCTGGAC

ATGCTGATTAACTCTAGATGA

>Cas9$_{m4}^{VP64}$N Sequences (SEQ ID NO: 3)

gccaccATGCCCAAGAAGAAGAGGAAGGTGGGAAGGGGGATGGACAAGAAGTACTCCATTG

GGCTCGCTATCGGCACAAACAGCGTCGGCTGGGCCGTCATTACGGACGAGTACAAGGTGCC

GAGCAAAAAATTCAAAGTTCTGGGCAATACCGATCGCCACAGCATAAAGAAGAACCTCATT

GGCGCCCTCCTGTTCGACTCCGGGGAGACGGCCGAAGCCACGCGGCTCAAAAGAACAGCAC

GGCGCAGATATACCCGCAGAAAGAATCGGATCTGCTACCTGCAGGAGATCTTTAGTAATGA

GATGGCTAAGGTGGATGACTCTTTCTTCCATAGGCTGGAGGAGTCCTTTTTGGTGGAGGAGG

ATAAAAAGCACGAGCGCCACCCAATCTTTGGCAATATCGTGGACGAGGTGGCGTACCATGA

AAAGTACCCAACCATATATCATCTGAGGAAGAAGCTTGTAGACAGTACTGATAAGGCTGAC

TTGCGGTTGATCTATCTCGCGCTGGCGCATATGATCAAATTTCGGGGACACTTCCTCATCGAG

GGGGACCTGAACCCAGACAACAGCGATGTCGACAAACTCTTTATCCAACTGGTTCAGACTTA

CAATCAGCTTTTCGAAGAGAACCCGATCAACGCATCCGGAGTTGACGCCAAAGCAATCCTG

AGCGCTAGGCTGTCCAAATCCCGGCGGCTCGAAAACCTCATCGCACAGCTCCCTGGGGAGA

AGAAGAACGGCCTGTTTGGTAATCTTATCGCCCTGTCACTCGGGCTGACCCCCAACTTTAAA

TCTAACTTCGACCTGGCCGAAGATGCCAAGCTTCAACTGAGCAAAGACACCTACGATGATGA

TCTCGACAATCTGCTGGCCCAGATCGGCGACCAGTACGCAGACCTTTTTTTGGCGGCAAAGA

ACCTGTCAGACGCCATTCTGCTGAGTGATATTCTGCGAGTGAACACGGAGATCACCAAAGCT

CCGCTGAGCGCTAGTATGATCAAGCGCTATGATGAGCACCACCAAGACTTGACTTTGCTGAA

GGCCCTTGTCAGACAGCAACTGCCTGAGAAGTACAAGGAAATTTTCTTCGATCAGTCTAAAA

ATGGCTACGCCGGATACATTGACGGCGGAGCAAGCCAGGAGGAATTTTACAAATTTATTAA

GCCCATCTTGGAAAAAATGGACGGCACCGAGGAGCTGCTGGTAAAGCTTAACAGAGAAGAT

CTGTTGCGCAAACAGCGCACTTTCGACAATGGAAGCATCCCCCACCAGATTCACCTGGGCGA

ACTGCACGCTATCCTCAGGCGGCAAGAGGATTTCTACCCCTTTTTGAAAGATAACAGGGAAA

AGATTGAGAAAATCCTCACATTTCGGATACCCTACTATGTAGGCCCCCTCGCCCGGGGAAAT

TCCAGATTCGCGTGGATGACTCGCAAATCAGAAGAGACCATCACTCCCTGGAACTTCGAGGA

AGTCGTGGATAAGGGGGCCTCTGCCCAGTCCTTCATCGAAAGGATGACTAACTTTGATAAAA

ATCTGCCTAACGAAAAGGTGCTTCCTAAACACTCTCTGCTGTACGAGTACTTCACAGTTTATA

ACGAGCTCACCAAGGTCAAATACGTCACAGAAGGGATGAGAAAGCCAGCATTCCTGTCTGG

AGAGCAGAAGAAAGCTATCGTGGACCTCCTCTTCAAGACGAACCGGAAAGTTACCGTGAAA

CAGCTCAAAGAAGACTATTTCAAAAAGATTGAATGTTTCGACTCTGTTGAAATCAGCGGAGT

GGAGGATCGCTTCAACGCATCCCTGGGAACGTATCACGATCTCCTGAAAATCATTAAAGACA

AGGACTTCCTGGACAATGAGGAGAACGAGGACATTCTTGAGGACATTGTCCTCACCCTTACG

-continued

```
TTGTTTGAAGATAGGGAGATGATTGAAGAACGCTTGAAAACTTACGCTCATCTCTTCGACGA
CAAAGTCATGAAACAGCTCAAGAGGCGCCGATATACAGGATGGGGGCGGCTGTCAAGAAAA
CTGATCAATGGGATCCGAGACAAGCAGAGTGGAAAGACAATCCTGGATTTTCTTAAGTCCG
ATGGATTTGCCAACCGGAACTTCATGCAGTTGATCCATGATGACTCTCTCACCTTTAAGGAG
GACATCCAGAAAGCACAAGTTTCTGGCCAGGGGACAGTCTTCACGAGCACATCGCTAATCT
TGCAGGTAGCCCAGCTATCAAAAAGGGAATACTGCAGACCGTTAAGGTCGTGGATGAACTC
GTCAAAGTAATGGGAAGGCATAAGCCCGAGAATATCGTTATCGAGATGGCCCGAGAGAACC
AAACTACCCAGAAGGGACAGAAGAACAGTAGGGAAAGGATGAAGAGGATTGAAGAGGGTA
TAAAAGAACTGGGGTCCCAAATCCTTAAGGAACACCCAGTTGAAAACACCCAGCTTCAGAA
TGAGAAGCTCTACCTGTACTACCTGCAGAACGGCAGGGACATGTACGTGGATCAGGAACTG
GACATCAATCGGCTCTCCGACTACGACGTGGCTGCTATCGTGCCCCAGTCTTTTCTCAAAGAT
GATTCTATTGATAATAAAGTGTTGACAAGATCCGATAAAgcTAGAGGGAAGAGTGATAACGT
CCCCTCAGAAGAAGTTGTCAAGAAAATGAAAAATTATTGGCGGCAGCTGCTGAACGCCAAA
CTGATCACACAACGGAAGTTCGATAATCTGACTAAGGCTGAACGAGGTGGCCTGTCTGAGTT
GGATAAAGCCGGCTTCATCAAAAGGCAGCTTGTTGAGACACGCCAGATCACCAAGCACGTG
GCCCAAATTCTCGATTCACGCATGAACACCAAGTACGATGAAAATGACAAACTGATTCGAG
AGGTGAAAGTTATTACTCTGAAGTCTAAGCTGGTCTCAGATTTCAGAAAGGACTTTCAGTTT
TATAAGGTGAGAGAGATCAACAATTACCACCATGCGCATGATGCCTACCTGAATGCAGTGGT
AGGCACTGCACTTATCAAAAAATATCCCAAGCTTGAATCTGAATTTGTTTACGGAGACTATA
AAGTGTACGATGTTAGGAAAATGATCGCAAAGTCTGAGCAGGAAATAGGCAAGGCCACCGC
TAAGTACTTCTTTTACAGCAATATTATGAATTTTTTCAAGACCGAGATTACACTGGCCAATGG
AGAGATTCGGAAGCGACCACTTATCGAAACAAACGGAGAAACAGGAGAAATCGTGTGGGA
CAAGGGTAGGGATTTCGCGACAGTCCGGAAGGTCCTGTCCATGCCGCAGGTAACATCGTTA
AAAAGACCGAAGTACAGACCGGAGGCTTCTCCAAGGAAAGTATCCTCCCGAAAAGGAACAG
CGACAAGCTGATCGCACGCAAAAAAGATTGGGACCCCAAGAAATACGGCGGATTCGATTCT
CCTACAGTCGCTTACAGTGTACTGGTTGTGCCAAAGTGGAGAAAGGGAAGTCTAAAAAAC
TCAAAAGCGTCAAGGAACTGCTGGGCATCACAATCATGGAGCGATCAAGCTTCGAAAAAAA
CCCCATCGACTTTCTCGAGGCGAAAGGATATAAAGAGGTCAAAAAAGACCTCATCATTAAG
CTTCCCAAGTACTCTCTCTTTGAGCTTGAAAACGGCCGGAAACGAATGCTCGCTAGTGCGGG
CGAGCTGCAGAAAGGTAACGAGCTGGCACTGCCCTCTAAATACGTTAATTTCTTGTATCTGG
CCAGCCACTATGAAAAGCTCAAAGGGTCTCCCGAAGATAATGAGCAGAAGCAGCTGTTCGT
GGAACAACACAAACACTACCTTGATGAGATCATCGAGCAAATAAGCGAATTCTCCAAAAGA
GTGATCCTCGCCGACGCTAACCTCGATAAGGTGCTTTCTGCTTACAATAAGCACAGGGATAA
GCCCATCAGGGAGCAGGCAGAAAACATTATCCACTTGTTTACTCTGACCAACTTGGGCGCGC
CTGCAGCTTCAAGTACTTCGACACCACCATAGACAGAAAGCGGTACACCTCTACAAAGGA
GGTCCTGGACGCCACACTGATTCATCAGTCAATTACGGGGCTCTATGAAACAAGAATCGACC
TCTCTCAGCTCGGTGGAGACAGCAGGGCTGACCCCAAGAAGAAGAGGAAGGTGGAGGCC
AGCGGTTCCGGACGGGCTGACGCATTGGACGATTTGATCTGGATATGCTGGGAAGTGACGCCCT
CGATGATTTTGACCTTGACATGCTTGGTTCGGATGCCCTTGATGACTTTGACCTCGACATGCTCGG
CAGTGACGCCCTTGATGATTTCGACCTGGACATGCTGATTAACTCTAGATGA
```

>Cas9$_{m4}^{VP64}$C

-continued (SEQ ID NO: 4)

```
gccaccATGGACAAGAAGTACTCCATTGGGCTCGCTATCGGCACAAACAGCGTCGGCTGGGCC
GTCATTACGGACGAGTACAAGGTGCCGAGCAAAAAATTCAAAGTTCTGGGCAATACCGATC
GCCACAGCATAAAGAAGAACCTCATTGGCGCCCTCCTGTTCGACTCCGGGGAGACGGCCGA
AGCCACGCGGCTCAAAAGAACAGCACGGCGCAGATATACCCGCAGAAAGAATCGGATCTGC
TACCTGCAGGAGATCTTTAGTAATGAGATGGCTAAGGTGGATGACTCTTTCTTCCATAGGCT
GGAGGAGTCCTTTTTGGTGGAGGAGGATAAAAAGCACGAGCGCCACCCAATCTTTGGCAAT
ATCGTGGACGAGGTGGCGTACCATGAAAAGTACCCAACCATATATCATCTGAGGAAGAAGC
TTGTAGACAGTACTGATAAGGCTGACTTGCGGTTGATCTATCTCGCGCTGGCGCATATGATC
AAATTTCGGGGACACTTCCTCATCGAGGGGGACCTGAACCCAGACAACAGCGATGTCGACA
AACTCTTTATCCAACTGGTTCAGACTTACAATCAGCTTTTCGAAGAGAACCCGATCAACGCA
TCCGGAGTTGACGCCAAAGCAATCCTGAGCGCTAGGCTGTCCAAATCCCGGCGGCTCGAAA
ACCTCATCGCACAGCTCCCTGGGGAGAAGAAGAACCTGCCTGTTTGGTAATCTTATCGCCCTG
TCACTCGGGCTGACCCCCAACTTTAAATCTAACTTCGACCTGGCCGAAGATGCCAAGCTTCA
ACTGAGCAAAGACACCTACGATGATGATCTCGACAATCTGCTGGCCCAGATCGGCGACCAG
TACGCAGACCTTTTTTTGGCGGCAAAGAACCTGTCAGACGCCATTCTGCTGAGTGATATTCT
GCGAGTGAACACGGAGATCACCAAAGCTCCGCTGAGCGCTAGTATGATCAAGCGCTATGAT
GAGCACCACCAAGACTTGACTTTGCTGAAGGCCCTTGTCAGACAGCAACTGCCTGAGAAGTA
CAAGGAAATTTTCTTCGATCAGTCTAAAAATGGCTACGCCGGATACATTGACGGCGGAGCAA
GCCAGGAGGAATTTTACAAATTTATTAAGCCCATCTTGGAAAAAATGGACGGCACCGAGGA
GCTGCTGGTAAAGCTTAACAGAGAAGATCTGTTGCGCAAACAGCGCACTTTCGACAATGGA
AGCATCCCCCACCAGATTCACCTGGGCGAACTGCACGCTATCCTCAGGCGGCAAGAGGATTT
CTACCCCTTTTTGAAAGATAACAGGGAAAAGATTGAGAAAATCCTCACATTTCGGATACCCT
ACTATGTAGGCCCCCTCGCCCGGGGAAATTCCAGATTCGCGTGGATGACTCGCAAATCAGAA
GAGACCATCACTCCCTGGAACTTCGAGGAAGTCGTGGATAAGGGGGCCTCTGCCCAGTCCTT
CATCGAAAGGATGACTAACTTTGATAAAAATCTGCCTAACGAAAAGGTGCTTCCTAAACACT
CTCTGCTGTACGAGTACTTCACAGTTTATAACGAGCTCACCAAGGTCAAATACGTCACAGAA
GGGATGAGAAAGCCAGCATTCCTGTCTGGAGAGCAGAAGAAAGCTATCGTGGACCTCCTCT
TCAAGACGAACCGGAAAGTTACCGTGAAACAGCTCAAAGAAGACTATTTCAAAAAGATTGA
ATGTTTCGACTCTGTTGAAATCAGCGGAGTGGAGGATCGCTTCAACGCATCCCTGGGAACGT
ATCACGATCTCCTGAAAATCATTAAAGACAAGGACTTCCTGGACAATGAGGAGAACGAGGA
CATTCTTGAGGACATTGTCCTCACCCTTACGTTGTTTGAAGATAGGGAGATGATTGAAGAAC
GCTTGAAAAdTTACGCTCATCTCTTCGACGACAAAGTCATGAAACAGCTCAAGAGGCGCCGA
TATACAGGATGGGGCGGCTGTCAAGAAAACTGATCAATGGGATCCGAGACAAGCAGAGTG
GAAAGACAATCCTGGATTTTCTTAAGTCCGATGGATTTGCCAACCGGAACTTCATGCAGTTG
ATCCATGATGACTCTCTCACCTTTAAGGAGGACATCCAGAAAGCACAAGTTTCTGGCCAGGG
GGACAGTCTTCACGAGCACATCGCTAATCTTGCAGGTAGCCCAGCTATCAAAAAGGGAATA
CTGCAGACCGTTAAGGTCGTGGATGAACTCGTCAAAGTAATGGGAAGGCATAAGCCCGAGA
ATATCGTTATCGAGATGGCCCGAGAGAACCAAACTACCCAGAAGGGACAGAAGAACAGTAG
GGAAAGGATGAAGAGGATTGAAGAGGGTATAAAAGAACTGGGGTCCCAAATCCTTAAGGA
ACACCCAGTTGAAAACACCCAGCTTCAGAATGAGAAGCTCTACCTGTACTACCTGCAGAACG
```

-continued
```
GCAGGGACATGTACGTGGATCAGGAACTGGACATCAATCGGCTCTCCGACTACGACGTGGC

TGCTATCGTGCCCCAGTCTTTTCTCAAAGATGATTCTATTGATAATAAAGTGTTGACAAGATC

CGATAAAgcTAGAGGGAAGAGTGATAACGTCCCCTCAGAAGAAGTTGTCAAGAAAATGAAA

AATTATTGGCGGCAGCTGCTGAACGCCAAACTGATCACACAACGGAAGTTCGATAATCTGAC

TAAGGCTGAACGAGGTGGCCTGTCTGAGTTGGATAAAGCCGGCTTCATCAAAAGGCAGCTT

GTTGAGACACGCCAGATCACCAAGCACGTGGCCCAAATTCTCGATTCACGCATGAACACCA

AGTACGATGAAAATGACAAACTGATTCGAGAGGTGAAAGTTATTACTCTGAAGTCTAAGCT

GGTCTCAGATTTCAGAAAGGACTTTCAGTTTTATAAGGTGAGAGAGATCAACAATTACCACC

ATGCGCATGATGCCTACCTGAATGCAGTGGTAGGCACTGCACTTATCAAAAAATATCCCAAG

CTTGAATCTGAATTTGTTTACGGAGACTATAAAGTGTACGATGTTAGGAAAATGATCGCAAA

GTCTGAGCAGGAAATAGGCAAGGCCACCGCTAAGTACTTCTTTTACAGCAATATTATGAATT

TTTTCAAGACCGAGATTACACTGGCCAATGGAGAGATTCGGAAGCGACCACTTATCGAAAC

AAACGGAGAAACAGGAGAAATCGTGTGGGACAAGGGTAGGGATTTCGCGACAGTCCGGAA

GGTCCTGTCCATGCCGCAGGTGAACATCGTTAAAAAGACCGAAGTACAGACCGGAGGCTTC

TCCAAGGAAAGTATCCTCCCGAAAAGGAACAGCGACAAGCTGATCGCACGCAAAAAGATT

GGGACCCCAAGAAATACGGCGGATTCGATTCTCCTACAGTCGCTTACAGTGTACTGGTTGTG

GCCAAAGTGGAGAAAGGGAAGTCTAAAAAACTCAAAAGCGTCAAGGAACTGCTGGGCATC

ACAATCATGGAGCGATCAAGCTTCGAAAAAAACCCCATCGACTTTCTCGAGGCGAAAGGAT

ATAAAGAGGTCAAAAAAGACCTCATCATTAAGCTTCCCAAGTACTCTCTCTTTGAGCTTGAA

AACGGCCGGAAACGAATGCTCGCTAGTGCGGGCGAGCTGCAGAAAGGTAACGAGCTGGCAC

TGCCCTCTAAATACGTTAATTTCTTGTATCTGGCCAGCCACTATGAAAAGCTCAAAGGGTCTC

CCGAAGATAATGAGCAGAAGCAGCTGTTCGTGGAACAACACAAACACTACCTTGATGAGAT

CATCGAGCAAATAAGCGAATTCTCCAAAAGAGTGATCCTCGCCGACGCTAACCTCGATAAG

GTGCTTTCTGCTTACAATAAGCACAGGGATAAGCCCATCAGGGAGCAGGCAGAAAACATTA

TCCACTTGTTTACTCTGACCAACTTGGGCGCGCCTGCAGCCTTCAAGTACTTCGACACCACCA

TAGACAGAAAGCGGTACACCTCTACAAAGGAGGTCCTGGACGCCACACTGATTCATCAGTC

AATTACGGGGCTCTATGAAACAAGAATCGACCTCTCTCAGCTCGGTGGAGACAGCAGGGCT

GACCCCAAGAAGAAGAGGAAGGTGGAGGCCAGCGGTTCCGGACGGGCTGACGCATTGGAC

GATTTTGATCTGGATATGCTGGGAAGTGACGCCCTCGATGATTTTGACCTTGACATGCTTGGTTCG

GATGCCCTTGATGACTTTGACCTCGACATGCTCGGCAGTGACGCCCTTGATGATTTCGACCTGGAC

ATGCTGATTAACTCTAGAGCGGCCGCAGATCCAAAAAAGAAGAGAAAGGTAGATCCAAAA

AAGAAGAGAAAGGTAGATCCAAAAAAGAAGAGAAAGGTAGATACGGCCGCATAG
```

B. Sequences of the MS2-activator constructs and corresponding gRNA backbone vector with 2×MS2 aptamer domains is provided below (NLS, VP64, gRNA spacer, and MS2-binding RNA stem loop domains are highlighted). Two versions of the former were constructed with the MS2$_{VP64}$N fusion protein format showing highest activity.

```
>MS2_VP64 N
                                       (SEQ ID NO: 5)
gccaccATGGGACCTAAGAAAAAGAGGAAGGTGGCGGCCGCTTCTAGAAT

GGCTTCTAACTTTACTCAGTTCGTTCTCGTCGACAATGGCGGAACTGGCG

ACGTGACTGTCGCCCCAAGCAACTTCGCTAACGGGATCGCTGAATGGATC

AGCTCTAACTCGCGTTCACAGGCTTACAAAGTAACCTGTAGCGTTCGTCA

GAGCTCTGCGCAGAATCGCAAATACACCATCAAAGTCGAGGTGCCTAAAG

GCGCCTGGCGTTCGTACTTAAATATGGAACTAACCATTCCAATTTTCGCC

ACGAATTCCGACTGCGAGCTTATTGTTAAGGCAATGCAAGGTCTCCTAAA

AGATGGAAACCCGATTCCCTCAGCAATCGCAGCAAACTCCGGCATCTACG

AGGCCAGCGGTTCCGGACGGGCTGACGCATTGGACGATTTTGATCTGGAT
```

-continued

ATGCTGGGAAGTGACGCCCTCGATGATTTTGACCTTGACATGCTTGGTTC

GGATGCCCTTGATGACTTTGACCTCGACATGCTCGGCAGTGACGCCCTTG

ATGATTTCGACCTGGACATGCTGATTAACTCTAGATGA

>MS2$_{VP64}$C (SEQ ID NO: 6)

gccaccATGGGACCTAAGAAAAAGAGGAAGGTGGCGGCCGCTTCTAGAAT

GGCTTCTAACTTTACTCAGTTCGTTCTCGTCGACAATGGCGGAACTGGCG

ACGTGACTGTCGCCCCAAGCAACTTCGCTAACGGGATCGCTGAATGGATC

AGCTCTAACTCGCGTTCACAGGCTTACAAAGTAACCTGTAGCGTTCGTCA

GAGCTCTGCGCAGAATCGCAAATACACCATCAAAGTCGAGGTGCCTAAAG

GCGCCTGGCGTTCGTACTTAAATATGGAACTAACCATTCCAATTTTCGCC

ACGAATTCCGACTGCGAGCTTATTGTTAAGGCAATGCAAGGTCTCCTAAA

AGATGGAAACCCGATTCCCTCAGCAATCGCAGCAAACTCCGGCATCTACG

AGGCCAGCGGTTCCGGACGGGCTGACGCATTGGACGATTTTGATCTGGAT

*ATGCTGGGAAGTGACGCCCTCGATGATTTTGACCTTGACATGCTTGGTTC*

*GGATGCCCTTGATGACTTTGACCTCGACATGCTCGGCAGTGACGCCCTTG*

*ATGATTTCGACCTGGACATGCTGATTAACTCTAGA*GCGGCCGCAGATCCA

AAAAAGAAGAGAAAGGTAGATCCAAAAAAGAAGAGAAAGGTAGATCCAAA

AAAGAAGAGAAAGGTAGATACGGCCGCATAG

>gRNA$_{2xMS2}$ (SEQ ID NO: 7)

TGTACAAAAAAGCAGGCTTTAAAGGAACCAATTCAGTCGACTGGATCCGG

TACCAAGGTCGGGCAGGAAGAGGGCCTATTTCCCATGATTCCTTCATATT

TGCATATACGATACAAGGCTGTTAGAGAGATAATTAGAATTAATTTGACT

GTAAACACAAAGATATTAGTACAAAATACGTGACGTAGAAAGTAATAATT

TCTTGGGTAGTTTGCAGTTTTAAAATTATGTTTTAAAATGGACTATCATA

TGCTTACCGTAACTTGAAAGTATTTCGATTTCTTGGCTTTATATATCTTG

TGGAAAGGACGAAACACCGNNNNNNNNNNNNNNNNNNNNGTTTTAGAGCT

AGAAATAGCAAGTTAAAATAAGGCTAGTCCGTTATCAACTTGAAAAAGTG

GCACCGAGTCGGTGCTCTGCAGGTCGACTCTAGAAAACATGAGGATCACC

CATGTCTGCAGTATTCCCGGGTTCATTAGATCCTAAGGTACCTAATTGCC

TAGAAAACATGAGGATCACCCATGTCTGCAGGTCGACTCTAGAAATTTTT

TCTAGAC

C. dTomato fluorescence based transcriptional activation reporter sequences are listed below (ISceI control-TF target, gRNA targets, minCMV promoter and FLAG tag+dTomato sequences are highlighted).

>TF Reporter 1

(SEQ ID NO: 8)

TAGGGATAACAGGGTAATAGT*GTCCCCTCCACCCCACAGTGGGG*CGAGGT

AGGCGTGTACGGTGGGAGGCCTATATAAGCAGAGCTCGTTTAGTGAACCG

TCAGATCGCCTGGAGAATTCgccaccatgGACTACAAGGATGACGACGAT

AAAACTTCCGGTGGCGGACTGGGTTCCACCGTGAGCAAGGGCGAGGAGGT

CATCAAAGAGTTCATGCGCTTCAAGGTGCGCATGGAGGGCTCCATGAACG

GCCACGAGTTCGAGATCGAGGGCGAGGGCGAGGGCCGCCCCTACGAGGGC

ACCCAGACCGCCAAGCTGAAGGTGACCAAGGGCGGCCCCCTGCCCTTCGC

CTGGGACATCCTGTCCCCCCAGTTCATGTACGGCTCCAAGGCGTACGTGA

AGCACCCCGCCGACATCCCCGATTACAAGAAGCTGTCCTTCCCCGAGGGC

TTCAAGTGGGAGCGCGTGATGAACTTCGAGGACGGCGGTCTGGTGACCGT

GACCCAGGACTCCTCCCTGCAGGACGGCACGCTGATCTACAAGGTGAAGA

TGCGCGGCACCAACTTCCCCCCCGACGGCCCCGTAATGCAGAAGAAGACC

ATGGGCTGGGAGGCCTCCACCGAGCGCCTGTACCCCCGCGACGGCGTGCT

GAAGGGCGAGATCCACCAGGCCCTGAAGCTGAAGGACGGCGGCCACTACC

TGGTGGAGTTCAAGACCATCTACATGGCCAAGAAGCCCGTGCAACTGCCC

GGCTACTACTACGTGGACACCAAGCTGGACATCACCTCCCACAACGAGGA

CTACACCATCGTGGAACAGTACGAGCGCTCCGAGGGCCGCCACCACCTGT

TCCTGTACGGCATGGACGAGCTGTACAAGTAA

>TF Reporter 2

(SEQ ID NO: 9)

TAGGGATAACAGGGTAATAGT*GGGGCCACTAGGGACAGGATTGG*CGAGGT

AGGCGTGTACGGTGGGAGGCCTATATAAGCAGAGCTCGTTTAGTGAACCG

TCAGATCGCCTGGAGAATTCgccaccatgGACTACAAGGATGACGACGAT

AAAACTTCCGGTGGCGGACTGGGTTCCACCGTGAGCAAGGGCGAGGAGGT

CATCAAAGAGTTCATGCGCTTCAAGGTGCGCATGGAGGGCTCCATGAACG

GCCACGAGTTCGAGATCGAGGGCGAGGGCGAGGGCCGCCCCTACGAGGGC

ACCCAGACCGCCAAGCTGAAGGTGACCAAGGGCGGCCCCCTGCCCTTCGC

CTGGGACATCCTGTCCCCCCAGTTCATGTACGGCTCCAAGGCGTACGTGA

AGCACCCCGCCGACATCCCCGATTACAAGAAGCTGTCCTTCCCCGAGGGC

TTCAAGTGGGAGCGCGTGATGAACTTCGAGGACGGCGGTCTGGTGACCGT

GACCCAGGACTCCTCCCTGCAGGACGGCACGCTGATCTACAAGGTGAAGA

TGCGCGGCACCAACTTCCCCCCCGACGGCCCCGTAATGCAGAAGAAGACC

ATGGGCTGGGAGGCCTCCACCGAGCGCCTGTACCCCCGCGACGGCGTGCT

GAAGGGCGAGATCCACCAGGCCCTGAAGCTGAAGGACGGCGGCCACTACC

TGGTGGAGTTCAAGACCATCTACATGGCCAAGAAGCCCGTGCAACTGCCC

GGCTACTACTACGTGGACACCAAGCTGGACATCACCTCCCACAACGAGGA

CTACACCATCGTGGAACAGTACGAGCGCTCCGAGGGCCGCCACCACCTGT

TCCTGTACGGCATGGACGAGCTGTACAAGTAA

D. General format of the reporter libraries used for TALE and Cas9-gRNA specificity assays is provided below (ISceI control-TF target, gRNA/TALE target site (23 bp for gRNAs and 18 bp for TALEs), minCMV promoter, RNA barcode, and dTomato sequences are highlighted).

>Specificity Reporter Libraries (SEQ ID NO: 10)

TAGGGATAACAGGGTAATAGT*NNNNNNNNNNNNNNNNNNNNNNN*CGAGGT

AGGCGTGTACGGTGGGAGGCCTATATAAGCAGAGCTCGTTTAGTGAACCG

TCAGATCGCCTGGAGAATTCgccaccatgGACTACAAGGATGACGACGAT

```
AAANNNNNNNNNNNNNNNNNNNNNNNNNNACTTCCGGTGGCGGACTGGGTTC
CACCGTGAGCAAGGGCGAGGAGGTCATCAAAGAGTTCATGCGCTTCAAGG
TGCGCATGGAGGGCTCCATGAACGGCCACGAGTTCGAGATCGAGGGCGAG
GGCGAGGGCCGCCCCTACGAGGGCACCCAGACCGCCAAGCTGAAGGTGAC
CAAGGGCGGCCCCCTGCCCTTCGCCTGGGACATCCTGTCCCCCCAGTTCA
TGTACGGCTCCAAGGCGTACGTGAAGCACCCCGCCGACATCCCCGATTAC
AAGAAGCTGTCCTTCCCCGAGGGCTTCAAGTGGGAGCGCGTGATGAACTT
CGAGGACGGCGGTCTGGTGACCGTGACCCAGGACTCCTCCCTGCAGGACG

GCACGCTGATCTACAAGGTGAAGATGCGCGGCACCAACTTCCCCCCCGAC
GGCCCCGTAATGCAGAAGAAGACCATGGGCTGGGAGGCCTCCACCGAGCG
CCTGTACCCCGCGACGGCGTGCTGAAGGGCGAGATCCACCAGGCCCTGA
AGCTGAAGGACGGCGGCCACTACCTGGTGGAGTTCAAGACCATCTACATG
GCCAAGAAGCCCGTGCAACTGCCCGGCTACTACTACGTGGACACCAAGCT
GGACATCACCTCCCACAACGAGGACTACACCATCGTGGAACAGTACGAGC
GCTCCGAGGGCCGCCACCACCTGTTCCTGTACGGCATGGACGAGCTGTAC
AAGTAAGAATTC
```

---

The invention claimed is:

1. A method of modulating expression of a target nucleic acid in a eukaryotic cell comprising
providing to the cell a nucleic acid encoding a guide RNA complementary to the target nucleic acid sequence and an aptamer comprising a target of an RNA binding domain, wherein the aptamer is attached to the 3' end or the 5' end of the guide RNA, wherein the guide RNA is a tracrRNA-crRNA fusion,
providing to the cell a nucleic acid encoding a transcriptional activator or repressor and an RNA binding domain, wherein the RNA binding domain binds to the target of the RNA binding domain,
providing to the cell a nucleic acid encoding a nuclease null Cas9 protein that interacts with the guide RNA, and
wherein the cell expresses the guide RNA having the aptamer attached to the 3' end or the 5' end of the guide RNA, the transcriptional activator or repressor having the RNA binding domain and the Cas9 protein, and
wherein the guide RNA including the transcriptional activator or repressor connected thereto and the Cas9 protein co-localize to the target nucleic acid sequence and wherein the transcriptional activator or repressor modulates expression of the target nucleic acid.

2. The method of claim 1 wherein the cell is a yeast cell, a plant cell or a mammalian cell.

3. The method or claim 1 wherein the cell is a human cell.

4. The method of claim 1 wherein the guide RNA is between about 10 to about 250 nucleotides.

5. The method of claim 1 wherein the guide RNA is between about 20 to about 100 nucleotides.

6. The method of claim 1 wherein the guide RNA is between about 100 to about 250 nucleotides.

7. The method of claim 1 wherein the target nucleic acid is genomic DNA, mitochondrial DNA, viral DNA or exogenous DNA.

8. A method of modulating expression of a target nucleic acid in a eukaryotic cell comprising
providing to the cell a nucleic acid encoding a transcriptional activator or repressor and an RNA binding domain,
providing to the cell a nucleic acid encoding a guide RNA having a spacer sequence fully complementary to viral DNA including the target nucleic acid sequence and an aptamer comprising a target of an RNA binding domain attached to the 3' end or the 5' end of the guide RNA, wherein the guide RNA is a tracrRNA-crRNA fusion, and wherein the RNA binding domain binds to the target of the RNA binding domain, wherein the cell expresses the guide RNA having the aptamer attached to the 3' end or the 5' end of the guide RNA and the transcriptional activator or repressor having the RNA binding domain,
providing to the cell a nuclease null Cas9 protein that interacts with the guide RNA, wherein the guide RNA including the transcriptional activator or repressor connected thereto and the Cas9 protein co-localize to the target nucleic acid sequence and wherein the transcriptional activator or repressor modulates expression of the target nucleic acid.

9. The method of claim 8
wherein the Cas9 protein is provided to the cell by introducing to the cell a nucleic acid encoding the Cas9 protein, and
wherein the cell expresses the Cas9 protein.

10. The method of claim 8 wherein the cell is a yeast cell, a plant cell or a mammalian cell.

11. The method or claim 8 wherein the cell is a human cell.

12. The method of claim 8 wherein the guide RNA is between about 10 to about 250 nucleotides.

13. The method of claim 8 wherein the guide RNA is between about 20 to about 100 nucleotides.

14. The method of claim 8 wherein the guide RNA is between about 100 to about 250 nucleotides.

15. The method of claim 1 wherein the aptamer comprises two copies of MS2 bacteriophage coat-protein binding RNA stem-loop.

16. The method of claim 1 wherein the RNA binding domain comprises MS2 bacteriophage coat-protein.

17. The method of claim 9 wherein the aptamer comprises two copies of MS2 bacteriophage coat-protein binding RNA stem-loop.

18. The method of claim 9 wherein the RNA binding domain comprises MS2 bacteriophage coat-protein.

19. A method of modulating expression of a target nucleic acid in a eukaryotic cell comprising
providing to the cell a guide RNA complementary to the target nucleic acid sequence, and an aptamer comprising a target of an RNA binding domain, wherein the aptamer is attached to the 3' end or the 5' end of the guide RNA, wherein the guide RNA is a tracrRNA-crRNA fusion,
providing to the cell a transcriptional activator or repressor and an RNA binding domain attached thereto, wherein the RNA binding domain binds to the target of the RNA binding domain,
providing to the cell a nuclease null Cas9 protein that interacts with the guide RNA,
wherein the guide RNA including the transcriptional activator or repressor connected thereto and the Cas9 protein co-localize to the target nucleic acid sequence and wherein the transcriptional activator or repressor modulates expression of the target nucleic acid.

20. The method of claim 19 wherein the cell is a yeast cell, a plant cell or a mammalian cell.

21. The method or claim 19 wherein the cell is a human cell.

22. The method of claim 19 wherein the guide RNA is between about 10 to about 250 nucleotides.

23. The method of claim 19 wherein the guide RNA is between about 20 to about 100 nucleotides.

24. The method of claim 19 wherein the guide RNA is between about 100 to about 250 nucleotides.

25. The method of claim 19 wherein the aptamer comprises two copies of MS2 bacteriophage coat-protein binding RNA stem-loop.

26. The method of claim 19 wherein the RNA binding domain comprises MS2 bacteriophage coat-protein.

27. The method of claim 19 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs having the transcriptional activator or repressor connected thereto modulate expression of the target nucleic acid.

28. The method of claim 19 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs having the transcriptional activator or repressor connected thereto modulate expression of different target nucleic acids.

29. The method of claim 1 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs having the transcriptional activator or repressor connected thereto modulate expression of the target nucleic acid.

30. The method of claim 1 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs having the transcriptional activator or repressor connected thereto modulate expression of different target nucleic acids.

31. The method of claim 8 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs having the transcriptional activator or repressor connected thereto modulate expression of the target nucleic acid.

32. The method of claim 8 wherein multiple guide RNAs are introduced to the cell with each guide RNA being complementary to a different target nucleic acid sequence and having an aptamer comprising a target of an RNA binding domain, wherein the aptamer is attached to the 3' end or the 5' end of the guide RNA, wherein each guide RNA is a tracrRNA-crRNA fusion, and wherein multiple guide RNAs having the transcriptional activator or repressor connected thereto modulate expression of different target nucleic acids.

* * * * *

UNITED STATES PATENT AND TRADEMARK OFFICE
CERTIFICATE OF CORRECTION

PATENT NO. : 10,640,789 B2
APPLICATION NO. : 15/049451
DATED : May 5, 2020
INVENTOR(S) : Church et al.

It is certified that error appears in the above-identified patent and that said Letters Patent is hereby corrected as shown below:

In the Specification

Under STATEMENT OF GOVERNMENT INTERESTS
Column 1, Line 15:
Please delete "This invention was made with government support under Grant No. P50 HG005550 from the National Institutes of health and DE-FG02-02ER63445 from the Department of Energy. The government has certain rights in the invention." and insert --This invention was made with government support under HG005550 awarded by National Institutes of Health (NIH) and under DE-FG02-02ER63445 awarded by U.S. Department of Energy (DOE). The government has certain rights in this invention.--

Signed and Sealed this
Twenty-seventh Day of September, 2022

Katherine Kelly Vidal
*Director of the United States Patent and Trademark Office*

SEQUENCE LISTING

<160> NUMBER OF SEQ ID NOS: 184

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp

```
                    260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
            325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
            405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
            485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
            565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
            645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
```

```
Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095
```

| | | | | | | | | | | | |
|---|---|---|---|---|---|---|---|---|---|---|---|
| Glu | Val | Gln | Thr | Gly | Gly | Phe | Ser | Lys | Glu | Ser | Ile | Leu | Pro | Lys |
| 1100 | | | | | 1105 | | | | | 1110 | | | | |

Glu Val Gln Thr Gly Gly Phe Ser Lys Glu Ser Ile Leu Pro Lys
 1100                1105                1110

Arg Asn Ser Asp Lys Leu Ile Ala Arg Lys Lys Asp Trp Asp Pro
 1115                1120                1125

Lys Lys Tyr Gly Gly Phe Asp Ser Pro Thr Val Ala Tyr Ser Val
 1130                1135                1140

Leu Val Val Ala Lys Val Glu Lys Gly Lys Ser Lys Lys Leu Lys
 1145                1150                1155

Ser Val Lys Glu Leu Leu Gly Ile Thr Ile Met Glu Arg Ser Ser
 1160                1165                1170

Phe Glu Lys Asn Pro Ile Asp Phe Leu Glu Ala Lys Gly Tyr Lys
 1175                1180                1185

Glu Val Lys Lys Asp Leu Ile Ile Lys Leu Pro Lys Tyr Ser Leu
 1190                1195                1200

Phe Glu Leu Glu Asn Gly Arg Lys Arg Met Leu Ala Ser Ala Gly
 1205                1210                1215

Glu Leu Gln Lys Gly Asn Glu Leu Ala Leu Pro Ser Lys Tyr Val
 1220                1225                1230

Asn Phe Leu Tyr Leu Ala Ser His Tyr Glu Lys Leu Lys Gly Ser
 1235                1240                1245

Pro Glu Asp Asn Glu Gln Lys Gln Leu Phe Val Glu Gln His Lys
 1250                1255                1260

His Tyr Leu Asp Glu Ile Ile Glu Gln Ile Ser Glu Phe Ser Lys
 1265                1270                1275

Arg Val Ile Leu Ala Asp Ala Asn Leu Asp Lys Val Leu Ser Ala
 1280                1285                1290

Tyr Asn Lys His Arg Asp Lys Pro Ile Arg Glu Gln Ala Glu Asn
 1295                1300                1305

Ile Ile His Leu Phe Thr Leu Thr Asn Leu Gly Ala Pro Ala Ala
 1310                1315                1320

Phe Lys Tyr Phe Asp Thr Thr Ile Asp Arg Lys Arg Tyr Thr Ser
 1325                1330                1335

Thr Lys Glu Val Leu Asp Ala Thr Leu Ile His Gln Ser Ile Thr
 1340                1345                1350

Gly Leu Tyr Glu Thr Arg Ile Asp Leu Ser Gln Leu Gly Gly Asp
 1355                1360                1365

<210> SEQ ID NO 2
<211> LENGTH: 4332
<212> TYPE: DNA
<213> ORGANISM: Artificial
<220> FEATURE:
<223> OTHER INFORMATION: VP64-activator construct

<400> SEQUENCE: 2

```
gccaccatgg acaagaagta ctccattggg ctcgctatcg gcacaaacag cgtcggctgg    60
gccgtcatta cggacgagta caaggtgccg agcaaaaaat tcaaagttct gggcaatacc   120
gatcgccaca gcataaagaa gaacctcatt ggcgccctcc tgttcgactc cggggagacg   180
gccgaagcca cgcggctcaa aagaacagca cggcgcagat atacccgcag aaagaatcgg   240
atctgctacc tgcaggagat ctttagtaat gagatggcta aggtggatga ctctttcttc   300
cataggctgg aggagtcctt tttggtggag gaggataaaa agcacgagcg ccacccaatc   360
tttggcaata tcgtggacga ggtggcgtac catgaaaagt acccaaccat atatcatctg   420
aggaagaagc ttgtagacag tactgataag gctgacttgc ggttgatcta tctcgcgctg   480
```

```
gcgcatatga tcaaatttcg gggacacttc ctcatcgagg gggacctgaa cccagacaac    540
agcgatgtcg acaaactctt tatccaactg gttcagactt acaatcagct tttcgaagag    600
aacccgatca acgcatccgg agttgacgcc aaagcaatcc tgagcgctag gctgtccaaa    660
tcccggcggc tcgaaaacct catcgcacag ctccctgggg agaagaagaa cggcctgttt    720
ggtaatctta tcgccctgtc actcgggctg accccaact ttaaatctaa cttcgacctg    780
gccgaagatg ccaagcttca actgagcaaa gacacctacg atgatgatct cgacaatctg    840
ctggcccaga tcggcgacca gtacgcagac cttttttttgg cggcaaagaa cctgtcagac    900
gccattctgc tgagtgatat tctgcgagtg aacacgagga tcaccaaagc tccgctgagc    960
gctagtatga tcaagcgcta tgatgagcac accaagact tgactttgct gaaggccctt   1020
gtcagacagc aactgcctga agtacaag gaaattttct tcgatcagtc taaaaatggc   1080
tacgccggat acattgacgg cggagcaagc caggaggaat tttacaaatt tattaagccc   1140
atcttggaaa aaatgacgg caccgaggag ctgctggtaa agcttaacag agaagatctg   1200
ttgcgcaaac agcgcacttt cgacaatgga agcatccccc accagattca cctgggcgaa   1260
ctgcacgcta tcctcaggcg gcaagaggat ttctacccct ttttgaaaga taacagggaa   1320
aagattgaga aaatcctcac atttcggata ccctactatg taggcccccct cgcccgggga   1380 aattccagat tcgcgtggat gactcgcaaa tcagaagaga ccatcactcc ctggaacttc   1440
gaggaagtcg tggataaggg ggcctctgcc cagtccttca tcgaaaggat gactaacttt   1500
gataaaaatc tgcctaacga aaggtgctt cctaaacact ctctgctgta cgagtacttc   1560
acagtttata acgagctcac caaggtcaaa tacgtcacag aagggatgag aaagccagca   1620
ttcctgtctg gagagcagaa gaaagctatc gtggacctcc tcttcaagac gaaccggaaa   1680
gttaccgtga acagctcaa agaagactat ttcaaaaaga ttgaatgttt cgactctgtt   1740
gaaatcagcg gagtggagga tcgcttcaac gcatccctgg gaacgtatca cgatctcctg   1800
aaaatcatta agacaagga cttcctggac aatgaggaga cgaggacat tcttgaggac   1860 attgtcctca cccttacgtt gtttgaagat agggagatga ttgaagaacg cttgaaaact   1920
tacgctcatc tcttcgacga caaagtcatg aaacagctca gaggcgccg atatacagga   1980 tgggggcggc tgtcaagaaa actgatcaat gggatccgag acaagcagag tggaaagaca   2040
atcctggatt ttcttaagtc cgatggattt gccaaccgga acttcatgca gttgatccat   2100
gatgactctc tcacctttaa ggaggacatc cagaaagcac aagtttctgg ccaggggac   2160 agtcttcacg agcacatcgc taatcttgca ggtagcccag ctatcaaaaa gggaatactg   2220
cagaccgtta aggtcgtgga tgaactcgtc aaagtaatgg aaggcataa gcccgagaat   2280 atcgttatcg agatggcccg agagaaccaa actacccaga agggacagaa gaacagtagg   2340
gaaaggatga agaggattga agagggtata aaagaactgg ggtcccaaat ccttaaggaa   2400
cacccagttg aaaacaccca gcttcagaat gagaagctct acctgtacta cctgcagaac   2460
ggcagggaca tgtacgtgga tcaggaactg gacatcaatc ggctctccga ctacgacgtg   2520
gctgctatcg tgcccagtc ttttctcaaa gatgattcta ttgataataa agtgttgaca   2580
agatccgata aagctagagg gaagagtgat aacgtcccct cagaagaagt tgtcaagaaa   2640
atgaaaaatt attggcggca gctgctgaac gccaaactga tcacacaacg gaagttcgat   2700
aatctgacta aggctgaacg aggtggcctg tctgagttgg ataaagccgg cttcatcaaa   2760
aggcagcttg ttgagacacg ccagatcacc aagcacgtgg cccaaattct cgattcacgc   2820
```

```
atgaacacca agtacgatga aaatgacaaa ctgattcgag aggtgaaagt tattactctg    2880
aagtctaagc tggtctcaga tttcagaaag gactttcagt tttataaggt gagagagatc    2940
aacaattacc accatgcgca tgatgcctac ctgaatgcag tggtaggcac tgcacttatc    3000
aaaaaatatc ccaagcttga atctgaattt gtttacggag actataaagt gtacgatgtt    3060
aggaaaatga tcgcaaagtc tgagcaggaa ataggcaagg ccaccgctaa gtacttcttt    3120
tacagcaata ttatgaattt tttcaagacc gagattacac tggccaatgg agagattcgg    3180
aagcgaccac ttatcgaaac aaacggagaa acaggagaaa tcgtgtggga caagggtagg    3240
gatttcgcga cagtccggaa ggtcctgtcc atgccgcagg tgaacatcgt taaaaagacc    3300
gaagtacaga ccggaggctt ctccaaggaa agtatcctcc cgaaaaggaa cagcgacaag    3360
ctgatcgcac gcaaaaaaga ttgggacccc aagaaatacg gcggattcga ttctcctaca    3420
gtcgcttaca gtgtactggt tgtggccaaa gtggagaaag ggaagtctaa aaaactcaaa    3480
agcgtcaagg aactgctggg catcacaatc atggagcgat caagcttcga aaaaaacccc    3540
atcgactttc tcgaggcgaa aggatataaa gaggtcaaaa aagacctcat cattaagctt    3600
cccaagtact ctctctttga gcttgaaaac ggccggaaac gaatgctcgc tagtgcgggc    3660
gagctgcaga aaggtaacga gctggcactg ccctctaaat acgttaattt cttgtatctg    3720
gccagccact atgaaaagct caaagggtct cccgaagata tgagcagaa gcagctgttc    3780 gtggaacaac acaaacacta ccttgatgag atcatcgagc aaataagcga attctccaaa    3840
agagtgatcc tcgccgacgc taacctcgat aaggtgcttt ctgcttacaa taagcacagg    3900
gataagccca tcagggagca ggcagaaaac attatccact tgtttactct gaccaacttg    3960
ggcgcgcctg cagccttcaa gtacttcgac accaccatag acagaaagcg gtacacctct    4020
acaaaggagg tcctggacgc cacactgatt catcagtcaa ttacgggct ctatgaaaca    4080 agaatcgacc tctctcagct cggtggagac agcagggctg accccaagaa gaagaggaag    4140
gtggaggcca gcggttccgg acgggctgac gcattggacg atttgatct ggatatgctg    4200 ggaagtgacg ccctcgatga ttttgacctt gacatgcttg gttcggatgc ccttgatgac    4260
tttgacctcg acatgctcgg cagtgacgcc cttgatgatt tcgacctgga catgctgatt    4320
aactctagat ga                                                        4332
```

<210> SEQ ID NO 3
<211> LENGTH: 4365
<212> TYPE: DNA
<213> ORGANISM: Artificial
<220> FEATURE:
<223> OTHER INFORMATION: VP64-activator construct

<400> SEQUENCE: 3

```
gccaccatgc ccaagaagaa gaggaaggtg gaaggggga tggacaagaa gtactccatt     60
gggctcgcta tcggcacaaa cagcgtcggc tgggccgtca ttacgacga gtacaaggtg    120 ccgagcaaaa aattcaaagt tctgggcaat accgatcgcc acagcataaa gaagaacctc    180
attggcgccc tcctgttcga ctccggggag acggccgaag ccacgcggct caaaagaaca    240
gcacggcgca gatatacccg cagaaagaat cggatctgct acctgcagga gatctttagt    300
aatgagatgg ctaaggtgga tgactctttc ttccataggc tggaggagtc cttttggtg    360 gaggaggata aaaagcacga gcgccaccca atctttggca atatcgtgga cgaggtggcg    420
taccatgaaa agtacccaac catatatcat ctgaggaaga agcttgtaga cagtactgat    480
aaggctgact tgcggttgat ctatctcgcg ctggcgcata tgatcaaatt cggggacac    540
```

```
ttcctcatcg agggggacct gaacccagac aacagcgatg tcgacaaact ctttatccaa      600
ctggttcaga cttacaatca gcttttcgaa gagaacccga tcaacgcatc cggagttgac      660
gccaaagcaa tcctgagcgc taggctgtcc aaatcccggc ggctcgaaaa cctcatcgca      720
cagctccctg gggagaagaa gaacggcctg tttggtaatc ttatcgccct gtcactcggg      780
ctgaccccca actttaaatc taacttcgac ctggccgaag atgccaagct tcaactgagc      840
aaagacacct acgatgatga tctcgacaat ctgctggccc agatcggcga ccagtacgca      900 gaccttttt tggcggcaaa gaacctgtca gacgccattc tgctgagtga tattctgcga       960
gtgaacacgg agatcaccaa agctccgctg agcgctagta tgatcaagcg ctatgatgag     1020
caccaccaag acttgacttt gctgaaggcc cttgtcagac agcaactgcc tgagaagtac     1080
aaggaaattt tcttcgatca gtctaaaaat ggctacgccg gatacattga cggcggagca     1140
agccaggagg aattttacaa atttattaag cccatcttgg aaaaaatgga cggcaccgag     1200
gagctgctgg taaagcttaa cagagaagat ctgttgcgca acagcgcac tttcgacaat      1260 ggaagcatcc cccaccagat tcacctgggc gaactgcacg ctatcctcag gcggcaagag     1320
gatttctacc ccttttttgaa agataacagg gaaaagattg agaaaatcct cacatttcgg     1380
atacgctact atgtaggccc cctcgcccgg ggaaattcca gattcgcgtg gatgactcgc     1440
aaatcagaag agaccatcac tccctggaac ttcgaggaag tcgtggataa ggggcctct      1500 gcccagtcct tcatcgaaag gatgactaac tttgataaaa atctgcctaa cgaaaaggtg     1560
cttcctaaac actctctgct gtacgagtac ttcacagttt ataacgagct caccaaggtc     1620
aaatacgtca cagaagggat gagaaagcca gcattcctgt ctggagagca aagaaaagct     1680
atcgtggacc tcctcttcaa gacgaaccgg aaagttaccg tgaaacagct caaagaagac     1740
tatttcaaaa agattgaatg tttcgactct gttgaaatca gcggagtgga ggatcgcttc     1800
aacgcatccc tgggaacgta tcacgatctc ctgaaaatca ttaaagacaa ggacttcctg     1860
gacaatgagg agaacgagga cattcttgag gacattgtcc tcacccttac gttgtttgaa     1920
gatagggaga tgattgaaga acgcttgaaa acttacgctc atctcttcga cgacaaagtc     1980
atgaaacagc tcaagaggcg ccgatataca ggatggggc ggctgtcaag aaaactgatc      2040
aatgggatcc gagacaagca gagtggaaag acaatcctgg attttcttaa gtccgatgga     2100
tttgccaacc ggaacttcat gcagttgatc catgatgact ctctcacctt taaggaggac     2160
atccagaaag cacaagtttc tggccagggg gacagtcttc acgagcacat cgctaatctt     2220
gcaggtagcc cagctatcaa aaagggaata ctgcagaccg ttaaggtcgt ggatgaactc     2280
gtcaaagtaa tgggaaggca taagcccgag aatatcgtta tcgagatggc ccgagagaac     2340
caaactaccc agaagggaca gaagaacagt agggaaagga tgaagaggat tgaagagggt     2400
ataaaagaac tggggtccca aatccttaag gaacacccag ttgaaaacac ccagcttcag     2460
aatgagaagc tctacctgta ctacctgcag aacggcaggg acatgtacgt ggatcaggaa     2520
ctggacatca atcggctctc cgactacgac gtggctgcta tcgtgcccca gtcttttctc     2580
aaagatgatt ctattgataa taaagtgttg acaagatccg ataaagctag agggaagagt     2640
gataacgtcc cctcagaaga agttgtcaag aaaatgaaaa attattggcg gcagctgctg     2700
aacgccaaac tgatcacaca acggaagttc gataatctga ctaaggctga acgaggtggc     2760
ctgtctgagt tggataaagc cggcttcatc aaaaaggcagc ttgttgagac acgccagatc     2820
accaagcacg tggcccaaat tctcgattca cgcatgaaca ccaagtacga tgaaaatgac     2880
```

| | |
|---|---|
| aaactgattc gagaggtgaa agttattact ctgaagtcta agctggtctc agatttcaga | 2940 |
| aaggactttc agttttataa ggtgagagag atcaacaatt accaccatgc gcatgatgcc | 3000 |
| tacctgaatg cagtggtagg cactgcactt atcaaaaaat atcccaagct tgaatctgaa | 3060 |
| tttgtttacg gagactataa agtgtacgat gttaggaaaa tgatcgcaaa gtctgagcag | 3120 |
| gaaataggca aggccaccgc taagtacttc ttttacagca atattatgaa ttttttcaag | 3180 |
| accgagatta cactgccaa tggagagatt cggaagcgac cacttatcga aacaaacgga | 3240 |
| gaaacaggag aaatcgtgtg ggacaagggt agggatttcg cgacagtccg aaggtcctg | 3300 |
| tccatgccgc aggtgaacat cgttaaaaag accgaagtac agaccggagg cttctccaag | 3360 |
| gaaagtatcc tcccgaaaag gaacagcgac aagctgatcg cacgcaaaaa agattgggac | 3420 |
| cccaagaaat acggcggatt cgattctcct acagtcgctt acagtgtact ggttgtggcc | 3480 |
| aaagtggaga aagggaagtc taaaaaactc aaaagcgtca aggaactgct gggcatcaca | 3540 |
| atcatggagc gatcaagctt cgaaaaaaac cccatcgact ttctcgaggc gaaaggatat | 3600 |
| aaagaggtca aaaagacct catcattaag cttcccaagt actctctctt tgagcttgaa | 3660 |
| aacggccgga aacgaatgct cgctagtgcg ggcgagctgc agaaaggtaa cgagctggca | 3720 |
| ctgccctcta aatacgttaa tttcttgtat ctggccagcc actatgaaaa gctcaaaggg | 3780 |
| tctcccgaag ataatgagca gaagcagctg ttcgtggaac aacacaaaca ctaccttgat | 3840 |
| gagatcatcg agcaaataag cgaattctcc aaaagagtga tcctcgccga cgctaacctc | 3900 |
| gataaggtgc tttctgctta caataagcac agggataagc ccatcaggga gcaggcagaa | 3960 |
| aacattatcc acttgtttac tctgaccaac ttgggcgcgc ctgcagcctt caagtacttc | 4020 |
| gacaccacca tagacagaaa gcggtacacc tctacaaagg aggtcctgga cgccacactg | 4080 |
| attcatcagt caattacggg gctctatgaa acaagaatcg acctctctca gctcggtgga | 4140 |
| gacagcaggg ctgaccccaa gaagaagagg aaggtggagg ccagcggttc cggacgggct | 4200 |
| gacgcattgg acgattttga tctggatatg ctggaagtg acgccctcga tgattttgac | 4260 |
| cttgacatgc ttggttcgga tgcccttgat gactttgacc tcgacatgct cggcagtgac | 4320 |
| gcccttgatg atttcgacct ggacatgctg attaactcta gatga | 4365 |

<210> SEQ ID NO 4
<211> LENGTH: 4425
<212> TYPE: DNA
<213> ORGANISM: Artificial
<220> FEATURE:
<223> OTHER INFORMATION: VP64-activator construct

<400> SEQUENCE: 4

| | |
|---|---|
| gccaccatgg acaagaagta ctccattggg ctcgctatcg gcacaaacag cgtcggctgg | 60 |
| gccgtcatta cggacgagta caaggtgccg agcaaaaaat tcaaagttct gggcaatacc | 120 |
| gatcgccaca gcataaagaa gaacctcatt ggcgccctcc tgttcgactc cggggagacg | 180 |
| gccgaagcca cgcggctcaa aagaacagca cggcgcagat atacccgcag aaagaatcgg | 240 |
| atctgctacc tgcaggagat ctttagtaat gagatggcta aggtggatga ctctttcttc | 300 |
| cataggctgg aggagtcctt tttggtggag gaggataaaa agcacgagcg ccacccaatc | 360 |
| tttggcaata tcgtggacga ggtggcgtac catgaaaagt acccaaccat atatcatctg | 420 |
| aggaagaagc ttgtagacag tactgataag gctgacttgc ggttgatcta tctcgcgctg | 480 |
| gcgcatatga tcaaatttcg gggacacttc ctcatcgagg gggacctgaa cccagacaac | 540 |
| agcgatgtcg acaaactctt tatccaactg gttcagactt acaatcagct tttcgaagag | 600 |

```
aacccgatca acgcatccgg agttgacgcc aaagcaatcc tgagcgctag gctgtccaaa    660
tcccggcggc tcgaaaacct catcgcacag ctccctgggg agaagaagaa cggcctgttt    720
ggtaatctta tcgccctgtc actcgggctg accccccaact ttaaatctaa cttcgacctg    780
gccgaagatg ccaagcttca actgagcaaa gacacctacg atgatgatct cgacaatctg    840
ctggcccaga tcggcgacca gtacgcagac ctttttttgg cggcaaagaa cctgtcagac    900
gccattctgc tgagtgatat tctgcgagtg aacacggaga tcaccaaagc tccgctgagc    960
gctagtatga tcaagcgcta tgatgagcac caccaagact tgactttgct gaaggccctt   1020
gtcagacagc aactgcctga gaagtacaag gaaattttct tcgatcagtc taaaaatggc   1080
tacgccggat acattgacgg cggagcaagc caggaggaat tttacaaatt tattaagccc   1140
atcttggaaa aaatggacgg caccgaggag ctgctggtaa agcttaacag agaagatctg   1200
ttgcgcaaac agcgcacttt cgacaatgga agcatccccc accagattca cctgggcgaa   1260
ctgcacgcta tcctcaggcg gcaagaggat ttctacccct ttttgaaaga taacagggaa   1320
aagattgaga aaatcctcac atttcggata ccctactatg taggccccct cgcccgggga   1380
aattccagat tcgcgtggat gactcgcaaa tcagaagaga ccatcactcc ctggaacttc   1440
gaggaagtcg tggataaggg ggcctctgcc cagtccttca tcgaaaggat gactaacttt   1500
gataaaaatc tgcctaacga aaaggtgctt cctaaacact ctctgctgta cgagtacttc   1560
acagtttata acgagctcac caaggtcaaa tacgtcacag aagggatgag aaagccagca   1620
ttcctgtctg gagagcagaa gaaagctatc gtggacctcc tcttcaagac gaaccggaaa   1680
gttaccgtga acagctcaa agaagactat ttcaaaaaga ttgaatgttt cgactctgtt   1740
gaaatcagcg gagtggagga tcgcttcaac gcatccctgg gaacgtatca cgatctcctg   1800
aaaatcatta agacaagga cttcctggac aatgaggaga cgaggacat tcttgaggac   1860 attgtcctca cccttacgtt gtttgaagat agggagatga ttgaagaacg cttgaaaact   1920
tacgctcatc tcttcgacga caaagtcatg aaacagctca gaggcgccg atatacagga   1980 tgggggcggc tgtcaagaaa actgatcaat gggatccgag acaagcagag tggaaagaca   2040
atcctggatt ttcttaagtc cgatggattt gccaaccgga acttcatgca gttgatccat   2100
gatgactctc tcacctttaa ggaggacatc cagaaagcac aagtttctgg ccagggggac   2160
agtcttcacg agcacatcgc taatcttgca ggtagcccag ctatcaaaaa gggaatactg   2220
cagaccgtta aggtcgtgga tgaactcgtc aaagtaatgg aaggcataa gcccgagaat   2280 atcgttatcg agatggcccg agagaaccaa actacccaga agggacagaa gaacagtagg   2340
gaaaggatga agaggattga agagggtata aaagaactgg ggtcccaaat ccttaaggaa   2400
cacccagttg aaaacaccca gcttcagaat gagaagctct acctgtacta cctgcagaac   2460
ggcagggaca tgtacgtgga tcaggaactg gacatcaatc ggctctccga ctacgacgtg   2520
gctgctatcg tgcccagtc ttttctcaaa gatgattcta ttgataataa agtgttgaca   2580
agatccgata aagctagagg gaagagtgat aacgtccct cagaagaagt tgtcaagaaa   2640
atgaaaaatt attggcggca gctgctgaac gccaaactga tcacacaacg gaagttcgat   2700
aatctgacta aggctgaacg aggtggcctg tctgagttgg ataaagccgg cttcatcaaa   2760
aggcagcttg ttgagacacg ccagatcacc aagcacgtgg cccaaattct cgattcacgc   2820
atgaacacca gtacgatga aaatgacaaa ctgattcgag aggtgaaagt tattactctg   2880
aagtctaagc tggtctcaga tttcagaaag gactttcagt tttataaggt gagagagatc   2940
```

```
aacaattacc accatgcgca tgatgcctac ctgaatgcag tggtaggcac tgcacttatc    3000
aaaaaatatc ccaagcttga atctgaattt gtttacggag actataaagt gtacgatgtt    3060
aggaaaatga tcgcaaagtc tgagcaggaa ataggcaagg ccaccgctaa gtacttcttt    3120
tacagcaata ttatgaattt tttcaagacc gagattacac tggccaatgg agagattcgg    3180
aagcgaccac ttatcgaaac aaacggagaa acaggagaaa tcgtgtggga caagggtagg    3240
gatttcgcga cagtccggaa ggtcctgtcc atgccgcagg tgaacatcgt taaaaagacc    3300
gaagtacaga ccggaggctt ctccaaggaa agtatcctcc cgaaaggaa cagcgacaag    3360 ctgatcgcac gcaaaaaga ttgggacccc aagaaatacg gcggattcga ttctcctaca    3420
gtcgcttaca gtgtactggt tgtggccaaa gtggagaaag ggaagtctaa aaaactcaaa    3480
agcgtcaagg aactgctggg catcacaatc atggagcgat caagcttcga aaaaaacccc    3540
atcgactttc tcgaggcgaa aggatataaa gaggtcaaaa aagacctcat cattaagctt    3600
cccaagtact ctctctttga gcttgaaaac ggccggaaac gaatgctcgc tagtgcgggc    3660
gagctgcaga aaggtaacga gctggcactg ccctctaaat acgttaattt cttgtatctg    3720
gccagccact atgaaaagct caaagggtct cccgaagata tgagcagaa gcagctgttc    3780 gtggaacaac acaaacacta ccttgatgag atcatcgagc aaataagcga attctccaaa    3840
agagtgatcc tcgccgacgc taacctcgat aaggtgcttt ctgcttacaa taagcacagg    3900
gataagccca tcagggagca ggcagaaaac attatccact tgtttactct gaccaacttg    3960
ggcgcgcctg cagccttcaa gtacttcgac accaccatag acagaaagcg gtacacctct    4020
acaaaggagg tcctggacgc cacactgatt catcagtcaa ttacgggct ctatgaaaca    4080 agaatcgacc tctctcagct cggtggagac agcagggctg accccaagaa gaagaggaag    4140
gtggaggcca gcggttccgg acgggctgac gcattggacg atttttgatct ggatatgctg    4200 ggaagtgacg ccctcgatga ttttgacctt gacatgcttg gttcggatgc ccttgatgac    4260
tttgacctcg acatgctcgg cagtgacgcc cttgatgatt tcgacctgga catgctgatt    4320
aactctagag cggccgcaga tccaaaaaag aagagaaagg tagatccaaa aaagaagaga    4380
aaggtagatc caaaaaagaa gagaaaggta gatacggccg catag                   4425
```

<210> SEQ ID NO 5
<211> LENGTH: 587
<212> TYPE: DNA
<213> ORGANISM: Artificial
<220> FEATURE:
<223> OTHER INFORMATION: MS2-activator construct

<400> SEQUENCE: 5

```
ccaccatggg acctaagaaa aagaggaagg tggcggccgc ttctagaatg gcttctaact      60
ttactcagtt cgttctcgtc gacaatggcg gaactggcga cgtgactgtc gccccaagca     120
acttcgctaa cgggatcgct gaatggatca gctctaactc gcgttcacag gcttacaaag     180
taacctgtag cgttcgtcag agctctgcgc agaatcgcaa atacaccatc aaagtcgagg     240
tgcctaaagg cgcctggcgt tcgtacttaa atatggaact aaccattcca attttcgcca     300
cgaattccga ctgcgagctt attgttaagg caatgcaagg tctcctaaaa gatgaaaacc     360
cgattccctc agcaatcgca gcaaactccg gcatctacga ggccagcggt tccggacggg     420
ctgacgcatt ggacgatttt gatctggata tgctggaag tgacgccctc gatgattttg     480
accttgacat gcttggttcg gatgcccttg atgactttga cctcgacatg ctcggcagtg     540
acgcccttga tgatttcgac ctggacatgc tgattaactc tagatga                   587
```

<210> SEQ ID NO 6
<211> LENGTH: 681
<212> TYPE: DNA
<213> ORGANISM: Artificial
<220> FEATURE:
<223> OTHER INFORMATION: MS2-activator construct

<400> SEQUENCE: 6

```
gccaccatgg gacctaagaa aaagaggaag gtggcggccg cttctagaat ggcttctaac      60
tttactcagt tcgttctcgt cgacaatggc ggaactggcg acgtgactgt cgccccaagc     120
aacttcgcta acgggatcgc tgaatggatc agctctaact cgcgttcaca ggcttacaaa     180
gtaacctgta gcgttcgtca gagctctgcg cagaatcgca atacaccat caaagtcgag      240
gtgcctaaag gcgcctggcg ttcgtactta aatatggaac taaccattcc aattttcgcc     300
acgaattccg actgcgagct tattgttaag gcaatgcaag gtctcctaaa agatggaaac     360
ccgattccct cagcaatcgc agcaaactcc ggcatctacg aggccagcgg ttccggacgg     420
gctgacgcat tggacgattt tgatctggat atgctgggaa gtgacgccct cgatgatttt     480
gaccttgaca tgcttggttc ggatgccctt gatgactttg acctcgacat gctcggcagt     540
gacgcccttg atgatttcga cctggacatg ctgattaact ctagagcggc cgcagatcca     600
aaaaagaaga gaaaggtaga tccaaaaaag aagagaaagg tagatccaaa aaagaagaga     660
aaggtagata cggccgcata g                                               681
```

<210> SEQ ID NO 7
<211> LENGTH: 557
<212> TYPE: DNA
<213> ORGANISM: Artificial
<220> FEATURE:
<223> OTHER INFORMATION: MS2-activator construct
<220> FEATURE:
<221> NAME/KEY: misc_feature
<222> LOCATION: (320)..(339)
<223> OTHER INFORMATION: wherein N is G, A, T or C

<400> SEQUENCE: 7

```
tgtacaaaaa agcaggcttt aaaggaacca attcagtcga ctggatccgg taccaaggtc      60
gggcaggaag agggcctatt tcccatgatt ccttcatatt tgcatatacg atacaaggct     120
gttagagaga taattagaat taatttgact gtaaacacaa agatattagt acaaaatacg     180
tgacgtagaa agtaataatt tcttgggtag tttgcagttt taaaattatg ttttaaaatg     240
gactatcata tgcttaccgt aacttgaaag tatttcgatt tcttggcttt atatatcttg     300
tggaaaggac gaaacaccgn nnnnnnnnn nnnnnnnnng ttttagagct agaaatagca     360
agttaaaata aggctagtcc gttatcaact tgaaaaagtg gcaccgagtc ggtgctctgc     420
aggtcgactc tagaaaacat gaggatcacc catgtctgca gtattcccgg gttcattaga     480
tcctaaggta cctaattgcc tagaaaacat gaggatcacc catgtctgca ggtcgactct     540
agaaattttt tctagac                                                   557
```

<210> SEQ ID NO 8
<211> LENGTH: 882
<212> TYPE: DNA
<213> ORGANISM: Artificial
<220> FEATURE:
<223> OTHER INFORMATION: Activation reporter construct

<400> SEQUENCE: 8

```
tagggataac agggtaatag tgtcccctcc accccacagt ggggcgaggt aggcgtgtac      60
ggtgggaggc ctatataagc agagctcgtt tagtgaaccg tcagatcgcc tggagaattc     120
gccaccatgg actacaagga tgacgacgat aaaacttccg gtggcggact gggttccacc     180
gtgagcaagg gcgaggaggt catcaaagag ttcatgcgct tcaaggtgcg catggagggc     240
tccatgaacg gccacgagtt cgagatcgag ggcgagggcg agggccgccc ctacgagggc     300
acccagaccg ccaagctgaa ggtgaccaag ggcggccccc tgcccttcgc ctgggacatc     360
ctgtcccccc agttcatgta cggctccaag gcgtacgtga agcaccccgc cgacatcccc     420
gattacaaga agctgtcctt ccccgagggc ttcaagtggg agcgcgtgat gaacttcgag     480
gacggcggtc tggtgaccgt gacccaggac tcctccctgc aggacggcac gctgatctac     540
aaggtgaaga tgcgcggcac caacttcccc cccgacggcc ccgtaatgca gaagaagacc     600
atgggctggg aggcctccac cgagcgcctg taccccgcg acggcgtgct gaagggcgag      660
atccaccagg ccctgaagct gaaggacggc ggccactacc tggtggagtt caagaccatc     720
tacatggcca agaagcccgt gcaactgccc ggctactact acgtggacac caagctggac     780
atcacctccc acaacgagga ctacaccatc gtggaacagt acgagcgctc cgagggccgc     840
caccacctgt tcctgtacgg catggacgag ctgtacaagt aa                         882
```

<210> SEQ ID NO 9
<211> LENGTH: 882
<212> TYPE: DNA
<213> ORGANISM: Artificial
<220> FEATURE:
<223> OTHER INFORMATION: Activation reporter construct

<400> SEQUENCE: 9

```
tagggataac agggtaatag tgggggccact agggacagga ttggcgaggt aggcgtgtac     60
ggtgggaggc ctatataagc agagctcgtt tagtgaaccg tcagatcgcc tggagaattc    120
gccaccatgg actacaagga tgacgacgat aaaacttccg gtggcggact gggttccacc    180
gtgagcaagg gcgaggaggt catcaaagag ttcatgcgct tcaaggtgcg catggagggc    240
tccatgaacg gccacgagtt cgagatcgag ggcgagggcg agggccgccc ctacgagggc    300
acccagaccg ccaagctgaa ggtgaccaag ggcggccccc tgcccttcgc ctgggacatc    360
ctgtcccccc agttcatgta cggctccaag gcgtacgtga agcaccccgc cgacatcccc    420
gattacaaga agctgtcctt ccccgagggc ttcaagtggg agcgcgtgat gaacttcgag    480
gacggcggtc tggtgaccgt gacccaggac tcctccctgc aggacggcac gctgatctac    540
aaggtgaaga tgcgcggcac caacttcccc cccgacggcc ccgtaatgca gaagaagacc    600
atgggctggg aggcctccac cgagcgcctg taccccgcg acggcgtgct gaagggcgag     660
atccaccagg ccctgaagct gaaggacggc ggccactacc tggtggagtt caagaccatc    720
tacatggcca agaagcccgt gcaactgccc ggctactact acgtggacac caagctggac    780
atcacctccc acaacgagga ctacaccatc gtggaacagt acgagcgctc cgagggccgc    840
caccacctgt tcctgtacgg catggacgag ctgtacaagt aa                        882
```

<210> SEQ ID NO 10
<211> LENGTH: 912
<212> TYPE: DNA
<213> ORGANISM: Artificial
<220> FEATURE:
<223> OTHER INFORMATION: Specificity reporter library
<220> FEATURE:
<221> NAME/KEY: misc_feature

```
<222> LOCATION: (22)..(44)
<223> OTHER INFORMATION: wherein N is G, A, T or C
<220> FEATURE:
<221> NAME/KEY: misc_feature
<222> LOCATION: (154)..(177)
<223> OTHER INFORMATION: wherein N is G, A, T or C

<400> SEQUENCE: 10
tagggataac agggtaatag tnnnnnnnnn nnnnnnnnnn nnnncgaggt aggcgtgtac      60
ggtgggaggc ctatataagc agagctcgtt tagtgaaccg tcagatcgcc tggagaattc     120
gccaccatgg actacaagga tgacgacgat aaannnnnnn nnnnnnnnnn nnnnnnnact     180
tccggtggcg gactgggttc caccgtgagc aagggcgagg aggtcatcaa agagttcatg     240
cgcttcaagg tgcgcatgga gggctccatg aacggccacg agttcgagat cgagggcgag     300
ggcgagggcc gcccctacga gggcacccag accgccaagc tgaaggtgac caagggcggc     360
cccctgccct cgcctggga catcctgtcc ccccagttca tgtacggctc caaggcgtac     420
gtgaagcacc ccgccgacat ccccgattac aagaagctgt ccttccccga gggcttcaag     480
tgggagcgcg tgatgaactt cgaggacggc ggtctggtga ccgtgaccca ggactcctcc     540
ctgcaggacg gcacgctgat ctacaaggtg aagatgcgcg gcaccaactt cccccccgac     600
ggccccgtaa tgcagaagaa gaccatgggc tgggaggcct ccaccgagcg cctgtacccc     660
cgcgacggcg tgctgaaggg cgagatccac caggccctga gctgaaggca ggcggccac      720
tacctggtgg agttcaagac catctacatg gccaagaagc ccgtgcaact gcccggctac     780
tactacgtgg acaccaagct ggacatcacc tcccacaacg aggactacac catcgtggaa     840
cagtacgagc gctccgaggg ccgccaccac ctgttcctgt acggcatgga cgagctgtac     900
aagtaagaat tc                                                         912

<210> SEQ ID NO 11
<211> LENGTH: 23
<212> TYPE: DNA
<213> ORGANISM: Artificial
<220> FEATURE:
<223> OTHER INFORMATION: Target probe

<400> SEQUENCE: 11
ctggcggatc actcgcggtt agg                                              23

<210> SEQ ID NO 12
<211> LENGTH: 23
<212> TYPE: DNA
<213> ORGANISM: Artificial
<220> FEATURE:
<223> OTHER INFORMATION: Target probe

<400> SEQUENCE: 12
cctcggcctc caaaagtgct agg                                              23

<210> SEQ ID NO 13
<211> LENGTH: 23
<212> TYPE: DNA
<213> ORGANISM: Artificial
<220> FEATURE:
<223> OTHER INFORMATION: Target probe

<400> SEQUENCE: 13
acgctgattc ctgcagatca ggg                                              23

<210> SEQ ID NO 14
```

```
<211> LENGTH: 23
<212> TYPE: DNA
<213> ORGANISM: Artificial
<220> FEATURE:
<223> OTHER INFORMATION: Target probe

<400> SEQUENCE: 14
ccaggaatac gtatccacca ggg                                              23

<210> SEQ ID NO 15
<211> LENGTH: 23
<212> TYPE: DNA
<213> ORGANISM: Artificial
<220> FEATURE:
<223> OTHER INFORMATION: Target probe

<400> SEQUENCE: 15
gccacaccca agcgatcaaa tgg                                              23

<210> SEQ ID NO 16
<211> LENGTH: 23
<212> TYPE: DNA
<213> ORGANISM: Artificial
<220> FEATURE:
<223> OTHER INFORMATION: Target probe

<400> SEQUENCE: 16
aaataataca ttctaaggta agg                                              23

<210> SEQ ID NO 17
<211> LENGTH: 23
<212> TYPE: DNA
<213> ORGANISM: Artificial
<220> FEATURE:
<223> OTHER INFORMATION: Target probe

<400> SEQUENCE: 17
gctactgggg aggctgaggc agg                                              23

<210> SEQ ID NO 18
<211> LENGTH: 23
<212> TYPE: DNA
<213> ORGANISM: Artificial
<220> FEATURE:
<223> OTHER INFORMATION: Target probe

<400> SEQUENCE: 18
tagcaataca gtcacattaa tgg                                              23

<210> SEQ ID NO 19
<211> LENGTH: 23
<212> TYPE: DNA
<213> ORGANISM: Artificial
<220> FEATURE:
<223> OTHER INFORMATION: Target probe

<400> SEQUENCE: 19
ctcatgtgat cccccogtct cgg                                              23

<210> SEQ ID NO 20
<211> LENGTH: 23
<212> TYPE: DNA
<213> ORGANISM: Artificial
<220> FEATURE:
<223> OTHER INFORMATION: Target probe

<400> SEQUENCE: 20
```

-continued ccgggcagag agtgaacgcg cgg                                              23

<210> SEQ ID NO 21
<211> LENGTH: 23
<212> TYPE: DNA
<213> ORGANISM: Artificial
<220> FEATURE:
<223> OTHER INFORMATION: Target probe

<400> SEQUENCE: 21
ttccttccct ctcccgtgct tgg                                              23

<210> SEQ ID NO 22
<211> LENGTH: 23
<212> TYPE: DNA
<213> ORGANISM: Artificial
<220> FEATURE:
<223> OTHER INFORMATION: Target probe

<400> SEQUENCE: 22
tctctgcaaa gcccctggag agg                                              23

<210> SEQ ID NO 23
<211> LENGTH: 23
<212> TYPE: DNA
<213> ORGANISM: Artificial
<220> FEATURE:
<223> OTHER INFORMATION: Target probe

<400> SEQUENCE: 23
aatgcagttg ccgagtgcag tgg                                              23

<210> SEQ ID NO 24
<211> LENGTH: 23
<212> TYPE: DNA
<213> ORGANISM: Artificial
<220> FEATURE:
<223> OTHER INFORMATION: Target probe

<400> SEQUENCE: 24
cctcagcctc ctaaagtgct ggg                                              23

<210> SEQ ID NO 25
<211> LENGTH: 23
<212> TYPE: DNA
<213> ORGANISM: Artificial
<220> FEATURE:
<223> OTHER INFORMATION: Target probe

<400> SEQUENCE: 25
gagtccaaat cctctttact agg                                              23

<210> SEQ ID NO 26
<211> LENGTH: 23
<212> TYPE: DNA
<213> ORGANISM: Artificial
<220> FEATURE:
<223> OTHER INFORMATION: Target probe

<400> SEQUENCE: 26
gagtgtctgg atttgggata agg                                              23

<210> SEQ ID NO 27
<211> LENGTH: 23
<212> TYPE: DNA

```
<213> ORGANISM: Artificial
<220> FEATURE:
<223> OTHER INFORMATION: Target probe

<400> SEQUENCE: 27
cagcacctca tctcccagtg agg                                         23

<210> SEQ ID NO 28
<211> LENGTH: 23
<212> TYPE: DNA
<213> ORGANISM: Artificial
<220> FEATURE:
<223> OTHER INFORMATION: Target probe

<400> SEQUENCE: 28
tctaaaaccc agggaatcat ggg                                         23

<210> SEQ ID NO 29
<211> LENGTH: 23
<212> TYPE: DNA
<213> ORGANISM: Artificial
<220> FEATURE:
<223> OTHER INFORMATION: Target probe

<400> SEQUENCE: 29
cacaaggcag ccagggatcc agg                                         23

<210> SEQ ID NO 30
<211> LENGTH: 23
<212> TYPE: DNA
<213> ORGANISM: Artificial
<220> FEATURE:
<223> OTHER INFORMATION: Target probe

<400> SEQUENCE: 30
gatggcaagc tgagaaacac tgg                                         23

<210> SEQ ID NO 31
<211> LENGTH: 23
<212> TYPE: DNA
<213> ORGANISM: Artificial
<220> FEATURE:
<223> OTHER INFORMATION: Target probe

<400> SEQUENCE: 31
tgaaatgcac gcatacaatt agg                                         23

<210> SEQ ID NO 32
<211> LENGTH: 23
<212> TYPE: DNA
<213> ORGANISM: Artificial
<220> FEATURE:
<223> OTHER INFORMATION: Target probe

<400> SEQUENCE: 32
ccagtccaga cctggccttc tgg                                         23

<210> SEQ ID NO 33
<211> LENGTH: 23
<212> TYPE: DNA
<213> ORGANISM: Artificial
<220> FEATURE:
<223> OTHER INFORMATION: Target probe

<400> SEQUENCE: 33
cccagaaaaa cagaccctga agg                                         23
```

<210> SEQ ID NO 34
<211> LENGTH: 23
<212> TYPE: DNA
<213> ORGANISM: Artificial
<220> FEATURE:
<223> OTHER INFORMATION: Target probe

<400> SEQUENCE: 34
aagggttgag cacttgttta ggg                                              23

<210> SEQ ID NO 35
<211> LENGTH: 23
<212> TYPE: DNA
<213> ORGANISM: Artificial
<220> FEATURE:
<223> OTHER INFORMATION: Target probe

<400> SEQUENCE: 35
atgtctgagt tttggttgag agg                                              23

<210> SEQ ID NO 36
<211> LENGTH: 23
<212> TYPE: DNA
<213> ORGANISM: Artificial
<220> FEATURE:
<223> OTHER INFORMATION: Target probe

<400> SEQUENCE: 36
ggtcccttga aggggaagta ggg                                              23

<210> SEQ ID NO 37
<211> LENGTH: 23
<212> TYPE: DNA
<213> ORGANISM: Artificial
<220> FEATURE:
<223> OTHER INFORMATION: Target probe

<400> SEQUENCE: 37
tggcagtcta ctcttgaaga tgg                                              23

<210> SEQ ID NO 38
<211> LENGTH: 23
<212> TYPE: DNA
<213> ORGANISM: Artificial
<220> FEATURE:
<223> OTHER INFORMATION: Target probe

<400> SEQUENCE: 38
ggcacagtgc cagaggtctg tgg                                              23

<210> SEQ ID NO 39
<211> LENGTH: 23
<212> TYPE: DNA
<213> ORGANISM: Artificial
<220> FEATURE:
<223> OTHER INFORMATION: Target probe

<400> SEQUENCE: 39
taaaaataaa aaaactaaca ggg                                              23

<210> SEQ ID NO 40
<211> LENGTH: 23
<212> TYPE: DNA
<213> ORGANISM: Artificial
<220> FEATURE:

-continued

<223> OTHER INFORMATION: Target probe

<400> SEQUENCE: 40
tctgtggggg acctgcactg agg    23

<210> SEQ ID NO 41
<211> LENGTH: 23
<212> TYPE: DNA
<213> ORGANISM: Artificial
<220> FEATURE:
<223> OTHER INFORMATION: Target probe

<400> SEQUENCE: 41
ggccagaggt caaggctagt ggg    23

<210> SEQ ID NO 42
<211> LENGTH: 23
<212> TYPE: DNA
<213> ORGANISM: Artificial
<220> FEATURE:
<223> OTHER INFORMATION: Target probe

<400> SEQUENCE: 42
cacgaccgaa acccttctta cgg    23

<210> SEQ ID NO 43
<211> LENGTH: 23
<212> TYPE: DNA
<213> ORGANISM: Artificial
<220> FEATURE:
<223> OTHER INFORMATION: Target probe

<400> SEQUENCE: 43
gttgaatgaa gacagtctag tgg    23

<210> SEQ ID NO 44
<211> LENGTH: 23
<212> TYPE: DNA
<213> ORGANISM: Artificial
<220> FEATURE:
<223> OTHER INFORMATION: Target probe

<400> SEQUENCE: 44
taagaacaga gcaagttacg tgg    23

<210> SEQ ID NO 45
<211> LENGTH: 23
<212> TYPE: DNA
<213> ORGANISM: Artificial
<220> FEATURE:
<223> OTHER INFORMATION: Target probe

<400> SEQUENCE: 45
tgtaaggtaa gagaggagag cgg    23

<210> SEQ ID NO 46
<211> LENGTH: 23
<212> TYPE: DNA
<213> ORGANISM: Artificial
<220> FEATURE:
<223> OTHER INFORMATION: Target probe

<400> SEQUENCE: 46
tgacacacca actcctgcac tgg    23

```
<210> SEQ ID NO 47
<211> LENGTH: 23
<212> TYPE: DNA
<213> ORGANISM: Artificial
<220> FEATURE:
<223> OTHER INFORMATION: Target probe

<400> SEQUENCE: 47
tttacccact tccttcgaaa agg                                              23

<210> SEQ ID NO 48
<211> LENGTH: 23
<212> TYPE: DNA
<213> ORGANISM: Artificial
<220> FEATURE:
<223> OTHER INFORMATION: Target probe

<400> SEQUENCE: 48
gtggctggca ggctggctct ggg                                              23

<210> SEQ ID NO 49
<211> LENGTH: 23
<212> TYPE: DNA
<213> ORGANISM: Artificial
<220> FEATURE:
<223> OTHER INFORMATION: Target probe

<400> SEQUENCE: 49
ctcccccggc ctcccccgcg cgg                                              23

<210> SEQ ID NO 50
<211> LENGTH: 23
<212> TYPE: DNA
<213> ORGANISM: Artificial
<220> FEATURE:
<223> OTHER INFORMATION: Target probe

<400> SEQUENCE: 50
caaaacccgg cagcgaggct ggg                                              23

<210> SEQ ID NO 51
<211> LENGTH: 23
<212> TYPE: DNA
<213> ORGANISM: Artificial
<220> FEATURE:
<223> OTHER INFORMATION: Target probe

<400> SEQUENCE: 51
aggagccgcc gcgcgctgat tgg                                              23

<210> SEQ ID NO 52
<211> LENGTH: 23
<212> TYPE: DNA
<213> ORGANISM: Artificial
<220> FEATURE:
<223> OTHER INFORMATION: Target probe

<400> SEQUENCE: 52
cacacacacc cacacgagat ggg                                              23

<210> SEQ ID NO 53
<211> LENGTH: 23
<212> TYPE: DNA
<213> ORGANISM: Artificial
<220> FEATURE:
<223> OTHER INFORMATION: Target probe
```

```
<400> SEQUENCE: 53
gaagaagcta aagagccaga ggg                                              23

<210> SEQ ID NO 54
<211> LENGTH: 23
<212> TYPE: DNA
<213> ORGANISM: Artificial
<220> FEATURE:
<223> OTHER INFORMATION: Target probe

<400> SEQUENCE: 54
atgagaattt caataacctc agg                                              23

<210> SEQ ID NO 55
<211> LENGTH: 23
<212> TYPE: DNA
<213> ORGANISM: Artificial
<220> FEATURE:
<223> OTHER INFORMATION: Target probe

<400> SEQUENCE: 55
tcccgctctg ttgcccaggc tgg                                              23

<210> SEQ ID NO 56
<211> LENGTH: 23
<212> TYPE: DNA
<213> ORGANISM: Artificial
<220> FEATURE:
<223> OTHER INFORMATION: Target probe

<400> SEQUENCE: 56
cagacaccca ccaccatgcg tgg                                              23

<210> SEQ ID NO 57
<211> LENGTH: 23
<212> TYPE: DNA
<213> ORGANISM: Artificial
<220> FEATURE:
<223> OTHER INFORMATION: Target probe

<400> SEQUENCE: 57
tcccaattta ctgggattac agg                                              23

<210> SEQ ID NO 58
<211> LENGTH: 23
<212> TYPE: DNA
<213> ORGANISM: Artificial
<220> FEATURE:
<223> OTHER INFORMATION: Target probe

<400> SEQUENCE: 58
tgatttaaaa gttggaaacg tgg                                              23

<210> SEQ ID NO 59
<211> LENGTH: 23
<212> TYPE: DNA
<213> ORGANISM: Artificial
<220> FEATURE:
<223> OTHER INFORMATION: Target probe

<400> SEQUENCE: 59
tctagttccc cacctagtct ggg                                              23

<210> SEQ ID NO 60
<211> LENGTH: 23
```

```
<212> TYPE: DNA
<213> ORGANISM: Artificial
<220> FEATURE:
<223> OTHER INFORMATION: Target probe

<400> SEQUENCE: 60
gattaactga gaattcacaa ggg                                              23

<210> SEQ ID NO 61
<211> LENGTH: 23
<212> TYPE: DNA
<213> ORGANISM: Artificial
<220> FEATURE:
<223> OTHER INFORMATION: Target probe

<400> SEQUENCE: 61
cgccaggagg ggtgggtcta agg                                              23

<210> SEQ ID NO 62
<211> LENGTH: 23
<212> TYPE: DNA
<213> ORGANISM: Artificial
<220> FEATURE:
<223> OTHER INFORMATION: Reporter construct

<400> SEQUENCE: 62
gtcccctcca ccccacagtg ggg                                              23

<210> SEQ ID NO 63
<211> LENGTH: 23
<212> TYPE: DNA
<213> ORGANISM: Artificial
<220> FEATURE:
<223> OTHER INFORMATION: Reporter construct

<400> SEQUENCE: 63
ggggccacta gggacaggat tgg                                              23

<210> SEQ ID NO 64
<211> LENGTH: 71
<212> TYPE: DNA
<213> ORGANISM: Artificial
<220> FEATURE:
<223> OTHER INFORMATION: Target oligonucleotide sequence

<400> SEQUENCE: 64
taatactttt atctgtcccc tccacccac agtggggcca ctaggacag gattggtgac        60 agaaaagccc c                                                           71

<210> SEQ ID NO 65
<211> LENGTH: 20
<212> TYPE: DNA
<213> ORGANISM: Artificial
<220> FEATURE:
<223> OTHER INFORMATION: Target oligonucleotide sequence

<400> SEQUENCE: 65
ggggccacta gggacaggat                                                  20

<210> SEQ ID NO 66
<211> LENGTH: 80
<212> TYPE: RNA
<213> ORGANISM: Artificial
<220> FEATURE:
<223> OTHER INFORMATION: Guide RNA
```

```
<400> SEQUENCE: 66
guuuuagagc uagaaauagc aaguuaaaau aaggcuagcu uguuaucaac uugaaaaagu    60
ggcaccgagu cggugcuuuu                                                80

<210> SEQ ID NO 67
<211> LENGTH: 23
<212> TYPE: DNA
<213> ORGANISM: Artificial
<220> FEATURE:
<223> OTHER INFORMATION: Target oligonucleotide sequence

<400> SEQUENCE: 67
gtcccctcca ccccacagtg cag                                            23

<210> SEQ ID NO 68
<211> LENGTH: 23
<212> TYPE: DNA
<213> ORGANISM: Artificial
<220> FEATURE:
<223> OTHER INFORMATION: Target oligonucleotide sequence

<400> SEQUENCE: 68
gtcccctcca ccccacagtg caa                                            23

<210> SEQ ID NO 69
<211> LENGTH: 23
<212> TYPE: DNA
<213> ORGANISM: Artificial
<220> FEATURE:
<223> OTHER INFORMATION: Target oligonucleotide sequence

<400> SEQUENCE: 69
gtcccctcca ccccacagtg cgg                                            23

<210> SEQ ID NO 70
<211> LENGTH: 52
<212> TYPE: DNA
<213> ORGANISM: Artificial
<220> FEATURE:
<223> OTHER INFORMATION: Target oligonucleotide sequence

<400> SEQUENCE: 70
tgtcccctcc accccacagt ggggccacta gggacaggat tggtgacaga aa            52

<210> SEQ ID NO 71
<211> LENGTH: 52
<212> TYPE: DNA
<213> ORGANISM: Artificial
<220> FEATURE:
<223> OTHER INFORMATION: Target oligonucleotide sequence

<400> SEQUENCE: 71
tgtccccccc accccacagt ggggccacta gggacaggat tggtgacaga aa            52

<210> SEQ ID NO 72
<211> LENGTH: 52
<212> TYPE: DNA
<213> ORGANISM: Artificial
<220> FEATURE:
<223> OTHER INFORMATION: Target oligonucleotide sequence

<400> SEQUENCE: 72
aaaaccctcc accccacagt ggggccacta gggacaggat tggtgacaga aa            52
```

<210> SEQ ID NO 73
<211> LENGTH: 52
<212> TYPE: DNA
<213> ORGANISM: Artificial
<220> FEATURE:
<223> OTHER INFORMATION: Target oligonucleotide sequence

<400> SEQUENCE: 73
tgtcccctcc tttttcagt ggggccacta gggacaggat tggtgacaga aa        52

<210> SEQ ID NO 74
<211> LENGTH: 23
<212> TYPE: DNA
<213> ORGANISM: Artificial
<220> FEATURE:
<223> OTHER INFORMATION: Target oligonucleotide sequence

<400> SEQUENCE: 74
caccggggtg gtgcccatcc tgg        23

<210> SEQ ID NO 75
<211> LENGTH: 23
<212> TYPE: DNA
<213> ORGANISM: Artificial
<220> FEATURE:
<223> OTHER INFORMATION: Target oligonucleotide sequence

<400> SEQUENCE: 75
ggtgcccatc ctggtcgagc tgg        23

<210> SEQ ID NO 76
<211> LENGTH: 23
<212> TYPE: DNA
<213> ORGANISM: Artificial
<220> FEATURE:
<223> OTHER INFORMATION: Target oligonucleotide sequence

<400> SEQUENCE: 76
cccatcctgg tcgagctgga cgg        23

<210> SEQ ID NO 77
<211> LENGTH: 23
<212> TYPE: DNA
<213> ORGANISM: Artificial
<220> FEATURE:
<223> OTHER INFORMATION: Target oligonucleotide sequence

<400> SEQUENCE: 77
ggccacaagt tcagcgtgtc cgg        23

<210> SEQ ID NO 78
<211> LENGTH: 23
<212> TYPE: DNA
<213> ORGANISM: Artificial
<220> FEATURE:
<223> OTHER INFORMATION: Target oligonucleotide sequence

<400> SEQUENCE: 78
cgcaaataag agctcaccta cgg        23

<210> SEQ ID NO 79
<211> LENGTH: 23
<212> TYPE: DNA
<213> ORGANISM: Artificial
<220> FEATURE:
<223> OTHER INFORMATION: Target oligonucleotide sequence

```
<400> SEQUENCE: 79
ctgaagttca tctgcaccac cgg                                              23

<210> SEQ ID NO 80
<211> LENGTH: 23
<212> TYPE: DNA
<213> ORGANISM: Artificial
<220> FEATURE:
<223> OTHER INFORMATION: Target oligonucleotide sequence

<400> SEQUENCE: 80
ccggcaagct gcccgtgccc tgg                                              23

<210> SEQ ID NO 81
<211> LENGTH: 23
<212> TYPE: DNA
<213> ORGANISM: Artificial
<220> FEATURE:
<223> OTHER INFORMATION: Target oligonucleotide sequence

<400> SEQUENCE: 81
gaccaggatg ggcaccaccc cgg                                              23

<210> SEQ ID NO 82
<211> LENGTH: 23
<212> TYPE: DNA
<213> ORGANISM: Artificial
<220> FEATURE:
<223> OTHER INFORMATION: Target oligonucleotide sequence

<400> SEQUENCE: 82
gccgtccagc tcgaccagga tgg                                              23

<210> SEQ ID NO 83
<211> LENGTH: 23
<212> TYPE: DNA
<213> ORGANISM: Artificial
<220> FEATURE:
<223> OTHER INFORMATION: Target oligonucleotide sequence

<400> SEQUENCE: 83
ggccggacac gctgaacttg tgg                                              23

<210> SEQ ID NO 84
<211> LENGTH: 23
<212> TYPE: DNA
<213> ORGANISM: Artificial
<220> FEATURE:
<223> OTHER INFORMATION: Target oligonucleotide sequence

<400> SEQUENCE: 84
taacagggta atgtcgaggc cgg                                              23

<210> SEQ ID NO 85
<211> LENGTH: 23
<212> TYPE: DNA
<213> ORGANISM: Artificial
<220> FEATURE:
<223> OTHER INFORMATION: Target oligonucleotide sequence

<400> SEQUENCE: 85
aggtgagctc ttatttgcgt agg                                              23

<210> SEQ ID NO 86
<211> LENGTH: 23
```

```
<212> TYPE: DNA
<213> ORGANISM: Artificial
<220> FEATURE:
<223> OTHER INFORMATION: Target oligonucleotide sequence

<400> SEQUENCE: 86
cttcagggtc agcttgccgt agg                                              23

<210> SEQ ID NO 87
<211> LENGTH: 23
<212> TYPE: DNA
<213> ORGANISM: Artificial
<220> FEATURE:
<223> OTHER INFORMATION: Target oligonucleotide sequence

<400> SEQUENCE: 87
gggcacgggc agcttgccgg tgg                                              23

<210> SEQ ID NO 88
<211> LENGTH: 23
<212> TYPE: DNA
<213> ORGANISM: Artificial
<220> FEATURE:
<223> OTHER INFORMATION: Target oligonucleotide sequence

<400> SEQUENCE: 88
gagatgatcg ccccttcttc tgg                                              23

<210> SEQ ID NO 89
<211> LENGTH: 20
<212> TYPE: DNA
<213> ORGANISM: Artificial
<220> FEATURE:
<223> OTHER INFORMATION: Target oligonucleotide sequence

<400> SEQUENCE: 89
gagatgatcg ccccttcttc                                                  20

<210> SEQ ID NO 90
<211> LENGTH: 20
<212> TYPE: DNA
<213> ORGANISM: Artificial
<220> FEATURE:
<223> OTHER INFORMATION: Target oligonucleotide sequence

<400> SEQUENCE: 90
gtgatgaccg gccgttcttc                                                  20

<210> SEQ ID NO 91
<211> LENGTH: 23
<212> TYPE: DNA
<213> ORGANISM: Artificial
<220> FEATURE:
<223> OTHER INFORMATION: Target oligonucleotide sequence

<400> SEQUENCE: 91
gtcccctcca ccccacagtg ggg                                              23

<210> SEQ ID NO 92
<211> LENGTH: 23
<212> TYPE: DNA
<213> ORGANISM: Artificial
<220> FEATURE:
<223> OTHER INFORMATION: Target oligonucleotide sequence

<400> SEQUENCE: 92
```

```
gagatgatcg cccgttcttc tgg                                              23

<210> SEQ ID NO 93
<211> LENGTH: 20
<212> TYPE: RNA
<213> ORGANISM: Artificial
<220> FEATURE:
<223> OTHER INFORMATION: RNA target sequence

<400> SEQUENCE: 93
guccccucca ccccacagug                                                  20

<210> SEQ ID NO 94
<211> LENGTH: 20
<212> TYPE: RNA
<213> ORGANISM: Artificial
<220> FEATURE:
<223> OTHER INFORMATION: RNA target sequence

<400> SEQUENCE: 94
guccccucca ccccacaguc                                                  20

<210> SEQ ID NO 95
<211> LENGTH: 20
<212> TYPE: RNA
<213> ORGANISM: Artificial
<220> FEATURE:
<223> OTHER INFORMATION: RNA target sequence

<400> SEQUENCE: 95
guccccucca ccccacagag                                                  20

<210> SEQ ID NO 96
<211> LENGTH: 20
<212> TYPE: RNA
<213> ORGANISM: Artificial
<220> FEATURE:
<223> OTHER INFORMATION: RNA target sequence

<400> SEQUENCE: 96
guccccucca ccccacacug                                                  20

<210> SEQ ID NO 97
<211> LENGTH: 20
<212> TYPE: RNA
<213> ORGANISM: Artificial
<220> FEATURE:
<223> OTHER INFORMATION: RNA target sequence

<400> SEQUENCE: 97
guccccucca ccccacugug                                                  20

<210> SEQ ID NO 98
<211> LENGTH: 20
<212> TYPE: RNA
<213> ORGANISM: Artificial
<220> FEATURE:
<223> OTHER INFORMATION: RNA target sequence

<400> SEQUENCE: 98
guccccucca ccccagagug                                                  20

<210> SEQ ID NO 99
<211> LENGTH: 20
<212> TYPE: RNA
<213> ORGANISM: Artificial
```

```
<220> FEATURE:
<223> OTHER INFORMATION: RNA target sequence

<400> SEQUENCE: 99
guccccucca ccccucagug                                                    20

<210> SEQ ID NO 100
<211> LENGTH: 20
<212> TYPE: RNA
<213> ORGANISM: Artificial
<220> FEATURE:
<223> OTHER INFORMATION: RNA target sequence

<400> SEQUENCE: 100
guccccucca cccgacagug                                                    20

<210> SEQ ID NO 101
<211> LENGTH: 20
<212> TYPE: RNA
<213> ORGANISM: Artificial
<220> FEATURE:
<223> OTHER INFORMATION: RNA target sequence

<400> SEQUENCE: 101
guccccucca ccgcacagug                                                    20

<210> SEQ ID NO 102
<211> LENGTH: 20
<212> TYPE: RNA
<213> ORGANISM: Artificial
<220> FEATURE:
<223> OTHER INFORMATION: RNA target sequence

<400> SEQUENCE: 102
guccccucca cgccacagug                                                    20

<210> SEQ ID NO 103
<211> LENGTH: 20
<212> TYPE: RNA
<213> ORGANISM: Artificial
<220> FEATURE:
<223> OTHER INFORMATION: RNA target sequence

<400> SEQUENCE: 103
guccccucca gcccacagug                                                    20

<210> SEQ ID NO 104
<211> LENGTH: 20
<212> TYPE: RNA
<213> ORGANISM: Artificial
<220> FEATURE:
<223> OTHER INFORMATION: RNA target sequence

<400> SEQUENCE: 104
guccccuccu ccccacagug                                                    20

<210> SEQ ID NO 105
<211> LENGTH: 20
<212> TYPE: RNA
<213> ORGANISM: Artificial
<220> FEATURE:
<223> OTHER INFORMATION: RNA target sequence

<400> SEQUENCE: 105
guccccucga ccccacagug                                                    20
```

```
<210> SEQ ID NO 106
<211> LENGTH: 20
<212> TYPE: RNA
<213> ORGANISM: Artificial
<220> FEATURE:
<223> OTHER INFORMATION: RNA target sequence

<400> SEQUENCE: 106
guccccucca ccccacagac                                              20

<210> SEQ ID NO 107
<211> LENGTH: 20
<212> TYPE: RNA
<213> ORGANISM: Artificial
<220> FEATURE:
<223> OTHER INFORMATION: RNA target sequence

<400> SEQUENCE: 107
guccccucca ccccacucug                                              20

<210> SEQ ID NO 108
<211> LENGTH: 20
<212> TYPE: RNA
<213> ORGANISM: Artificial
<220> FEATURE:
<223> OTHER INFORMATION: RNA target sequence

<400> SEQUENCE: 108
guccccucca ccccugagug                                              20

<210> SEQ ID NO 109
<211> LENGTH: 20
<212> TYPE: RNA
<213> ORGANISM: Artificial
<220> FEATURE:
<223> OTHER INFORMATION: RNA target sequence

<400> SEQUENCE: 109
guccccucca ccggacagug                                              20

<210> SEQ ID NO 110
<211> LENGTH: 20
<212> TYPE: RNA
<213> ORGANISM: Artificial
<220> FEATURE:
<223> OTHER INFORMATION: RNA target sequence

<400> SEQUENCE: 110
guccccucca ggccacagug                                              20

<210> SEQ ID NO 111
<211> LENGTH: 20
<212> TYPE: RNA
<213> ORGANISM: Artificial
<220> FEATURE:
<223> OTHER INFORMATION: RNA target sequence

<400> SEQUENCE: 111
guccccucgu ccccacagug                                              20

<210> SEQ ID NO 112
<211> LENGTH: 23
<212> TYPE: DNA
<213> ORGANISM: Artificial
<220> FEATURE:
<223> OTHER INFORMATION: Target oligonucleotide sequence
```

```
<400> SEQUENCE: 112
ggggccacta gggacaggat ggg                                              23

<210> SEQ ID NO 113
<211> LENGTH: 20
<212> TYPE: RNA
<213> ORGANISM: Artificial
<220> FEATURE:
<223> OTHER INFORMATION: RNA target sequence

<400> SEQUENCE: 113
gagaugaucg ccccuucuuc                                                  20

<210> SEQ ID NO 114
<211> LENGTH: 20
<212> TYPE: RNA
<213> ORGANISM: Artificial
<220> FEATURE:
<223> OTHER INFORMATION: RNA target sequence

<400> SEQUENCE: 114
gagaugaucg ccccuucuug                                                  20

<210> SEQ ID NO 115
<211> LENGTH: 20
<212> TYPE: RNA
<213> ORGANISM: Artificial
<220> FEATURE:
<223> OTHER INFORMATION: RNA target sequence

<400> SEQUENCE: 115
gagaugaucg ccccuucuac                                                  20

<210> SEQ ID NO 116
<211> LENGTH: 20
<212> TYPE: RNA
<213> ORGANISM: Artificial
<220> FEATURE:
<223> OTHER INFORMATION: RNA target sequence

<400> SEQUENCE: 116
gagaugaucg ccccuucauc                                                  20

<210> SEQ ID NO 117
<211> LENGTH: 20
<212> TYPE: RNA
<213> ORGANISM: Artificial
<220> FEATURE:
<223> OTHER INFORMATION: RNA target sequence

<400> SEQUENCE: 117
gagaugaucg ccccuuguuc                                                  20

<210> SEQ ID NO 118
<211> LENGTH: 20
<212> TYPE: RNA
<213> ORGANISM: Artificial
<220> FEATURE:
<223> OTHER INFORMATION: RNA target sequence

<400> SEQUENCE: 118
gagaugaucg ccccuacuuc                                                  20

<210> SEQ ID NO 119
```

```
<211> LENGTH: 20
<212> TYPE: RNA
<213> ORGANISM: Artificial
<220> FEATURE:
<223> OTHER INFORMATION: RNA target sequence

<400> SEQUENCE: 119
gagaugaucg ccccaucuuc                                              20

<210> SEQ ID NO 120
<211> LENGTH: 20
<212> TYPE: RNA
<213> ORGANISM: Artificial
<220> FEATURE:
<223> OTHER INFORMATION: RNA target sequence

<400> SEQUENCE: 120
gagaugaucg cccguucuuc                                              20

<210> SEQ ID NO 121
<211> LENGTH: 20
<212> TYPE: RNA
<213> ORGANISM: Artificial
<220> FEATURE:
<223> OTHER INFORMATION: RNA target sequence

<400> SEQUENCE: 121
gagaugaucg ccgcuucuuc                                              20

<210> SEQ ID NO 122
<211> LENGTH: 20
<212> TYPE: RNA
<213> ORGANISM: Artificial
<220> FEATURE:
<223> OTHER INFORMATION: RNA target sequence

<400> SEQUENCE: 122
gagaugaucg cgccuucuuc                                              20

<210> SEQ ID NO 123
<211> LENGTH: 20
<212> TYPE: RNA
<213> ORGANISM: Artificial
<220> FEATURE:
<223> OTHER INFORMATION: RNA target sequence

<400> SEQUENCE: 123
gagaugaucg gcccuucuuc                                              20

<210> SEQ ID NO 124
<211> LENGTH: 20
<212> TYPE: RNA
<213> ORGANISM: Artificial
<220> FEATURE:
<223> OTHER INFORMATION: RNA target sequence

<400> SEQUENCE: 124
gagaugaucc ccccuucuuc                                              20

<210> SEQ ID NO 125
<211> LENGTH: 20
<212> TYPE: RNA
<213> ORGANISM: Artificial
<220> FEATURE:
<223> OTHER INFORMATION: RNA target sequence

<400> SEQUENCE: 125
```
gagaugaugg ccccuucuuc                                               20

<210> SEQ ID NO 126
<211> LENGTH: 20
<212> TYPE: RNA
<213> ORGANISM: Artificial
<220> FEATURE:
<223> OTHER INFORMATION: RNA target sequence

<400> SEQUENCE: 126
gagaugaucg ccccuucuag                                               20

<210> SEQ ID NO 127
<211> LENGTH: 20
<212> TYPE: RNA
<213> ORGANISM: Artificial
<220> FEATURE:
<223> OTHER INFORMATION: RNA target sequence

<400> SEQUENCE: 127
gagaugaucg ccccuugauc                                               20

<210> SEQ ID NO 128
<211> LENGTH: 20
<212> TYPE: RNA
<213> ORGANISM: Artificial
<220> FEATURE:
<223> OTHER INFORMATION: RNA target sequence

<400> SEQUENCE: 128
gagaugaucg ccccaacuuc                                               20

<210> SEQ ID NO 129
<211> LENGTH: 20
<212> TYPE: RNA
<213> ORGANISM: Artificial
<220> FEATURE:
<223> OTHER INFORMATION: RNA target sequence

<400> SEQUENCE: 129
gagaugaucg ccgguucuuc                                               20

<210> SEQ ID NO 130
<211> LENGTH: 20
<212> TYPE: RNA
<213> ORGANISM: Artificial
<220> FEATURE:
<223> OTHER INFORMATION: RNA target sequence

<400> SEQUENCE: 130
gagaugaucg ggccuucuuc                                               20

<210> SEQ ID NO 131
<211> LENGTH: 20
<212> TYPE: RNA
<213> ORGANISM: Artificial
<220> FEATURE:
<223> OTHER INFORMATION: RNA target sequence

<400> SEQUENCE: 131
gagaugaugc ccccuucuuc                                               20

<210> SEQ ID NO 132
<211> LENGTH: 23
<212> TYPE: DNA

```
<213> ORGANISM: Artificial
<220> FEATURE:
<223> OTHER INFORMATION: Target oligonucleotide sequence

<400> SEQUENCE: 132
gagatgatcg cccctttcttc tgg                                              23

<210> SEQ ID NO 133
<211> LENGTH: 20
<212> TYPE: RNA
<213> ORGANISM: Artificial
<220> FEATURE:
<223> OTHER INFORMATION: RNA target sequence

<400> SEQUENCE: 133
ggggccacua gggacaggau                                                   20

<210> SEQ ID NO 134
<211> LENGTH: 19
<212> TYPE: RNA
<213> ORGANISM: Artificial
<220> FEATURE:
<223> OTHER INFORMATION: RNA target sequence

<400> SEQUENCE: 134
gggccacuag ggacaggau                                                    19

<210> SEQ ID NO 135
<211> LENGTH: 18
<212> TYPE: RNA
<213> ORGANISM: Artificial
<220> FEATURE:
<223> OTHER INFORMATION: RNA target sequence

<400> SEQUENCE: 135
ggccacuagg gacaggau                                                     18

<210> SEQ ID NO 136
<211> LENGTH: 17
<212> TYPE: RNA
<213> ORGANISM: Artificial
<220> FEATURE:
<223> OTHER INFORMATION: RNA target sequence

<400> SEQUENCE: 136
gccacuaggg acaggau                                                      17

<210> SEQ ID NO 137
<211> LENGTH: 20
<212> TYPE: RNA
<213> ORGANISM: Artificial
<220> FEATURE:
<223> OTHER INFORMATION: RNA target sequence

<400> SEQUENCE: 137
gagaugaucg ccccuucuuc                                                   20

<210> SEQ ID NO 138
<211> LENGTH: 18
<212> TYPE: RNA
<213> ORGANISM: Artificial
<220> FEATURE:
<223> OTHER INFORMATION: RNA target sequence

<400> SEQUENCE: 138
gaugaucgcc ccuucuuc                                                     18
```

<210> SEQ ID NO 139
<211> LENGTH: 15
<212> TYPE: RNA
<213> ORGANISM: Artificial
<220> FEATURE:
<223> OTHER INFORMATION: RNA target sequence

<400> SEQUENCE: 139
gaucgccccu ucuuc                                                        15

<210> SEQ ID NO 140
<211> LENGTH: 11
<212> TYPE: RNA
<213> ORGANISM: Artificial
<220> FEATURE:
<223> OTHER INFORMATION: RNA target sequence

<400> SEQUENCE: 140
gccccuucuu c                                                            11

<210> SEQ ID NO 141
<211> LENGTH: 21
<212> TYPE: DNA
<213> ORGANISM: Artificial
<220> FEATURE:
<223> OTHER INFORMATION: Target oligonucleotide sequence

<400> SEQUENCE: 141 gtccctcca ccccacagtg c                                                  21

<210> SEQ ID NO 142
<211> LENGTH: 14
<212> TYPE: DNA
<213> ORGANISM: Artificial
<220> FEATURE:
<223> OTHER INFORMATION: Target oligonucleotide sequence
<220> FEATURE:
<221> NAME/KEY: misc_feature
<222> LOCATION: (5)..(10)
<223> OTHER INFORMATION: wherein N id G, A, T or C

<400> SEQUENCE: 142
tgtcnnnnnn accc                                                         14

<210> SEQ ID NO 143
<211> LENGTH: 14
<212> TYPE: DNA
<213> ORGANISM: Artificial
<220> FEATURE:
<223> OTHER INFORMATION: Target oligonucleotide sequence

<400> SEQUENCE: 143
tgtcaaaaaa accc                                                         14

<210> SEQ ID NO 144
<211> LENGTH: 14
<212> TYPE: DNA
<213> ORGANISM: Artificial
<220> FEATURE:
<223> OTHER INFORMATION: Target oligonucleotide sequence

<400> SEQUENCE: 144 tgtcggggggg accc                                                        14

<210> SEQ ID NO 145

-continued

```
<211> LENGTH: 14
<212> TYPE: DNA
<213> ORGANISM: Artificial
<220> FEATURE:
<223> OTHER INFORMATION: Target oligonucleotide sequence

<400> SEQUENCE: 145
tgtcaaaaaa accc                                                   14

<210> SEQ ID NO 146
<211> LENGTH: 14
<212> TYPE: DNA
<213> ORGANISM: Artificial
<220> FEATURE:
<223> OTHER INFORMATION: Target oligonucleotide sequence

<400> SEQUENCE: 146
tgtcgggggg accc                                                   14

<210> SEQ ID NO 147
<211> LENGTH: 14
<212> TYPE: DNA
<213> ORGANISM: Artificial
<220> FEATURE:
<223> OTHER INFORMATION: Target oligonucleotide sequence

<400> SEQUENCE: 147 tgtcccccccc accc                                                  14

<210> SEQ ID NO 148
<211> LENGTH: 14
<212> TYPE: DNA
<213> ORGANISM: Artificial
<220> FEATURE:
<223> OTHER INFORMATION: Target oligonucleotide sequence

<400> SEQUENCE: 148
tgtctttttt accc                                                   14

<210> SEQ ID NO 149
<211> LENGTH: 14
<212> TYPE: DNA
<213> ORGANISM: Artificial
<220> FEATURE:
<223> OTHER INFORMATION: Target oligonucleotide sequence

<400> SEQUENCE: 149
tgtccccccc accc                                                   14

<210> SEQ ID NO 150
<211> LENGTH: 14
<212> TYPE: DNA
<213> ORGANISM: Artificial
<220> FEATURE:
<223> OTHER INFORMATION: Target oligonucleotide sequence

<400> SEQUENCE: 150
tgtctttttt accc                                                   14

<210> SEQ ID NO 151
<211> LENGTH: 23
<212> TYPE: DNA
<213> ORGANISM: Artificial
<220> FEATURE:
<223> OTHER INFORMATION: Target oligonucleotide sequence

<400> SEQUENCE: 151
```

```
ggatcctgtg tccccgagct ggg                                              23
```

<210> SEQ ID NO 152
<211> LENGTH: 23
<212> TYPE: DNA
<213> ORGANISM: Artificial
<220> FEATURE:
<223> OTHER INFORMATION: Target oligonucleotide sequence

<400> SEQUENCE: 152

```
gttaatgtgg ctctggttct ggg                                              23
```

<210> SEQ ID NO 153
<211> LENGTH: 23
<212> TYPE: DNA
<213> ORGANISM: Artificial
<220> FEATURE:
<223> OTHER INFORMATION: Target oligonucleotide sequence

<400> SEQUENCE: 153

```
ggggccacta gggacaggat tgg                                              23
```

<210> SEQ ID NO 154
<211> LENGTH: 23
<212> TYPE: DNA
<213> ORGANISM: Artificial
<220> FEATURE:
<223> OTHER INFORMATION: Target oligonucleotide sequence

<400> SEQUENCE: 154

```
cttcctagtc tcctgatatt ggg                                              23
```

<210> SEQ ID NO 155
<211> LENGTH: 23
<212> TYPE: DNA
<213> ORGANISM: Artificial
<220> FEATURE:
<223> OTHER INFORMATION: Target oligonucleotide sequence

<400> SEQUENCE: 155

```
tggtcccagc tcggggacac agg                                              23
```

<210> SEQ ID NO 156
<211> LENGTH: 23
<212> TYPE: DNA
<213> ORGANISM: Artificial
<220> FEATURE:
<223> OTHER INFORMATION: Target oligonucleotide sequence

<400> SEQUENCE: 156

```
agaaccagag ccacattaac cgg                                              23
```

<210> SEQ ID NO 157
<211> LENGTH: 23
<212> TYPE: DNA
<213> ORGANISM: Artificial
<220> FEATURE:
<223> OTHER INFORMATION: Target oligonucleotide sequence

<400> SEQUENCE: 157

```
gtcaccaatc ctgtccctag tgg                                              23
```

<210> SEQ ID NO 158
<211> LENGTH: 23
<212> TYPE: DNA

```
<213> ORGANISM: Artificial
<220> FEATURE:
<223> OTHER INFORMATION: Target oligonucleotide sequence

<400> SEQUENCE: 158
agacccaata tcaggagact agg                                              23

<210> SEQ ID NO 159
<211> LENGTH: 75
<212> TYPE: DNA
<213> ORGANISM: Artificial
<220> FEATURE:
<223> OTHER INFORMATION: Target oligonucleotide sequence

<400> SEQUENCE: 159
gggatcctgt gtccccgagc tgggaccacc ttatattccc agggccggtt aatgtggctc      60
tggttctggg tactt                                                       75

<210> SEQ ID NO 160
<211> LENGTH: 69
<212> TYPE: DNA
<213> ORGANISM: Artificial
<220> FEATURE:
<223> OTHER INFORMATION: Target oligonucleotide sequence

<400> SEQUENCE: 160
gggatcctgt gtccccgagc tgggaccacc ttatattccc agggccggtt aatgtggttc      60
tgggtactt                                                              69

<210> SEQ ID NO 161
<211> LENGTH: 113
<212> TYPE: DNA
<213> ORGANISM: Artificial
<220> FEATURE:
<223> OTHER INFORMATION: Target oligonucleotide sequence

<400> SEQUENCE: 161
gggatcctgt gtccccgagc tgggaccacc ttatattccc agggcagggc cggttggacc      60
accttatatt cccagggcag ggccggttaa tgtggctctg gttctgggta ctt             113

<210> SEQ ID NO 162
<211> LENGTH: 34
<212> TYPE: DNA
<213> ORGANISM: Artificial
<220> FEATURE:
<223> OTHER INFORMATION: Target oligonucleotide sequence

<400> SEQUENCE: 162
gggatcctgt gtccccgtct ggttctgggt actt                                  34

<210> SEQ ID NO 163
<211> LENGTH: 47
<212> TYPE: DNA
<213> ORGANISM: Artificial
<220> FEATURE:
<223> OTHER INFORMATION: Target oligoncleotide sequence

<400> SEQUENCE: 163
gggatcctgt gtccccgagc tgggaccacc ttatattctg ggtactt                    47

<210> SEQ ID NO 164
<211> LENGTH: 17
<212> TYPE: DNA
<213> ORGANISM: Artificial
```

```
<220> FEATURE:
<223> OTHER INFORMATION: Target oligonucleotide sequence

<400> SEQUENCE: 164
gggatcctgt ggtactt                                                  17

<210> SEQ ID NO 165
<211> LENGTH: 93
<212> TYPE: DNA
<213> ORGANISM: Artificial
<220> FEATURE:
<223> OTHER INFORMATION: Target oligonucleotide sequence

<400> SEQUENCE: 165
agggccggtt aatgtggctc tggttctggg tactttatc tgtccctcc accccacagt    60 ggggccacta gggacaggat tggtgacaga aaa                                93

<210> SEQ ID NO 166
<211> LENGTH: 83
<212> TYPE: DNA
<213> ORGANISM: Artificial
<220> FEATURE:
<223> OTHER INFORMATION: Target oligonucleotide sequence

<400> SEQUENCE: 166
agggccggtt aatgaatgtg gctctggttc tgggtacttt tatctgtccc ctccacccca   60
cagtggggcc actagacaga aaa                                           83

<210> SEQ ID NO 167
<211> LENGTH: 76
<212> TYPE: DNA
<213> ORGANISM: Artificial
<220> FEATURE:
<223> OTHER INFORMATION: Target oligonucleotide sequence

<400> SEQUENCE: 167
agggccggtt aatgtggctc tggttctggg tactttatc tgtcccccag tggggccact    60
gattggtgac agaaaa                                                   76

<210> SEQ ID NO 168
<211> LENGTH: 29
<212> TYPE: DNA
<213> ORGANISM: Artificial
<220> FEATURE:
<223> OTHER INFORMATION: Target oligonucleotide sequence

<400> SEQUENCE: 168
agggccggtt caggattggt gacagaaaa                                     29

<210> SEQ ID NO 169
<211> LENGTH: 34
<212> TYPE: DNA
<213> ORGANISM: Artificial
<220> FEATURE:
<223> OTHER INFORMATION: Target oligonucleotide sequence

<400> SEQUENCE: 169
agggccggtt aatgtggcga ttggtgacag aaaa                               34

<210> SEQ ID NO 170
<211> LENGTH: 63
<212> TYPE: DNA
<213> ORGANISM: Artificial
<220> FEATURE:
```

```
<223> OTHER INFORMATION: Target oligonucleotide sequence

<400> SEQUENCE: 170
agggccggtt aatgtggctc tggttctggg tactttatc tgtccccgat tggtgacaga       60
aaa                                                                    63

<210> SEQ ID NO 171
<211> LENGTH: 84
<212> TYPE: DNA
<213> ORGANISM: Artificial
<220> FEATURE:
<223> OTHER INFORMATION: Target oligonucleotide sequence

<400> SEQUENCE: 171
agggccggtt aatgtggctc tggttctggg tactttatc tgtcccctcc accccacagt       60
ggggacagga ttggtgacag aaaa                                             84

<210> SEQ ID NO 172
<211> LENGTH: 27
<212> TYPE: DNA
<213> ORGANISM: Artificial
<220> FEATURE:
<223> OTHER INFORMATION: Target oligonucleotide sequence

<400> SEQUENCE: 172
agggccggtt aatgtggtga cagaaaa                                          27

<210> SEQ ID NO 173
<211> LENGTH: 105
<212> TYPE: DNA
<213> ORGANISM: Artificial
<220> FEATURE:
<223> OTHER INFORMATION: Target oligonucleotide sequence

<400> SEQUENCE: 173
agggccggtt aatgtggctc tggttctggg tactttatc tgtcccctcc accccagggg       60
acagtctgtc ccctccaccc caggacagg attggtgaca gaaaa                      105

<210> SEQ ID NO 174
<211> LENGTH: 80
<212> TYPE: DNA
<213> ORGANISM: Artificial
<220> FEATURE:
<223> OTHER INFORMATION: Target oligonucleotide sequence

<400> SEQUENCE: 174
agggccggtt aatgtggctc tggttctggg tactttatc tgtcccctcc accactaggg       60
acaggattgg tgacagaaaa                                                  80

<210> SEQ ID NO 175
<211> LENGTH: 53
<212> TYPE: DNA
<213> ORGANISM: Artificial
<220> FEATURE:
<223> OTHER INFORMATION: Target oligonucleotide sequence

<400> SEQUENCE: 175
cccacagtgg ggccactagg gacaggattg gtgacagaaa agccccatac ccc             53

<210> SEQ ID NO 176
<211> LENGTH: 22
<212> TYPE: DNA
<213> ORGANISM: Artificial
```

```
<220> FEATURE:
<223> OTHER INFORMATION: Target oligonucleotide sequence

<400> SEQUENCE: 176
cccacagtgg ggccactacc cc                                              22

<210> SEQ ID NO 177
<211> LENGTH: 96
<212> TYPE: DNA
<213> ORGANISM: Artificial
<220> FEATURE:
<223> OTHER INFORMATION: Target oligonucleotide sequence

<400> SEQUENCE: 177
cccacagtgg ggccactagt agaaaagccc catccttagg cctcccccat ccttaggcct    60
cctccttcct agtctcctga tattgggtct aacccc                              96

<210> SEQ ID NO 178
<211> LENGTH: 94
<212> TYPE: DNA
<213> ORGANISM: Artificial
<220> FEATURE:
<223> OTHER INFORMATION: Target oligonucleotide sequence

<400> SEQUENCE: 178
cccacagtgg ggccactagg gacaggattg gtgacagaaa agccccatcc ttaggcctcc    60
tccttcctag tctcctgata ttgggtctaa cccc                                94

<210> SEQ ID NO 179
<211> LENGTH: 62
<212> TYPE: DNA
<213> ORGANISM: Artificial
<220> FEATURE:
<223> OTHER INFORMATION: Target oligonucleotide sequence

<400> SEQUENCE: 179
cccacagtgg ggccaccctt aggcctcctc cttcctagtc tcctgatatt gggtctaacc    60
cc                                                                   62

<210> SEQ ID NO 180
<211> LENGTH: 38
<212> TYPE: DNA
<213> ORGANISM: Artificial
<220> FEATURE:
<223> OTHER INFORMATION: Target oligonucleotide sequence

<400> SEQUENCE: 180
cccacagtgg ggccactagt gatattgggt ctaacccc                            38

<210> SEQ ID NO 181
<211> LENGTH: 94
<212> TYPE: DNA
<213> ORGANISM: Artificial
<220> FEATURE:
<223> OTHER INFORMATION: target oligonucleotide sequence

<400> SEQUENCE: 181
cccacagtgg ggccactagg gacaggattg gtgacaaaaa agccccatcc ttacgcctcc    60
```

```
tccttcctag tctcctgata ttgggtctaa cccc                                  94

<210> SEQ ID NO 182
<211> LENGTH: 65
<212> TYPE: DNA
<213> ORGANISM: Artificial
<220> FEATURE:
<223> OTHER INFORMATION: Target oligonucleotide sequence

<400> SEQUENCE: 182
cccacagtgg ggccactagg gacaggcctc ctccttccta gtctcctgat attgggtcta     60
acccc                                                                 65

<210> SEQ ID NO 183
<211> LENGTH: 102
<212> TYPE: DNA
<213> ORGANISM: Artificial
<220> FEATURE:
<223> OTHER INFORMATION: Target oligonucleotide sequence

<400> SEQUENCE: 183
cccacagtgg ggccactagg gacaggggga caggattggt gacagaaaag ccccatcctt     60
aggcctcctc cttcctagtc tctgatatt gggtctaacc cc                        102

<210> SEQ ID NO 184
<211> LENGTH: 76
<212> TYPE: DNA
<213> ORGANISM: Artificial
<220> FEATURE:
<223> OTHER INFORMATION: Target oligonucleotide sequence

<400> SEQUENCE: 184
cccacaggat tggtgacaga aaagcccat ccttaggcct cctccttcct agtctcctga      60
tattgggtct aacccc                                                     76
```